US011198874B2

(12) United States Patent
Tallent et al.

(10) Patent No.: US 11,198,874 B2
(45) Date of Patent: Dec. 14, 2021

(54) SCN8A SPLICE MODULATING OLIGONUCLEOTIDES AND METHODS OF USE THEREOF

(71) Applicant: LifeSplice Pharma LLC, Malvern, PA (US)

(72) Inventors: Melanie Tallent, Malvern, PA (US); Nicole Lykens, Malvern, PA (US); Gordon Lutz, Malvern, PA (US)

(73) Assignee: LifeSplice Pharma LLC, Malvern, PA (US)

( * ) Notice: Subject to any disclaimer, the term of this patent is extended or adjusted under 35 U.S.C. 154(b) by 0 days.

(21) Appl. No.: 15/504,952

(22) PCT Filed: Oct. 17, 2015

(86) PCT No.: PCT/IB2015/001917
§ 371 (c)(1),
(2) Date: Feb. 17, 2017

(87) PCT Pub. No.: WO2016/027168
PCT Pub. Date: Feb. 25, 2016

(65) Prior Publication Data

US 2017/0240904 A1 Aug. 24, 2017

Related U.S. Application Data

(60) Provisional application No. 62/039,819, filed on Aug. 20, 2014.

(51) Int. Cl.

| | |
|---|---|
| ***C12N 15/11*** | (2006.01) |
| ***C12N 15/113*** | (2010.01) |
| ***A61K 31/7105*** | (2006.01) |
| ***C12N 15/85*** | (2006.01) |
| ***A61K 48/00*** | (2006.01) |

(52) U.S. Cl.
CPC ...... *C12N 15/1138* (2013.01); *A61K 31/7105* (2013.01); *A61K 48/00* (2013.01); *C12N 15/113* (2013.01); *C12N 15/85* (2013.01); *C12N 2310/11* (2013.01); *C12N 2310/315* (2013.01); *C12N 2310/321* (2013.01); *C12N 2320/33* (2013.01)

(58) Field of Classification Search
CPC . C12N 15/111; C12N 15/113; C12N 2310/11; C12N 2320/33; C12N 2710/24161
See application file for complete search history.

(56) References Cited

U.S. PATENT DOCUMENTS

| | | | | |
|---|---|---|---|---|
| 8,680,254 B2 | | 3/2014 | Lutz et al. | |
| 9,359,603 B2 | | 6/2016 | Lutz et al. | |
| 2005/0112633 A1 | | 5/2005 | Armour et al. | |
| 2007/0031844 A1* | | 2/2007 | Khvorova | A61K 31/713 435/6.11 |
| 2008/0113351 A1* | | 5/2008 | Naito | A61K 31/713 435/6.11 |
| 2009/0306005 A1* | | 12/2009 | Bhanot | C12N 15/1137 514/44 R |
| 2009/0306179 A1* | | 12/2009 | Bhanot | C12N 15/1137 514/44 A |
| 2012/0316223 A1 | | 12/2012 | Lutz et al. | |
| 2014/0249210 A1 | | 9/2014 | Lutz et al. | |
| 2015/0099791 A1* | | 4/2015 | Krieg | C12N 15/113 514/44 A |
| 2015/0152410 A1* | | 6/2015 | Krieg | C12N 15/113 514/44 R |
| 2016/0002625 A1* | | 1/2016 | Crooke | C12N 15/113 514/44 A |
| 2016/0032286 A1* | | 2/2016 | Montgomery | C12N 15/113 514/44 A |
| 2017/0037411 A1 | | 2/2017 | Lutz et al. | |

FOREIGN PATENT DOCUMENTS

WO WO-2010/083338 A2 7/2010

OTHER PUBLICATIONS

Predicted: Homo sapiens RAR related orphan receptor A (RORA), transcript variant X8, mRNA, NCBI Reference Sequence: XM_011521879.2, retrieved from www.ncbi.nlm.nih.gov on Oct. 25, 2017.*
Homo sapiens SHANK associated RH domain interactor (SHARPIN), transcript variant 1, mRNA, NCBI Reference Sequence: NM_030974.3, retrieved from www.ncbi.nlm.nih.gov on Oct. 25, 2017.*
Homo sapiens transmembrane protein 248 (TMEM248), mRNA, NCBI Reference Sequence: NM_017994.4, retrieved from www.ncbi.nlm.nih.gov on Oct. 25, 2017.*
Predicted: Amborella trichopoda cytochrome P450 97B2, chloroplastic (LOC18444387), transcript variant X3, mRNA, NCBI Reference Sequence: XM_020673772.1, retrieved from www.ncbi.nlm.nih.gov on Oct. 25, 2017.*
Predicted: Limulus polyphemus tubulin-specific chaperone C-like (LOC106458145), transcript variant X7, mRNA, NCBI Reference Sequence: XM_022384293.1, retrieved from www.ncbi.nlm.nih.gov on Oct. 25, 2017.*

(Continued)

*Primary Examiner* — Dana H Shin
(74) *Attorney, Agent, or Firm* — Clark & Elbing LLP; Susan M. Michaud

(57) ABSTRACT

A splice modulating oligonucleotide (SMO), is provided having a sequence designed to modulate the splicing of a SCN8A pre-mRNA, wherein the SMO sequence specifically binds to a sequence in the SCN8A pre-mRNA. Certain embodiments of the invention provide methods of using the SMOs described herein, including methods of treating or preventing epilepsy or a Dravet Spectrum disorder in subject (e.g., a mammal, e.g., a human), including the administration of an SMO or composition described herein to the subject. A method of using the SMOs is described herein to treat spinal cord injury, cancer, amyotrophic lateral sclerosis, Alzheimer's disease, traumatic brain injury, autism, hemiplegic migraine, multiple sclerosis, CNS infections, Parkinson's and Huntington's disease, or other neurological diseases or disorders in which excitotoxicity or hyperexcitability contributes to the pathology.

17 Claims, 49 Drawing Sheets

Specification includes a Sequence Listing.

(56) References Cited

OTHER PUBLICATIONS

Predicted: Myzus persicae coiled-coil domain-containing protein 39-like (LOC111040808), transcript variant X5, mRNA, NCBI Reference Sequence: XM_022324870.1, retrieved from www.ncbi.nlm.nih.gov on Oct. 25, 2017.*
O'Brien et al., Rbfox proteins regulate alternative splicing of neuronal sodium channel SCN8A, 2012 (available online on Oct. 21, 2011), vol. 49, pp. 120-126.*
Minovitsky et al., The splicing regulatory element, UGCAUG, is phylogenetically and spatially conserved in introns that flank tissue-specific alterantive exons, 2005, Nucleic Acids Research, vol. 33, pp. 714-724.*
Hua et al., Antisense masking of an hnRNP A1/A2 intronic splicing silencer corrects SMN2 splicing in transgenic mice, 2008, The American Journal of Human Genetics, vol. 82, pp. 834-848.*
Aartsma-Rus et al., Guidelines for antisense oligonucleotide design and insight into splice-modulating mechanisms, Molecular Therapy, vol. 17, pp. 548-553. (Year: 2009).*
Wilton et al., Antisense oligonucleotide-induced exon skipping across the human dystrophin gene transcript, Molecular Therapy, vol. 15, pp. 1288-1296. (Year: 2007).*
Communication pursuant to Article 113 EPC dated Jun. 7, 2017 for European Application No. 15833669.3, Tallent et al., "Splice Modulating Oligonucleotides and Methods of Use Thereof," filed Oct. 17, 2015 (4 pages).
Decision dated Sep. 19, 2017 for European Application No. 15833669.3, Tallent et al., "Splice Modulating Oligonucleotides and Methods of Use Thereof," filed Oct. 17, 2015 (4 pages).
Gehman et al., "The splicing regulator Rbfox2 is required for both cerebellar development and mature motor function," Genes Dev. 26(5):445-60 (2012).
International Search Report and Written Opinion dated Feb. 23, 2016, for International Application No. PCT/IB2015/001917, Tallent et al., "Splice Modulating Oligonucleotides and Methods of Use Thereof," filed Oct. 17, 2015 (10 pages).
Invitation to File a Request dated Mar. 24, 2017 for European Application No. 15833669.3, Tallent et al., "Splice Modulating Oligonucleotides and Methods of Use Thereof," filed Oct. 17, 2015 (2 pages).
Notification of Decision on Request dated Jan. 14, 2016 for International Application No. PCT/IB2015/001917, Tallent et al., "Splice Modulating Oligonucleotides and Methods of Use Thereof," filed Oct. 17, 2015 (4 pages).
O'Brien et al., "Rbfox proteins regulate alternative splicing of neuronal sodium channel SCN8A," available in PMC Feb. 1, 2013, published in final edited form as: Mol Cell Neurosci. 49(2):120-6 (2012) (16 pages).
Plummer et al., "Alternative splicing of the sodium channel SCN8A predicts a truncated two-domain protein in fetal brain and non-neuronal cells," J Biol Chem. 272(38):24008-15 (1997).
Project Information for Project No. 1 R21NS087162-01A1, Tallent et al., "Directing splicing of SCN8A to treat Dravet Syndrome," award notice dated Sep. 22, 2014, NIH Reporter, available on <https://projectreporter.nih.gov/project_info_description.cfm?aid=8824327&icde=33055476> (2 pages).
Request for International Application No. PCT/IB2015/001917, dated Oct. 16, 2015, Tallent et al., "Splice Modulating Oligonucleotides and Methods of Use Thereof," filed Oct. 17, 2015 (2 pages).
Submission for European Patent Application No. 15833669.3 dated Apr. 20, 2017, Tallent et al., "Splice Modulating Oligonucleotides and Methods of Use Thereof," filed Oct. 17, 2015 (36 pages).
Zubovic et al., "Mutually exclusive splicing regulates the Nav 1.6 sodium channel function through a combinatorial mechanism that involves three distinct splicing regulatory elements and their ligands," Nucleic Acids Res. 40(13):6255-69 (2012).
Bauman et al., "Therapeutic potential of splice-switching oligonucleotides," Oligonucleotides. 19(1):1-13 (2009) (14 pages).
Lykens et al., "AMPA GluA1-flip targeted oligonucleotide therapy reduces neonatal seizures and hyperexcitability," PLoS One. 12(2):e0171538 (22 pages) (2017).
Oliva et al., "Sodium channels and the neurobiology of epilepsy," Epilepsia. 53(11 ):1849-59 (2012).
Siva et al., "Exon-skipping antisense oligonucleotides to correct missplicing in neurogenetic diseases," Nucleic Acid Ther. 24(1):69-86 (2014).
Supplementary European Search Report dated Mar. 16, 2018 for European Patent Application No. 15833669.3, Tallent et al., "Splice modulating oligonucleotides and methods of use thereof," filed Oct. 17, 2015 (8 pages).
Zubovic, Lorena, Thesis: "Characterization of the mechanisms behind the alternative splicing of the mutually exclusive exons 18N and 18A in the sodium channel gene SCN8A and mutually exclusive exons 5N and 5A in the sodium channel gene SCN9A," Doctor of Philosophy, International Centre for Genetic Engineering and Biotechnology, ICGEB, Open University (UK), 2011 (186 pages).

* cited by examiner

FIG. 2A.
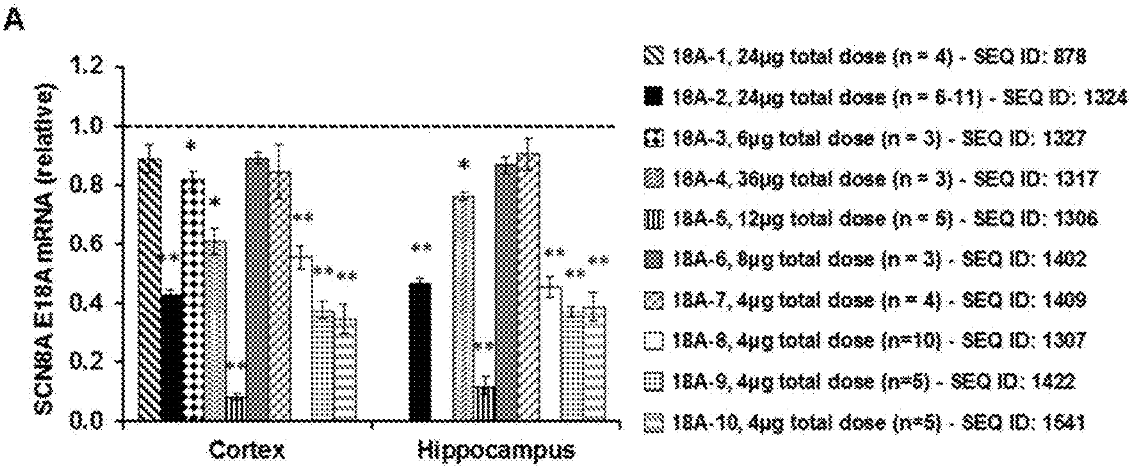
FIG. 2B. FIG. 2C. FIG. 2D.
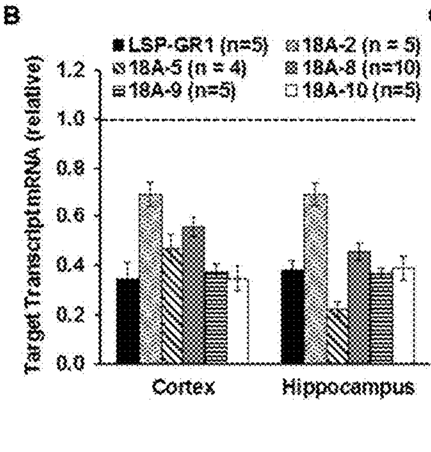
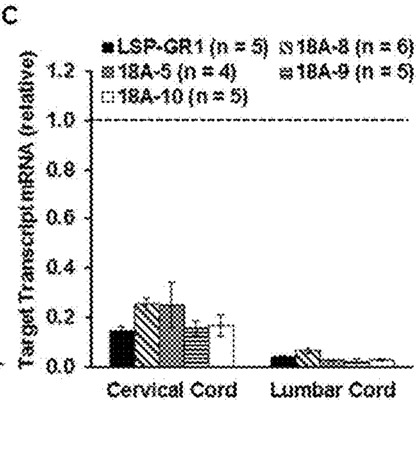
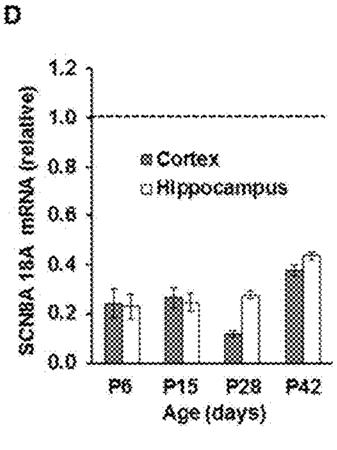

FIG. 3A.

SCN8A Human Sequences: 7nt of the Intron 5' to Exon 5A + entire 92 nt of Exon 5A + 5nt of Intron 5

| SEQ ID NO: | Orientation of Nucleic Acid Target Sequence | Sequence |
|---|---|---|
| 1 | DNA: Target Seq: 3' - 5' orientation | GAGTGGACCTTAATGTCTCTATCAAAAGTTTCGAGCCTCT TGGGACTTACAAGAGTCGCGACTCTGTAACGGGTCCAGGT GTTTGAGACAGTGTATAGACATCA |
| 1 | DNA: Target Seq: 5' - 3' orientation | ACTACAGATATGTGACAGAGTTTGTGGACCTGGGCAATGT CTCAGCGCTGAGAACATTCAGGGTTCTCCGAGCTTTGAAA ACTATCTCTGTAATTCCAGGTGAG |
| 2 | RNA: Compliment: 5' - 3' orientation | CUCACCUGGAAUUACAGAGAUAGUUUUCAAAGCUCGGAGA ACCCUGAAUGUUCUCAGCGCUGAGACAUUGCCCAGGUCCA CAAACUCUGUCACAUAUCUGUAGU |

FIG. 3B.

| SCN8A E5A 24 mer Table | | |
|---|---|---|
| SEQ ID NO: | 5' - 3' SMO sequences | Length (nt) |
| 3 | CUCACCUGGAAUUACAGAGAUAGU | 24 |
| 4 | UCACCUGGAAUUACAGAGAUAGUU | 24 |
| 5 | CACCUGGAAUUACAGAGAUAGUUU | 24 |
| 6 | ACCUGGAAUUACAGAGAUAGUUUU | 24 |
| 7 | CCUGGAAUUACAGAGAUAGUUUUC | 24 |
| 8 | CUGGAAUUACAGAGAUAGUUUUCA | 24 |
| 9 | UGGAAUUACAGAGAUAGUUUUCAA | 24 |
| 10 | GGAAUUACAGAGAUAGUUUUCAAA | 24 |
| 11 | GAAUUACAGAGAUAGUUUUCAAAG | 24 |
| 12 | AAUUACAGAGAUAGUUUUCAAAGC | 24 |
| 13 | AUUACAGAGAUAGUUUUCAAAGCU | 24 |
| 14 | UUACAGAGAUAGUUUUCAAAGCUC | 24 |
| 15 | UACAGAGAUAGUUUUCAAAGCUCG | 24 |
| 16 | ACAGAGAUAGUUUUCAAAGCUCGG | 24 |
| 17 | CAGAGAUAGUUUUCAAAGCUCGGA | 24 |
| 18 | AGAGAUAGUUUUCAAAGCUCGGAG | 24 |
| 19 | GAGAUAGUUUUCAAAGCUCGGAGA | 24 |
| 20 | AGAUAGUUUUCAAAGCUCGGAGAA | 24 |
| 21 | GAUAGUUUUCAAAGCUCGGAGAAC | 24 |
| 22 | AUAGUUUUCAAAGCUCGGAGAACC | 24 |
| 23 | UAGUUUUCAAAGCUCGGAGAACCC | 24 |
| 24 | AGUUUUCAAAGCUCGGAGAACCCU | 24 |
| 25 | GUUUUCAAAGCUCGGAGAACCCUG | 24 |

FIG. 3B (continued)

| SCN8A E5A 24 mer Table | | |
|---|---|---|
| SEQ ID NO: | 5' - 3' SMO sequences | Length (nt) |
| 26 | UUUUCAAAGCUCGGAGAACCCUGA | 24 |
| 27 | UUUCAAAGCUCGGAGAACCCUGAA | 24 |
| 28 | UUCAAAGCUCGGAGAACCCUGAAU | 24 |
| 29 | UCAAAGCUCGGAGAACCCUGAAUG | 24 |
| 30 | CAAAGCUCGGAGAACCCUGAAUGU | 24 |
| 31 | AAAGCUCGGAGAACCCUGAAUGUU | 24 |
| 32 | AAGCUCGGAGAACCCUGAAUGUUC | 24 |
| 33 | AGCUCGGAGAACCCUGAAUGUUCU | 24 |
| 34 | GCUCGGAGAACCCUGAAUGUUCUC | 24 |
| 35 | CUCGGAGAACCCUGAAUGUUCUCA | 24 |
| 36 | UCGGAGAACCCUGAAUGUUCUCAG | 24 |
| 37 | CGGAGAACCCUGAAUGUUCUCAGC | 24 |
| 38 | GGAGAACCCUGAAUGUUCUCAGCG | 24 |
| 39 | GAGAACCCUGAAUGUUCUCAGCGC | 24 |
| 40 | AGAACCCUGAAUGUUCUCAGCGCU | 24 |
| 41 | GAACCCUGAAUGUUCUCAGCGCUG | 24 |
| 42 | AACCCUGAAUGUUCUCAGCGCUGA | 24 |
| 43 | ACCCUGAAUGUUCUCAGCGCUGAG | 24 |
| 44 | CCCUGAAUGUUCUCAGCGCUGAGA | 24 |
| 45 | CCUGAAUGUUCUCAGCGCUGAGAC | 24 |
| 46 | CUGAAUGUUCUCAGCGCUGAGACA | 24 |
| 47 | UGAAUGUUCUCAGCGCUGAGACAU | 24 |
| 48 | GAAUGUUCUCAGCGCUGAGACAUU | 24 |
| 49 | AAUGUUCUCAGCGCUGAGACAUUG | 24 |
| 50 | AUGUUCUCAGCGCUGAGACAUUGC | 24 |
| 51 | UGUUCUCAGCGCUGAGACAUUGCC | 24 |
| 52 | GUUCUCAGCGCUGAGACAUUGCCC | 24 |
| 53 | UUCUCAGCGCUGAGACAUUGCCCA | 24 |
| 54 | UCUCAGCGCUGAGACAUUGCCCAG | 24 |
| 55 | CUCAGCGCUGAGACAUUGCCCAGG | 24 |
| 56 | UCAGCGCUGAGACAUUGCCCAGGU | 24 |
| 57 | CAGCGCUGAGACAUUGCCCAGGUC | 24 |
| 58 | AGCGCUGAGACAUUGCCCAGGUCC | 24 |
| 59 | GCGCUGAGACAUUGCCCAGGUCCA | 24 |
| 60 | CGCUGAGACAUUGCCCAGGUCCAC | 24 |
| 61 | GCUGAGACAUUGCCCAGGUCCACA | 24 |
| 62 | CUGAGACAUUGCCCAGGUCCACAA | 24 |
| 63 | UGAGACAUUGCCCAGGUCCACAAA | 24 |
| 64 | GAGACAUUGCCCAGGUCCACAAAC | 24 |
| 65 | AGACAUUGCCCAGGUCCACAAACU | 24 |
| 66 | GACAUUGCCCAGGUCCACAAACUC | 24 |
| 67 | ACAUUGCCCAGGUCCACAAACUCU | 24 |
| 68 | CAUUGCCCAGGUCCACAAACUCUG | 24 |

FIG 3B (continued)

| SCN8A E5A 24 mer Table | | |
|---|---|---|
| SEQ ID NO: | 5' - 3' SMO sequences | Length (nt) |
| 69 | AUUGCCCAGGUCCACAAACUCUGU | 24 |
| 70 | UUGCCCAGGUCCACAAACUCUGUC | 24 |
| 71 | UGCCCAGGUCCACAAACUCUGUCA | 24 |
| 72 | GCCCAGGUCCACAAACUCUGUCAC | 24 |
| 73 | CCCAGGUCCACAAACUCUGUCACA | 24 |
| 74 | CCAGGUCCACAAACUCUGUCACAU | 24 |
| 75 | CAGGUCCACAAACUCUGUCACAUA | 24 |
| 76 | AGGUCCACAAACUCUGUCACAUAU | 24 |
| 77 | GGUCCACAAACUCUGUCACAUAUC | 24 |
| 78 | GUCCACAAACUCUGUCACAUAUCU | 24 |
| 79 | UCCACAAACUCUGUCACAUAUCUG | 24 |
| 80 | CCACAAACUCUGUCACAUAUCUGU | 24 |
| 81 | CACAAACUCUGUCACAUAUCUGUA | 24 |
| 82 | ACAAACUCUGUCACAUAUCUGUAG | 24 |
| 83 | CAAACUCUGUCACAUAUCUGUAGU | 24 |

FIG. 3C.

| SCN8A E5A 23 mer Table | | |
|---|---|---|
| SEQ ID NO: | 5' - 3' SMO sequences | Length (nt) |
| 84 | CUCACCUGGAAUUACAGAGAUAG | 23 |
| 85 | UCACCUGGAAUUACAGAGAUAGU | 23 |
| 86 | CACCUGGAAUUACAGAGAUAGUU | 23 |
| 87 | ACCUGGAAUUACAGAGAUAGUUU | 23 |
| 88 | CCUGGAAUUACAGAGAUAGUUUU | 23 |
| 89 | CUGGAAUUACAGAGAUAGUUUUC | 23 |
| 90 | UGGAAUUACAGAGAUAGUUUUCA | 23 |
| 91 | GGAAUUACAGAGAUAGUUUUCAA | 23 |
| 92 | GAAUUACAGAGAUAGUUUUCAAA | 23 |
| 93 | AAUUACAGAGAUAGUUUUCAAAG | 23 |
| 94 | AUUACAGAGAUAGUUUUCAAAGC | 23 |
| 95 | UUACAGAGAUAGUUUUCAAAGCU | 23 |
| 96 | UACAGAGAUAGUUUUCAAAGCUC | 23 |
| 97 | ACAGAGAUAGUUUUCAAAGCUCG | 23 |
| 98 | CAGAGAUAGUUUUCAAAGCUCGG | 23 |
| 99 | AGAGAUAGUUUUCAAAGCUCGGA | 23 |
| 100 | GAGAUAGUUUUCAAAGCUCGGAG | 23 |
| 101 | AGAUAGUUUUCAAAGCUCGGAGA | 23 |
| 102 | GAUAGUUUUCAAAGCUCGGAGAA | 23 |
| 103 | AUAGUUUUCAAAGCUCGGAGAAC | 23 |
| 104 | UAGUUUUCAAAGCUCGGAGAACC | 23 |

FIG. 3C (continued)

| SCN8A E5A 23 mer Table | | |
|---|---|---|
| SEQ ID NO: | 5' - 3' SMO sequences | Length (nt) |
| 105 | AGUUUUCAAAGCUCGGAGAACCC | 23 |
| 106 | GUUUUCAAAGCUCGGAGAACCCU | 23 |
| 107 | UUUUCAAAGCUCGGAGAACCCUG | 23 |
| 108 | UUUCAAAGCUCGGAGAACCCUGA | 23 |
| 109 | UUCAAAGCUCGGAGAACCCUGAA | 23 |
| 110 | UCAAAGCUCGGAGAACCCUGAAU | 23 |
| 111 | CAAAGCUCGGAGAACCCUGAAUG | 23 |
| 112 | AAAGCUCGGAGAACCCUGAAUGU | 23 |
| 113 | AAGCUCGGAGAACCCUGAAUGUU | 23 |
| 114 | AGCUCGGAGAACCCUGAAUGUUC | 23 |
| 115 | GCUCGGAGAACCCUGAAUGUUCU | 23 |
| 116 | CUCGGAGAACCCUGAAUGUUCUC | 23 |
| 117 | UCGGAGAACCCUGAAUGUUCUCA | 23 |
| 118 | CGGAGAACCCUGAAUGUUCUCAG | 23 |
| 119 | GGAGAACCCUGAAUGUUCUCAGC | 23 |
| 120 | GAGAACCCUGAAUGUUCUCAGCG | 23 |
| 121 | AGAACCCUGAAUGUUCUCAGCGC | 23 |
| 122 | GAACCCUGAAUGUUCUCAGCGCU | 23 |
| 123 | AACCCUGAAUGUUCUCAGCGCUG | 23 |
| 124 | ACCCUGAAUGUUCUCAGCGCUGA | 23 |
| 125 | CCCUGAAUGUUCUCAGCGCUGAG | 23 |
| 126 | CCUGAAUGUUCUCAGCGCUGAGA | 23 |
| 127 | CUGAAUGUUCUCAGCGCUGAGAC | 23 |
| 128 | UGAAUGUUCUCAGCGCUGAGACA | 23 |
| 129 | GAAUGUUCUCAGCGCUGAGACAU | 23 |
| 130 | AAUGUUCUCAGCGCUGAGACAUU | 23 |
| 131 | AUGUUCUCAGCGCUGAGACAUUG | 23 |
| 132 | UGUUCUCAGCGCUGAGACAUUGC | 23 |
| 133 | GUUCUCAGCGCUGAGACAUUGCC | 23 |
| 134 | UUCUCAGCGCUGAGACAUUGCCC | 23 |
| 135 | UCUCAGCGCUGAGACAUUGCCCA | 23 |
| 136 | CUCAGCGCUGAGACAUUGCCCAG | 23 |
| 137 | UCAGCGCUGAGACAUUGCCCAGG | 23 |
| 138 | CAGCGCUGAGACAUUGCCCAGGU | 23 |
| 139 | AGCGCUGAGACAUUGCCCAGGUC | 23 |
| 140 | GCGCUGAGACAUUGCCCAGGUCC | 23 |
| 141 | CGCUGAGACAUUGCCCAGGUCCA | 23 |
| 142 | GCUGAGACAUUGCCCAGGUCCAC | 23 |
| 143 | CUGAGACAUUGCCCAGGUCCACA | 23 |
| 144 | UGAGACAUUGCCCAGGUCCACAA | 23 |
| 145 | GAGACAUUGCCCAGGUCCACAAA | 23 |
| 146 | AGACAUUGCCCAGGUCCACAAAC | 23 |
| 147 | GACAUUGCCCAGGUCCACAAACU | 23 |
| 148 | ACAUUGCCCAGGUCCACAAACUC | 23 |

FIG. 3C (continued)

| SCN8A E5A 23 mer Table | | |
|---|---|---|
| SEQ ID NO: | 5' - 3' SMO sequences | Length (nt) |
| 149 | CAUUGCCCAGGUCCACAAACUCU | 23 |
| 150 | AUUGCCCAGGUCCACAAACUCUG | 23 |
| 151 | UUGCCCAGGUCCACAAACUCUGU | 23 |
| 152 | UGCCCAGGUCCACAAACUCUGUC | 23 |
| 153 | GCCCAGGUCCACAAACUCUGUCA | 23 |
| 154 | CCCAGGUCCACAAACUCUGUCAC | 23 |
| 155 | CCAGGUCCACAAACUCUGUCACA | 23 |
| 156 | CAGGUCCACAAACUCUGUCACAU | 23 |
| 157 | AGGUCCACAAACUCUGUCACAUA | 23 |
| 158 | GGUCCACAAACUCUGUCACAUAU | 23 |
| 159 | GUCCACAAACUCUGUCACAUAUC | 23 |
| 160 | UCCACAAACUCUGUCACAUAUCU | 23 |
| 161 | CCACAAACUCUGUCACAUAUCUG | 23 |
| 162 | CACAAACUCUGUCACAUAUCUGU | 23 |
| 163 | ACAAACUCUGUCACAUAUCUGUA | 23 |
| 164 | CAAACUCUGUCACAUAUCUGUAG | 23 |
| 165 | AAACUCUGUCACAUAUCUGUAGU | 23 |

FIG. 3D.

| SCN8A E5A 22 mer Table | | |
|---|---|---|
| SEQ ID NO: | 5' - 3' SMO sequences | Length (nt) |
| 166 | CUCACCUGGAAUUACAGAGAUA | 22 |
| 167 | UCACCUGGAAUUACAGAGAUAG | 22 |
| 168 | CACCUGGAAUUACAGAGAUAGU | 22 |
| 169 | ACCUGGAAUUACAGAGAUAGUU | 22 |
| 170 | CCUGGAAUUACAGAGAUAGUUU | 22 |
| 171 | CUGGAAUUACAGAGAUAGUUUU | 22 |
| 172 | UGGAAUUACAGAGAUAGUUUUC | 22 |
| 173 | GGAAUUACAGAGAUAGUUUUCA | 22 |
| 174 | GAAUUACAGAGAUAGUUUUCAA | 22 |
| 175 | AAUUACAGAGAUAGUUUUCAAA | 22 |
| 176 | AUUACAGAGAUAGUUUUCAAAG | 22 |
| 177 | UUACAGAGAUAGUUUUCAAAGC | 22 |
| 178 | UACAGAGAUAGUUUUCAAAGCU | 22 |
| 179 | ACAGAGAUAGUUUUCAAAGCUC | 22 |
| 180 | CAGAGAUAGUUUUCAAAGCUCG | 22 |
| 181 | AGAGAUAGUUUUCAAAGCUCGG | 22 |
| 182 | GAGAUAGUUUUCAAAGCUCGGA | 22 |
| 183 | AGAUAGUUUUCAAAGCUCGGAG | 22 |
| 184 | GAUAGUUUUCAAAGCUCGGAGA | 22 |

FIG. 3D (continued)

| SCN8A E5A 22 mer Table | | |
|---|---|---|
| SEQ ID NO: | 5' - 3' SMO sequences | Length (nt) |
| 185 | AUAGUUUUCAAAGCUCGGAGAA | 22 |
| 186 | UAGUUUUCAAAGCUCGGAGAAC | 22 |
| 187 | AGUUUUCAAAGCUCGGAGAACC | 22 |
| 188 | GUUUUCAAAGCUCGGAGAACCC | 22 |
| 189 | UUUUCAAAGCUCGGAGAACCCU | 22 |
| 190 | UUUCAAAGCUCGGAGAACCCUG | 22 |
| 191 | UUCAAAGCUCGGAGAACCCUGA | 22 |
| 192 | UCAAAGCUCGGAGAACCCUGAA | 22 |
| 193 | CAAAGCUCGGAGAACCCUGAAU | 22 |
| 194 | AAAGCUCGGAGAACCCUGAAUG | 22 |
| 195 | AAGCUCGGAGAACCCUGAAUGU | 22 |
| 196 | AGCUCGGAGAACCCUGAAUGUU | 22 |
| 197 | GCUCGGAGAACCCUGAAUGUUC | 22 |
| 198 | CUCGGAGAACCCUGAAUGUUCU | 22 |
| 199 | UCGGAGAACCCUGAAUGUUCUC | 22 |
| 200 | CGGAGAACCCUGAAUGUUCUCA | 22 |
| 201 | GGAGAACCCUGAAUGUUCUCAG | 22 |
| 202 | GAGAACCCUGAAUGUUCUCAGC | 22 |
| 203 | AGAACCCUGAAUGUUCUCAGCG | 22 |
| 204 | GAACCCUGAAUGUUCUCAGCGC | 22 |
| 205 | AACCCUGAAUGUUCUCAGCGCU | 22 |
| 206 | ACCCUGAAUGUUCUCAGCGCUG | 22 |
| 207 | CCCUGAAUGUUCUCAGCGCUGA | 22 |
| 208 | CCUGAAUGUUCUCAGCGCUGAG | 22 |
| 209 | CUGAAUGUUCUCAGCGCUGAGA | 22 |
| 210 | UGAAUGUUCUCAGCGCUGAGAC | 22 |
| 211 | GAAUGUUCUCAGCGCUGAGACA | 22 |
| 212 | AAUGUUCUCAGCGCUGAGACAU | 22 |
| 213 | AUGUUCUCAGCGCUGAGACAUU | 22 |
| 214 | UGUUCUCAGCGCUGAGACAUUG | 22 |
| 215 | GUUCUCAGCGCUGAGACAUUGC | 22 |
| 216 | UUCUCAGCGCUGAGACAUUGCC | 22 |
| 217 | UCUCAGCGCUGAGACAUUGCCC | 22 |
| 218 | CUCAGCGCUGAGACAUUGCCCA | 22 |
| 219 | UCAGCGCUGAGACAUUGCCCAG | 22 |
| 220 | CAGCGCUGAGACAUUGCCCAGG | 22 |
| 221 | AGCGCUGAGACAUUGCCCAGGU | 22 |
| 222 | GCGCUGAGACAUUGCCCAGGUC | 22 |
| 223 | CGCUGAGACAUUGCCCAGGUCC | 22 |
| 224 | GCUGAGACAUUGCCCAGGUCCA | 22 |
| 225 | CUGAGACAUUGCCCAGGUCCAC | 22 |
| 226 | UGAGACAUUGCCCAGGUCCACA | 22 |
| 227 | GAGACAUUGCCCAGGUCCACAA | 22 |

FIG. 3D (continued)

| SCN8A E5A 22 mer Table | | |
|---|---|---|
| SEQ ID NO: | 5' - 3' SMO sequences | Length (nt) |
| 228 | AGACAUUGCCCAGGUCCACAAA | 22 |
| 229 | GACAUUGCCCAGGUCCACAAAC | 22 |
| 230 | ACAUUGCCCAGGUCCACAAACU | 22 |
| 231 | CAUUGCCCAGGUCCACAAACUC | 22 |
| 232 | AUUGCCCAGGUCCACAAACUCU | 22 |
| 233 | UUGCCCAGGUCCACAAACUCUG | 22 |
| 234 | UGCCCAGGUCCACAAACUCUGU | 22 |
| 235 | GCCCAGGUCCACAAACUCUGUC | 22 |
| 236 | CCCAGGUCCACAAACUCUGUCA | 22 |
| 237 | CCAGGUCCACAAACUCUGUCAC | 22 |
| 238 | CAGGUCCACAAACUCUGUCACA | 22 |
| 239 | AGGUCCACAAACUCUGUCACAU | 22 |
| 240 | GGUCCACAAACUCUGUCACAUA | 22 |
| 241 | GUCCACAAACUCUGUCACAUAU | 22 |
| 242 | UCCACAAACUCUGUCACAUAUC | 22 |
| 243 | CCACAAACUCUGUCACAUAUCU | 22 |
| 244 | CACAAACUCUGUCACAUAUCUG | 22 |
| 245 | ACAAACUCUGUCACAUAUCUGU | 22 |
| 246 | CAAACUCUGUCACAUAUCUGUA | 22 |
| 247 | AAACUCUGUCACAUAUCUGUAG | 22 |
| 248 | AACUCUGUCACAUAUCUGUAGU | 22 |

FIG. 3E.

| SCN8A E5A 21 mer Table | | |
|---|---|---|
| SEQ ID | 5' - 3' SMO sequences | Length (nt) |
| . 249 | CUCACCUGGAAUUACAGAGAU | 21 |
| 250 | UCACCUGGAAUUACAGAGAUA | 21 |
| 251 | CACCUGGAAUUACAGAGAUAG | 21 |
| 252 | ACCUGGAAUUACAGAGAUAGU | 21 |
| 253 | CCUGGAAUUACAGAGAUAGUU | 21 |
| 254 | CUGGAAUUACAGAGAUAGUUU | 21 |
| 255 | UGGAAUUACAGAGAUAGUUUU | 21 |
| 256 | GGAAUUACAGAGAUAGUUUUC | 21 |
| 257 | GAAUUACAGAGAUAGUUUUCA | 21 |
| 258 | AAUUACAGAGAUAGUUUUCAA | 21 |
| 259 | AUUACAGAGAUAGUUUUCAAA | 21 |
| 260 | UUACAGAGAUAGUUUUCAAAG | 21 |
| 261 | UACAGAGAUAGUUUUCAAAGC | 21 |
| 262 | ACAGAGAUAGUUUUCAAAGCU | 21 |

FIG. 3E (continued)

| SCN8A E5A 21 mer Table | | |
|---|---|---|
| SEQ ID | 5' - 3' SMO sequences | Length (nt) |
| 263 | CAGAGAUAGUUUUCAAAGCUC | 21 |
| 264 | AGAGAUAGUUUUCAAAGCUCG | 21 |
| 265 | GAGAUAGUUUUCAAAGCUCGG | 21 |
| 266 | AGAUAGUUUUCAAAGCUCGGA | 21 |
| 267 | GAUAGUUUUCAAAGCUCGGAG | 21 |
| 268 | AUAGUUUUCAAAGCUCGGAGA | 21 |
| 269 | UAGUUUUCAAAGCUCGGAGAA | 21 |
| 270 | AGUUUUCAAAGCUCGGAGAAC | 21 |
| 271 | GUUUUCAAAGCUCGGAGAACC | 21 |
| 272 | UUUUCAAAGCUCGGAGAACCC | 21 |
| 273 | UUUCAAAGCUCGGAGAACCCU | 21 |
| 274 | UUCAAAGCUCGGAGAACCCUG | 21 |
| 275 | UCAAAGCUCGGAGAACCCUGA | 21 |
| 276 | CAAAGCUCGGAGAACCCUGAA | 21 |
| 277 | AAAGCUCGGAGAACCCUGAAU | 21 |
| 278 | AAGCUCGGAGAACCCUGAAUG | 21 |
| 279 | AGCUCGGAGAACCCUGAAUGU | 21 |
| 280 | GCUCGGAGAACCCUGAAUGUU | 21 |
| 281 | CUCGGAGAACCCUGAAUGUUC | 21 |
| 282 | UCGGAGAACCCUGAAUGUUCU | 21 |
| 283 | CGGAGAACCCUGAAUGUUCUC | 21 |
| 284 | GGAGAACCCUGAAUGUUCUCA | 21 |
| 285 | GAGAACCCUGAAUGUUCUCAG | 21 |
| 286 | AGAACCCUGAAUGUUCUCAGC | 21 |
| 287 | GAACCCUGAAUGUUCUCAGCG | 21 |
| 288 | AACCCUGAAUGUUCUCAGCGC | 21 |
| 289 | ACCCUGAAUGUUCUCAGCGCU | 21 |
| 290 | CCCUGAAUGUUCUCAGCGCUG | 21 |
| 291 | CCUGAAUGUUCUCAGCGCUGA | 21 |
| 292 | CUGAAUGUUCUCAGCGCUGAG | 21 |
| 293 | UGAAUGUUCUCAGCGCUGAGA | 21 |
| 294 | GAAUGUUCUCAGCGCUGAGAC | 21 |
| 295 | AAUGUUCUCAGCGCUGAGACA | 21 |
| 296 | AUGUUCUCAGCGCUGAGACAU | 21 |
| 297 | UGUUCUCAGCGCUGAGACAUU | 21 |
| 298 | GUUCUCAGCGCUGAGACAUUG | 21 |
| 299 | UUCUCAGCGCUGAGACAUUGC | 21 |
| 300 | UCUCAGCGCUGAGACAUUGCC | 21 |
| 301 | CUCAGCGCUGAGACAUUGCCC | 21 |
| 302 | UCAGCGCUGAGACAUUGCCCA | 21 |
| 303 | CAGCGCUGAGACAUUGCCCAG | 21 |
| 304 | AGCGCUGAGACAUUGCCCAGG | 21 |
| 305 | GCGCUGAGACAUUGCCCAGGU | 21 |

FIG. 3E (continued)

| SCN8A E5A 21 mer Table | | |
|---|---|---|
| SEQ ID | 5' - 3' SMO sequences | Length (nt) |
| 306 | CGCUGAGACAUUGCCCAGGUC | 21 |
| 307 | GCUGAGACAUUGCCCAGGUCC | 21 |
| 308 | CUGAGACAUUGCCCAGGUCCA | 21 |
| 309 | UGAGACAUUGCCCAGGUCCAC | 21 |
| 310 | GAGACAUUGCCCAGGUCCACA | 21 |
| 311 | AGACAUUGCCCAGGUCCACAA | 21 |
| 312 | GACAUUGCCCAGGUCCACAAA | 21 |
| 313 | ACAUUGCCCAGGUCCACAAAC | 21 |
| 314 | CAUUGCCCAGGUCCACAAACU | 21 |
| 315 | AUUGCCCAGGUCCACAAACUC | 21 |
| 316 | UUGCCCAGGUCCACAAACUCU | 21 |
| 317 | UGCCCAGGUCCACAAACUCUG | 21 |
| 318 | GCCCAGGUCCACAAACUCUGU | 21 |
| 319 | CCCAGGUCCACAAACUCUGUC | 21 |
| 320 | CCAGGUCCACAAACUCUGUCA | 21 |
| 321 | CAGGUCCACAAACUCUGUCAC | 21 |
| 322 | AGGUCCACAAACUCUGUCACA | 21 |
| 323 | GGUCCACAAACUCUGUCACAU | 21 |
| 324 | GUCCACAAACUCUGUCACAUA | 21 |
| 325 | UCCACAAACUCUGUCACAUAU | 21 |
| 326 | CCACAAACUCUGUCACAUAUC | 21 |
| 327 | CACAAACUCUGUCACAUAUCU | 21 |
| 328 | ACAAACUCUGUCACAUAUCUG | 21 |
| 329 | CAAACUCUGUCACAUAUCUGU | 21 |
| 330 | AAACUCUGUCACAUAUCUGUA | 21 |
| 331 | AACUCUGUCACAUAUCUGUAG | 21 |
| 332 | ACUCUGUCACAUAUCUGUAGU | 21 |

FIG. 3F.

| SCN8A E5A 20 mer Table | | |
|---|---|---|
| SEQ ID NO: | 5' - 3' SMO sequences | Length (nt) |
| 333 | CUCACCUGGAAUUACAGAGA | 20 |
| 334 | UCACCUGGAAUUACAGAGAU | 20 |
| 335 | CACCUGGAAUUACAGAGAUA | 20 |
| 336 | ACCUGGAAUUACAGAGAUAG | 20 |

FIG. 3F (continued)

| SCN8A E5A 20 mer Table | | |
|---|---|---|
| SEQ ID NO: | 5' - 3' SMO sequences | Length (nt) |
| 337 | CCUGGAAUUACAGAGAUAGU | 20 |
| 338 | CUGGAAUUACAGAGAUAGUU | 20 |
| 339 | UGGAAUUACAGAGAUAGUUU | 20 |
| 340 | GGAAUUACAGAGAUAGUUUU | 20 |
| 341 | GAAUUACAGAGAUAGUUUUC | 20 |
| 342 | AAUUACAGAGAUAGUUUUCA | 20 |
| 343 | AUUACAGAGAUAGUUUUCAA | 20 |
| 344 | UUACAGAGAUAGUUUUCAAA | 20 |
| 345 | UACAGAGAUAGUUUUCAAAG | 20 |
| 346 | ACAGAGAUAGUUUUCAAAGC | 20 |
| 347 | CAGAGAUAGUUUUCAAAGCU | 20 |
| 348 | AGAGAUAGUUUUCAAAGCUC | 20 |
| 349 | GAGAUAGUUUUCAAAGCUCG | 20 |
| 350 | AGAUAGUUUUCAAAGCUCGG | 20 |
| 351 | GAUAGUUUUCAAAGCUCGGA | 20 |
| 352 | AUAGUUUUCAAAGCUCGGAG | 20 |
| 353 | UAGUUUUCAAAGCUCGGAGA | 20 |
| 354 | AGUUUUCAAAGCUCGGAGAA | 20 |
| 355 | GUUUUCAAAGCUCGGAGAAC | 20 |
| 356 | UUUUCAAAGCUCGGAGAACC | 20 |
| 357 | UUUCAAAGCUCGGAGAACCC | 20 |
| 358 | UUCAAAGCUCGGAGAACCCU | 20 |
| 359 | UCAAAGCUCGGAGAACCCUG | 20 |
| 360 | CAAAGCUCGGAGAACCCUGA | 20 |
| 361 | AAAGCUCGGAGAACCCUGAA | 20 |
| 362 | AAGCUCGGAGAACCCUGAAU | 20 |
| 363 | AGCUCGGAGAACCCUGAAUG | 20 |
| 364 | GCUCGGAGAACCCUGAAUGU | 20 |
| 365 | CUCGGAGAACCCUGAAUGUU | 20 |
| 366 | UCGGAGAACCCUGAAUGUUC | 20 |
| 367 | CGGAGAACCCUGAAUGUUCU | 20 |
| 368 | GGAGAACCCUGAAUGUUCUC | 20 |
| 369 | GAGAACCCUGAAUGUUCUCA | 20 |
| 370 | AGAACCCUGAAUGUUCUCAG | 20 |
| 371 | GAACCCUGAAUGUUCUCAGC | 20 |
| 372 | AACCCUGAAUGUUCUCAGCG | 20 |
| 373 | ACCCUGAAUGUUCUCAGCGC | 20 |
| 374 | CCCUGAAUGUUCUCAGCGCU | 20 |
| 375 | CCUGAAUGUUCUCAGCGCUG | 20 |
| 376 | CUGAAUGUUCUCAGCGCUGA | 20 |
| 377 | UGAAUGUUCUCAGCGCUGAG | 20 |
| 378 | GAAUGUUCUCAGCGCUGAGA | 20 |
| 379 | AAUGUUCUCAGCGCUGAGAC | 20 |

FIG. 3F (continued)

| SCN8A E5A 20 mer Table | | |
|---|---|---|
| SEQ ID NO: | 5' - 3' SMO sequences | Length (nt) |
| 380 | AUGUUCUCAGCGCUGAGACA | 20 |
| 381 | UGUUCUCAGCGCUGAGACAU | 20 |
| 382 | GUUCUCAGCGCUGAGACAUU | 20 |
| 383 | UUCUCAGCGCUGAGACAUUG | 20 |
| 384 | UCUCAGCGCUGAGACAUUGC | 20 |
| 385 | CUCAGCGCUGAGACAUUGCC | 20 |
| 386 | UCAGCGCUGAGACAUUGCCC | 20 |
| 387 | CAGCGCUGAGACAUUGCCCA | 20 |
| 388 | AGCGCUGAGACAUUGCCCAG | 20 |
| 389 | GCGCUGAGACAUUGCCCAGG | 20 |
| 390 | CGCUGAGACAUUGCCCAGGU | 20 |
| 391 | GCUGAGACAUUGCCCAGGUC | 20 |
| 392 | CUGAGACAUUGCCCAGGUCC | 20 |
| 393 | UGAGACAUUGCCCAGGUCCA | 20 |
| 394 | GAGACAUUGCCCAGGUCCAC | 20 |
| 395 | AGACAUUGCCCAGGUCCACA | 20 |
| 396 | GACAUUGCCCAGGUCCACAA | 20 |
| 397 | ACAUUGCCCAGGUCCACAAA | 20 |
| 398 | CAUUGCCCAGGUCCACAAAC | 20 |
| 399 | AUUGCCCAGGUCCACAAACU | 20 |
| 400 | UUGCCCAGGUCCACAAACUC | 20 |
| 401 | UGCCCAGGUCCACAAACUCU | 20 |
| 402 | GCCCAGGUCCACAAACUCUG | 20 |
| 403 | CCCAGGUCCACAAACUCUGU | 20 |
| 404 | CCAGGUCCACAAACUCUGUC | 20 |
| 405 | CAGGUCCACAAACUCUGUCA | 20 |
| 406 | AGGUCCACAAACUCUGUCAC | 20 |
| 407 | GGUCCACAAACUCUGUCACA | 20 |
| 408 | GUCCACAAACUCUGUCACAU | 20 |
| 409 | UCCACAAACUCUGUCACAUA | 20 |
| 410 | CCACAAACUCUGUCACAUAU | 20 |
| 411 | CACAAACUCUGUCACAUAUC | 20 |
| 412 | ACAAACUCUGUCACAUAUCU | 20 |
| 413 | CAAACUCUGUCACAUAUCUG | 20 |
| 414 | AAACUCUGUCACAUAUCUGU | 20 |
| 415 | AACUCUGUCACAUAUCUGUA | 20 |
| 416 | ACUCUGUCACAUAUCUGUAG | 20 |
| 417 | CUCUGUCACAUAUCUGUAGU | 20 |

FIG. 3G

| SCN8A E5A 19 mer Table | | |
|---|---|---|
| SEQ ID No: | 5' - 3' SMO sequences | Length (nt) |
| 418 | CUCACCUGGAAUUACAGAG | 19 |
| 419 | UCACCUGGAAUUACAGAGA | 19 |
| 420 | CACCUGGAAUUACAGAGAU | 19 |
| 421 | ACCUGGAAUUACAGAGAUA | 19 |
| 422 | CCUGGAAUUACAGAGAUAG | 19 |
| 423 | CUGGAAUUACAGAGAUAGU | 19 |
| 424 | UGGAAUUACAGAGAUAGUU | 19 |
| 425 | GGAAUUACAGAGAUAGUUU | 19 |
| 426 | GAAUUACAGAGAUAGUUUU | 19 |
| 427 | AAUUACAGAGAUAGUUUUC | 19 |
| 428 | AUUACAGAGAUAGUUUUCA | 19 |
| 429 | UUACAGAGAUAGUUUUCAA | 19 |
| 430 | UACAGAGAUAGUUUUCAAA | 19 |
| 431 | ACAGAGAUAGUUUUCAAAG | 19 |
| 432 | CAGAGAUAGUUUUCAAAGC | 19 |
| 433 | AGAGAUAGUUUUCAAAGCU | 19 |
| 434 | GAGAUAGUUUUCAAAGCUC | 19 |
| 435 | AGAUAGUUUUCAAAGCUCG | 19 |
| 436 | GAUAGUUUUCAAAGCUCGG | 19 |
| 437 | AUAGUUUUCAAAGCUCGGA | 19 |
| 438 | UAGUUUUCAAAGCUCGGAG | 19 |
| 439 | AGUUUUCAAAGCUCGGAGA | 19 |
| 440 | GUUUUCAAAGCUCGGAGAA | 19 |
| 441 | UUUUCAAAGCUCGGAGAAC | 19 |
| 442 | UUUCAAAGCUCGGAGAACC | 19 |
| 443 | UUCAAAGCUCGGAGAACCC | 19 |
| 444 | UCAAAGCUCGGAGAACCCU | 19 |
| 445 | CAAAGCUCGGAGAACCCUG | 19 |
| 446 | AAAGCUCGGAGAACCCUGA | 19 |
| 447 | AAGCUCGGAGAACCCUGAA | 19 |
| 448 | AGCUCGGAGAACCCUGAAU | 19 |
| 449 | GCUCGGAGAACCCUGAAUG | 19 |
| 450 | CUCGGAGAACCCUGAAUGU | 19 |
| 451 | UCGGAGAACCCUGAAUGUU | 19 |
| 452 | CGGAGAACCCUGAAUGUUC | 19 |
| 453 | GGAGAACCCUGAAUGUUCU | 19 |
| 454 | GAGAACCCUGAAUGUUCUC | 19 |
| 455 | AGAACCCUGAAUGUUCUCA | 19 |
| 456 | GAACCCUGAAUGUUCUCAG | 19 |
| 457 | AACCCUGAAUGUUCUCAGC | 19 |
| 458 | ACCCUGAAUGUUCUCAGCG | 19 |
| 459 | CCCUGAAUGUUCUCAGCGC | 19 |
| 460 | CCUGAAUGUUCUCAGCGCU | 19 |
| 461 | CUGAAUGUUCUCAGCGCUG | 19 |

FIG. 3G (continued)

| SCN8A E5A 19 mer Table | | |
|---|---|---|
| SEQ ID No: | 5' - 3' SMO sequences | Length (nt) |
| 462 | UGAAUGUUCUCAGCGCUGA | 19 |
| 463 | GAAUGUUCUCAGCGCUGAG | 19 |
| 464 | AAUGUUCUCAGCGCUGAGA | 19 |
| 465 | AUGUUCUCAGCGCUGAGAC | 19 |
| 466 | UGUUCUCAGCGCUGAGACA | 19 |
| 467 | GUUCUCAGCGCUGAGACAU | 19 |
| 468 | UUCUCAGCGCUGAGACAUU | 19 |
| 469 | UCUCAGCGCUGAGACAUUG | 19 |
| 470 | CUCAGCGCUGAGACAUUGC | 19 |
| 471 | UCAGCGCUGAGACAUUGCC | 19 |
| 472 | CAGCGCUGAGACAUUGCCC | 19 |
| 473 | AGCGCUGAGACAUUGCCCA | 19 |
| 474 | GCGCUGAGACAUUGCCCAG | 19 |
| 475 | CGCUGAGACAUUGCCCAGG | 19 |
| 476 | GCUGAGACAUUGCCCAGGU | 19 |
| 477 | CUGAGACAUUGCCCAGGUC | 19 |
| 478 | UGAGACAUUGCCCAGGUCC | 19 |
| 479 | GAGACAUUGCCCAGGUCCA | 19 |
| 480 | AGACAUUGCCCAGGUCCAC | 19 |
| 481 | GACAUUGCCCAGGUCCACA | 19 |
| 482 | ACAUUGCCCAGGUCCACAA | 19 |
| 483 | CAUUGCCCAGGUCCACAAA | 19 |
| 484 | AUUGCCCAGGUCCACAAAC | 19 |
| 485 | UUGCCCAGGUCCACAAACU | 19 |
| 486 | UGCCCAGGUCCACAAACUC | 19 |
| 487 | GCCCAGGUCCACAAACUCU | 19 |
| 488 | CCCAGGUCCACAAACUCUG | 19 |
| 489 | CCAGGUCCACAAACUCUGU | 19 |
| 490 | CAGGUCCACAAACUCUGUC | 19 |
| 491 | AGGUCCACAAACUCUGUCA | 19 |
| 492 | GGUCCACAAACUCUGUCAC | 19 |
| 493 | GUCCACAAACUCUGUCACA | 19 |
| 494 | UCCACAAACUCUGUCACAU | 19 |
| 495 | CCACAAACUCUGUCACAUA | 19 |
| 496 | CACAAACUCUGUCACAUAU | 19 |
| 497 | ACAAACUCUGUCACAUAUC | 19 |
| 498 | CAAACUCUGUCACAUAUCU | 19 |
| 499 | AAACUCUGUCACAUAUCUG | 19 |
| 500 | AACUCUGUCACAUAUCUGU | 19 |
| 501 | ACUCUGUCACAUAUCUGUA | 19 |
| 502 | CUCUGUCACAUAUCUGUAG | 19 |
| 503 | UCUGUCACAUAUCUGUAGU | 19 |

FIG. 3H.

| SCN8A E5A 18 mer Table | | |
|---|---|---|
| SEQ ID NO: | 5' - 3' SMO sequences | Length (nt) |
| 504 | CUCACCUGGAAUUACAGA | 18 |
| 505 | UCACCUGGAAUUACAGAG | 18 |
| 506 | CACCUGGAAUUACAGAGA | 18 |
| 507 | ACCUGGAAUUACAGAGAU | 18 |
| 508 | CCUGGAAUUACAGAGAUA | 18 |
| 509 | CUGGAAUUACAGAGAUAG | 18 |
| 510 | UGGAAUUACAGAGAUAGU | 18 |
| 511 | GGAAUUACAGAGAUAGUU | 18 |
| 512 | GAAUUACAGAGAUAGUUU | 18 |
| 513 | AAUUACAGAGAUAGUUUU | 18 |
| 514 | AUUACAGAGAUAGUUUUC | 18 |
| 515 | UUACAGAGAUAGUUUUCA | 18 |
| 516 | UACAGAGAUAGUUUUCAA | 18 |
| 517 | ACAGAGAUAGUUUUCAAA | 18 |
| 518 | CAGAGAUAGUUUUCAAAG | 18 |
| 519 | AGAGAUAGUUUUCAAAGC | 18 |
| 520 | GAGAUAGUUUUCAAAGCU | 18 |
| 521 | AGAUAGUUUUCAAAGCUC | 18 |
| 522 | GAUAGUUUUCAAAGCUCG | 18 |
| 523 | AUAGUUUUCAAAGCUCGG | 18 |
| 524 | UAGUUUUCAAAGCUCGGA | 18 |
| 525 | AGUUUUCAAAGCUCGGAG | 18 |
| 526 | GUUUUCAAAGCUCGGAGA | 18 |
| 527 | UUUUCAAAGCUCGGAGAA | 18 |
| 528 | UUUCAAAGCUCGGAGAAC | 18 |
| 529 | UUCAAAGCUCGGAGAACC | 18 |
| 530 | UCAAAGCUCGGAGAACCC | 18 |
| 531 | CAAAGCUCGGAGAACCCU | 18 |
| 532 | AAAGCUCGGAGAACCCUG | 18 |
| 533 | AAGCUCGGAGAACCCUGA | 18 |
| 534 | AGCUCGGAGAACCCUGAA | 18 |
| 535 | GCUCGGAGAACCCUGAAU | 18 |
| 536 | CUCGGAGAACCCUGAAUG | 18 |
| 537 | UCGGAGAACCCUGAAUGU | 18 |
| 538 | CGGAGAACCCUGAAUGUU | 18 |
| 539 | GGAGAACCCUGAAUGUUC | 18 |
| 540 | GAGAACCCUGAAUGUUCU | 18 |
| 541 | AGAACCCUGAAUGUUCUC | 18 |
| 542 | GAACCCUGAAUGUUCUCA | 18 |
| 543 | AACCCUGAAUGUUCUCAG | 18 |
| 544 | ACCCUGAAUGUUCUCAGC | 18 |

FIG. 3H (continued)

| SCN8A E5A 18 mer Table | | |
|---|---|---|
| SEQ ID NO: | 5' - 3' SMO sequences | Length (nt) |
| 545 | CCCUGAAUGUUCUCAGCG | 18 |
| 546 | CCUGAAUGUUCUCAGCGC | 18 |
| 547 | CUGAAUGUUCUCAGCGCU | 18 |
| 548 | UGAAUGUUCUCAGCGCUG | 18 |
| 549 | GAAUGUUCUCAGCGCUGA | 18 |
| 550 | AAUGUUCUCAGCGCUGAG | 18 |
| 551 | AUGUUCUCAGCGCUGAGA | 18 |
| 552 | UGUUCUCAGCGCUGAGAC | 18 |
| 553 | GUUCUCAGCGCUGAGACA | 18 |
| 554 | UUCUCAGCGCUGAGACAU | 18 |
| 555 | UCUCAGCGCUGAGACAUU | 18 |
| 556 | CUCAGCGCUGAGACAUUG | 18 |
| 557 | UCAGCGCUGAGACAUUGC | 18 |
| 558 | CAGCGCUGAGACAUUGCC | 18 |
| 559 | AGCGCUGAGACAUUGCCC | 18 |
| 560 | GCGCUGAGACAUUGCCCA | 18 |
| 561 | CGCUGAGACAUUGCCCAG | 18 |
| 562 | GCUGAGACAUUGCCCAGG | 18 |
| 563 | CUGAGACAUUGCCCAGGU | 18 |
| 564 | UGAGACAUUGCCCAGGUC | 18 |
| 565 | GAGACAUUGCCCAGGUCC | 18 |
| 566 | AGACAUUGCCCAGGUCCA | 18 |
| 567 | GACAUUGCCCAGGUCCAC | 18 |
| 568 | ACAUUGCCCAGGUCCACA | 18 |
| 569 | CAUUGCCCAGGUCCACAA | 18 |
| 570 | AUUGCCCAGGUCCACAAA | 18 |
| 571 | UUGCCCAGGUCCACAAAC | 18 |
| 572 | UGCCCAGGUCCACAAACU | 18 |
| 573 | GCCCAGGUCCACAAACUC | 18 |
| 574 | CCCAGGUCCACAAACUCU | 18 |
| 575 | CCAGGUCCACAAACUCUG | 18 |
| 576 | CAGGUCCACAAACUCUGU | 18 |
| 577 | AGGUCCACAAACUCUGUC | 18 |
| 578 | GGUCCACAAACUCUGUCA | 18 |
| 579 | GUCCACAAACUCUGUCAC | 18 |
| 580 | UCCACAAACUCUGUCACA | 18 |
| 581 | CCACAAACUCUGUCACAU | 18 |
| 582 | CACAAACUCUGUCACAUA | 18 |
| 583 | ACAAACUCUGUCACAUAU | 18 |
| 584 | CAAACUCUGUCACAUAUC | 18 |
| 585 | AAACUCUGUCACAUAUCU | 18 |
| 586 | AACUCUGUCACAUAUCUG | 18 |
| 587 | ACUCUGUCACAUAUCUGU | 18 |
| 588 | CUCUGUCACAUAUCUGUA | 18 |

FIG. 3H (continued)

| SCN8A E5A 18 mer Table | | |
|---|---|---|
| SEQ ID NO: | 5' - 3' SMO sequences | Length (nt) |
| 589 | UCUGUCACAUAUCUGUAG | 18 |
| 590 | CUGUCACAUAUCUGUAGU | 18 |

FIG. 3I.

| SCN8A E5A 17 mer Table | | |
|---|---|---|
| SEQ ID No: | 5' - 3' SMO sequences | Length (nt) |
| 591 | CUCACCUGGAAUUACAG | 17 |
| 592 | UCACCUGGAAUUACAGA | 17 |
| 593 | CACCUGGAAUUACAGAG | 17 |
| 594 | ACCUGGAAUUACAGAGA | 17 |
| 595 | CCUGGAAUUACAGAGAU | 17 |
| 596 | CUGGAAUUACAGAGAUA | 17 |
| 597 | UGGAAUUACAGAGAUAG | 17 |
| 598 | GGAAUUACAGAGAUAGU | 17 |
| 599 | GAAUUACAGAGAUAGUU | 17 |
| 600 | AAUUACAGAGAUAGUUU | 17 |
| 601 | AUUACAGAGAUAGUUUU | 17 |
| 602 | UUACAGAGAUAGUUUUC | 17 |
| 603 | UACAGAGAUAGUUUUCA | 17 |
| 604 | ACAGAGAUAGUUUUCAA | 17 |
| 605 | CAGAGAUAGUUUUCAAA | 17 |
| 606 | AGAGAUAGUUUUCAAAG | 17 |
| 607 | GAGAUAGUUUUCAAAGC | 17 |
| 608 | AGAUAGUUUUCAAAGCU | 17 |
| 609 | GAUAGUUUUCAAAGCUC | 17 |
| 610 | AUAGUUUUCAAAGCUCG | 17 |
| 611 | UAGUUUUCAAAGCUCGG | 17 |
| 612 | AGUUUUCAAAGCUCGGA | 17 |
| 613 | GUUUUCAAAGCUCGGAG | 17 |
| 614 | UUUUCAAAGCUCGGAGA | 17 |
| 615 | UUUCAAAGCUCGGAGAA | 17 |
| 616 | UUCAAAGCUCGGAGAAC | 17 |
| 617 | UCAAAGCUCGGAGAACC | 17 |
| 618 | CAAAGCUCGGAGAACCC | 17 |
| 619 | AAAGCUCGGAGAACCCU | 17 |
| 620 | AAGCUCGGAGAACCCUG | 17 |
| 621 | AGCUCGGAGAACCCUGA | 17 |
| 622 | GCUCGGAGAACCCUGAA | 17 |
| 623 | CUCGGAGAACCCUGAAU | 17 |

FIG. 3I (continued)

| SCN8A E5A 17 mer Table | | |
|---|---|---|
| SEQ ID No: | 5' - 3' SMO sequences | Length (nt) |
| 624 | UCGGAGAACCCUGAAUG | 17 |
| 625 | CGGAGAACCCUGAAUGU | 17 |
| 626 | GGAGAACCCUGAAUGUU | 17 |
| 627 | GAGAACCCUGAAUGUUC | 17 |
| 628 | AGAACCCUGAAUGUUCU | 17 |
| 629 | GAACCCUGAAUGUUCUC | 17 |
| 630 | AACCCUGAAUGUUCUCA | 17 |
| 631 | ACCCUGAAUGUUCUCAG | 17 |
| 632 | CCCUGAAUGUUCUCAGC | 17 |
| 633 | CCUGAAUGUUCUCAGCG | 17 |
| 634 | CUGAAUGUUCUCAGCGC | 17 |
| 635 | UGAAUGUUCUCAGCGCU | 17 |
| 636 | GAAUGUUCUCAGCGCUG | 17 |
| 637 | AAUGUUCUCAGCGCUGA | 17 |
| 638 | AUGUUCUCAGCGCUGAG | 17 |
| 639 | UGUUCUCAGCGCUGAGA | 17 |
| 640 | GUUCUCAGCGCUGAGAC | 17 |
| 641 | UUCUCAGCGCUGAGACA | 17 |
| 642 | UCUCAGCGCUGAGACAU | 17 |
| 643 | CUCAGCGCUGAGACAUU | 17 |
| 644 | UCAGCGCUGAGACAUUG | 17 |
| 645 | CAGCGCUGAGACAUUGC | 17 |
| 646 | AGCGCUGAGACAUUGCC | 17 |
| 647 | GCGCUGAGACAUUGCCC | 17 |
| 648 | CGCUGAGACAUUGCCCA | 17 |
| 649 | GCUGAGACAUUGCCCAG | 17 |
| 650 | CUGAGACAUUGCCCAGG | 17 |
| 651 | UGAGACAUUGCCCAGGU | 17 |
| 652 | GAGACAUUGCCCAGGUC | 17 |
| 653 | AGACAUUGCCCAGGUCC | 17 |
| 654 | GACAUUGCCCAGGUCCA | 17 |
| 655 | ACAUUGCCCAGGUCCAC | 17 |
| 656 | CAUUGCCCAGGUCCACA | 17 |
| 657 | AUUGCCCAGGUCCACAA | 17 |
| 658 | UUGCCCAGGUCCACAAA | 17 |
| 659 | UGCCCAGGUCCACAAAC | 17 |
| 660 | GCCCAGGUCCACAAACU | 17 |
| 661 | CCCAGGUCCACAAACUC | 17 |
| 662 | CCAGGUCCACAAACUCU | 17 |
| 663 | CAGGUCCACAAACUCUG | 17 |
| 664 | AGGUCCACAAACUCUGU | 17 |
| 665 | GGUCCACAAACUCUGUC | 17 |
| 666 | GUCCACAAACUCUGUCA | 17 |
| 667 | UCCACAAACUCUGUCAC | 17 |

FIG. 3I (continued)

| SCN8A E5A 17 mer Table | | |
|---|---|---|
| SEQ ID No: | 5' - 3' SMO sequences | Length (nt) |
| 668 | CCACAAACUCUGUCACA | 17 |
| 669 | CACAAACUCUGUCACAU | 17 |
| 670 | ACAAACUCUGUCACAUA | 17 |
| 671 | CAAACUCUGUCACAUAU | 17 |
| 672 | AAACUCUGUCACAUAUC | 17 |
| 673 | AACUCUGUCACAUAUCU | 17 |
| 674 | ACUCUGUCACAUAUCUG | 17 |
| 675 | CUCUGUCACAUAUCUGU | 17 |
| 676 | UCUGUCACAUAUCUGUA | 17 |
| 677 | CUGUCACAUAUCUGUAG | 17 |
| 678 | UGUCACAUAUCUGUAGU | 17 |

FIG. 3J.

| SCN8A E5A 16 mer Table | | |
|---|---|---|
| SEQ ID NO: | 5' - 3' SMO sequences | Length (nt) |
| 679 | CUCACCUGGAAUUACA | 16 |
| 680 | UCACCUGGAAUUACAG | 16 |
| 681 | CACCUGGAAUUACAGA | 16 |
| 682 | ACCUGGAAUUACAGAG | 16 |
| 683 | CCUGGAAUUACAGAGA | 16 |
| 684 | CUGGAAUUACAGAGAU | 16 |
| 685 | UGGAAUUACAGAGAUA | 16 |
| 686 | GGAAUUACAGAGAUAG | 16 |
| 687 | GAAUUACAGAGAUAGU | 16 |
| 688 | AAUUACAGAGAUAGUU | 16 |
| 689 | AUUACAGAGAUAGUUU | 16 |
| 690 | UUACAGAGAUAGUUUU | 16 |
| 691 | UACAGAGAUAGUUUUC | 16 |
| 692 | ACAGAGAUAGUUUUCA | 16 |
| 693 | CAGAGAUAGUUUUCAA | 16 |
| 694 | AGAGAUAGUUUUCAAA | 16 |
| 695 | GAGAUAGUUUUCAAAG | 16 |
| 696 | AGAUAGUUUUCAAAGC | 16 |
| 697 | GAUAGUUUUCAAAGCU | 16 |
| 698 | AUAGUUUUCAAAGCUC | 16 |
| 699 | UAGUUUUCAAAGCUCG | 16 |
| 700 | AGUUUUCAAAGCUCGG | 16 |
| 701 | GUUUUCAAAGCUCGGA | 16 |
| 702 | UUUUCAAAGCUCGGAG | 16 |
| 703 | UUUCAAAGCUCGGAGA | 16 |

FIG. 3J (continued)

| SCN8A E5A 16 mer Table | | |
|---|---|---|
| SEQ ID NO: | 5' - 3' SMO sequences | Length (nt) |
| 704 | UUCAAAGCUCGGAGAA | 16 |
| 705 | UCAAAGCUCGGAGAAC | 16 |
| 706 | CAAAGCUCGGAGAACC | 16 |
| 707 | AAAGCUCGGAGAACCC | 16 |
| 708 | AAGCUCGGAGAACCCU | 16 |
| 709 | AGCUCGGAGAACCCUG | 16 |
| 710 | GCUCGGAGAACCCUGA | 16 |
| 711 | CUCGGAGAACCCUGAA | 16 |
| 712 | UCGGAGAACCCUGAAU | 16 |
| 713 | CGGAGAACCCUGAAUG | 16 |
| 714 | GGAGAACCCUGAAUGU | 16 |
| 715 | GAGAACCCUGAAUGUU | 16 |
| 716 | AGAACCCUGAAUGUUC | 16 |
| 717 | GAACCCUGAAUGUUCU | 16 |
| 718 | AACCCUGAAUGUUCUC | 16 |
| 719 | ACCCUGAAUGUUCUCA | 16 |
| 720 | CCCUGAAUGUUCUCAG | 16 |
| 721 | CCUGAAUGUUCUCAGC | 16 |
| 722 | CUGAAUGUUCUCAGCG | 16 |
| 723 | UGAAUGUUCUCAGCGC | 16 |
| 724 | GAAUGUUCUCAGCGCU | 16 |
| 725 | AAUGUUCUCAGCGCUG | 16 |
| 726 | AUGUUCUCAGCGCUGA | 16 |
| 727 | UGUUCUCAGCGCUGAG | 16 |
| 728 | GUUCUCAGCGCUGAGA | 16 |
| 729 | UUCUCAGCGCUGAGAC | 16 |
| 730 | UCUCAGCGCUGAGACA | 16 |
| 731 | CUCAGCGCUGAGACAU | 16 |
| 732 | UCAGCGCUGAGACAUU | 16 |
| 733 | CAGCGCUGAGACAUUG | 16 |
| 734 | AGCGCUGAGACAUUGC | 16 |
| 735 | GCGCUGAGACAUUGCC | 16 |
| 736 | CGCUGAGACAUUGCCC | 16 |
| 737 | GCUGAGACAUUGCCCA | 16 |
| 738 | CUGAGACAUUGCCCAG | 16 |
| 739 | UGAGACAUUGCCCAGG | 16 |
| 740 | GAGACAUUGCCCAGGU | 16 |
| 741 | AGACAUUGCCCAGGUC | 16 |
| 742 | GACAUUGCCCAGGUCC | 16 |
| 743 | ACAUUGCCCAGGUCCA | 16 |
| 744 | CAUUGCCCAGGUCCAC | 16 |
| 745 | AUUGCCCAGGUCCACA | 16 |
| 746 | UUGCCCAGGUCCACAA | 16 |
| 747 | UGCCCAGGUCCACAAA | 16 |

FIG. 3J (continued)

| SCN8A E5A 16 mer Table | | |
|---|---|---|
| SEQ ID NO: | 5' - 3' SMO sequences | Length (nt) |
| 748 | GCCCAGGUCCACAAAC | 16 |
| 749 | CCCAGGUCCACAAACU | 16 |
| 750 | CCAGGUCCACAAACUC | 16 |
| 751 | CAGGUCCACAAACUCU | 16 |
| 752 | AGGUCCACAAACUCUG | 16 |
| 753 | GGUCCACAAACUCUGU | 16 |
| 754 | GUCCACAAACUCUGUC | 16 |
| 755 | UCCACAAACUCUGUCA | 16 |
| 756 | CCACAAACUCUGUCAC | 16 |
| 757 | CACAAACUCUGUCACA | 16 |
| 758 | ACAAACUCUGUCACAU | 16 |
| 759 | CAAACUCUGUCACAUA | 16 |
| 760 | AAACUCUGUCACAUAU | 16 |
| 761 | AACUCUGUCACAUAUC | 16 |
| 762 | ACUCUGUCACAUAUCU | 16 |
| 763 | CUCUGUCACAUAUCUG | 16 |
| 764 | UCUGUCACAUAUCUGU | 16 |
| 765 | CUGUCACAUAUCUGUA | 16 |
| 766 | UGUCACAUAUCUGUAG | 16 |
| 767 | GUCACAUAUCUGUAGU | 16 |

FIG. 3K.

| SCN8A E5A 15 mer Table | | |
|---|---|---|
| SEQ ID No: | 5' - 3' SMO sequences | Length (nt) |
| 768 | CUCACCUGGAAUUAC | 15 |
| 769 | UCACCUGGAAUUACA | 15 |
| 770 | CACCUGGAAUUACAG | 15 |
| 771 | ACCUGGAAUUACAGA | 15 |
| 772 | CCUGGAAUUACAGAG | 15 |
| 773 | CUGGAAUUACAGAGA | 15 |
| 774 | UGGAAUUACAGAGAU | 15 |
| 775 | GGAAUUACAGAGAUA | 15 |
| 776 | GAAUUACAGAGAUAG | 15 |
| 777 | AAUUACAGAGAUAGU | 15 |
| 778 | AUUACAGAGAUAGUU | 15 |
| 779 | UUACAGAGAUAGUUU | 15 |
| 780 | UACAGAGAUAGUUUU | 15 |
| 781 | ACAGAGAUAGUUUUC | 15 |
| 782 | CAGAGAUAGUUUUCA | 15 |
| 783 | AGAGAUAGUUUUCAA | 15 |
| 784 | GAGAUAGUUUUCAAA | 15 |
| 785 | AGAUAGUUUUCAAAG | 15 |

FIG. 3K (continued)

| SCN8A E5A 15 mer Table | | |
|---|---|---|
| SEQ ID No: | 5' - 3' SMO sequences | Length (nt) |
| 786 | GAUAGUUUUCAAAGC | 15 |
| 787 | AUAGUUUUCAAAGCU | 15 |
| 788 | UAGUUUUCAAAGCUC | 15 |
| 789 | AGUUUUCAAAGCUCG | 15 |
| 790 | GUUUUCAAAGCUCGG | 15 |
| 791 | UUUUCAAAGCUCGGA | 15 |
| 792 | UUUCAAAGCUCGGAG | 15 |
| 793 | UUCAAAGCUCGGAGA | 15 |
| 794 | UCAAAGCUCGGAGAA | 15 |
| 795 | CAAAGCUCGGAGAAC | 15 |
| 796 | AAAGCUCGGAGAACC | 15 |
| 797 | AAGCUCGGAGAACCC | 15 |
| 798 | AGCUCGGAGAACCCU | 15 |
| 799 | GCUCGGAGAACCCUG | 15 |
| 800 | CUCGGAGAACCCUGA | 15 |
| 801 | UCGGAGAACCCUGAA | 15 |
| 802 | CGGAGAACCCUGAAU | 15 |
| 803 | GGAGAACCCUGAAUG | 15 |
| 804 | GAGAACCCUGAAUGU | 15 |
| 805 | AGAACCCUGAAUGUU | 15 |
| 806 | GAACCCUGAAUGUUC | 15 |
| 807 | AACCCUGAAUGUUCU | 15 |
| 808 | ACCCUGAAUGUUCUC | 15 |
| 809 | CCCUGAAUGUUCUCA | 15 |
| 810 | CCUGAAUGUUCUCAG | 15 |
| 811 | CUGAAUGUUCUCAGC | 15 |
| 812 | UGAAUGUUCUCAGCG | 15 |
| 813 | GAAUGUUCUCAGCGC | 15 |
| 814 | AAUGUUCUCAGCGCU | 15 |
| 815 | AUGUUCUCAGCGCUG | 15 |
| 816 | UGUUCUCAGCGCUGA | 15 |
| 817 | GUUCUCAGCGCUGAG | 15 |
| 818 | UUCUCAGCGCUGAGA | 15 |
| 819 | UCUCAGCGCUGAGAC | 15 |
| 820 | CUCAGCGCUGAGACA | 15 |
| 821 | UCAGCGCUGAGACAU | 15 |
| 822 | CAGCGCUGAGACAUU | 15 |
| 823 | AGCGCUGAGACAUUG | 15 |
| 824 | GCGCUGAGACAUUGC | 15 |
| 825 | CGCUGAGACAUUGCC | 15 |
| 826 | GCUGAGACAUUGCCC | 15 |
| 827 | CUGAGACAUUGCCCA | 15 |
| 828 | UGAGACAUUGCCCAG | 15 |
| 829 | GAGACAUUGCCCAGG | 15 |

FIG. 3K (continued)

| SCN8A E5A 15 mer Table | | |
|---|---|---|
| SEQ ID No: | 5' - 3' SMO sequences | Length (nt) |
| 830 | AGACAUUGCCCAGGU | 15 |
| 831 | GACAUUGCCCAGGUC | 15 |
| 832 | ACAUUGCCCAGGUCC | 15 |
| 833 | CAUUGCCCAGGUCCA | 15 |
| 834 | AUUGCCCAGGUCCAC | 15 |
| 835 | UUGCCCAGGUCCACA | 15 |
| 836 | UGCCCAGGUCCACAA | 15 |
| 837 | GCCCAGGUCCACAAA | 15 |
| 838 | CCCAGGUCCACAAAC | 15 |
| 839 | CCAGGUCCACAAACU | 15 |
| 840 | CAGGUCCACAAACUC | 15 |
| 841 | AGGUCCACAAACUCU | 15 |
| 842 | GGUCCACAAACUCUG | 15 |
| 843 | GUCCACAAACUCUGU | 15 |
| 844 | UCCACAAACUCUGUC | 15 |
| 845 | CCACAAACUCUGUCA | 15 |
| 846 | CACAAACUCUGUCAC | 15 |
| 847 | ACAAACUCUGUCACA | 15 |
| 848 | CAAACUCUGUCACAU | 15 |
| 849 | AAACUCUGUCACAUA | 15 |
| 850 | AACUCUGUCACAUAU | 15 |
| 851 | ACUCUGUCACAUAUC | 15 |
| 852 | CUCUGUCACAUAUCU | 15 |
| 853 | UCUGUCACAUAUCUG | 15 |
| 854 | CUGUCACAUAUCUGU | 15 |
| 855 | UGUCACAUAUCUGUA | 15 |
| 856 | GUCACAUAUCUGUAG | 15 |
| 857 | UCACAUAUCUGUAGU | 15 |

FIG. 4A.

Human SCN8A target sequences at intronic sites close to the 5' splice site, and corresponding preferred SCN8A SMO sequences for skipping Exon 18A

| SEQ ID NO: | Orientation of Nucleic Acid Target Sequence | Sequence |
|---|---|---|
| 858 | DNA: Target Seq: 3' - 5' orientation | TTGTCAAAGGTGACCGTACGTCTTCCTAG |
| 858 | DNA: Target Seq: 5' - 3' orientation | GATCCTTCTGCATGCCAGTGGAAACTGTT |
| 859 | RNA: Compliment: 5' - 3' orientation | AACAGUUUCCACUGGCAUGCAGAAGGAUC |

| SEQ ID NO: | 5' - 3' SMOs for Intronic E18A close to 5'ss | Length (nt) |
|---|---|---|
| 860 | AACAGUUUCCACUGGCAUGCAGAA | 24 |
| 861 | ACAGUUUCCACUGGCAUGCAGAAG | 24 |
| 862 | CAGUUUCCACUGGCAUGCAGAAGG | 24 |
| 863 | AGUUUCCACUGGCAUGCAGAAGGA | 24 |
| 864 | GUUUCCACUGGCAUGCAGAAGGAU | 24 |
| 865 | UUUCCACUGGCAUGCAGAAGGAUC | 24 |
| | | |
| 866 | AACAGUUUCCACUGGCAUGCAGA | 23 |
| 867 | ACAGUUUCCACUGGCAUGCAGAA | 23 |
| 868 | CAGUUUCCACUGGCAUGCAGAAG | 23 |
| 869 | AGUUUCCACUGGCAUGCAGAAGG | 23 |
| 870 | GUUUCCACUGGCAUGCAGAAGGA | 23 |
| 871 | UUUCCACUGGCAUGCAGAAGGAU | 23 |
| 872 | UUCCACUGGCAUGCAGAAGGAUC | 23 |
| | | |
| 873 | AACAGUUUCCACUGGCAUGCAG | 22 |
| 874 | ACAGUUUCCACUGGCAUGCAGA | 22 |
| 875 | CAGUUUCCACUGGCAUGCAGAA | 22 |
| 876 | AGUUUCCACUGGCAUGCAGAAG | 22 |
| 877 | AGUUUCCACUGGCAUGCAGAAG | 22 |
| 878 | GUUUCCACUGGCAUGCAGAAGG | 22 |
| 879 | UUCCACUGGCAUGCAGAAGGAU | 22 |
| 880 | UCCACUGGCAUGCAGAAGGAUC | 22 |
| | | |
| 881 | AACAGUUUCCACUGGCAUGCA | 21 |
| 882 | ACAGUUUCCACUGGCAUGCAG | 21 |
| 883 | CAGUUUCCACUGGCAUGCAGA | 21 |
| 884 | AGUUUCCACUGGCAUGCAGAA | 21 |
| 885 | GUUUCCACUGGCAUGCAGAAG | 21 |
| 886 | UUUCCACUGGCAUGCAGAAGG | 21 |
| 887 | UUCCACUGGCAUGCAGAAGGA | 21 |

FIG. 4A (continued)

| SEQ ID NO: | 5' - 3' SMOs for Intronic E18A close to 5'ss | Length (nt) |
|---|---|---|
| 888 | UCCACUGGCAUGCAGAAGGAU | 21 |
| 889 | CCACUGGCAUGCAGAAGGAUC | 21 |
| | | |
| 890 | AACAGUUUCCACUGGCAUGC | 20 |
| 891 | ACAGUUUCCACUGGCAUGCA | 20 |
| 892 | CAGUUUCCACUGGCAUGCAG | 20 |
| 893 | AGUUUCCACUGGCAUGCAGA | 20 |
| 894 | GUUUCCACUGGCAUGCAGAA | 20 |
| 895 | UUUCCACUGGCAUGCAGAAG | 20 |
| 896 | UUCCACUGGCAUGCAGAAGG | 20 |
| 897 | UCCACUGGCAUGCAGAAGGA | 20 |
| 898 | CCACUGGCAUGCAGAAGGAU | 20 |
| 899 | CACUGGCAUGCAGAAGGAUC | 20 |
| | | |
| 900 | AACAGUUUCCACUGGCAUG | 19 |
| 901 | ACAGUUUCCACUGGCAUGC | 19 |
| 902 | CAGUUUCCACUGGCAUGCA | 19 |
| 903 | AGUUUCCACUGGCAUGCAG | 19 |
| 904 | GUUUCCACUGGCAUGCAGA | 19 |
| 905 | UUUCCACUGGCAUGCAGAA | 19 |
| 906 | UUCCACUGGCAUGCAGAAG | 19 |
| 907 | UCCACUGGCAUGCAGAAGG | 19 |
| 908 | CCACUGGCAUGCAGAAGGA | 19 |
| 909 | CACUGGCAUGCAGAAGGAU | 19 |
| 910 | ACUGGCAUGCAGAAGGAUC | 19 |
| | | |
| 911 | AACAGUUUCCACUGGCAU | 18 |
| 912 | ACAGUUUCCACUGGCAUG | 18 |
| 913 | CAGUUUCCACUGGCAUGC | 18 |
| 914 | AGUUUCCACUGGCAUGCA | 18 |
| 915 | GUUUCCACUGGCAUGCAG | 18 |
| 916 | UUUCCACUGGCAUGCAGA | 18 |
| 917 | UUCCACUGGCAUGCAGAA | 18 |
| 918 | UCCACUGGCAUGCAGAAG | 18 |
| 919 | CCACUGGCAUGCAGAAGG | 18 |
| 920 | CACUGGCAUGCAGAAGGA | 18 |
| 921 | ACUGGCAUGCAGAAGGAU | 18 |
| 922 | CUGGCAUGCAGAAGGAUC | 18 |
| | | |
| 923 | AACAGUUUCCACUGGCA | 17 |
| 924 | ACAGUUUCCACUGGCAU | 17 |
| 925 | CAGUUUCCACUGGCAUG | 17 |
| 926 | AGUUUCCACUGGCAUGC | 17 |
| 927 | GUUUCCACUGGCAUGCA | 17 |
| 928 | UUUCCACUGGCAUGCAG | 17 |

FIG. 4A (continued)

| SEQ ID NO: | 5' - 3' SMOs for Intronic E18A close to 5'ss | Length (nt) |
|---|---|---|
| 929 | UUCCACUGGCAUGCAGA | 17 |
| 930 | UCCACUGGCAUGCAGAA | 17 |
| 931 | CCACUGGCAUGCAGAAG | 17 |
| 932 | CACUGGCAUGCAGAAGG | 17 |
| 933 | ACUGGCAUGCAGAAGGA | 17 |
| 934 | CUGGCAUGCAGAAGGAU | 17 |
| 935 | UGGCAUGCAGAAGGAUC | 17 |
| | | |
| 936 | AACAGUUUCCACUGGC | 16 |
| 937 | ACAGUUUCCACUGGCA | 16 |
| 938 | CAGUUUCCACUGGCAU | 16 |
| 939 | AGUUUCCACUGGCAUG | 16 |
| 940 | GUUUCCACUGGCAUGC | 16 |
| 941 | UUUCCACUGGCAUGCA | 16 |
| 942 | UUCCACUGGCAUGCAG | 16 |
| 943 | UCCACUGGCAUGCAGA | 16 |
| 944 | CCACUGGCAUGCAGAA | 16 |
| 945 | CACUGGCAUGCAGAAG | 16 |
| 946 | ACUGGCAUGCAGAAGG | 16 |
| 947 | CUGGCAUGCAGAAGGA | 16 |
| 948 | UGGCAUGCAGAAGGAU | 16 |
| 949 | GGCAUGCAGAAGGAUC | 16 |
| | | |
| 950 | AACAGUUUCCACUGG | 15 |
| 951 | ACAGUUUCCACUGGC | 15 |
| 952 | CAGUUUCCACUGGCA | 15 |
| 953 | AGUUUCCACUGGCAU | 15 |
| 954 | GUUUCCACUGGCAUG | 15 |
| 955 | UUUCCACUGGCAUGC | 15 |
| 956 | UUCCACUGGCAUGCA | 15 |
| 957 | UCCACUGGCAUGCAG | 15 |
| 958 | CCACUGGCAUGCAGA | 15 |
| 959 | CACUGGCAUGCAGAA | 15 |
| 960 | ACUGGCAUGCAGAAG | 15 |
| 961 | CUGGCAUGCAGAAGG | 15 |
| 962 | UGGCAUGCAGAAGGA | 15 |
| 963 | GGCAUGCAGAAGGAU | 15 |
| 964 | GCAUGCAGAAGGAUC | 15 |

FIG. 4B.

Human SCN8A target sequences at the 5' splice site, and corresponding preferred SCN8A SMO sequences for skipping Exon 18A

| SEQ ID NO: | Orientation of Nucleic Acid Target Sequence | Sequence |
|---|---|---|
| 965 | DNA: Target Seq: 3' - 5' orientation | AGAATGGGAGTAGGGAAGTTTAGCACTATTCCGAGAATTCCCAGAGT |
| 965 | DNA: Target Seq: 5' - 3' orientation | TGAGACCCTTAAGAGCCTTATCACGATTTGAAGGGATGAGGGTAAGA |
| 966 | RNA: Compliment: 5' - 3' orientation | UCUUACCCUCAUCCCUUCAAAUCGUGAUAAGGCUCUUAAGGGUCUCA |

| SEQ ID NO: | 5' - 3' SMOs for E18A covering 5'ss | Length (nt) |
|---|---|---|
| 967 | UCUUACCCUCAUCCCUUCAAAUCG | 24 |
| 968 | CUUACCCUCAUCCCUUCAAAUCGU | 24 |
| 969 | UUACCCUCAUCCCUUCAAAUCGUG | 24 |
| 970 | UACCCUCAUCCCUUCAAAUCGUGA | 24 |
| 971 | ACCCUCAUCCCUUCAAAUCGUGAU | 24 |
| 972 | CCCUCAUCCCUUCAAAUCGUGAUA | 24 |
| 973 | CCUCAUCCCUUCAAAUCGUGAUAA | 24 |
| 974 | CUCAUCCCUUCAAAUCGUGAUAAG | 24 |
| 975 | UCAUCCCUUCAAAUCGUGAUAAGG | 24 |
| 976 | CAUCCCUUCAAAUCGUGAUAAGGC | 24 |
| 977 | AUCCCUUCAAAUCGUGAUAAGGCU | 24 |
| 978 | UCCCUUCAAAUCGUGAUAAGGCUC | 24 |
| 979 | CCCUUCAAAUCGUGAUAAGGCUCU | 24 |
| 980 | CCUUCAAAUCGUGAUAAGGCUCUU | 24 |
| 981 | CUUCAAAUCGUGAUAAGGCUCUUA | 24 |
| 982 | UUCAAAUCGUGAUAAGGCUCUUAA | 24 |
| 983 | UCAAAUCGUGAUAAGGCUCUUAAG | 24 |
| 984 | CAAAUCGUGAUAAGGCUCUUAAGG | 24 |
| 985 | AAAUCGUGAUAAGGCUCUUAAGGG | 24 |
| 986 | AAUCGUGAUAAGGCUCUUAAGGGU | 24 |
| 987 | AUCGUGAUAAGGCUCUUAAGGGUC | 24 |
| 988 | UCGUGAUAAGGCUCUUAAGGGUCU | 24 |
| 989 | CGUGAUAAGGCUCUUAAGGGUCUC | 24 |
| 990 | GUGAUAAGGCUCUUAAGGGUCUCA | 24 |
| | | |
| 991 | UCUUACCCUCAUCCCUUCAAAUC | 23 |
| 992 | CUUACCCUCAUCCCUUCAAAUCG | 23 |
| 993 | UUACCCUCAUCCCUUCAAAUCGU | 23 |
| 994 | UACCCUCAUCCCUUCAAAUCGUG | 23 |
| 995 | ACCCUCAUCCCUUCAAAUCGUGA | 23 |
| 996 | CCCUCAUCCCUUCAAAUCGUGAU | 23 |

FIG. 4B (continued)

| SEQ ID NO: | 5' - 3' SMOs for E18A covering 5'ss | Length (nt) |
|---|---|---|
| 997 | CCUCAUCCCUUCAAAUCGUGAUA | 23 |
| 998 | CUCAUCCCUUCAAAUCGUGAUAA | 23 |
| 999 | UCAUCCCUUCAAAUCGUGAUAAG | 23 |
| 1000 | CAUCCCUUCAAAUCGUGAUAAGG | 23 |
| 1001 | AUCCCUUCAAAUCGUGAUAAGGC | 23 |
| 1002 | UCCCUUCAAAUCGUGAUAAGGCU | 23 |
| 1003 | CCCUUCAAAUCGUGAUAAGGCUC | 23 |
| 1004 | CCUUCAAAUCGUGAUAAGGCUCU | 23 |
| 1005 | CUUCAAAUCGUGAUAAGGCUCUU | 23 |
| 1006 | UUCAAAUCGUGAUAAGGCUCUUA | 23 |
| 1007 | UCAAAUCGUGAUAAGGCUCUUAA | 23 |
| 1008 | CAAAUCGUGAUAAGGCUCUUAAG | 23 |
| 1009 | AAAUCGUGAUAAGGCUCUUAAGG | 23 |
| 1010 | AAUCGUGAUAAGGCUCUUAAGGG | 23 |
| 1011 | AUCGUGAUAAGGCUCUUAAGGGU | 23 |
| 1012 | UCGUGAUAAGGCUCUUAAGGGUC | 23 |
| 1013 | CGUGAUAAGGCUCUUAAGGGUCU | 23 |
| 1014 | GUGAUAAGGCUCUUAAGGGUCUC | 23 |
| 1015 | UGAUAAGGCUCUUAAGGGUCUCA | 23 |
| | | |
| 1016 | UCUUACCCUCAUCCCUUCAAAU | 22 |
| 1017 | CUUACCCUCAUCCCUUCAAAUC | 22 |
| 1018 | UUACCCUCAUCCCUUCAAAUCG | 22 |
| 1019 | UACCCUCAUCCCUUCAAAUCGU | 22 |
| 1020 | UACCCUCAUCCCUUCAAAUCGU | 22 |
| 1021 | ACCCUCAUCCCUUCAAAUCGUG | 22 |
| 1022 | CCUCAUCCCUUCAAAUCGUGAU | 22 |
| 1023 | CUCAUCCCUUCAAAUCGUGAUA | 22 |
| 1024 | UCAUCCCUUCAAAUCGUGAUAA | 22 |
| 1025 | CAUCCCUUCAAAUCGUGAUAAG | 22 |
| 1026 | AUCCCUUCAAAUCGUGAUAAGG | 22 |
| 1027 | UCCCUUCAAAUCGUGAUAAGGC | 22 |
| 1028 | CCCUUCAAAUCGUGAUAAGGCU | 22 |
| 1029 | CCUUCAAAUCGUGAUAAGGCUC | 22 |
| 1030 | CUUCAAAUCGUGAUAAGGCUCU | 22 |
| 1031 | UUCAAAUCGUGAUAAGGCUCUU | 22 |
| 1032 | UCAAAUCGUGAUAAGGCUCUUA | 22 |
| 1033 | CAAAUCGUGAUAAGGCUCUUAA | 22 |
| 1034 | AAAUCGUGAUAAGGCUCUUAAG | 22 |
| 1035 | AAUCGUGAUAAGGCUCUUAAGG | 22 |
| 1036 | AUCGUGAUAAGGCUCUUAAGGG | 22 |
| 1037 | UCGUGAUAAGGCUCUUAAGGGU | 22 |
| 1038 | CGUGAUAAGGCUCUUAAGGGUC | 22 |
| 1039 | GUGAUAAGGCUCUUAAGGGUCU | 22 |
| 1040 | UGAUAAGGCUCUUAAGGGUCUC | 22 |

FIG. 4B (continued)

| SEQ ID NO: | 5' - 3' SMOs for E18A covering 5'ss | Length (nt) |
|---|---|---|
| 1041 | GAUAAGGCUCUUAAGGGUCUCA | 22 |
| | | |
| 1042 | UCUUACCCUCAUCCCUUCAAA | 21 |
| 1043 | CUUACCCUCAUCCCUUCAAAU | 21 |
| 1044 | UUACCCUCAUCCCUUCAAAUC | 21 |
| 1045 | UACCCUCAUCCCUUCAAAUCG | 21 |
| 1046 | ACCCUCAUCCCUUCAAAUCGU | 21 |
| 1047 | CCCUCAUCCCUUCAAAUCGUG | 21 |
| 1048 | CCUCAUCCCUUCAAAUCGUGA | 21 |
| 1049 | CUCAUCCCUUCAAAUCGUGAU | 21 |
| 1050 | UCAUCCCUUCAAAUCGUGAUA | 21 |
| 1051 | CAUCCCUUCAAAUCGUGAUAA | 21 |
| 1052 | AUCCCUUCAAAUCGUGAUAAG | 21 |
| 1053 | UCCCUUCAAAUCGUGAUAAGG | 21 |
| 1054 | CCCUUCAAAUCGUGAUAAGGC | 21 |
| 1055 | CCUUCAAAUCGUGAUAAGGCU | 21 |
| 1056 | CUUCAAAUCGUGAUAAGGCUC | 21 |
| 1057 | UUCAAAUCGUGAUAAGGCUCU | 21 |
| 1058 | UCAAAUCGUGAUAAGGCUCUU | 21 |
| 1059 | CAAAUCGUGAUAAGGCUCUUA | 21 |
| 1060 | AAAUCGUGAUAAGGCUCUUAA | 21 |
| 1061 | AAUCGUGAUAAGGCUCUUAAG | 21 |
| 1062 | AUCGUGAUAAGGCUCUUAAGG | 21 |
| 1063 | UCGUGAUAAGGCUCUUAAGGG | 21 |
| 1064 | CGUGAUAAGGCUCUUAAGGGU | 21 |
| 1065 | GUGAUAAGGCUCUUAAGGGUC | 21 |
| 1066 | UGAUAAGGCUCUUAAGGGUCU | 21 |
| 1067 | GAUAAGGCUCUUAAGGGUCUC | 21 |
| 1068 | AUAAGGCUCUUAAGGGUCUCA | 21 |
| | | |
| 1069 | UCUUACCCUCAUCCCUUCAA | 20 |
| 1070 | CUUACCCUCAUCCCUUCAAA | 20 |
| 1071 | UUACCCUCAUCCCUUCAAAU | 20 |
| 1072 | UACCCUCAUCCCUUCAAAUC | 20 |
| 1073 | ACCCUCAUCCCUUCAAAUCG | 20 |
| 1074 | CCCUCAUCCCUUCAAAUCGU | 20 |
| 1075 | CCUCAUCCCUUCAAAUCGUG | 20 |
| 1076 | CUCAUCCCUUCAAAUCGUGA | 20 |
| 1077 | UCAUCCCUUCAAAUCGUGAU | 20 |
| 1078 | CAUCCCUUCAAAUCGUGAUA | 20 |
| 1079 | AUCCCUUCAAAUCGUGAUAA | 20 |
| 1080 | UCCCUUCAAAUCGUGAUAAG | 20 |
| 1081 | CCCUUCAAAUCGUGAUAAGG | 20 |
| 1082 | CCUUCAAAUCGUGAUAAGGC | 20 |
| 1083 | CUUCAAAUCGUGAUAAGGCU | 20 |

FIG. 4B (continued)

| SEQ ID NO: | 5' - 3' SMOs for E18A covering 5'ss | Length (nt) |
|---|---|---|
| 1084 | UUCAAAUCGUGAUAAGGCUC | 20 |
| 1085 | UCAAAUCGUGAUAAGGCUCU | 20 |
| 1086 | CAAAUCGUGAUAAGGCUCUU | 20 |
| 1087 | AAAUCGUGAUAAGGCUCUUA | 20 |
| 1088 | AAUCGUGAUAAGGCUCUUAA | 20 |
| 1089 | AUCGUGAUAAGGCUCUUAAG | 20 |
| 1090 | UCGUGAUAAGGCUCUUAAGG | 20 |
| 1091 | CGUGAUAAGGCUCUUAAGGG | 20 |
| 1092 | GUGAUAAGGCUCUUAAGGGU | 20 |
| 1093 | UGAUAAGGCUCUUAAGGGUC | 20 |
| 1094 | GAUAAGGCUCUUAAGGGUCU | 20 |
| 1095 | AUAAGGCUCUUAAGGGUCUC | 20 |
| 1096 | UAAGGCUCUUAAGGGUCUCA | 20 |
| | | |
| 1097 | UCUUACCCUCAUCCCUUCA | 19 |
| 1098 | CUUACCCUCAUCCCUUCAA | 19 |
| 1099 | UUACCCUCAUCCCUUCAAA | 19 |
| 1100 | UACCCUCAUCCCUUCAAAU | 19 |
| 1101 | ACCCUCAUCCCUUCAAAUC | 19 |
| 1102 | CCCUCAUCCCUUCAAAUCG | 19 |
| 1103 | CCUCAUCCCUUCAAAUCGU | 19 |
| 1104 | CUCAUCCCUUCAAAUCGUG | 19 |
| 1105 | UCAUCCCUUCAAAUCGUGA | 19 |
| 1106 | CAUCCCUUCAAAUCGUGAU | 19 |
| 1107 | AUCCCUUCAAAUCGUGAUA | 19 |
| 1108 | UCCCUUCAAAUCGUGAUAA | 19 |
| 1109 | CCCUUCAAAUCGUGAUAAG | 19 |
| 1110 | CCUUCAAAUCGUGAUAAGG | 19 |
| 1111 | CUUCAAAUCGUGAUAAGGC | 19 |
| 1112 | UUCAAAUCGUGAUAAGGCU | 19 |
| 1113 | UCAAAUCGUGAUAAGGCUC | 19 |
| 1114 | CAAAUCGUGAUAAGGCUCU | 19 |
| 1115 | AAAUCGUGAUAAGGCUCUU | 19 |
| 1116 | AAUCGUGAUAAGGCUCUUA | 19 |
| 1117 | AUCGUGAUAAGGCUCUUAA | 19 |
| 1118 | UCGUGAUAAGGCUCUUAAG | 19 |
| 1119 | CGUGAUAAGGCUCUUAAGG | 19 |
| 1120 | GUGAUAAGGCUCUUAAGGG | 19 |
| 1121 | UGAUAAGGCUCUUAAGGGU | 19 |
| 1122 | GAUAAGGCUCUUAAGGGUC | 19 |
| 1123 | AUAAGGCUCUUAAGGGUCU | 19 |
| 1124 | UAAGGCUCUUAAGGGUCUC | 19 |
| 1125 | AAGGCUCUUAAGGGUCUCA | 19 |
| | | |
| 1126 | UCUUACCCUCAUCCCUUC | 18 |

FIG. 4B (continued)

| SEQ ID NO: | 5' - 3' SMOs for E18A covering 5'ss | Length (nt) |
|---|---|---|
| 1127 | CUUACCCUCAUCCCUUCA | 18 |
| 1128 | UUACCCUCAUCCCUUCAA | 18 |
| 1129 | UACCCUCAUCCCUUCAAA | 18 |
| 1130 | ACCCUCAUCCCUUCAAAU | 18 |
| 1131 | CCCUCAUCCCUUCAAAUC | 18 |
| 1132 | CCUCAUCCCUUCAAAUCG | 18 |
| 1133 | CUCAUCCCUUCAAAUCGU | 18 |
| 1134 | UCAUCCCUUCAAAUCGUG | 18 |
| 1135 | CAUCCCUUCAAAUCGUGA | 18 |
| 1136 | AUCCCUUCAAAUCGUGAU | 18 |
| 1137 | UCCCUUCAAAUCGUGAUA | 18 |
| 1138 | CCCUUCAAAUCGUGAUAA | 18 |
| 1139 | CCUUCAAAUCGUGAUAAG | 18 |
| 1140 | CUUCAAAUCGUGAUAAGG | 18 |
| 1141 | UUCAAAUCGUGAUAAGGC | 18 |
| 1142 | UCAAAUCGUGAUAAGGCU | 18 |
| 1143 | CAAAUCGUGAUAAGGCUC | 18 |
| 1144 | AAAUCGUGAUAAGGCUCU | 18 |
| 1145 | AAUCGUGAUAAGGCUCUU | 18 |
| 1146 | AUCGUGAUAAGGCUCUUA | 18 |
| 1147 | UCGUGAUAAGGCUCUUAA | 18 |
| 1148 | CGUGAUAAGGCUCUUAAG | 18 |
| 1149 | GUGAUAAGGCUCUUAAGG | 18 |
| 1150 | UGAUAAGGCUCUUAAGGG | 18 |
| 1151 | GAUAAGGCUCUUAAGGGU | 18 |
| 1152 | AUAAGGCUCUUAAGGGUC | 18 |
| 1153 | UAAGGCUCUUAAGGGUCU | 18 |
| 1154 | AAGGCUCUUAAGGGUCUC | 18 |
| 1155 | AGGCUCUUAAGGGUCUCA | 18 |
| | | |
| 1156 | UCUUACCCUCAUCCCUU | 17 |
| 1157 | CUUACCCUCAUCCCUUC | 17 |
| 1158 | UUACCCUCAUCCCUUCA | 17 |
| 1159 | UACCCUCAUCCCUUCAA | 17 |
| 1160 | ACCCUCAUCCCUUCAAA | 17 |
| 1161 | CCCUCAUCCCUUCAAAU | 17 |
| 1162 | CCUCAUCCCUUCAAAUC | 17 |
| 1163 | CUCAUCCCUUCAAAUCG | 17 |
| 1164 | UCAUCCCUUCAAAUCGU | 17 |
| 1165 | CAUCCCUUCAAAUCGUG | 17 |
| 1166 | AUCCCUUCAAAUCGUGA | 17 |
| 1167 | UCCCUUCAAAUCGUGAU | 17 |
| 1168 | CCCUUCAAAUCGUGAUA | 17 |
| 1169 | CCUUCAAAUCGUGAUAA | 17 |
| 1170 | CUUCAAAUCGUGAUAAG | 17 |

FIG. 4B (continued)

| SEQ ID NO: | 5' - 3' SMOs for E18A covering 5'ss | Length (nt) |
|---|---|---|
| 1171 | UUCAAAUCGUGAUAAGG | 17 |
| 1172 | UCAAAUCGUGAUAAGGC | 17 |
| 1173 | CAAAUCGUGAUAAGGCU | 17 |
| 1174 | AAAUCGUGAUAAGGCUC | 17 |
| 1175 | AAUCGUGAUAAGGCUCU | 17 |
| 1176 | AUCGUGAUAAGGCUCUU | 17 |
| 1177 | UCGUGAUAAGGCUCUUA | 17 |
| 1178 | CGUGAUAAGGCUCUUAA | 17 |
| 1179 | GUGAUAAGGCUCUUAAG | 17 |
| 1180 | UGAUAAGGCUCUUAAGG | 17 |
| 1181 | GAUAAGGCUCUUAAGGG | 17 |
| 1182 | AUAAGGCUCUUAAGGGU | 17 |
| 1183 | UAAGGCUCUUAAGGGUC | 17 |
| 1184 | AAGGCUCUUAAGGGUCU | 17 |
| 1185 | AGGCUCUUAAGGGUCUC | 17 |
| 1186 | GGCUCUUAAGGGUCUCA | 17 |
| | | |
| 1187 | UCUUACCCUCAUCCCU | 16 |
| 1188 | CUUACCCUCAUCCCUU | 16 |
| 1189 | UUACCCUCAUCCCUUC | 16 |
| 1190 | UACCCUCAUCCCUUCA | 16 |
| 1191 | ACCCUCAUCCCUUCAA | 16 |
| 1192 | CCCUCAUCCCUUCAAA | 16 |
| 1193 | CCUCAUCCCUUCAAAU | 16 |
| 1194 | CUCAUCCCUUCAAAUC | 16 |
| 1195 | UCAUCCCUUCAAAUCG | 16 |
| 1196 | CAUCCCUUCAAAUCGU | 16 |
| 1197 | AUCCCUUCAAAUCGUG | 16 |
| 1198 | UCCCUUCAAAUCGUGA | 16 |
| 1199 | CCCUUCAAAUCGUGAU | 16 |
| 1200 | CCUUCAAAUCGUGAUA | 16 |
| 1201 | CUUCAAAUCGUGAUAA | 16 |
| 1202 | UUCAAAUCGUGAUAAG | 16 |
| 1203 | UCAAAUCGUGAUAAGG | 16 |
| 1204 | CAAAUCGUGAUAAGGC | 16 |
| 1205 | AAAUCGUGAUAAGGCU | 16 |
| 1206 | AAUCGUGAUAAGGCUC | 16 |
| 1207 | AUCGUGAUAAGGCUCU | 16 |
| 1208 | UCGUGAUAAGGCUCUU | 16 |
| 1209 | CGUGAUAAGGCUCUUA | 16 |
| 1210 | GUGAUAAGGCUCUUAA | 16 |
| 1211 | UGAUAAGGCUCUUAAG | 16 |
| 1212 | GAUAAGGCUCUUAAGG | 16 |
| 1213 | AUAAGGCUCUUAAGGG | 16 |
| 1214 | UAAGGCUCUUAAGGGU | 16 |

FIG. 4B (continued)

| SEQ ID NO: | 5' - 3' SMOs for E18A covering 5'ss | Length (nt) |
|---|---|---|
| 1215 | AAGGCUCUUAAGGGUC | 16 |
| 1216 | AGGCUCUUAAGGGUCU | 16 |
| 1217 | GGCUCUUAAGGGUCUC | 16 |
| 1218 | GCUCUUAAGGGUCUCA | 16 |
| | | |
| 1219 | UCUUACCCUCAUCCC | 15 |
| 1220 | CUUACCCUCAUCCCU | 15 |
| 1221 | UUACCCUCAUCCCUU | 15 |
| 1222 | UACCCUCAUCCCUUC | 15 |
| 1223 | ACCCUCAUCCCUUCA | 15 |
| 1224 | CCCUCAUCCCUUCAA | 15 |
| 1225 | CCUCAUCCCUUCAAA | 15 |
| 1226 | CUCAUCCCUUCAAAU | 15 |
| 1227 | UCAUCCCUUCAAAUC | 15 |
| 1228 | CAUCCCUUCAAAUCG | 15 |
| 1229 | AUCCCUUCAAAUCGU | 15 |
| 1230 | UCCCUUCAAAUCGUG | 15 |
| 1231 | CCCUUCAAAUCGUGA | 15 |
| 1232 | CCUUCAAAUCGUGAU | 15 |
| 1233 | CUUCAAAUCGUGAUA | 15 |
| 1234 | UUCAAAUCGUGAUAA | 15 |
| 1235 | UCAAAUCGUGAUAAG | 15 |
| 1236 | CAAAUCGUGAUAAGG | 15 |
| 1237 | AAAUCGUGAUAAGGC | 15 |
| 1238 | AAUCGUGAUAAGGCU | 15 |
| 1239 | AUCGUGAUAAGGCUC | 15 |
| 1240 | UCGUGAUAAGGCUCU | 15 |
| 1241 | CGUGAUAAGGCUCUU | 15 |
| 1242 | GUGAUAAGGCUCUUA | 15 |
| 1243 | UGAUAAGGCUCUUAA | 15 |
| 1244 | GAUAAGGCUCUUAAG | 15 |
| 1245 | AUAAGGCUCUUAAGG | 15 |
| 1246 | UAAGGCUCUUAAGGG | 15 |
| 1247 | AAGGCUCUUAAGGGU | 15 |
| 1248 | AGGCUCUUAAGGGUC | 15 |
| 1249 | GGCUCUUAAGGGUCU | 15 |
| 1250 | GCUCUUAAGGGUCUC | 15 |
| 1251 | CUCUUAAGGGUCUCA | 15 |

FIG. 4C.

Human SCN8A target sequences within Exon 18A, and corresponding preferred SCN8A SMO sequences for skipping Exon 18A FIG. 4C (continued)

| SEQ ID NO: | Orientation of Nucleic Acid Target Sequence | Sequence |
|---|---|---|
| 1252 | DNA: Target Seq: 3' - 5' orientation | ACTATTCCGAGAATTCCCAGAGTTTCGAGAATCCCAGGATT CCCTGAAATACCGTGGATCAAGGCTCATCGGGTCCCGT |
| 1252 | DNA: Target Seq: 5' - 3' orientation | TGCCCTGGGCTACTCGGAACTAGGTGCCATAAAGTCCCTTA GGACCCTAAGAGCTTTGAGACCCTTAAGAGCCTTATCA |
| 1253 | RNA: Compliment: 5' - 3' orientation | UGAUAAGGCUCUUAAGGGUCUCAAAGCUCUUAGGGUCCUAA GGGACUUUAUGGCACCUAGUUCCGAGUAGCCCAGGGCA |

| SEQ ID NO: | 5' - 3' SMOs for Internal exon | Length (nt) |
|---|---|---|
| 1254 | UGAUAAGGCUCUUAAGGGUCUCAA | 24 |
| 1255 | GAUAAGGCUCUUAAGGGUCUCAAA | 24 |
| 1256 | AUAAGGCUCUUAAGGGUCUCAAAG | 24 |
| 1257 | UAAGGCUCUUAAGGGUCUCAAAGC | 24 |
| 1258 | AAGGCUCUUAAGGGUCUCAAAGCU | 24 |
| 1259 | AGGCUCUUAAGGGUCUCAAAGCUC | 24 |
| 1260 | GGCUCUUAAGGGUCUCAAAGCUCU | 24 |
| 1261 | GCUCUUAAGGGUCUCAAAGCUCUU | 24 |
| 1262 | CUCUUAAGGGUCUCAAAGCUCUUA | 24 |
| 1263 | UCUUAAGGGUCUCAAAGCUCUUAG | 24 |
| 1264 | CUUAAGGGUCUCAAAGCUCUUAGG | 24 |
| 1265 | UUAAGGGUCUCAAAGCUCUUAGGG | 24 |
| 1266 | UAAGGGUCUCAAAGCUCUUAGGGU | 24 |
| 1267 | AAGGGUCUCAAAGCUCUUAGGGUC | 24 |
| 1268 | AGGGUCUCAAAGCUCUUAGGGUCC | 24 |
| 1269 | GGGUCUCAAAGCUCUUAGGGUCCU | 24 |
| 1270 | GGUCUCAAAGCUCUUAGGGUCCUA | 24 |
| 1271 | GUCUCAAAGCUCUUAGGGUCCUAA | 24 |
| 1272 | UCUCAAAGCUCUUAGGGUCCUAAG | 24 |
| 1273 | CUCAAAGCUCUUAGGGUCCUAAGG | 24 |
| 1274 | UCAAAGCUCUUAGGGUCCUAAGGG | 24 |
| 1275 | CAAAGCUCUUAGGGUCCUAAGGGA | 24 |
| 1276 | AAAGCUCUUAGGGUCCUAAGGGAC | 24 |
| 1277 | AAGCUCUUAGGGUCCUAAGGGACU | 24 |
| 1278 | AGCUCUUAGGGUCCUAAGGGACUU | 24 |
| 1279 | GCUCUUAGGGUCCUAAGGGACUUU | 24 |
| 1280 | CUCUUAGGGUCCUAAGGGACUUUA | 24 |
| 1281 | UCUUAGGGUCCUAAGGGACUUUAU | 24 |
| 1282 | CUUAGGGUCCUAAGGGACUUUAUG | 24 |
| 1283 | UUAGGGUCCUAAGGGACUUUAUGG | 24 |
| 1284 | UAGGGUCCUAAGGGACUUUAUGGC | 24 |
| 1285 | AGGGUCCUAAGGGACUUUAUGGCA | 24 |
| 1286 | GGGUCCUAAGGGACUUUAUGGCAC | 24 |
| 1287 | GGUCCUAAGGGACUUUAUGGCACC | 24 |

FIG. 4C (continued)

| SEQ ID NO: | 5' - 3' SMOs for Internal exon | Length (nt) |
|---|---|---|
| 1288 | GUCCUAAGGGACUUUAUGGCACCU | 24 |
| 1289 | UCCUAAGGGACUUUAUGGCACCUA | 24 |
| 1290 | CCUAAGGGACUUUAUGGCACCUAG | 24 |
| 1291 | CUAAGGGACUUUAUGGCACCUAGU | 24 |
| 1292 | UAAGGGACUUUAUGGCACCUAGUU | 24 |
| 1293 | AAGGGACUUUAUGGCACCUAGUUC | 24 |
| 1294 | AGGGACUUUAUGGCACCUAGUUCC | 24 |
| 1295 | GGGACUUUAUGGCACCUAGUUCCG | 24 |
| 1296 | GGACUUUAUGGCACCUAGUUCCGA | 24 |
| 1297 | GACUUUAUGGCACCUAGUUCCGAG | 24 |
| 1298 | ACUUUAUGGCACCUAGUUCCGAGU | 24 |
| 1299 | CUUUAUGGCACCUAGUUCCGAGUA | 24 |
| 1300 | UUUAUGGCACCUAGUUCCGAGUAG | 24 |
| 1301 | UUAUGGCACCUAGUUCCGAGUAGC | 24 |
| 1302 | UAUGGCACCUAGUUCCGAGUAGCC | 24 |
| 1303 | AUGGCACCUAGUUCCGAGUAGCCC | 24 |
| 1304 | UGGCACCUAGUUCCGAGUAGCCCA | 24 |
| 1305 | GGCACCUAGUUCCGAGUAGCCCAG | 24 |
| 1306 | GCACCUAGUUCCGAGUAGCCCAGG | 24 |
| 1307 | CACCUAGUUCCGAGUAGCCCAGGG | 24 |
| 1308 | ACCUAGUUCCGAGUAGCCCAGGGC | 24 |
| 1309 | CCUAGUUCCGAGUAGCCCAGGGCA | 24 |
| | | |
| 1310 | UGAUAAGGCUCUUAAGGGUCUCA | 23 |
| 1311 | GAUAAGGCUCUUAAGGGUCUCAA | 23 |
| 1312 | AUAAGGCUCUUAAGGGUCUCAAA | 23 |
| 1313 | UAAGGCUCUUAAGGGUCUCAAAG | 23 |
| 1314 | AAGGCUCUUAAGGGUCUCAAAGC | 23 |
| 1315 | AGGCUCUUAAGGGUCUCAAAGCU | 23 |
| 1316 | GGCUCUUAAGGGUCUCAAAGCUC | 23 |
| 1317 | GCUCUUAAGGGUCUCAAAGCUCU | 23 |
| 1318 | CUCUUAAGGGUCUCAAAGCUCUU | 23 |
| 1319 | UCUUAAGGGUCUCAAAGCUCUUA | 23 |
| 1320 | CUUAAGGGUCUCAAAGCUCUUAG | 23 |
| 1321 | UUAAGGGUCUCAAAGCUCUUAGG | 23 |
| 1322 | UAAGGGUCUCAAAGCUCUUAGGG | 23 |
| 1323 | AAGGGUCUCAAAGCUCUUAGGGU | 23 |
| 1324 | AGGGUCUCAAAGCUCUUAGGGUC | 23 |
| 1325 | GGGUCUCAAAGCUCUUAGGGUCC | 23 |
| 1326 | GGUCUCAAAGCUCUUAGGGUCCU | 23 |
| 1327 | GUCUCAAAGCUCUUAGGGUCCUA | 23 |
| 1328 | UCUCAAAGCUCUUAGGGUCCUAA | 23 |
| 1329 | CUCAAAGCUCUUAGGGUCCUAAG | 23 |
| 1330 | UCAAAGCUCUUAGGGUCCUAAGG | 23 |
| 1331 | CAAAGCUCUUAGGGUCCUAAGGG | 23 |

FIG. 4C (continued)

| SEQ ID NO: | 5' - 3' SMOs for Internal exon | Length (nt) |
|---|---|---|
| 1332 | AAAGCUCUUAGGGUCCUAAGGGA | 23 |
| 1333 | AAGCUCUUAGGGUCCUAAGGGAC | 23 |
| 1334 | AGCUCUUAGGGUCCUAAGGGACU | 23 |
| 1335 | GCUCUUAGGGUCCUAAGGGACUU | 23 |
| 1336 | CUCUUAGGGUCCUAAGGGACUUU | 23 |
| 1337 | UCUUAGGGUCCUAAGGGACUUUA | 23 |
| 1338 | CUUAGGGUCCUAAGGGACUUUAU | 23 |
| 1339 | UUAGGGUCCUAAGGGACUUUAUG | 23 |
| 1340 | UAGGGUCCUAAGGGACUUUAUGG | 23 |
| 1341 | AGGGUCCUAAGGGACUUUAUGGC | 23 |
| 1342 | GGGUCCUAAGGGACUUUAUGGCA | 23 |
| 1343 | GGUCCUAAGGGACUUUAUGGCAC | 23 |
| 1344 | GUCCUAAGGGACUUUAUGGCACC | 23 |
| 1345 | UCCUAAGGGACUUUAUGGCACCU | 23 |
| 1346 | CCUAAGGGACUUUAUGGCACCUA | 23 |
| 1347 | CUAAGGGACUUUAUGGCACCUAG | 23 |
| 1348 | UAAGGGACUUUAUGGCACCUAGU | 23 |
| 1349 | AAGGGACUUUAUGGCACCUAGUU | 23 |
| 1350 | AGGGACUUUAUGGCACCUAGUUC | 23 |
| 1351 | GGGACUUUAUGGCACCUAGUUCC | 23 |
| 1352 | GGACUUUAUGGCACCUAGUUCCG | 23 |
| 1353 | GACUUUAUGGCACCUAGUUCCGA | 23 |
| 1354 | ACUUUAUGGCACCUAGUUCCGAG | 23 |
| 1355 | CUUUAUGGCACCUAGUUCCGAGU | 23 |
| 1356 | UUUAUGGCACCUAGUUCCGAGUA | 23 |
| 1357 | UUAUGGCACCUAGUUCCGAGUAG | 23 |
| 1358 | UAUGGCACCUAGUUCCGAGUAGC | 23 |
| 1359 | AUGGCACCUAGUUCCGAGUAGCC | 23 |
| 1360 | UGGCACCUAGUUCCGAGUAGCCC | 23 |
| 1361 | GGCACCUAGUUCCGAGUAGCCCA | 23 |
| 1362 | GCACCUAGUUCCGAGUAGCCCAG | 23 |
| 1363 | CACCUAGUUCCGAGUAGCCCAGG | 23 |
| 1364 | ACCUAGUUCCGAGUAGCCCAGGG | 23 |
| 1365 | CCUAGUUCCGAGUAGCCCAGGGC | 23 |
| 1366 | CUAGUUCCGAGUAGCCCAGGGCA | 23 |
| | | |
| 1367 | UGAUAAGGCUCUUAAGGGUCUC | 22 |
| 1368 | GAUAAGGCUCUUAAGGGUCUCA | 22 |
| 1369 | AUAAGGCUCUUAAGGGUCUCAA | 22 |
| 1370 | UAAGGCUCUUAAGGGUCUCAAA | 22 |
| 1371 | AAGGCUCUUAAGGGUCUCAAAG | 22 |
| 1372 | AGGCUCUUAAGGGUCUCAAAGC | 22 |
| 1373 | GGCUCUUAAGGGUCUCAAAGCU | 22 |
| 1374 | GCUCUUAAGGGUCUCAAAGCUC | 22 |
| 1375 | CUCUUAAGGGUCUCAAAGCUCU | 22 |

FIG. 4C (continued)

| SEQ ID NO: | 5' - 3' SMOs for Internal exon | Length (nt) |
|---|---|---|
| 1376 | UCUUAAGGGUCUCAAAGCUCUU | 22 |
| 1377 | CUUAAGGGUCUCAAAGCUCUUA | 22 |
| 1378 | UUAAGGGUCUCAAAGCUCUUAG | 22 |
| 1379 | UAAGGGUCUCAAAGCUCUUAGG | 22 |
| 1380 | AAGGGUCUCAAAGCUCUUAGGG | 22 |
| 1381 | AGGGUCUCAAAGCUCUUAGGGU | 22 |
| 1382 | GGGUCUCAAAGCUCUUAGGGUC | 22 |
| 1383 | GGUCUCAAAGCUCUUAGGGUCC | 22 |
| 1384 | GUCUCAAAGCUCUUAGGGUCCU | 22 |
| 1385 | UCUCAAAGCUCUUAGGGUCCUA | 22 |
| 1386 | CUCAAAGCUCUUAGGGUCCUAA | 22 |
| 1387 | UCAAAGCUCUUAGGGUCCUAAG | 22 |
| 1388 | CAAAGCUCUUAGGGUCCUAAGG | 22 |
| 1389 | AAAGCUCUUAGGGUCCUAAGGG | 22 |
| 1390 | AAGCUCUUAGGGUCCUAAGGGA | 22 |
| 1391 | AGCUCUUAGGGUCCUAAGGGAC | 22 |
| 1392 | GCUCUUAGGGUCCUAAGGGACU | 22 |
| 1393 | CUCUUAGGGUCCUAAGGGACUU | 22 |
| 1394 | UCUUAGGGUCCUAAGGGACUUU | 22 |
| 1395 | CUUAGGGUCCUAAGGGACUUUA | 22 |
| 1396 | UUAGGGUCCUAAGGGACUUUAU | 22 |
| 1397 | UAGGGUCCUAAGGGACUUUAUG | 22 |
| 1398 | AGGGUCCUAAGGGACUUUAUGG | 22 |
| 1399 | GGGUCCUAAGGGACUUUAUGGC | 22 |
| 1400 | GGUCCUAAGGGACUUUAUGGCA | 22 |
| 1401 | GUCCUAAGGGACUUUAUGGCAC | 22 |
| 1402 | UCCUAAGGGACUUUAUGGCACC | 22 |
| 1403 | CCUAAGGGACUUUAUGGCACCU | 22 |
| 1404 | CUAAGGGACUUUAUGGCACCUA | 22 |
| 1405 | UAAGGGACUUUAUGGCACCUAG | 22 |
| 1406 | AAGGGACUUUAUGGCACCUAGU | 22 |
| 1407 | AGGGACUUUAUGGCACCUAGUU | 22 |
| 1408 | GGGACUUUAUGGCACCUAGUUC | 22 |
| 1409 | GGACUUUAUGGCACCUAGUUCC | 22 |
| 1410 | GACUUUAUGGCACCUAGUUCCG | 22 |
| 1411 | ACUUUAUGGCACCUAGUUCCGA | 22 |
| 1412 | CUUUAUGGCACCUAGUUCCGAG | 22 |
| 1413 | UUUAUGGCACCUAGUUCCGAGU | 22 |
| 1414 | UUAUGGCACCUAGUUCCGAGUA | 22 |
| 1415 | UAUGGCACCUAGUUCCGAGUAG | 22 |
| 1416 | AUGGCACCUAGUUCCGAGUAGC | 22 |
| 1417 | UGGCACCUAGUUCCGAGUAGCC | 22 |
| 1418 | GGCACCUAGUUCCGAGUAGCCC | 22 |
| 1419 | GCACCUAGUUCCGAGUAGCCCA | 22 |
| 1420 | CACCUAGUUCCGAGUAGCCCAG | 22 |

FIG. 4C (continued)

| SEQ ID NO: | 5' - 3' SMOs for Internal exon | Length (nt) |
|---|---|---|
| 1421 | ACCUAGUUCCGAGUAGCCCAGG | 22 |
| 1422 | CCUAGUUCCGAGUAGCCCAGGG | 22 |
| 1423 | CUAGUUCCGAGUAGCCCAGGGC | 22 |
| 1424 | UAGUUCCGAGUAGCCCAGGGCA | 22 |
| | | |
| 1425 | UGAUAAGGCUCUUAAGGGUCU | 21 |
| 1426 | GAUAAGGCUCUUAAGGGUCUC | 21 |
| 1427 | AUAAGGCUCUUAAGGGUCUCA | 21 |
| 1428 | UAAGGCUCUUAAGGGUCUCAA | 21 |
| 1429 | AAGGCUCUUAAGGGUCUCAAA | 21 |
| 1430 | AGGCUCUUAAGGGUCUCAAAG | 21 |
| 1431 | GGCUCUUAAGGGUCUCAAAGC | 21 |
| 1432 | GCUCUUAAGGGUCUCAAAGCU | 21 |
| 1433 | CUCUUAAGGGUCUCAAAGCUC | 21 |
| 1434 | UCUUAAGGGUCUCAAAGCUCU | 21 |
| 1435 | CUUAAGGGUCUCAAAGCUCUU | 21 |
| 1436 | UUAAGGGUCUCAAAGCUCUUA | 21 |
| 1437 | UAAGGGUCUCAAAGCUCUUAG | 21 |
| 1438 | AAGGGUCUCAAAGCUCUUAGG | 21 |
| 1439 | AGGGUCUCAAAGCUCUUAGGG | 21 |
| 1440 | GGGUCUCAAAGCUCUUAGGGU | 21 |
| 1441 | GGUCUCAAAGCUCUUAGGGUC | 21 |
| 1442 | GUCUCAAAGCUCUUAGGGUCC | 21 |
| 1443 | UCUCAAAGCUCUUAGGGUCCU | 21 |
| 1444 | CUCAAAGCUCUUAGGGUCCUA | 21 |
| 1445 | UCAAAGCUCUUAGGGUCCUAA | 21 |
| 1446 | CAAAGCUCUUAGGGUCCUAAG | 21 |
| 1447 | AAAGCUCUUAGGGUCCUAAGG | 21 |
| 1448 | AAGCUCUUAGGGUCCUAAGGG | 21 |
| 1449 | AGCUCUUAGGGUCCUAAGGGA | 21 |
| 1450 | GCUCUUAGGGUCCUAAGGGAC | 21 |
| 1451 | CUCUUAGGGUCCUAAGGGACU | 21 |
| 1452 | UCUUAGGGUCCUAAGGGACUU | 21 |
| 1453 | CUUAGGGUCCUAAGGGACUUU | 21 |
| 1454 | UUAGGGUCCUAAGGGACUUUA | 21 |
| 1455 | UAGGGUCCUAAGGGACUUUAU | 21 |
| 1456 | AGGGUCCUAAGGGACUUUAUG | 21 |
| 1457 | GGGUCCUAAGGGACUUUAUGG | 21 |
| 1458 | GGUCCUAAGGGACUUUAUGGC | 21 |
| 1459 | GUCCUAAGGGACUUUAUGGCA | 21 |
| 1460 | UCCUAAGGGACUUUAUGGCAC | 21 |
| 1461 | CCUAAGGGACUUUAUGGCACC | 21 |
| 1462 | CUAAGGGACUUUAUGGCACCU | 21 |
| 1463 | UAAGGGACUUUAUGGCACCUA | 21 |
| 1464 | AAGGGACUUUAUGGCACCUAG | 21 |

FIG. 4C (continued)

| SEQ ID NO: | 5' - 3' SMOs for Internal exon | Length (nt) |
|---|---|---|
| 1465 | AGGGACUUUAUGGCACCUAGU | 21 |
| 1466 | GGGACUUUAUGGCACCUAGUU | 21 |
| 1467 | GGACUUUAUGGCACCUAGUUC | 21 |
| 1468 | GACUUUAUGGCACCUAGUUCC | 21 |
| 1469 | ACUUUAUGGCACCUAGUUCCG | 21 |
| 1470 | CUUUAUGGCACCUAGUUCCGA | 21 |
| 1471 | UUUAUGGCACCUAGUUCCGAG | 21 |
| 1472 | UUAUGGCACCUAGUUCCGAGU | 21 |
| 1473 | UAUGGCACCUAGUUCCGAGUA | 21 |
| 1474 | AUGGCACCUAGUUCCGAGUAG | 21 |
| 1475 | UGGCACCUAGUUCCGAGUAGC | 21 |
| 1476 | GGCACCUAGUUCCGAGUAGCC | 21 |
| 1477 | GCACCUAGUUCCGAGUAGCCC | 21 |
| 1478 | CACCUAGUUCCGAGUAGCCCA | 21 |
| 1479 | ACCUAGUUCCGAGUAGCCCAG | 21 |
| 1480 | CCUAGUUCCGAGUAGCCCAGG | 21 |
| 1481 | CUAGUUCCGAGUAGCCCAGGG | 21 |
| 1482 | UAGUUCCGAGUAGCCCAGGGC | 21 |
| 1483 | AGUUCCGAGUAGCCCAGGGCA | 21 |
| | | |
| 1484 | UGAUAAGGCUCUUAAGGGUC | 20 |
| 1485 | GAUAAGGCUCUUAAGGGUCU | 20 |
| 1486 | AUAAGGCUCUUAAGGGUCUC | 20 |
| 1487 | UAAGGCUCUUAAGGGUCUCA | 20 |
| 1488 | AAGGCUCUUAAGGGUCUCAA | 20 |
| 1489 | AGGCUCUUAAGGGUCUCAAA | 20 |
| 1490 | GGCUCUUAAGGGUCUCAAAG | 20 |
| 1491 | GCUCUUAAGGGUCUCAAAGC | 20 |
| 1492 | CUCUUAAGGGUCUCAAAGCU | 20 |
| 1493 | UCUUAAGGGUCUCAAAGCUC | 20 |
| 1494 | CUUAAGGGUCUCAAAGCUCU | 20 |
| 1495 | UUAAGGGUCUCAAAGCUCUU | 20 |
| 1496 | UAAGGGUCUCAAAGCUCUUA | 20 |
| 1497 | AAGGGUCUCAAAGCUCUUAG | 20 |
| 1498 | AGGGUCUCAAAGCUCUUAGG | 20 |
| 1499 | GGGUCUCAAAGCUCUUAGGG | 20 |
| 1500 | GGUCUCAAAGCUCUUAGGGU | 20 |
| 1501 | GUCUCAAAGCUCUUAGGGUC | 20 |
| 1502 | UCUCAAAGCUCUUAGGGUCC | 20 |
| 1503 | CUCAAAGCUCUUAGGGUCCU | 20 |
| 1504 | UCAAAGCUCUUAGGGUCCUA | 20 |
| 1505 | CAAAGCUCUUAGGGUCCUAA | 20 |
| 1506 | AAAGCUCUUAGGGUCCUAAG | 20 |
| 1507 | AAGCUCUUAGGGUCCUAAGG | 20 |
| 1508 | AGCUCUUAGGGUCCUAAGGG | 20 |

FIG. 4C (continued)

| SEQ ID NO: | 5' - 3' SMOs for Internal exon | Length (nt) |
|---|---|---|
| 1509 | GCUCUUAGGGUCCUAAGGGA | 20 |
| 1510 | CUCUUAGGGUCCUAAGGGAC | 20 |
| 1511 | UCUUAGGGUCCUAAGGGACU | 20 |
| 1512 | CUUAGGGUCCUAAGGGACUU | 20 |
| 1513 | UUAGGGUCCUAAGGGACUUU | 20 |
| 1514 | UAGGGUCCUAAGGGACUUUA | 20 |
| 1515 | AGGGUCCUAAGGGACUUUAU | 20 |
| 1516 | GGGUCCUAAGGGACUUUAUG | 20 |
| 1517 | GGUCCUAAGGGACUUUAUGG | 20 |
| 1518 | GUCCUAAGGGACUUUAUGGC | 20 |
| 1519 | UCCUAAGGGACUUUAUGGCA | 20 |
| 1520 | CCUAAGGGACUUUAUGGCAC | 20 |
| 1521 | CUAAGGGACUUUAUGGCACC | 20 |
| 1522 | UAAGGGACUUUAUGGCACCU | 20 |
| 1523 | AAGGGACUUUAUGGCACCUA | 20 |
| 1524 | AGGGACUUUAUGGCACCUAG | 20 |
| 1525 | GGGACUUUAUGGCACCUAGU | 20 |
| 1526 | GGACUUUAUGGCACCUAGUU | 20 |
| 1527 | GACUUUAUGGCACCUAGUUC | 20 |
| 1528 | ACUUUAUGGCACCUAGUUCC | 20 |
| 1529 | CUUUAUGGCACCUAGUUCCG | 20 |
| 1530 | UUUAUGGCACCUAGUUCCGA | 20 |
| 1531 | UUAUGGCACCUAGUUCCGAG | 20 |
| 1532 | UAUGGCACCUAGUUCCGAGU | 20 |
| 1533 | AUGGCACCUAGUUCCGAGUA | 20 |
| 1534 | UGGCACCUAGUUCCGAGUAG | 20 |
| 1535 | GGCACCUAGUUCCGAGUAGC | 20 |
| 1536 | GCACCUAGUUCCGAGUAGCC | 20 |
| 1537 | CACCUAGUUCCGAGUAGCCC | 20 |
| 1538 | ACCUAGUUCCGAGUAGCCCA | 20 |
| 1539 | CCUAGUUCCGAGUAGCCCAG | 20 |
| 1540 | CUAGUUCCGAGUAGCCCAGG | 20 |
| 1541 | UAGUUCCGAGUAGCCCAGGG | 20 |
| 1542 | AGUUCCGAGUAGCCCAGGGC | 20 |
| 1543 | GUUCCGAGUAGCCCAGGGCA | 20 |
| | | |
| 1544 | UGAUAAGGCUCUUAAGGGU | 19 |
| 1545 | GAUAAGGCUCUUAAGGGUC | 19 |
| 1546 | AUAAGGCUCUUAAGGGUCU | 19 |
| 1547 | UAAGGCUCUUAAGGGUCUC | 19 |
| 1548 | AAGGCUCUUAAGGGUCUCA | 19 |
| 1549 | AGGCUCUUAAGGGUCUCAA | 19 |
| 1550 | GGCUCUUAAGGGUCUCAAA | 19 |
| 1551 | GCUCUUAAGGGUCUCAAAG | 19 |
| 1552 | CUCUUAAGGGUCUCAAAGC | 19 |

FIG. 4C (continued)

| SEQ ID NO: | 5' - 3' SMOs for Internal exon | Length (nt) |
|---|---|---|
| 1553 | UCUUAAGGGUCUCAAAGCU | 19 |
| 1554 | CUUAAGGGUCUCAAAGCUC | 19 |
| 1555 | UUAAGGGUCUCAAAGCUCU | 19 |
| 1556 | UAAGGGUCUCAAAGCUCUU | 19 |
| 1557 | AAGGGUCUCAAAGCUCUUA | 19 |
| 1558 | AGGGUCUCAAAGCUCUUAG | 19 |
| 1559 | GGGUCUCAAAGCUCUUAGG | 19 |
| 1560 | GGUCUCAAAGCUCUUAGGG | 19 |
| 1561 | GUCUCAAAGCUCUUAGGGU | 19 |
| 1562 | UCUCAAAGCUCUUAGGGUC | 19 |
| 1563 | CUCAAAGCUCUUAGGGUCC | 19 |
| 1564 | UCAAAGCUCUUAGGGUCCU | 19 |
| 1565 | CAAAGCUCUUAGGGUCCUA | 19 |
| 1566 | AAAGCUCUUAGGGUCCUAA | 19 |
| 1567 | AAGCUCUUAGGGUCCUAAG | 19 |
| 1568 | AGCUCUUAGGGUCCUAAGG | 19 |
| 1569 | GCUCUUAGGGUCCUAAGGG | 19 |
| 1570 | CUCUUAGGGUCCUAAGGGA | 19 |
| 1571 | UCUUAGGGUCCUAAGGGAC | 19 |
| 1572 | CUUAGGGUCCUAAGGGACU | 19 |
| 1573 | UUAGGGUCCUAAGGGACUU | 19 |
| 1574 | UAGGGUCCUAAGGGACUUU | 19 |
| 1575 | AGGGUCCUAAGGGACUUUA | 19 |
| 1576 | GGGUCCUAAGGGACUUUAU | 19 |
| 1577 | GGUCCUAAGGGACUUUAUG | 19 |
| 1578 | GUCCUAAGGGACUUUAUGG | 19 |
| 1579 | UCCUAAGGGACUUUAUGGC | 19 |
| 1580 | CCUAAGGGACUUUAUGGCA | 19 |
| 1581 | CUAAGGGACUUUAUGGCAC | 19 |
| 1582 | UAAGGGACUUUAUGGCACC | 19 |
| 1583 | AAGGGACUUUAUGGCACCU | 19 |
| 1584 | AGGGACUUUAUGGCACCUA | 19 |
| 1585 | GGGACUUUAUGGCACCUAG | 19 |
| 1586 | GGACUUUAUGGCACCUAGU | 19 |
| 1587 | GACUUUAUGGCACCUAGUU | 19 |
| 1588 | ACUUUAUGGCACCUAGUUC | 19 |
| 1589 | CUUUAUGGCACCUAGUUCC | 19 |
| 1590 | UUUAUGGCACCUAGUUCCG | 19 |
| 1591 | UUAUGGCACCUAGUUCCGA | 19 |
| 1592 | UAUGGCACCUAGUUCCGAG | 19 |
| 1593 | AUGGCACCUAGUUCCGAGU | 19 |
| 1594 | UGGCACCUAGUUCCGAGUA | 19 |
| 1595 | GGCACCUAGUUCCGAGUAG | 19 |
| 1596 | GCACCUAGUUCCGAGUAGC | 19 |
| 1597 | CACCUAGUUCCGAGUAGCC | 19 |

FIG. 4C (continued)

| SEQ ID NO: | 5' - 3' SMOs for Internal exon | Length (nt) |
|---|---|---|
| 1598 | ACCUAGUUCCGAGUAGCCC | 19 |
| 1599 | CCUAGUUCCGAGUAGCCCA | 19 |
| 1600 | CUAGUUCCGAGUAGCCCAG | 19 |
| 1601 | UAGUUCCGAGUAGCCCAGG | 19 |
| 1602 | AGUUCCGAGUAGCCCAGGG | 19 |
| 1603 | GUUCCGAGUAGCCCAGGGC | 19 |
| 1604 | UUCCGAGUAGCCCAGGGCA | 19 |
| | | |
| 1605 | UGAUAAGGCUCUUAAGGG | 18 |
| 1606 | GAUAAGGCUCUUAAGGGU | 18 |
| 1607 | AUAAGGCUCUUAAGGGUC | 18 |
| 1608 | UAAGGCUCUUAAGGGUCU | 18 |
| 1609 | AAGGCUCUUAAGGGUCUC | 18 |
| 1610 | AGGCUCUUAAGGGUCUCA | 18 |
| 1611 | GGCUCUUAAGGGUCUCAA | 18 |
| 1612 | GCUCUUAAGGGUCUCAAA | 18 |
| 1613 | CUCUUAAGGGUCUCAAAG | 18 |
| 1614 | UCUUAAGGGUCUCAAAGC | 18 |
| 1615 | CUUAAGGGUCUCAAAGCU | 18 |
| 1616 | UUAAGGGUCUCAAAGCUC | 18 |
| 1617 | UAAGGGUCUCAAAGCUCU | 18 |
| 1618 | AAGGGUCUCAAAGCUCUU | 18 |
| 1619 | AGGGUCUCAAAGCUCUUA | 18 |
| 1620 | GGGUCUCAAAGCUCUUAG | 18 |
| 1621 | GGUCUCAAAGCUCUUAGG | 18 |
| 1622 | GUCUCAAAGCUCUUAGGG | 18 |
| 1623 | UCUCAAAGCUCUUAGGGU | 18 |
| 1624 | CUCAAAGCUCUUAGGGUC | 18 |
| 1625 | UCAAAGCUCUUAGGGUCC | 18 |
| 1626 | CAAAGCUCUUAGGGUCCU | 18 |
| 1627 | AAAGCUCUUAGGGUCCUA | 18 |
| 1628 | AAGCUCUUAGGGUCCUAA | 18 |
| 1629 | AGCUCUUAGGGUCCUAAG | 18 |
| 1630 | GCUCUUAGGGUCCUAAGG | 18 |
| 1631 | CUCUUAGGGUCCUAAGGG | 18 |
| 1632 | UCUUAGGGUCCUAAGGGA | 18 |
| 1633 | CUUAGGGUCCUAAGGGAC | 18 |
| 1634 | UUAGGGUCCUAAGGGACU | 18 |
| 1635 | UAGGGUCCUAAGGGACUU | 18 |
| 1636 | AGGGUCCUAAGGGACUUU | 18 |
| 1637 | GGGUCCUAAGGGACUUUA | 18 |
| 1638 | GGUCCUAAGGGACUUUAU | 18 |
| 1639 | GUCCUAAGGGACUUUAUG | 18 |
| 1640 | UCCUAAGGGACUUUAUGG | 18 |
| 1641 | CCUAAGGGACUUUAUGGC | 18 |

FIG. 4C (continued)

| SEQ ID NO: | 5' - 3' SMOs for Internal exon | Length (nt) |
|---|---|---|
| 1642 | CUAAGGGACUUUAUGGCA | 18 |
| 1643 | UAAGGGACUUUAUGGCAC | 18 |
| 1644 | AAGGGACUUUAUGGCACC | 18 |
| 1645 | AGGGACUUUAUGGCACCU | 18 |
| 1646 | GGGACUUUAUGGCACCUA | 18 |
| 1647 | GGACUUUAUGGCACCUAG | 18 |
| 1648 | GACUUUAUGGCACCUAGU | 18 |
| 1649 | ACUUUAUGGCACCUAGUU | 18 |
| 1650 | CUUUAUGGCACCUAGUUC | 18 |
| 1651 | UUUAUGGCACCUAGUUCC | 18 |
| 1652 | UUAUGGCACCUAGUUCCG | 18 |
| 1653 | UAUGGCACCUAGUUCCGA | 18 |
| 1654 | AUGGCACCUAGUUCCGAG | 18 |
| 1655 | UGGCACCUAGUUCCGAGU | 18 |
| 1656 | GGCACCUAGUUCCGAGUA | 18 |
| 1657 | GCACCUAGUUCCGAGUAG | 18 |
| 1658 | CACCUAGUUCCGAGUAGC | 18 |
| 1659 | ACCUAGUUCCGAGUAGCC | 18 |
| 1660 | CCUAGUUCCGAGUAGCCC | 18 |
| 1661 | CUAGUUCCGAGUAGCCCA | 18 |
| 1662 | UAGUUCCGAGUAGCCCAG | 18 |
| 1663 | AGUUCCGAGUAGCCCAGG | 18 |
| 1664 | GUUCCGAGUAGCCCAGGG | 18 |
| 1665 | UUCCGAGUAGCCCAGGGC | 18 |
| 1666 | UCCGAGUAGCCCAGGGCA | 18 |
| | | |
| 1667 | UGAUAAGGCUCUUAAGG | 17 |
| 1668 | GAUAAGGCUCUUAAGGG | 17 |
| 1669 | AUAAGGCUCUUAAGGGU | 17 |
| 1670 | UAAGGCUCUUAAGGGUC | 17 |
| 1671 | AAGGCUCUUAAGGGUCU | 17 |
| 1672 | AGGCUCUUAAGGGUCUC | 17 |
| 1673 | GGCUCUUAAGGGUCUCA | 17 |
| 1674 | GCUCUUAAGGGUCUCAA | 17 |
| 1675 | CUCUUAAGGGUCUCAAA | 17 |
| 1676 | UCUUAAGGGUCUCAAAG | 17 |
| 1677 | CUUAAGGGUCUCAAAGC | 17 |
| 1678 | UUAAGGGUCUCAAAGCU | 17 |
| 1679 | UAAGGGUCUCAAAGCUC | 17 |
| 1680 | AAGGGUCUCAAAGCUCU | 17 |
| 1681 | AGGGUCUCAAAGCUCUU | 17 |
| 1682 | GGGUCUCAAAGCUCUUA | 17 |
| 1683 | GGUCUCAAAGCUCUUAG | 17 |
| 1684 | GUCUCAAAGCUCUUAGG | 17 |
| 1685 | UCUCAAAGCUCUUAGGG | 17 |

FIG. 4C (continued)

| SEQ ID NO: | 5' - 3' SMOs for Internal exon | Length (nt) |
|---|---|---|
| 1686 | CUCAAAGCUCUUAGGGU | 17 |
| 1687 | UCAAAGCUCUUAGGGUC | 17 |
| 1688 | CAAAGCUCUUAGGGUCC | 17 |
| 1689 | AAAGCUCUUAGGGUCCU | 17 |
| 1690 | AAGCUCUUAGGGUCCUA | 17 |
| 1691 | AGCUCUUAGGGUCCUAA | 17 |
| 1692 | GCUCUUAGGGUCCUAAG | 17 |
| 1693 | CUCUUAGGGUCCUAAGG | 17 |
| 1694 | UCUUAGGGUCCUAAGGG | 17 |
| 1695 | CUUAGGGUCCUAAGGGA | 17 |
| 1696 | UUAGGGUCCUAAGGGAC | 17 |
| 1697 | UAGGGUCCUAAGGGACU | 17 |
| 1698 | AGGGUCCUAAGGGACUU | 17 |
| 1699 | GGGUCCUAAGGGACUUU | 17 |
| 1700 | GGUCCUAAGGGACUUUA | 17 |
| 1701 | GUCCUAAGGGACUUUAU | 17 |
| 1702 | UCCUAAGGGACUUUAUG | 17 |
| 1703 | CCUAAGGGACUUUAUGG | 17 |
| 1704 | CUAAGGGACUUUAUGGC | 17 |
| 1705 | UAAGGGACUUUAUGGCA | 17 |
| 1706 | AAGGGACUUUAUGGCAC | 17 |
| 1707 | AGGGACUUUAUGGCACC | 17 |
| 1708 | GGGACUUUAUGGCACCU | 17 |
| 1709 | GGACUUUAUGGCACCUA | 17 |
| 1710 | GACUUUAUGGCACCUAG | 17 |
| 1711 | ACUUUAUGGCACCUAGU | 17 |
| 1712 | CUUUAUGGCACCUAGUU | 17 |
| 1713 | UUUAUGGCACCUAGUUC | 17 |
| 1714 | UUAUGGCACCUAGUUCC | 17 |
| 1715 | UAUGGCACCUAGUUCCG | 17 |
| 1716 | AUGGCACCUAGUUCCGA | 17 |
| 1717 | UGGCACCUAGUUCCGAG | 17 |
| 1718 | GGCACCUAGUUCCGAGU | 17 |
| 1719 | GCACCUAGUUCCGAGUA | 17 |
| 1720 | CACCUAGUUCCGAGUAG | 17 |
| 1721 | ACCUAGUUCCGAGUAGC | 17 |
| 1722 | CCUAGUUCCGAGUAGCC | 17 |
| 1723 | CUAGUUCCGAGUAGCCC | 17 |
| 1724 | UAGUUCCGAGUAGCCCA | 17 |
| 1725 | AGUUCCGAGUAGCCCAG | 17 |
| 1726 | GUUCCGAGUAGCCCAGG | 17 |
| 1727 | UUCCGAGUAGCCCAGGG | 17 |
| 1728 | UCCGAGUAGCCCAGGGC | 17 |
| 1729 | CCGAGUAGCCCAGGGCA | 17 |
| | | |

FIG. 4C (continued)

| SEQ ID NO: | 5' - 3' SMOs for Internal exon | Length (nt) |
|---|---|---|
| 1730 | UGAUAAGGCUCUUAAG | 16 |
| 1731 | GAUAAGGCUCUUAAGG | 16 |
| 1732 | AUAAGGCUCUUAAGGG | 16 |
| 1733 | UAAGGCUCUUAAGGGU | 16 |
| 1734 | AAGGCUCUUAAGGGUC | 16 |
| 1735 | AGGCUCUUAAGGGUCU | 16 |
| 1736 | GGCUCUUAAGGGUCUC | 16 |
| 1737 | GCUCUUAAGGGUCUCA | 16 |
| 1738 | CUCUUAAGGGUCUCAA | 16 |
| 1739 | UCUUAAGGGUCUCAAA | 16 |
| 1740 | CUUAAGGGUCUCAAAG | 16 |
| 1741 | UUAAGGGUCUCAAAGC | 16 |
| 1742 | UAAGGGUCUCAAAGCU | 16 |
| 1743 | AAGGGUCUCAAAGCUC | 16 |
| 1744 | AGGGUCUCAAAGCUCU | 16 |
| 1745 | GGGUCUCAAAGCUCUU | 16 |
| 1746 | GGUCUCAAAGCUCUUA | 16 |
| 1747 | GUCUCAAAGCUCUUAG | 16 |
| 1748 | UCUCAAAGCUCUUAGG | 16 |
| 1749 | CUCAAAGCUCUUAGGG | 16 |
| 1750 | UCAAAGCUCUUAGGGU | 16 |
| 1751 | CAAAGCUCUUAGGGUC | 16 |
| 1752 | AAAGCUCUUAGGGUCC | 16 |
| 1753 | AAGCUCUUAGGGUCCU | 16 |
| 1754 | AGCUCUUAGGGUCCUA | 16 |
| 1755 | GCUCUUAGGGUCCUAA | 16 |
| 1756 | CUCUUAGGGUCCUAAG | 16 |
| 1757 | UCUUAGGGUCCUAAGG | 16 |
| 1758 | CUUAGGGUCCUAAGGG | 16 |
| 1759 | UUAGGGUCCUAAGGGA | 16 |
| 1760 | UAGGGUCCUAAGGGAC | 16 |
| 1761 | AGGGUCCUAAGGGACU | 16 |
| 1762 | GGGUCCUAAGGGACUU | 16 |
| 1763 | GGUCCUAAGGGACUUU | 16 |
| 1764 | GUCCUAAGGGACUUUA | 16 |
| 1765 | UCCUAAGGGACUUUAU | 16 |
| 1766 | CCUAAGGGACUUUAUG | 16 |
| 1767 | CUAAGGGACUUUAUGG | 16 |
| 1768 | UAAGGGACUUUAUGGC | 16 |
| 1769 | AAGGGACUUUAUGGCA | 16 |
| 1770 | AGGGACUUUAUGGCAC | 16 |
| 1771 | GGGACUUUAUGGCACC | 16 |
| 1772 | GGACUUUAUGGCACCU | 16 |
| 1773 | GACUUUAUGGCACCUA | 16 |
| 1774 | ACUUUAUGGCACCUAG | 16 |

FIG. 4C (continued)

| SEQ ID NO: | 5' - 3' SMOs for Internal exon | Length (nt) |
|---|---|---|
| 1775 | CUUUAUGGCACCUAGU | 16 |
| 1776 | UUUAUGGCACCUAGUU | 16 |
| 1777 | UUAUGGCACCUAGUUC | 16 |
| 1778 | UAUGGCACCUAGUUCC | 16 |
| 1779 | AUGGCACCUAGUUCCG | 16 |
| 1780 | UGGCACCUAGUUCCGA | 16 |
| 1781 | GGCACCUAGUUCCGAG | 16 |
| 1782 | GCACCUAGUUCCGAGU | 16 |
| 1783 | CACCUAGUUCCGAGUA | 16 |
| 1784 | ACCUAGUUCCGAGUAG | 16 |
| 1785 | CCUAGUUCCGAGUAGC | 16 |
| 1786 | CUAGUUCCGAGUAGCC | 16 |
| 1787 | UAGUUCCGAGUAGCCC | 16 |
| 1788 | AGUUCCGAGUAGCCCA | 16 |
| 1789 | GUUCCGAGUAGCCCAG | 16 |
| 1790 | UUCCGAGUAGCCCAGG | 16 |
| 1791 | UCCGAGUAGCCCAGGG | 16 |
| 1792 | CCGAGUAGCCCAGGGC | 16 |
| 1793 | CGAGUAGCCCAGGGCA | 16 |
| | | |
| 1794 | UGAUAAGGCUCUUAA | 15 |
| 1795 | GAUAAGGCUCUUAAG | 15 |
| 1796 | AUAAGGCUCUUAAGG | 15 |
| 1797 | UAAGGCUCUUAAGGG | 15 |
| 1798 | AAGGCUCUUAAGGGU | 15 |
| 1799 | AGGCUCUUAAGGGUC | 15 |
| 1800 | GGCUCUUAAGGGUCU | 15 |
| 1801 | GCUCUUAAGGGUCUC | 15 |
| 1802 | CUCUUAAGGGUCUCA | 15 |
| 1803 | UCUUAAGGGUCUCAA | 15 |
| 1804 | CUUAAGGGUCUCAAA | 15 |
| 1805 | UUAAGGGUCUCAAAG | 15 |
| 1806 | UAAGGGUCUCAAAGC | 15 |
| 1807 | AAGGGUCUCAAAGCU | 15 |
| 1808 | AGGGUCUCAAAGCUC | 15 |
| 1809 | GGGUCUCAAAGCUCU | 15 |
| 1810 | GGUCUCAAAGCUCUU | 15 |
| 1811 | GUCUCAAAGCUCUUA | 15 |
| 1812 | UCUCAAAGCUCUUAG | 15 |
| 1813 | CUCAAAGCUCUUAGG | 15 |
| 1814 | UCAAAGCUCUUAGGG | 15 |
| 1815 | CAAAGCUCUUAGGGU | 15 |
| 1816 | AAAGCUCUUAGGGUC | 15 |
| 1817 | AAGCUCUUAGGGUCC | 15 |
| 1818 | AGCUCUUAGGGUCCU | 15 |

FIG. 4C (continued)

| SEQ ID NO: | 5' - 3' SMOs for Internal exon | Length (nt) |
|---|---|---|
| 1819 | GCUCUUAGGGUCCUA | 15 |
| 1820 | CUCUUAGGGUCCUAA | 15 |
| 1821 | UCUUAGGGUCCUAAG | 15 |
| 1822 | CUUAGGGUCCUAAGG | 15 |
| 1823 | UUAGGGUCCUAAGGG | 15 |
| 1824 | UAGGGUCCUAAGGGA | 15 |
| 1825 | AGGGUCCUAAGGGAC | 15 |
| 1826 | GGGUCCUAAGGGACU | 15 |
| 1827 | GGUCCUAAGGGACUU | 15 |
| 1828 | GUCCUAAGGGACUUU | 15 |
| 1829 | UCCUAAGGGACUUUA | 15 |
| 1830 | CCUAAGGGACUUUAU | 15 |
| 1831 | CUAAGGGACUUUAUG | 15 |
| 1832 | UAAGGGACUUUAUGG | 15 |
| 1833 | AAGGGACUUUAUGGC | 15 |
| 1834 | AGGGACUUUAUGGCA | 15 |
| 1835 | GGGACUUUAUGGCAC | 15 |
| 1836 | GGACUUUAUGGCACC | 15 |
| 1837 | GACUUUAUGGCACCU | 15 |
| 1838 | ACUUUAUGGCACCUA | 15 |
| 1839 | CUUUAUGGCACCUAG | 15 |
| 1840 | UUUAUGGCACCUAGU | 15 |
| 1841 | UUAUGGCACCUAGUU | 15 |
| 1842 | UAUGGCACCUAGUUC | 15 |
| 1843 | AUGGCACCUAGUUCC | 15 |
| 1844 | UGGCACCUAGUUCCG | 15 |
| 1845 | GGCACCUAGUUCCGA | 15 |
| 1846 | GCACCUAGUUCCGAG | 15 |
| 1847 | CACCUAGUUCCGAGU | 15 |
| 1848 | ACCUAGUUCCGAGUA | 15 |
| 1849 | CCUAGUUCCGAGUAG | 15 |
| 1850 | CUAGUUCCGAGUAGC | 15 |
| 1851 | UAGUUCCGAGUAGCC | 15 |
| 1852 | AGUUCCGAGUAGCCC | 15 |
| 1853 | GUUCCGAGUAGCCCA | 15 |
| 1854 | UUCCGAGUAGCCCAG | 15 |
| 1855 | UCCGAGUAGCCCAGG | 15 |
| 1856 | CCGAGUAGCCCAGGG | 15 |
| 1857 | CGAGUAGCCCAGGGC | 15 |
| 1858 | GAGUAGCCCAGGGCA | 15 |

SCN8A SPLICE MODULATING OLIGONUCLEOTIDES AND METHODS OF USE THEREOF

RELATED APPLICATIONS

This application claims priority benefit of U.S. Provisional Application Ser. No. 62/039,819 filed Aug. 20, 2014; the contents of which are hereby incorporated by reference.

SEQUENCE LISTING

The instant application contains a Sequence Listing which has been submitted electronically in ASCII format and is hereby incorporated by reference in its entirety. Said ASCII copy, created on Jun. 4, 2019 is named 50972-002001 _UPDATED_Sequence_Listing_5.9.19 _ST25 and is 418,054 bytes in size.

FIELD OF THE INVENTION

The present invention in general relates in general to therapeutic compositions, and in particular to a sequence designed to modulate the splicing of a SCN8A pre-mRNA.

BACKGROUND

A unified "loss-of-function hypothesis" for the spectrum of pediatric epilepsies caused by SCN1A mutations has recently been proposed (Catterall et. al., 2010). These Dravet Spectrum disorders resulting from SCN1A loss-of-function mutations include febrile seizures, generalized epilepsy with febrile seizure plus (GEFS+), and Dravet syndrome (severe myoclonic epilepsy of infancy or SMEI), in order of increasing severity (Meisler and Kearney 2005). GEFS+ patients typically exhibit febrile seizures and mild cognitive impairment in childhood; seizures can either spontaneously resolve or progress to generalized epilepsy over time (Singh et. al., 1999). SMEI is a relatively rare but catastrophic form of childhood epilepsy characterized by the development of seizures in previously healthy infants that advance to include multiple seizure types such as myoclonus, partial seizures, febrile induced, and the absence episodes by age 2. Progressive developmental and behavioral impairments manifest along with the recurrent and varied seizure episodes that are typically unresponsive to currently available antiepileptic drugs (Dravet et. al., 2005). Additionally, motor abnormalities occur in 20-60% SMEI children (Dravet et. al., 2005). Greater availability of genetic testing and advances in mutational screening now allow for better detection and earlier diagnosis of this severe childhood epilepsy, making early intervention and cure a possibility. Thus, there is a significant and urgent need for the development of novel therapeutic approaches in these patients.

De novo loss-of-function mutations in various sites within the SCN1A gene account for about 70% of SMEI (De 2011) and 10% of GEFS+(Catterall et. al., 2010). The SCN1A gene encodes the a subunit for a voltage-gated sodium (VGS or Nav) channel (Nav1.1), one of a family of 10 paralogous pore-forming alpha subunits (SCN) expressed in the human central nervous system (CNS)), peripheral nerves, and other areas of the body such as the heart. The alpha subunits; SCN1A (Nav1.1), SCN2A (Nav1.2), SCN3A (Nav1.3), SCN4A (Nav1.4), SCN5A (Nav1.5), SCN6/7A, SCN8A (Nav1.6), SCN9A (Nav1.7), SCN10A (Nav1.8), and SCN11/12A (Nav 1.9) as a component of their respective VSG channels, which are critical regulators of neuronal excitability. SCN8A is a VGS channel subunit which functionally opposes the currents produced by SCN1A containing channels. SCN8A-containing (Nav1.6) channels are highly expressed in excitatory neurons (including hippocampal and purkinje neurons), and function to drive excitatory neuron repetitive firing (Chen et. al., 2008; Raman et. al., 1997). Conversely, the majority of SCN1A-containing sodium channels are expressed in GABAergic inhibitory neurons, particularly in hippocampal (Yu et. al., 2006) and purkinje interneurons (Raman et. al., 1997). In SCN1A R168H mutant mice, a GEFS+ model, sodium channel activity in interneurons is impaired, leading to decreased GABAergic inhibition, and the overall effect of the mutation is hyperexcitability and increased seizure susceptibility (Martin et. al., 2010; Tang et. al., 2009). Similarly, SCN1A knockout (KO) SMEI mice exhibit significantly reduced firing and sodium current density in cortical and hippocampal interneurons, with no change in excitatory pyramidal neurons (Ogiwara et. al., 2007; Yu et. al., 2006), suggesting a common lack of inhibitory balance as the cause of SMEI and GEFS+. Interestingly, reducing SCN8A function can "rescue" pro-seizure phenotypes in both SCN1A R168H and SCN1A knockout mice (Hawkins et. al., 2011; Martin et. al., 2007; Meisler et. al., 2010). SCN8A partial loss-of-function mutations alone cause ataxia and neuromuscular degeneration, but increased kainate- and flurothyl-induced seizure thresholds in mice (Martin et. al., 2007). However, crossing either SCN1A knockouts or SCN1A R168H mutant mice with an SCN8A partial loss-of-function mutant mouse, normalized flurothyl-induced seizure thresholds and extended lifespan in both lines (Hawkins et. al., 2011; Martin et. al., 2007; Meisler et. al., 2010). Thus, it appears from these studies that reducing SCN8A levels to diminish SCN8A-mediated excitation therapeutically rebalances inhibitory deficits caused by loss-of-function SCN1A mutations.

The VGS channel a subunits undergo several alternative pre-mRNA splicing events, some of these splicing events regulate the inhibitory and excitatory balance of sodium currents in the CNS. Importantly, SCN8A pre-mRNA undergoes mutually exclusive alternative splicing at both exon 5 and exon 18 during development to form 5N (neonatal), or 5A (adult) and 18N (neonatal), or 18A (adult) isoforms, respectively. Inclusion of the 18N exon introduces a premature stop codon into the transcript to yield a nonfunctional truncated SCN8A 18N isoform (Plummer et. al., 1997), whereas inclusion of 5N leads to lower gain SCNA channels and reduced neuronal excitability (Fletcher et. al., 2011; Gazina et. al., 2010; Xu et. al., 2007). Evaluation in a heterologous expression system, revealed that channels formed from SCN2A 5N isoforms are less excitable than those containing the 5A isoform leading to the hypothesis that exon 5A/N alternative splicing across VGS channels subunits (particularly SCN1A, SCN2A, SCN3A and SCN8A) determines neuronal excitability and seizure susceptibility in human infants (Xu et. al., 2007)'. Such splicing has been proposed as one mechanism that counters the normally high excitability of neonatal neurons and helps to reduce seizure susceptibility in normal human infants. A single nucleotide polymorphism (SNP) in the exon 5N splice site donor region (IVS5N+5 G>A) is responsible for the wide variation of the proportion of SCN1A 5N expression in the adult human brain (Heinzen et. al., 2007). In samples from human temporal cortex, it was demonstrated that the "A" SNP disrupts exon 5N splicing, such that individuals with the "AA" genotype are reduced to 0.7% of total SCN1A mRNA expression in the 5N isoform, in contrast to the "GG" genotype which averages 41% 5N expression (Heinzen et. al., 2007). Importantly, the SCN1A IVS5N+5 G>A polymorphism "AA" genotype which reduces 5N and increases 5A isoform expression also confers a 3-fold greater risk of febrile seizures in childhood (as occurs in Dravet Spectrum epilepsies) over the "GG" genotype providing functional evidence that exon 5 splicing confers changes in neuronal excitability (Schlachter et. al., 2009).

For the four major voltage-gated sodium channel alpha subunits in the CNS (SCN1A, SCN2A, SCN3A and SCN8A) it has been shown that 18A levels begin to rise between P7.5-P10 and that expression levels of both the 18A and 18N isoforms near adult levels and complete the developmental switch between P20-P30 in mice (Bender et. al., 2012; Plummer et. al., 1997). The change from predominantly 5N to 5A isoform expression for SCN8A is also developmentally regulated. The 5A/5N expression ratio in fetal cynolomous monkey was demonstrated to be only 1.44, while the expression ration in adult cynolomous monkey brain was 8.52 (Raymond et. al., 2004), indicating that there is a significant reversal in the expression pattern over the neonatal period to decrease 5N expression in favor of 5A isoform expression. These developmental switches in SCN8A and SCN1A isoform expression in rodents coincides with the reduced survival and increased susceptibility to seizures seen in GEFS+/SMEI mice (Martin et. al., 2010; Oakley et. al., 2009; Yu et. al., 2006) and correspond well with both the peak in human SCN1A expression at 7-9 months of age (Wang et. al., 2011) and the onset of seizures in GEFS+/SMEI patients (Bender et. al., 2012).

SCN1A is a member of a family of voltage gated Na+ (VGS) channel a subunits, and is expressed largely in inhibitory GABAergic interneurons of the central nervous system (CNS). SCN8 channels, conversely, are expressed on excitatory neurons, and thus these two VGS channel subunits reciprocally regulate network excitation. Accordingly, partial loss of SCN8A function can "rescue" pro-febrile seizure phenotypes in both SCN1A R168H mutant mice and SCN1A knockout mice (Hawkins et. al., 2011; Martin et. al., 2007; Meisler et. al., 2010).

In spite of the advances in understanding clinical manifestations of SCN channel pathways and variants, there exists a need for compositions and treatments based on those compositions for treating of diseases and disorders associated with SCN channels, such as neurological disorders or cancer In particular, there is a need for treatments for Dravet Spectrum disorders.

SUMMARY

Accordingly, certain embodiments of the invention provide a splice modulating oligonucleotide (SMO), comprising a sequence designed to modulate the splicing of a SCN8A pre-mRNA, wherein the SMO sequence specifically binds to a sequence in the SCN8A pre-mRNA.

Certain embodiments of the invention provide a composition comprising an SMO described herein.

Certain embodiments of the invention provide a pharmaceutical composition comprising an SMO described herein and a pharmaceutically acceptable carrier.

Certain embodiments of the invention provide a method of modulating splicing of an SCN8A pre-mRNA comprising contacting a cell with an effective amount of an SMO or a composition described herein.

Certain embodiments of the invention provide a method of treating or preventing a disease, disorder or condition in subject (e.g., a mammal, e.g., a human), comprising administering an SMO or composition as described herein to the subject.

Certain embodiments of the invention provide an SMO or a composition as described herein for the prophylactic or therapeutic treatment of a disease, disorder or condition in a subject.

Certain embodiments of the invention provide the use of an SMO or a composition as described herein to prepare a medicament for treating disease, disorder or condition in a subject.

Certain embodiments of the invention provide an SMO or a composition as described herein for use in medical therapy.

Certain embodiments of the invention provide an SMO or a composition as described herein for use in treating a disease, disorder or condition.

BRIEF DESCRIPTION OF THE DRAWINGS

FIG. 1D. Fewer mice progressed to severe seizure stages after a single KA dose (3 mg/kg) at P10 when pre-treated with 2 μg of LSP-GR1 at P1, P3, and P5 (n=11 per group; $p<0.001$). FIG. 1E. "Second hit" KA dose required to reach SE at P12 in mice given 4 μg of LSP-GR1 2 hr post-SE at P10, was 40% greater than for saline ($p<0.05$), and 20% greater than in naïve (no SE) mice ($p<0.05$; n=7 per group). FIG. 2 C. Whole-cell patch-clamp recordings of aEPSCs from CA1 pyramidal neurons in P12 mice. SE induction at P10, followed 2 hr later by ICV injection of saline, produced a large increase in aEPSC amplitude compared to naïve (no SE) mice ($p<0.001$). SE-induced potentiation of aEPSCs was completely prevented by injection of 4 μg of LSP-GR1 at 2 hrs post-SE (n=5-7 mice per group), suggesting that LSP-GR1 treatment could prevent epileptogenesis. Asterisks in FIG. 1E and FIG. 1F indicate significance compared to saline-treated SE-experienced group.

FIGS. 2A-D. Comparison of top candidate SCN8A exon 18A skipping SMOs. FIG. 2A. Ten SMOs were tested in vivo for ability to direct SCN8A exon 18A skipping via paradigms involving 1, 2, or 3 bilateral ICY injections at doses of 2 or 4 μg per ventricle in neonatal pups between the ages of P3-7. Several SMOs demonstrated statistically significant exon 18A skipping; 18A-2 (SEQ ID: 1324), 18A-3 (SEQ ID: 1327), 18A-4 (SEQ ID: 1317), 18A-5 (SEQ ID: 1306), 18A-8 (SEQ ID: 1307), 18A-9 (SEQ ID: 1422), and 18A-10 (SEQ ID: 1541), at the doses tested.

FIG. 2B. A single submaximal dose (2 μg bilateral—4 μg total) was given by ICV injection in P3-5 neonatal mouse pups for each candidate compound to examine small differences in splicing efficiency for the most potent of the compounds during initial screening, relative to saline (negative control, dotted line at 1.0) and compared to LSP-GR1 (positive control). The 18A-5 (SEQ ID: 1306), 18A-8 (SEQ ID: 1307), 18A-9 (SEQ ID: 1422), and 18A-10 (SEQ ID: 1541) SMOs all showed similar on target splicing efficacy. While 18A-5 (SEQ ID: 1306), seemed to produce greatest splicing in the hippocampus, there was proportionally less splicing in the cortex. Thus, the 18A-5 (SEQ ID: 1306), 18A-8 (SEQ ID: 1307), 18A-9 (SEQ ID: 1422), and 18A-10 (SEQ ID: 1541) SMOs all showed similar on target splicing efficacy at a low dose, providing several SMO options to select from as therapeutics. FIG. 2C. Dose-response comparison after high dose (50 μg) intrathecal delivery in adult mice shows that 18A-9 (SEQ ID: 1422), and 18A-10 (SEQ ID: 1541) produce equivalent or slightly better splicing than LSP-GR1 in the cervical and lumbar spinal cord. Target transcript mRNA is SCN8A exon 18A of 18A SMO and GluA1-flip for LSP-GR1. Duration of action of high single dose SCN8A-18A-9 SMO. FIG. 2D. C57BL/6 mice were harvested at P6, P15, P28, and P42 after a single 4 μg bilateral ICV injection of SCN8A-18A-9 ((SEQ ID: 1422, 8 μg total) at P3-5. The 18A-9 (SEQ ID: 1422) SMO splicing effect was maintained out to 28 days without decrement though significant exon 18A skipping is still present at P42. SCN8A-18A transcript expression is normalized to saline controls (line=1.0)

FIG. 2E. Seven SMOs were tested in vivo for ability to direct SCN8A exon 5A skipping via paradigms involving 1 or 2 bilateral ICV injections at doses of 2 or 4 μg per ventricle in neonatal pups between the ages of P3-5. Only SCN8A-5A-2 (SEQ ID: 33), and 5A-7 (SEQ ID: 26) showed statistically significant exon 5A skipping at the doses tested. FIG. 2F. Dose-response of the candidate exon 5A splicing SMO, SCN8A-5A-2 (SEQ ID: 33), was measured after bilateral ICV injection (n=4-6 per dose); single 2 μg/ventricle dose (4 μg total), 2×4 μg/ventricle dose (16 μg total), and 3×4 μg/ventricle dose (24 μg total) between ages P3-P10 in neonatal mouse pups. SCN8A-5A transcript expression is normalized to saline controls (line=1.0). Significance determined by students t-test with * $p<0.05$, ** $p<0.005$ after Bonferoni correction for multiple measures.

FIGS. 3A-K. SCN8A E5A Splicing SMOs. FIG. 3A. Human SCN8A target sequences for E5A splicing: 7 nt of the Intron 5' to Exon 5A+entire 92 nt of Exon 5A+5 nt of Intron 5. FIG. 3B. SCN8A E5A 24 mer SMO sequences. FIG. 3C. SCN8A E5A 23 mer SMO sequences. FIG. 3 D. SCN8A E5A 22 mer SMO sequences. FIG. 3E. SCN8A E5A 21 mer SMO sequences. FIG. 3F. SCN8A E5A 20 mer SMO sequences. FIG. 3G. SCN8A E5A 19 mer SMO sequences. FIG. 3H. SCN8A E5A 18 mer SMO sequences.

FIG. 3I. SCN8A E5A 17 mer SMO sequences. FIG. 3J. SCN8A E5A 16 mer SMO sequences. FIG. 3K. SCN8A E5A 15 mer SMO sequences.

FIGS. 4A-D. SCN8A E18A Splicing SMOs. FIG. 4A. Human SCN8A target sequences internal to Intron 18 near the 5' splice site, and corresponding preferred SCN8AN SMO sequences for skipping Exon 18A. FIG. 4B. Human SCN8A target sequences at the 5' splice site, and corresponding preferred SCN8AN SMO sequences for skipping Exon 18A. The entire target sequence covers 5' splice site, and is 100% conserved between mouse and human. It is noted that the 5' splice site cannot be targeted while being specific for SCN8A because of too much identity with SCN1A. FIG. 4C. Human SCN8A target sequences within Exon 18A, and corresponding preferred SCN8AN SMO sequences for skipping Exon 18A. The entire target sequence is exonic, and is 100% conserved between mouse and human. FIG. 4D. SCN8A target sequences from human and SMO sequences for skipping Exon 18A, at 3' ss.

DETAILED DESCRIPTION OF THE PREFERRED EMBODIMENTS

Figure 1A:
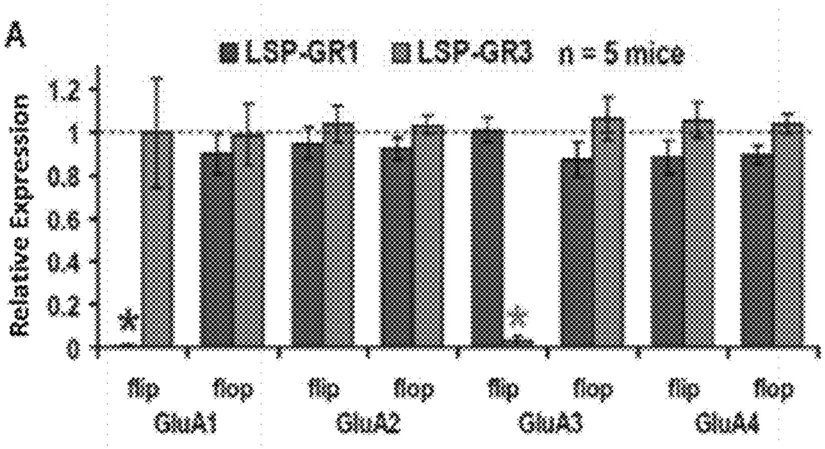
FIG. 1A. Bilateral ICV injections of GR1 and GR3 (2 μg per ventricle) in separate groups of mice (n=5 mice per group) produced nearly 100% reduction in GluA1-flip and GluA3-flip transcripts, respectively, without significant effect on other GluA flip or flop transcript (dotted line shows saline control in all panels). For each subset, LSP-GR1 is shown on the left as a dark grey bar and LSP-GR3 is shown on the right as a light grey bar.

The present invention has utility as a medical treatment of seizure disorders, neurological disorders, and cancers; as well as novel compositions for the detection of susceptibility thereto. SCN1A loss-of-function mutations are the major cause of Dravet spectrum pediatric epilepsies, including generalized epilepsy with febrile seizure plus (GEFS+) and severe myoclonic epilepsy of infancy (SMEI) or Dravet syndrome (Claes et. al., 2001). The major therapeutic indication for modulating the splicing of SCN8A is to correct the excitatory/inhibitory imbalance in the brain caused by loss-of-function mutations in SCN1A. The relationship of SCN1A and SCN8A can to be thought of as opposing aspects that must balance exactly for normal brain function. If the amount of normal SCN1A function is reduced due to a mutation, then the present invention serves to reduce SCN8A function, to rebalance the scale. An inventive process to control SCN8A function is by controlling the mRNA splicing to code for an alpha subunit protein that either doesn't allow the resulting VGS channel to function as a sodium channel or exhibits reduced sodium channel kinetics. Based on SCN1A knock out mouse studies, reducing SCN8 mediated excitation is a logical strategy for rebalancing the reduced inhibitory input caused by SCN1A mutations. However, general sodium channel blockers are largely ineffective at treating Dravet Syndrome due to non-specific effects on Nav sodium channel function, thus there is a need to develop compounds which can specifically and precisely modulate the contributions of the SCN8A subunit to sodium channel function. A novel approach to achieving the needed target specificity is through the development of splice modulating oligonucleotides (SMOs). SCN8A subunits are naturally alternatively spliced at two specific sites of interest. Exon 18 is alternatively spliced to form 18N (neonatal) and 18A (adult) isoforms. Inclusion of the 18N exon yields a truncated nonfunctional SCN8A-18N (Plummer et. al., 1997). Directing splicing to exclude (skip) exon 18A of SCN8A will result in inclusion of the desired 18N isoform. Similarly, there are two alternate exons (5N/5A) which are present in SCN8A pre-mRNA. This splicing event also occurs in related SCN genes and is known to control sodium channel kinetics. Based on similarities in amino acid composition to other SCN genes, the SCN8A 5N-containing mRNA is predicted to yield a lower gain sodium channel and the 5A isoform a higher gain sodium channel (Gazina et. al., 2010; Xu et. al., 2007). Thus, as described herein, reduction of the 18A isoform to favor production of the 18N isoform could be used as a strategy to ameliorate the effects of SCN1A mutations. Similarly, reducing expression of the SCN8A 5A isoform will decrease sodium currents, with a milder and more controlled modulation of channel properties versus creating non-functional isoforms. SMOs are designed to overcome several barriers to successful drug development. In contrast to classic antisense compounds and siRNAs, SMOs do not recruit degradation enzymes (RNAseH, dicer) and therefore do not cause off-target degradation of transcripts. SMOs bind to their targets with exceptional potency, specificity, and negligible off-target effects (Eckstein 2007)

As a major advantage, our proposed SMOs will be designed for complete selectivity in targeting SCN8A isoform expression without affecting any other highly related VGS channel subunits. Additionally, regulation of SCN8A exon 18A splicing is differentially controlled in non-neuronal cells, thus SMOs can be designed specifically to modulate splicing in the CNS such that release from the CNS during normal metabolism is unlikely to have on-target effects outside of the CNS (Zubovic et. al., 2012), and vice versa. Moreover, the SCN8A gene is nearly 100% conserved between mouse and human surrounding the SMO target sites, such that SMOs validated in the mouse model will be directly applicable to the clinic. The strategy of specifically reducing function only of the Na+ channel subunit that counterbalances SCN1A input (SCN8A) should be more effective with fewer adverse effects than non-selective VGS channel blockers. Further, by changing alternative splicing, an SMO directed against exon 5A will specifically reduce excitatory channel properties, rather than simply decreasing overall Nav1.6 channel function. In addition to treating Dravet spectrum epilepsies, the modulation of SCN8A pre-mRNA splicing may also be used to treat a variety of diseases and disorders. Specifically, the SMOs described herein, which target SCN8A pre-mRNA, may also be used to treat certain neurological disorders and cancer as described below.

Accordingly, the present invention encompasses a class of compounds known as splice modulating oligonucleotides (SMOs) that modulate pre-mRNA splicing, thereby affecting expression and functionality of a specific protein in a cell; where the pre-mRNA is SCN8A. and the protein is Nav1.6 An SMO specifically binds to a complementary sequence on a pre-mRNA at an exon or intron splice suppressor or splice enhancer site, or at an intron-exon splice site, or at a variety of sites on the pre-mRNA containing various other motifs that are predicted to affect splicing. For example, when an SMO specifically binds to a splice enhancer site, or an intron-exon splice site, the adjacent exon is excluded from the resulting mRNA. Additionally, an SMO may specifically bind to a splice suppressor site or an intron-exon site and the adjacent exon is included in the resulting mRNA. Finally, an SMO may specifically bind to a splice enhancer site or an intron-exon splice site and shift the reading frame of the pre-mRNA so that the resulting protein is truncated. In some cases, the resulting protein is a limited-function, or non-functional protein relative to the native protein. The location of an exonic or intronic splice enhancer or suppressor motif may be found anywhere within the exon and the flanking introns. Similarly, an SMO may either fully or partially overlap a predicted exonic or intronic splice enhancer or suppressor site in proximity to an intron-exon boundary and/or be complementary to the predicted 3' or 5' splice Sites.

Splice Modulating Oligonucleotides and Compositions Thereof

The present invention is directed, in specific embodiments to oligonucleotides referred to herein as splice modulating oligonucleotides (SMOs), suitable for use in modulating splicing of a target transcript pre-mRNA. Here, SCN8A pre-mRNA splicing is modulated to correct the excitatory/inhibitory imbalance in the brain caused by loss-of-function mutations in SCN1A. Further SCN8A pre-mRNA splicing is modulated to treat any disease or disorder to which reducing or increasing input from SCN8A containing voltage gated sodium channels is therapeutic. SCN8A pre-mRNA splicing is also modulated as a tool for studying SCN8A both in vitro and in vivo.

It is appreciated that such SMOs are operative as therapeutics, gene therapy, genotyping a subject, and as part of a business method in which any of the aforementioned tasks are accomplished in exchange for financial remuneration. For example, certain embodiments of the invention provide an SMO based on the consensus sequence of sodium channel, voltage-gated, type VIII (Nav1.6), alpha subunit (SCN8A) (OMIM: 600702; Genbank AB027567.1), including upstream and downstream nucleotides (see, e.g., FIGS. 3A-K. and 4A-D). The present invention also includes a pharmaceutical composition including an SMO suitable for modulating splicing of a target pre-mRNA both in vitro and in vivo (e.g., SCN8A pre-mRNA). For example, these SMOs are used according to the methods of the invention to modulate splicing of SCN8A pre-mRNA. In one embodiment, these SMOs are used according to the methods of the invention to modulate splicing of SCN8A pre-mRNA to exclude exon 5A or exon 18A or a combination thereof. In vivo methodologies are useful for both general splice site modulatory purposes, as well as in therapeutic applications in which modulating splicing of a target pre-mRNA is desirable (e.g., to modulate the splicing of SCN8A to treat a disorder such as Dravet spectrum epilepsy).

(FIGS. 3A-K and 4A-D) depict exemplary SMOs useful for modulating splicing of SCN8A pre-mRNA (e.g., to exclude exon 5A or exon 18A).

Accordingly, certain embodiments of the invention provide a splice modulating oligonucleotide (SMO) that specifically binds to a SCN8A pre-mRNA (i.e., a pre-mRNA that undergoes splicing to form an mRNA encoding a SCN8A protein).

In certain embodiments, the inventive SMO specifically binds a complementary sequence of the SCN8A pre-mRNA.

In certain embodiments, the SMO includes a sequence designed to modulate the splicing of an SCN8A pre-mRNA. In certain embodiments, the SMO includes a sequence that specifically binds to an exon, an intron, a 5' untranslated region (UTR), a 3' UTR, a splice junction, an exon:exon splice junction, an exonic splicing silencer (ESS), an exonic splicing enhancer (ESE), an intronic splicing silencer (ISS), an intronic splicing enhancer (ISE), or a combination of any of the aforementioned in the SCN8A pre-mRNA. In certain embodiments, the SMO includes a sequence that specifically binds to exon 5A, exon 5N, exon 18A, exon 18N, intron 4, intron 5, intron 4A, intron 4N, intron 5A, intron 5N, intron 17, intron 18, intron 17A, intron 17N, intron 18A, intron 18N or a combination of any of the aforementioned of the SCN8A pre-mRNA (see, e.g., Example 1 and FIGS. 3A-K. and 4A-D).

With respect to an inventive SMO, the term "hybridizing" refers to the association between two single-stranded nucleotide molecules of sufficiently complementary sequence to permit such hybridization under pre-determined conditions generally used in the art. In particular, the term refers to hybridization of an SMO with a substantially complementary sequence contained within a complementary sequence of a target complementary sequence of the SCN8A pre-mRNA molecule, to the substantial exclusion of hybridization of the SMO with a pre-mRNA that has a non-complementary sequence. Appropriate conditions enabling specific hybridization of single stranded nucleic acid molecules of varying complementarity are well known in the art. It is appreciated that these conditions are largely dictated by cellular conditions for in vivo applications.

With respect to the inventive SMO, the term "complementary" or "complementarity" refers to a degree of anti-parallel relationship between a strand of SMO and a pre-mRNA molecule In some instances, the complementarity between an inventive SMO and a pre-mRNA is between 80 and 99.9%, while in other instance, the complementarity to a pre-mRNA by an inventive SMO is 100%.

The SMO of the invention may be defined generally as a nucleotide sequence (or oligonucleotide) a portion of which is capable of hybridizing with the target nucleic acid to exact an antisense activity on the target nucleic acid.

Alternatively, the inventive SMO may be defined functionally as a nucleotide sequence (or oligonucleotide) a portion of which is complementary to and capable of hybridizing with the target nucleic acid sequence to exact a splice modulation in the target RNA of at least 10% for a given subject as measured by target RNA levels. In a preferred embodiment, the target nucleic acid an SCN8A pre-mRNA.

With respect to the inventive SMO, the term "splice modulation" refers to molecular manipulation of pre-mRNA splicing to direct the final composition of the mRNA transcript. It is appreciated that complementarity to the target pre-mRNA alone is not sufficient to produce an inventive SMO. The location of SMO binding (ie blocking splicing motifs in the pre-mRNA, and thermodynamics of binding at that site, as well as secondary structure of the pre-mRNA are among the factors that determine whether splice modulation occurs and the magnitude thereof For instance, one common formula for calculating the stringency conditions required to achieve hybridization between nucleic acid molecules of a specified sequence homology is set forth below (Sambrook et al., Molecular Cloning Manual #1, 1989):

$$Tm=81.5° \text{ C.}+16.6 \text{ Log [Na+]}+0.41(\% \ G+C)-0.63(\% \text{ formamide})-600/\#\text{bp in duplex}$$

As an illustration of the above formula, using [Na+]=[0.368] and 50% formamide, with GC content of 42% and an, average probe size of 200 bases, the Tm is 57° C. The Tm of a DNA duplex decreases by 1-1.5° C. with every 1% decrease in homology. Thus, targets with greater than about 75% sequence identity would be observed using a hybridization temperature of 42° C. Additional examples of stringency conditions for polynucleotide hybridization are provided in Sambrook, et al., 2001, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference.

The stringency of the ex vivo hybridization and wash depend primarily on the salt concentration and temperature of the solutions. In general, to maximize the rate of annealing of the SMO with a target therefor, the hybridization is usually carried out at salt and temperature conditions that are 20-25° C. below the calculated Tm of the hybrid. Wash conditions should be as stringent as possible for the degree of identity of the probe for the target. In general, wash conditions are selected to be approximately 12-20° C. below the Tm of the hybrid. In regards to the nucleic acids of the current invention, a moderate stringency hybridization is defined as hybridization in 6×SSC, 5×Denhardt's solution, 0.5% SDS and 100 μg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 μg/ml denatured salmon sperm DNA at 42° C., and washed in 1.times.SSC and 0.5% SDS at 65° C. for 15 minutes. A very high stringency hybridization is defined as hybridization in 6×SSC, 5×Denhardt's solution, 0.5% SDS and 100 μg/ml denatured salmon sperm DNA at 42° C., and washed in 0.1×SSC and 0.5% SDS at 65° C. for 15 minutes.

Examples of additional conditions under which a nucleotide sequence (or oligonucleotide or SMO sequence) is capable of hybridizing with the target RNA, include 400 mM NaCl, 40 mM PIPES pH 6.4, 1 mM EDTA, 50° C. or 70° C. hybridization for 12-16 hours; followed by washing) and hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids less than 50 base pairs in length should be 5-10° C. less than the melting temperature (Tm) of the hybrid, as determined according to the following equations. At less than 18 base pairs in length, Tm (° C.)=2 (number of A+T bases)+4 (number of G+C bases). Between 18 and 49 base pairs in length, Tm (° C.)=81.5+16.6 (log 10 [Na+])+0.41 (% G+C)−(600/N), where N is the number of bases in the hybrid, and [Na+] is the concentration of sodium ions in the hybridization buffer ([Na+] for 1×SSC=0.165 M).

In certain inventive embodiments, the SMO includes a sequence designed to modulate the splicing of an SCN8A pre-mRNA (e.g., to exclude exon 5A or exon 18A), wherein the SMO has at least about 60% (e.g., about 70%, 80%, 90%, 95%, 96%, 97%, 98%, 99% or 100%) complementarity to an SCN8A pre-mRNA, and wherein the SMO sequence is 14 to 26 nucleotides long (e.g., about 14, 15, 16, 17, 18, 19, 20, 21, 22, 23, 24, 25 or 26 nucleotides long).

In certain inventive embodiments, the SMO includes a sequence designed to bind with complementarity to an SCN8A pre-mRNA and modulate the splicing of exon 5A/5N in the SCN8A pre-mRNA. In certain inventive embodiments, the SMO includes a sequence designed to bind with complementarity to an SCN8A pre-mRNA and exclude exon 5A from a resulting SCN8A mRNA. In certain inventive embodiments, the SMO includes a sequence designed to bind with complementarity to an SCN8A pre-mRNA and include exon 5N in a resulting SCN8A mRNA. In certain inventive embodiments, the SMO includes a sequence that specifically binds to a 3' or 5' splice site of SCN8A exon 5A. In certain inventive embodiments, the SMO includes a sequence that specifically binds to an exon 5A exonic splice enhancer (ESE) sequence within an SCN8A pre-mRNA. In certain inventive embodiments, the SMO includes a sequence that specifically binds to an exon 5A intronic splice enhancer (ISE) sequence within an SCN8A pre-mRNA. In certain inventive embodiments, the SMO includes a sequence that specifically binds to an exon 5N intronic splice silencer (ISS) sequence within an SCN8A pre-mRNA. In certain inventive embodiments, the SMO includes a sequence that specifically binds to an exon 5N exonic splice silencer (ESS) sequence within an SCN8A pre-mRNA. In certain inventive embodiments, the SMO includes a sequence that specifically binds to exon 5A of the SCN8A pre-mRNA (e.g., binds to a complementary sequence in exon 5A (either partially or wholly within exon 5A)).

In certain inventive embodiments, the SMO includes a sequence designed to modulate the splicing of exon 18A/18N in the SCN8A pre-mRNA. In certain inventive embodiments, the SMO includes a sequence designed to bind with complementarity to an SCN8A pre-mRNA and exclude exon 18A from the resulting SCN8A mRNA. In certain inventive embodiments, the SMO includes a sequence designed to bind with complementarity to an SCN8A pre-mRNA and include exon 18N in a resulting SCN8A mRNA. In certain inventive embodiments, the nucleic acid includes a sequence that specifically binds to a 3' or 5' splice site of SCN8A exon 18A. In certain inventive embodiments, the nucleic acid includes a sequence that specifically binds to an exon 18A exonic splice enhancer (ESE) sequence within an SCN8A pre-mRNA. In certain inventive embodiments, the nucleic acid includes a sequence that specifically binds to an exon 18A intronic splice enhancer (ISE) sequence within an SCN8A pre-mRNA. In certain inventive embodiments, the SMO includes a sequence that specifically binds to an exon 18N intronic splice silencer (ISS) sequence within an SCN8A pre-mRNA. In certain inventive embodiments, the SMO includes a sequence that specifically binds to an exon 18N exonic splice silencer (ESS) sequence within an SCN8A pre-mRNA. In certain inventive embodiments, the SMO includes a sequence that specifically binds to exon 18A of the SCN8A pre-mRNA (e.g., binds to a complementary sequence in exon 18A (either partially or wholly within exon 18A)).

In certain inventive embodiments, the SMO includes a sequence that has at least about 60% complementarity with a SCN8A pre-mRNA sequence. In certain inventive embodiments, the sequence has at least about 65, 70, 75, 80, 81, 82, 83, 84, 85, 86, 87, 88, 89, 90, 91, 92, 93, 94, 95, 96, 97, 98, 99 or 100% complementarity with a SCN8A pre-mRNA sequence.

In certain inventive embodiments, the SMO includes a sequence that has at least about 60% complementarity with SEQ ID NO:1, 858, 965, 1252, or 1859. In certain inventive embodiments, the sequence has at least about 65, 70, 75, 80, 81, 82, 83, 84, 85, 86, 87, 88, 89, 90, 91, 92, 93, 94, 95, 96, 97, 98, 99 or 100% complementarity with SEQ ID NO:1, 858, 965, 1252, or 1859.

In certain inventive embodiments, the SMO includes a sequence that has at least about 60% sequence identity with SEQ ID NOs:2, 859, 966, 1253, or 1860. In certain inventive embodiments, the sequence has at least about 65, 70, 75, 80, 81, 82, 83, 84, 85, 86, 87, 88, 89, 90, 91, 92, 93, 94, 95, 96, 97, 98, 99 or 100% sequence identity with SEQ ID NOs: 2, 859, 966, 1253, or 1860.

In certain inventive embodiments, the SMO sequence is about 14 to about 26 nucleotides long (e.g., about 14, 15, 16, 17, 18, 19, 20, 21, 22, 23, 24, 25 or 26 nucleotides long). In certain inventive embodiments, the SMO is about 15 to about 24 nucleotides long.

In certain inventive embodiments, the SMO is about 14 to about 26 nucleotides and includes between about 6 and 24 contiguous nucleotides (i.e., about 6, 7, 8, 9, 10, 11, 12, 13, 14, 15, 16, 17, 18, 19, 20, 21, 22, 23 or 24 contiguous nucleotides) of any one of SEQ ID NOs: 3-857. In certain inventive embodiments, the SMO includes between about 10 to about 24 contiguous nucleotides of any one of SEQ ID NOs: 3-857. In certain inventive embodiments, the SMO includes about 11, 12, 13, 14, 15, 16, 17, 18, 19, 20, 21, 22, 23 or 24 contiguous nucleotides of any one of SEQ ID NOs: 3-857.

In certain inventive embodiments, the SMO is about 14 to about 26 nucleotides and includes between about 6 and 24 contiguous nucleotides (i.e., about 6, 7, 8, 9, 10, 11, 12, 13, 14, 15, 16, 17, 18, 19, 20, 21, 22, 23 or 24 contiguous nucleotides) of any one of SEQ ID NOs:860-964, 967-1251, 1254-1858 and 1861-2140. In certain inventive embodiments, the SMO includes between about 10 to 24 contiguous nucleotides of any one of SEQ ID NOs: 860-964, 967-1251, 1254-1858 and 1861-2140. In certain inventive embodiments, the SMO includes about 11, 12, 13, 14, 15, 16, 17, 18, 19, 20, 21, 22, 23 or 24 contiguous nucleotides of any one of SEQ ID NOs: 860-964, 967-1251, 1254-1858 and 1861-2140.

In certain inventive embodiments, the SMO includes a sequence that has at least 60% sequence identity with any one of SEQ ID NOs: 3-857. In certain inventive embodiments, the sequence has at least 65, 70, 75, 80, 81, 82, 83, 84, 85, 86, 87, 88, 89, 90, 91, 92, 93, 94, 95, 96, 97, 98, 99 or 100% sequence identity with any one of SEQ ID NOs: 3-857. In certain inventive embodiments, the sequence is selected from any one of SEQ ID NOs: 3-857.

In certain inventive embodiments, the SMO is a sequence that has at least 60% sequence identity with any one of SEQ ID NOs: 3-857. In certain inventive embodiments, the sequence has at least 65, 70, 75, 80, 81, 82, 83, 84, 85, 86, 87, 88, 89, 90, 91, 92, 93, 94, 95, 96, 97, 98 or 99% sequence identity with any one of SEQ ID NOs: 3-857. In certain inventive embodiments, the sequence is selected from any one of SEQ ID NOs: 3-857.

In certain inventive embodiments, the SMO includes a sequence that has at least 60% sequence identity with any one of SEQ ID NOs: 860-964, 967-1251, 1254-1858 and 1861-2140. In certain inventive embodiments, the sequence has at least 65, 70, 75, 80, 81, 82, 83, 84, 85, 86, 87, 88, 89, 90, 91, 92, 93, 94, 95, 96, 97, 98, 99 or 100% sequence identity with any one of SEQ ID NOs:860-964, 967-1251, 1254-1858 and 1861-2140. In certain inventive embodiments, the sequence is selected from any one of SEQ ID NOs: 860-964, 967-1251, 1254-1858 and 1861-2140.

In certain inventive embodiments, the SMO has a sequence that has at least 60% sequence identity with any one of SEQ ID NOs: 860-964, 967-1251, 1254-1858 and 1861-2140. In certain inventive embodiments, the sequence has at least 65, 70, 75, 80, 81, 82, 83, 84, 85, 86, 87, 88, 89, 90, 91, 92, 93, 94, 95, 96, 97, 98 or 99% sequence identity with any one of SEQ ID NOs:860-964, 967-1251, 1254-1858 and 1861-2140. In certain inventive embodiments, the sequence is selected from any one of SEQ ID NOs: 860-964, 967-1251, 1254-1858 and 1861-2140.

In certain inventive embodiments, the sequence is selected from any one of SEQ ID NOs: 860-964.

In certain inventive embodiments, the sequence is selected from any one of SEQ ID NOs: 967-1251.

In certain inventive embodiments, the sequence is selected from any one of SEQ ID NOs: 1254-1858. In certain inventive embodiments, the sequence is SEQ ID NO: 1324.

In certain inventive embodiments, the sequence is selected from any one of SEQ ID NOs: 1861-2140.

Certain inventive embodiments of the invention provide a composition including an SMO described herein. In certain inventive embodiments, the composition is a pharmaceutical composition. In certain inventive embodiments, the pharmaceutical composition includes a pharmaceutically acceptable carrier.

The route of SMO administration is oral, rectal, intraventricular, intracranial, intratumoral, intrathecal, intracisternal, epidural, intravaginal, parenteral, intravenous, intramuscular, subcutaneous, local, intraperitoneal, transdermal, by inhalation or as a buccal or nasal spray. The exact amount of SMO required will vary from subject to subject, depending on the age, weight and general condition of the subject, the severity of the disease that is being treated, the mode of administration, and the like. An appropriate amount may be determined by one of ordinary skill in the art using only routine experimentation given the teachings herein.

Depending on the intended mode of administration or delivery, the SMO can be in pharmaceutical compositions in the form of solid, semi-solid or liquid dosage forms, such as, for example, tablets, suppositories, pills, capsules, powders, liquids, or suspensions, preferably in unit dosage form suitable for single administration of a precise dosage. The compositions will include an effective amount of the selected SMO in combination with a pharmaceutically acceptable carrier and, in addition, may include other medicinal agents, pharmaceutical agents, carriers, or diluents. By "pharmaceutically acceptable" is meant a material that is not biologically, or otherwise undesirable, which can be administered to a subject along with the selected SMO without causing significant undesirable biological effects or interacting in a deleterious manner with any of the other components of the pharmaceutical composition in which it is contained.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols, suitable mixtures thereof, vegetable oils and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants; as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethylene glycols, and the like.

Solid dosage forms such as tablets, dragees, capsules, pills, and granules can be prepared with coatings and shells, such as enteric coatings and others well known in the art. They may contain opacifying agents, and can also be of such composition that they release the SMO in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, ethyl carbonate, ethyl acetate, benzyl alcohol, benzyl benzoate, propyleneglycol, 1,3-butyleneglycol, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the compositions can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethylene glycol or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Synthesis of SMOs

An oligonucleotide of the invention, i.e. the SMO, can be synthesized using any procedure known in the art, including chemical synthesis, enzymatic ligation, organic synthesis, and biological synthesis.

In one embodiment, an RNA molecule, e.g., an SMO, is prepared chemically. Methods of synthesizing RNA and DNA molecules are known in the art, in particular, the chemical synthesis methods as described in Verma and Eckstein (1998) Annul Rev. Biochem. 67:99-134. RNA can be purified from a mixture by extraction with a solvent or resin, precipitation, electrophoresis, chromatography, or a combination thereof.

Alternatively, the RNA may be used with no or a minimum of purification to avoid losses due to sample processing.

Modifications of SMOs

In certain inventive embodiments, the oligonucleotides of the present invention (i.e. SMOs) are modified to improve stability in serum or growth medium for cell cultures, or otherwise to enhance stability during delivery to subjects and/or cell cultures. In order to enhance the stability, the 3'-residues may be stabilized against degradation, e.g., they may be selected such that they include only purine nucleotides, particularly adenosine or guanosine nucleotides. Alternatively, substitution of pyrimidine nucleotides by modified analogues, e.g., substitution of uridine by 2'-deoxythymidine, or cytosine by 5'-methylcytosine, can be tolerated without affecting the efficiency of oligonucleotide reagent-induced modulation of splice site selection. For example, the absence of a 2' hydroxyl may significantly enhance the nuclease resistance of the oligonucleotides in tissue culture medium.

In an embodiment of the present invention, the oligonucleotides, e.g., SMOs, may contain at least one modified nucleotide analogue at any position within the sequence, including the entirety of the SMO sequence. The nucleotide analogues may be located at positions where the target-specific activity, e.g., the splice modulating activity is not substantially effected, e.g., in a region at the 5'-end and/or the 3'-end of the oligonucleotide molecule, or a combination of such sites to increase stability against enzymatic degradation while preserving functionality compared to a base SMO containing only nucleotides naturally occurring in the host. Particularly, the ends may be stabilized by incorporating modified nucleotide analogues.

Specific nucleotide analogues operative herein include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides, the phosphodiester group connecting to adjacent ribonucleotides is replaced by a modified group, e.g., of phosphorothioate group. In preferred sugar-modified ribonucleotides, the 2' OH-group is replaced by a group of $CH_3$, H, OR, R, halo, SH, SR, $NH_2$, NHR, $NR_2$ or ON, where R is $C_1$-$C_6$ alkyl, $C_2$-$C_6$ alkenyl or $C_2$-$C_6$ alkynyl and halo is F, Cl, Br or I. In a preferred embodiment, the 2' OH-group is replaced by O—$CH_3$ also known as 2'O-methyl modification Other specific nucleotide analogues include nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to phosphorothioate derivatives and acridine substituted nucleotides, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluraci $I_5$-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine, uridine and/or cytidine modified at the 5-position, e.g., 5-(2-amino) propyl uridine, 5-bromo uridine; adenosine and/or guanosines modified at the 8 position, e.g., 8-bromo guanosine; deaza nucleotides, e.g., 7-deaza-adenosine; 0- and N-alkylated nucleotides, e.g., N6-methyl adenosine. It should be noted that the above modifications may be combined. Oligonucleotides of the invention also may be modified with chemical moieties (e.g., cholesterol) that improve the in vivo pharmacological properties of the oligonucleotides. Within the oligonucleotides (e.g., oligoribonucleotides) of the invention, as few as one and as many as all nucleotides of the oligonucleotide can be modified. For example, a 20-mer oligonucleotide (e.g., oligoribonucleotide) of the invention may contain 1, 2, 3, 4, 5, 6, 7, 8, 9, 10, 1 1, 12, 13, 14, 15, 16, 17, 18, 19 or 20 modified nucleotides. In preferred embodiments, the modified oligonucleotides (e.g., oligoribonucleotides) of the invention will contain as few modified nucleotides as are necessary to achieve a desired level of in vivo stability and/or bio-accessibility while maintaining cost effectiveness. SMOs of the invention include oligonucleotides synthesized to include any combination of modified bases disclosed herein in order to optimize function. In one embodiment, an SMO of the invention includes at least two different modified bases. In another embodiment, an SMO of the invention may include alternating 2' O-methyl substitutions and LNA bases or constrained ethyl nucleic acid (cEt) bases.

An oligonucleotide of the invention can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, Nucleic Acids Res. 15:6625-6641). The oligonucleotide can also include a 2'-O-methylribonucleotide (Inoue et al., 1987, Nucleic Acids Res. 15:6131-6148) or a chimeric RNA-DNA analogue (Inoue et al., 1987, FEBS Lett. 215:327-330).

In various embodiments, the oligonucleotides of the invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acid molecules (see Hyrup et al., 1996, Bioorganic & Medicinal Chemistry 4(1): 5-23). As used herein, the terms “peptide nucleic acids” or “PNAs” refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O’Keefe et al. (1996) Proc. Natl. Acad. Sci. USA 93:14670-675. In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) Nucleic Acids Res. 24(17):3357-63. For example, a DNA chain can be synthesized on a solid support using standard phosphoramidite coupling chemistry and modified nucleoside analogs. Compounds such as 5'-(4-methoxytrityl) amino-5'-deoxy-thymidine phosphoramidite can be used as a link between the PNA and the 5' end of DNA (Mag et al, 1989, Nucleic Acids Res. 17:5973-88). PNA monomers are then coupled in a step-wise manner to produce a chimeric molecule with a 5' PNA segment and a 3' DNA segment (Finn et al., 1996, Nucleic Acids Res. 24(17): 3357-63). Alternatively, chimeric molecules can be synthesized with a 5' DNA segment and a 3' PNA segment (Peterser et al., 1975, Bioorganic Med. Chem. Lett. 5: 1 1 19-1 1124).

The oligonucleotides of the invention can also be formulated as morpholino oligonucleotides. In such embodiments, the riboside moiety of each subunit of an oligonucleotide of the oligonucleotide is converted to a morpholine moiety (morpholine $C_4$H9NO; refer to Heasman, J. 2002 Developmental Biology 243, 209-214, the entire contents of which are incorporated herein by reference).

In certain inventive embodiments, an operative SMO has an oligonucleotide modification that includes Locked Nucleic Acids (LNAs) in which the 2'-hydroxyl group is linked to the 3' or 4' carbon atom of the sugar ring thereby forming a bicyclic sugar moiety. The linkage is preferably a methylene $(\sim CH_2\sim)_n$ group (such as an ethyl or methoxymethyl group) bridging the 2' oxygen atom and the 4' carbon atom wherein n is 1 or 2. LNAs and preparation thereof are described in WO 98/39352 and WO 99/14226, the entire contents of which are incorporated by reference herein. In other embodiments, the oligonucleotide can include other appended groups such as peptides (e.g., for targeting host cell receptors in vivo), or agents facilitating transport across the cell membrane (see, e.g., Letsinger et al., 1989, Proc. Natl. Acad. Sci. USA 86:6553-6556; Lemaitre et al., 1987, Proc. Natl. Acad. Sci. USA 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, Bio/Techniques 6:958-976) or intercalating agents (see, e.g., Zon, 1988, Pharm. Res. 5:539-549). To this end, the oligonucleotide can be conjugated to another molecule, e.g., a peptide, hybridization triggered cross-linking agent, transport agent, hybridization-triggered cleavage agent, etc.

The invention also includes molecular beacon nucleic acid molecules having at least one region which is complementary to a nucleic acid molecule of the invention, such that the molecular beacon is useful for quantitating the presence of the nucleic acid molecule of the invention in a sample. A "molecular beacon" nucleic acid is a nucleic acid molecule including a pair of complementary regions and having a fluorophore and a fluorescent quencher associated therewith. The fluorophore and quencher are associated with different portions of the nucleic acid in such an orientation that when the complementary regions are annealed with one another, fluorescence of the fluorophore is quenched by the quencher. When the complementary regions of the nucleic acid molecules are not annealed with one another, fluorescence of the fluorophore is quenched to a lesser degree. Molecular beacon nucleic acid molecules are described, for example, in U.S. Pat. No. 5,876,930.

In certain inventive embodiments, the SMO includes at least one nucleotide that contains a non-naturally occurring modification including at least one of a chemical composition of phosphorothioate phosphorothioate 2'-MOE, locked nucleic acid (LNA) peptide nucleic acid (PNA), phosphorodiamidate morpholino, or any combination thereof.

In certain inventive embodiments, the SMO includes at least one 2'-O-methyl nucleotide. In certain inventive embodiments, the SMO includes at least two 2'-O-methyl nucleotides. In certain inventive embodiments, the SMO includes at least three 2'-O-methyl nucleotides. In certain inventive embodiments, at least about 10, 20, 30, 40, 50, 60, 70, 80, 90 or 100% of the SMO nucleotides are 2'-O-methyl modified.

In certain inventive embodiments, the SMO includes at least one nucleotide with a phosphorothioate linkage. In certain inventive embodiments, the SMO includes at least two nucleotides with phosphorothioate linkages. In certain inventive embodiments, the SMO includes at least three nucleotides with phosphorothioate linkages. In certain inventive embodiments, at least about 10, 20, 30, 40, 50, 60, 70, 80, 90 or 100% of the SMO nucleotides include phosphorothioate linkages.

In certain inventive embodiments, the SMO includes at least one phosphorothioate 2'-O-methyl modified nucleotide. In certain inventive embodiments, the SMO includes at least two phosphorothioate 2'-O-methyl modified nucleotides. In certain inventive embodiments, the SMO includes at least three phosphorothioate 2'-O-methyl modified nucleotides. In certain inventive embodiments, at least about 10, 20, 30, 40, 50, 60, 70, 80, 90 or 100% of the SMO nucleotides are phosphorothioate 2'-O-methyl modified.

In certain inventive embodiments, modifications include a bicyclic sugar moiety similar to the LNA has also been described (see U.S. Pat. No. 6,043,060) where the bridge is a single methylene group which connect the 3'-hydroxyl group to the 4' carbon atom of the sugar ring thereby forming a 3'-C,4'-C-oxymethylene linkage. In certain inventive embodiments oligonucleotide modifications include cyclohexene nucleic acids (CeNA), in which the furanose ring of a DNA or RNA molecule is replaced with a cyclohexenyl ring to increase stability of the resulting complexes with RNA and DNA complements (Wang et al., *J. Am. Chem. Soc.,* 2000, 122, 8595-8602). In certain inventive embodiments other bicyclic and tricyclic nucleoside analogs are included in the SMO.

The target RNA (e.g., pre-mRNA, e.g., SCN8A pre-mRNA) splice-modifying interaction guided by oligonucleotides of the invention is highly sequence specific. In general, oligonucleotides containing nucleotide sequences perfectly complementary, having 100% complementarity to a portion of the target RNA are exposed to target RNA for blocking of sequence elements within the target RNA. However, it is appreciated that 100% sequence complementarity between the oligonucleotide and the target RNA is not required to practice the present invention. Thus, the invention may tolerate sequence variations that might be expected due to genetic mutation, wobble base pairing, strain polymorphism, or evolutionary divergence. In wobble base pairing non-Watson-Crick nucleotide pairing occurs in which U can pair with both A and G, so A can be substituted with G, and inosine (I) can pair with any base. For example, oligonucleotide sequences with insertions, deletions, and single point mutations relative to the target sequence may also be effective for SMO-mediated splice modulation. Alternatively, oligonucleotide sequences with nucleotide analog substitutions or insertions can be effective for splice modulation. Greater than 70% sequence identity (or complementarity), e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% sequence identity, and any and all whole or partial increments there between the oligonucleotide and the target RNA, e.g., target pre-mRNA, is preferred.

It is further understood in the art that incorporation of nucleotide affinity modifications may allow for a greater number of mismatches compared to an unmodified compound. Certain oligonucleotide (SMO) sequences may be more tolerant to mismatches than other oligonucleotide sequences. One of ordinary skill in the art is capable of determining an appropriate number of mismatches between oligonucleotides, between an SMO and a target nucleic acid, such as by determining melting temperature (Tm) and evaluating the effect of chemical modifications on the Tm and hybridization stringency. Tm can be calculated by techniques that are familiar to one of ordinary skill in the art. Techniques and calculations as described in Freier et al. (Nucleic Acids Research, 1997, 25, 22: 4429-4443) allow one of ordinary skill in the art to evaluate nucleotide modifications for their ability to increase the Tm of an RNA: RNA or an RNA: DNA duplex.

In certain inventive embodiments, “sequence identity” or “identity” in the context of two nucleic acid sequences makes reference to a specified percentage of residues in the two sequences that are the same when aligned by sequence comparison algorithms or by visual inspection. For example, sequence identity may be used to reference a specified percentage of residues that are the same across the entirety of the two sequences when aligned.

In certain inventive embodiments, the term “substantial identity” of polynucleotide sequences means that a polynucleotide includes a sequence that has at least 70%, 71%, 72%, 73%, 74%, 75%, 76%, 77%, 78%, or 79%; at least 80%, 81%, 82%, 83%, 84%, 85%, 86%, 87%, 88%, or 89%; at least 90%, 91%, 92%, 93%, or 94%; or even at least 95%, 96%, 97%, 98%, or 99% sequence identity, compared to a reference sequence using one of the alignment programs described using standard parameters.

Sequence identity, including determination of sequence complementarity or homology for nucleic acid sequences, may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=number of identical positions/total number of positions×100), optionally penalizing the score for the number of gaps introduced and/or length of gaps introduced. The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. WI. Biol. 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM 120 weight residue table, a gap length penalty of 12, and a gap penalty of 4 can be used.

In another embodiment, the sequence identity for two sequences is based on the greatest number of consecutive identical nucleotides between the two sequences (without inserting gaps). For example, the percent sequence identity between Sequence A and B below would be 87.5% (Sequence B is 14/16 identical to Sequence A), whereas the percent sequence identity between Sequence A and C would be 25% (Sequence C is 4/16 identical to Sequence A).

```
Example Sequence A:
                         (SEQ ID NO: 2141)
GCATGCATGCATGCAT

Example Sequence B:
                         (SEQ ID NO: 2142)
GCATGCATGCATGC

Example Sequence C:
                         (SEQ ID NO: 2143)
GCATTTGCAGCAGC
```

In yet another embodiment, nucleic acids, oligonucleotides, SMOs, or a portion thereof, may have a defined percent identity to a SEQ ID NO, or a another LifeSplice compound. As used herein, a sequence is identical to the SMO sequence disclosed herein if it has the same nucleobase pairing ability. This identity may be over, the entire length of the nucleotide sequence, or in a portion of the nucleotide sequence e.g., nucleobases 1-20 of a 300-mer may be compared to a 20-mer to determine percent identity of the nucleic acid to the SEQ ID NO described herein. Percent identity is calculated according to the number of nucleotide bases that have identical base pairing corresponding to the SEQ ID NO or SMO compound to which it is being compared. The non-identical bases may be adjacent to each other, dispersed throughout the nucleotide sequence, or both. For example, a 18-mer having the same sequence as nucleobases 3-20 of a 24-mer SMO is 75% identical to the 24-mer SMO. Alternatively, a 24-mer containing six nucleobases not identical to another 24-mer is also 75% identical to the 24-mer. Similarly a 15-mer having the same sequence as nucleobases 1-15 of a 100-mer is 15% identical to the 100-mer. Such calculations are well within the ability of those skilled in the art.

It is further understood by those skilled in the art that a nucleic acid sequence need not have an identical sequence to those described herein to function similarly to the SMO compound described herein. Shortened versions of SMO compounds taught herein, or non-identical versions of the SMO compounds taught herein, are also provided. Non-identical versions can include at least one base replaced with a different base with different pairing activity (e.g., G can be replaced by C, A, or T), wobble base pairing, or sequences are those wherein each base does not have the same pairing activity (e.g. by the nucleic acid sequence being shorter or having at least one abasic site) as the SMOs disclosed herein.

Alternatively, the oligonucleotide may be defined functionally as a nucleotide sequence (or oligonucleotide sequence) a portion of which is capable of hybridizing with the target RNA (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in IX SSC or 50° C. in IX SSC, 50% formamide followed by washing at 70° C. in 0.3×SSC or hybridization at 70° C. in 4×SSC or 50° C. in 4×SSC, 50% formamide followed by washing at 67° C. in IX SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(number of A+T bases)+4(number of G+C bases). For hybrids between 18 and 49 base pairs in length, Tm(° C.)=81.5+16.6(log 10[$Na^+$])+0.41(% G+C)−(600/N), where N is the number of bases in the hybrid, and [$Na^+$] is the concentration of sodium ions in the hybridization buffer ([$Na^+$] for IX SSC=0.165 M). Additional examples of stringency conditions for polynucleotide hybridization are provided in Sambrook, et al., 2001, Molecular Cloning: A Laboratory Manual, Cold Spring Harbor Laboratory Press, Cold Spring Harbor, N.Y., chapters 9 and 1 1, and Current Protocols in Molecular Biology, 1995, F. M. Ausubel et al., eds., John Wiley & Sons, Inc., sections 2.10 and 6.3-6.4, incorporated herein by reference. The length of the identical nucleotide sequences may be at least about 10, 12, 15, 17, 20, 22, 25, 27, 30, 32, 35, 37, 40, 42, 45, 47 or 50 bases.

Methods of Use

Methods of Modulating SCN8A Pre-mRNA Splicing

The present invention provides compositions and methods for modulating SCN8A pre-mRNA splicing using an SMO of the invention (e.g., to abrogate disease-causing mutations in a protein, such as SCN1A). For example, an SMO may modulate pre-mRNA splicing by removing an exon (e.g., exon 5A or exon 18A) or including an exon (e.g., exon 5N or exon 18N) in order to alter protein isoform expression (e.g., to enhance expression of isoforms with reduced excitatory function). For example, an SMO as described herein may modulate SCN8A pre-mRNA by excluding exon 5A in the resulting SCN8A mRNA. These SMOs may be used to modify SCN8A channel properties, i.e., to reduce sodium currents. In other embodiments, an SMO described herein may modulate SCN8A pre-mRNA by excluding exon 18A in the resulting SCN8A mRNA. These SMOs may be used to generate a truncated SCN8A protein that is non-functional as a sodium channel, or that is not even translated into a SCN8 protein.

Accordingly, certain inventive embodiments of the invention provide a method of modulating splicing of an SCN8A pre-mRNA, either in vitro or in vivo including contacting a cell with an effective amount of an SMO or composition described herein. In certain inventive embodiments, the SMO specifically binds to a SCN8A pre-mRNA sequence (e.g., at an intron/exon splice site, ESE and/or ISE), thereby excluding exon 5A or exon 18A from a resulting SCN8A mRNA.

Certain inventive embodiments of the invention provide a method of modulating splicing of an SCN8A pre-mRNA including contacting a cell with an effective amount of an SMO that specifically binds to a complementary sequence on the pre-mRNA at a intron-exon splice site, ESE and/or ISE, wherein when the SMO specifically binds to the complementary sequence, exon-18A or exon-5A is excluded from the resulting mRNA, and wherein the resulting mRNA encodes an SCN8A protein.

Certain inventive embodiments of the invention provide a method of modulating splicing of an SCN8A pre-mRNA including contacting a cell with an effective amount of an SMO that specifically binds to a complementary sequence on the pre-mRNA at a intron-exon splice site, ESE and/or ISE, wherein when the SMO specifically binds to the complementary sequence, exon-18N or exon-5N is included in the resulting mRNA, and wherein the resulting mRNA encodes an SCN8A protein.

Certain inventive embodiments of the invention provide a method of reducing neuronal excitability including contacting a cell with an effective amount of an SMO or composition described herein.

Methods of Treating Diseases and Disorders

The relationship between SCN8A pre-mRNA splicing and the Dravet spectrum epilepsies is described above; however, SCN8A dysregulation or dysfunction is also associated with other diseases and disorders as described below.

Hyperexcitability Including Other Epilepsies.

SCN8A loss-of function mutation or knockout results in increased seizure threshold to chemoconvulsant induced seizures (Martin et. al., 2007), thus the SMOs that modulate SCN8A isoform expression (e.g., decrease E5A or E18A; FIGS. 3A-K. and 4A-D) are viable therapeutics for other types of refractory pediatric and adult epilepsies; some that have dysfunctional SCN1A and others that do not. More broadly, these SMOs have the potential be treat various diseases or disorders in which CNS hyperexcitability and/or excitotoxicity have been implicated as having a significant contribution to disease pathology through dysfunction of SCN1A or SCN8A. Additionally, there are hundreds of SCN1A and SCN8A mutations attributed to a variety of epilepsy syndromes aside from the Dravet spectrum epilepsies (Oliva et. al., 2012).

Further it has recently been demonstrated that selective reduction of SCN8A expression in the hippocampus is responsible for the anti-seizure effect of SCN8A reduction (Makinson et. al., 2014) and is a strategy that could be accomplished in humans with intractable epilepsies. While complete SCN8A KO causes a severe phenotype in mice including motor system degeneration and early lethality (Martin et. al., 2007; Meisler et. al., 2004), loss of function mutations have been found in humans with only mild impact on cognition (Trudeau et. al., 2006).

Additionally, pathogenic SCN8A gain-of-function mutations have been found in patients with epileptic encephalopathy (Estacion et. al., 2014; Ohba et. al., 2014; Vaher et.

al., 2013; Veeramah et. al., 2012). Epileptic encephalopathy is characterized by onset of variable types of seizures in infancy including generalized tonic-clonic, atypical absence, partial, apneic attack, febrile convulsion, and loss of tone and consciousness, which are refractory to typical anti-seizure drugs (Ohba et. al., 2014) and (SUDEP) sudden unexplained death of epilepsy (Oliva et. al., 2012; Veeramah et. al., 2012). Patients may also exhibit developmental delay or regression in infancy, resulting in severe intellectual disability, cerebellar and cerebral atrophy (Ohba et. al., 2014) and movement disorders (Vaher et. al., 2013). Thus, the use of SMOs to reduce expression of either the SCN8A 18A or 5A isoforms could mitigate the disease causing effects of SCN8A gain-of-function mutations. SMO dosing for CNS manifestations can be accomplished by direct bolus intrathecal injection as infrequently as every 1-6 months or by continuous infusion via pump (ie Omaya Reservoir) directly into the hippocampus. Dosing for peripheral indications (ie SUDEP from cardiac arrhythmia) can be achieved through subcutaneous or intravenous injections as infrequently as every 1-6 months, or a multiple loading dose strategy could also be used.

Spinal Cord Injury. Blockade of continuous post-traumatic SCN channel activation in general prevents the neuronal acidosis, swelling, and Ca2+ excitotoxicity that contributes to spinal cord injury (Wilson and Fehlings 2014). Thus, SMOs in the present invention that mediate splice modulation of SCN8A channel alpha subunits to reduce functional channel expression (E18A) or modulate channel properties (E5A) are strong therapeutic candidates. SMO dosing for spinal cord injury can be accomplished by direct bolus intrathecal injection at a frequency of every 1-6 months, or as otherwise necessary.

Cancer. Voltage-gated sodium channels are also expressed in non-excitable cells such as macrophages and neoplastic cells. A functional splice variant containing E18A of SCN8A, is required for podosome and invadopodia formation in macrophages. SCN8A is as the alpha subunit of NaV1.6. Absence of functional NaV1.6 through a naturally occurring mutation (med) in mouse peritoneal macrophages inhibited podosome formation (Carrithers et. al., 2009). Invasion of the extracellular matrix by differentiated THP-1 cells, an invasive melanoma cell line, also was inhibited by knockdown of SCN8A, thus SCN8A and by extension, NaV1.6, participates in the control of podosome and invadopodia formation (Carrithers et. al., 2009). Similarly, reduction in SCN8A 18A isoform expression via an SMO-mediated splice modulation should help prevent metastatic ability of even non-neuronal cancer cells. Depending on the location of said cancer, SMO dosing for CNS manifestations can be accomplished by direct bolus intrathecal injection at a frequency of every 1-6 months, continuous ICV infusion via pump (ie Omaya Reservoir), or bolus delivery (ie Omaya Reservoir) directly into the tumor vasculature. Dosing for peripheral indications can be achieved through monthly subcutaneous injections.

Amyotrophic Lateral Sclerosis (ALS).

Riluzole, the only drug approved to treat ALS (albeit with very modest efficacy), is thought to work in part by antagonizing SCN channel alpha subunits, particularly SCN8A (Nutini et. al., 2011; Sierra et. al., 2012). Thus, the specific modulation of SCN8A properties conferred by the SMOs in the instant invention is expected to provide neuroprotection to α-motor neurons that are selectively lost is this fatal neurodegenerative disease. Importantly, the SMOs recited herein that reduce SCN8A 5A and 18A isoforms also are expected to provide a potent anti-inflammatory response in the CNS (see Section 10 below), and therefore are expected to provide therapeutic benefit to ALS patients via a dual mechanism. SMO dosing for ALS can be accomplished by direct bolus intrathecal injection at a frequency of every 1-6 months, or as otherwise necessary for efficacy and patient compliance.

Alzheimer's Disease (AD).

Reduced SCN1A (the alpha subunit of Nav1.1) expression in inhibitory interneurons and parvalbumin cells are found both in mouse models of AD and AD patients (Verret et. al., 2012). Similarly, restoring normal levels of SCN1A in the brain of AD mice reduced epileptiform discharges, memory deficits, and increased survival. Thus, among the serious maladies in AD, neuronal network excitatory imbalance produces debilitating brain pathology. An innovative SMO-based therapeutic approach to rebalance the net inhibitory plus excitatory synaptic drive from reduced SCN1A expression in AD, is to reduce the counterbalancing SCN8A synaptic drive using optimal SMOs that reduce either SCN8A E18A (FIGS. 4A-D) or the SCN8A E5A (FIG. 3A-K) isoform expression, reducing overall synaptic input from the SCN8A-containing VGS channels. There is strong literature-based rationale from Dravet syndrome mouse models that reduced inhibitory drive as a result of diminished SCN1A-containing VGS channels may be mitigated by concurrently reducing SCN8A excitatory drive with minimal adverse effects. In the case of the present invention, this strategy may feasibly be accomplished via reducing SCN8A E5A- or E18A-containing isoforms of SCN8A. SMO dosing for CNS manifestations can be accomplished by direct bolus intrathecal injection at a frequency of every 1-6 months or continuous infusion via pump (ie Omaya Reservoir) directly into the lateral ventricles, or as otherwise necessary for efficacy and patient compliance.

Traumatic Brain injury (TBI).

Depolarization of voltage-gated sodium (VGS) channels and the resultant increased neuronal Na+ influx are critical early events in the initiation of deleterious cellular changes after TBI (Mao et. al., 2010). In particular NaV1.6 (SCN8A) expression is upregulated within hours of percussive TBI insult (Mao et. al., 2010). Thus, a rational and innovative strategy to prevent subsequent cellular damage in the acute post-injury period is to reduce the excessive Na+ influx through SCN8A-containing VGS channels by SMO-mediated skipping of exon 5A (FIG. 3A-K) or 18A (FIG. 4A-D). SMO dosing for CNS manifestations can be accomplished by direct bolus intrathecal injection at a frequency of every 1-6 months or continuous infusion via pump (ie Omaya Reservoir) directly into the lateral ventricles, or as otherwise necessary for efficacy and patient compliance.

Autism.

Autism has been linked to de novo SCN1A mutations (O'Roak et. al., 2011; O'Roak et. al., 2012). Not surprisingly, patients with Dravet spectrum epilepsies may also exhibit autistic behaviors due to SCN1A mutations (Han et. al., 2012), thus rebalancing the excitatory and inhibitory inputs in the brain can be accomplished through reducing SCN8A E18A or E5A expression which could provide therapeutic benefit to autistic patients. SMO dosing for CNS manifestations can be accomplished by direct bolus intrathecal injection at a frequency of every 1-6 months or continuous infusion via pump (ie Omaya Reservoir) directly into the lateral ventricles, or as otherwise necessary for efficacy and patient compliance.

Hemiplegic migraine. Familial Hemiplegic Migraine (FHM) has been linked in some families to missense mutations in the SCN1A gene, leading to alterations in SCN1A- containing VGS channel function (Gargus and Tournay 2007; Silberstein and Dodick 2013), which may be corrected by reducing Na+ currents through the counterbalancing SCN8A-containing VGS channels. SMO dosing for CNS manifestations can be accomplished by direct bolus intrathecal injection at a frequency of every 1-6 months or continuous infusion via pump (ie Omaya Reservoir) directly into the lateral ventricles, or as otherwise necessary for efficacy and patient compliance.

Multiple Sclerosis.

SCN8A-containing VGS channels in demyelinated axons (a hallmark of multiple sclerosis; MS) activates a Na+-Ca2+ exchanger that imports Ca2+ into the axon, leading to axonal injury and eventually axonal degeneration (Waxman 2006). SCN8A is upregulated in microglia of MS patients and in animal models of MS (Black and Waxman 2012). Thus, reducing SCN8A function with SMOs (see, e.g., FIGS. 3A-K. and 4A-D), would both reduce microglial activation and axonal injury/degeneration; providing therapeutic benefit to MS patients via two distinct mechanisms. SMO dosing for CNS manifestations can be accomplished by direct bolus intrathecal injection at a frequency of every 1-6 months or continuous infusion via pump (ie Omaya Reservoir) directly into the lateral ventricles, or as otherwise necessary for efficacy and patient compliance.

Peripheral Neuropathic Pain (Including Post-Herpetic Neuralgia and Diabetic Neuropathy):

There is indirect evidence of increased persistent $Na^+$ currents at nodes of Ranvier due to changes in expression of $Na_v1.6$ in diabetic neuropathy (Morris et. al., 2012). Development of neuropathic pain depends on axonal hyperexcitability due to increased nodal $Na^+$ currents, which is potentiated by lack of glycemic control, and this cascade is suggested to be responsible for neuropathic pain/paresthesia in diabetic neuropathy (Misawa et. al., 2009). Post-herpetic neuralgia (PHN) results from reactivation of the dormant varicella zoster (chickenpox) virus in the dorsal root ganglion (DRG) years after initial infection, and is often unresponsive to current to analgesics and current anti-virals (Garry et. al., 2005). Varicella zoster virus infection is associated with a significant increase in $Na_v$ 1.6 mRNA, which significantly increased Na+ current amplitude (Kennedy et. al., 2013). Therefore, reduction of sodium current through $Na_v$ 1.6 channels and corresponding SCN8A subunit via SMO-mediated splice direction specifically to reduce expression of 18A and 5A containing isoforms could be therapeutic for peripheral neuropathic pain. Dosing for peripheral indications can be achieved through monthly subcutaneous injections. SMO dosing may also be accomplished by direct bolus intrathecal injection or epidural injection at the affected spinal level at a frequency of every 1-6 months, or as otherwise necessary for efficacy and patient compliance.

Carpal Tunnel:

In carpal tunnel syndrome, persistent Na+ current becomes altered across the carpal tunnel region leading to injury, inflammation, and ectopic impulse generation (Kuwabara et. al., 2006). $Na_v1.6$ (and SCN8A) is highly expressed in the peripheral nodes of Ranvier (Morris et. al., 2012). Sodium channel blockers such as Mexiletine, have been sown to be useful, thus SMO treatment to alter splicing of SCN8A, specifically to reduce expression of 18A or 5A containing isoforms individually or in combination may produce long term relief of symptoms or prevent need for surgery. Dosing for peripheral indications can be achieved through monthly local subcutaneous, intramuscular, or intracapsular injections. SMO dosing may also be accomplished by epidural injection at the affected spinal level at a frequency of every 1-6 months, or as otherwise necessary for efficacy and patient compliance.

Cardiovascular Disease or Disorder (e.g., Hypertension, Congestive Heart Failure, Ischemia/Reperfusion, Arrhythmias):

Arrhythmia and Ischemia and reperfusion injury: It is thought that ventricular and atrial expression of $Na_v1.6$, in part, allows for a slow persistent Na+ current based $Na_v$ channel leak leading to arrhythmia or contributing to ischemia and reperfusion injury (Morris et. al., 2012). However, current sodium channel blocking strategies to ameliorate cardiac ischemic and reperfusion damage, including block of the Na+/H+ exchanger, have so far been therapeutically ineffective (Weiss et. al., 2010) necessitating novel therapeutic approaches. Riluzole, through preferential block of persistent Na+ current, was shown to provide dose-dependent protection against cardiac ischemia and reperfusion injury in animal models, suggesting block of the SCN8A/Nav 1.6 mediate persistent sodium current would be a viable method of ameliorating cardiac ischemic/reperfusion damage (Weiss et. al., 2010). Through inhibition of Na+ current in the ventricles even in patients with structurally compromised hearts, Ranolazine, an FDA-approved anti-anginal agent, can suppress arrhythmias associated with acute coronary syndrome, long QT syndrome, heart failure, ischemia/reperfusion in the ventricles and also suppress atrial tachyarrhythmias and atrial fibrillation (Antzelevitch et. al., 2011). Thus, reducing persistent or late Na+ current specifically in cardiomyocytes through splice-modulation of SCN8A E18A/N or E5A/N, could allow for greater Na+ channel modulation and provide long-term antiarrhythmic therapy for intractable cases, and acutely prevent ischemia-reperfusion injury after heart attack. SMO dosing for cardiac indications can be achieved through monthly subcutaneous injections, or as otherwise necessary for efficacy and patient compliance.

Other Diseases with a Neuroinflammatory Component.

SCN8A expression is upregulated in activated microglia, and blocking SCN8A activity with nonselective Na+ channel blockers prevents microglia activation (Black and Waxman 2012). Thus, many neurological diseases/disorders with a neuroinflammatory component, including but not limited to CNS infections, stroke, ALS, Alzheimer's disease, Parkinson's disease, Huntington's disease (Fernandes et. al., 2014), and aging and age-related disorders (Norden and Godbout 2013) may be treatable using the highly selective SCN8A SMOs (FIGS. 3A-K. and 4A-D) of the present invention.

Accordingly, the present invention also provides compositions and methods of treating a subject at risk of susceptible to, or having a disease, disorder, or condition associated with SCN8A pre-mRNA expression or SCN8A protein expression or function. In one embodiment, a SCN8A pre-mRNA may be an alternatively spliced, aberrantly spliced, overexpressed or unwanted pre-mRNA (e.g., a SCN8A pre-mRNA including exon 5A or exon 18A) that encodes a protein that results in, causes, produces, or predisposes a subject to a disease or disorder. In another embodiment, splicing of a SCN8A pre-mRNA is not a cause of a disease or disorder, but modulation of the splicing of the SCN8A pre-mRNA reduces at least one symptom of the disease or disorder.

In another embodiment, the invention provides a method of preventing in a subject, a disease, disorder, or condition associated with SCN8A pre-mRNA splicing, the method including administering to the subject an SMO or composition described, or vector, or transgene encoding same.

Accordingly, certain inventive embodiments of the invention provide a method of treating or preventing a disease, disorder or condition in subject (e.g., a mammal, e.g., a human), including administering an SMO or composition described herein to the subject.

In certain inventive embodiments, the disease, disorder or condition is a neurological disease, disorder or condition. For example, in certain inventive embodiments, the neurological disease, disorder or condition is epilepsy (e.g., a Dravet spectrum epilepsy), a disease or disorder associated with CNS hyperexcitability and/or excitotoxicity, a spinal cord injury, amyotrophic lateral sclerosis (ALS), Alzheimer's disease (AD), traumatic brain injury (TBI), autism, hemiplegic migraine, multiple sclerosis or a neuroinflammatory associated disease or disorder. In certain inventive embodiments, the neuroinflammatory associated disease or disorder is a CNS infection, stroke, ALS, AD, Parkinson's disease, Huntington's disease, aging or aging related disorders.

In certain inventive embodiments, the disease, disorder or condition is pain mediated by SCN8A regulation. For example, in certain inventive embodiments the pain mediated disease, disorder or condition is peripheral neuropathic pain or carpal tunnel syndrome.

In certain inventive embodiments, the disease, disorder or condition is cardiovascular mediated by SCN8A regulation. For example, in certain inventive embodiments the cardiovascular mediated disease, disorder or condition is hypertension, congestive heart failure, ischemia/reperfusion, or arrhythmia.

In certain inventive embodiments, the disease, disorder or condition is cancer mediated by SCN8A regulation. In certain inventive embodiments, the cancer is brain cancer mediated by SCN8A regulation.

Certain inventive embodiments of the invention provide a method of treating or preventing epilepsy or a Dravet Spectrum disorder in subject (e.g., a mammal, e.g., a human), including administering an SMO or composition described herein to the subject.

In certain inventive embodiments, the Dravet Spectrum disorder is caused by a SCN1A mutation. In certain inventive embodiments, the Dravet Spectrum disorder is febrile seizures, generalized epilepsy with febrile seizure plus (GEFS+) or Dravet syndrome (severe myoclonic epilepsy of infancy or SMEI).

In certain inventive embodiments, the administration reduces SCN8A excitatory function.

In certain inventive embodiments, the SMO specifically binds to a SCN8A pre-mRNA sequence, wherein when the SMO specifically binds to the SCN8A pre-mRNA sequence, exon 5A is excluded in the resulting SCN8A mRNA, and wherein the resulting mRNA encodes a SCN8A protein.

In certain inventive embodiments, the SMO specifically binds to a SCN8A pre-mRNA sequence, wherein when the SMO specifically binds to the SCN8A pre-mRNA sequence, exon 18A is excluded in the resulting SCN8A mRNA, and wherein the resulting mRNA encodes a SCN8A protein.

In certain inventive embodiments, the SCN8A protein has reduced excitatory function.

Certain inventive embodiments of the invention provide an SMO as described herein for the prophylactic or therapeutic treatment of a disease or disorder in a subject mediated by SCN8A regulation.

Certain inventive embodiments of the invention provide the use of an SMO as described herein to prepare a medicament for treating a disease or disorder in a subject mediated by SCN8A regulation.

Certain inventive embodiments of the invention provide an SMO as described herein for use in medical therapy.

Certain inventive embodiments of the invention provide an SMO as described herein for use in treating a disease or disorder mediated by SCN8A regulation.

Methods of Administration

Examples of methods for introducing oligonucleotides into cells encompass in vivo and ex vivo methods. The oligonucleotides of the invention, i.e. SMOs, are typically administered to a subject or generated in situ such that they hybridize with or bind to SCN8A pre-mRNA. In one embodiment, the SMO enhances exclusion of exon 5A or enhances inclusion of exon 5N during splicing of a SCN8A pre-mRNA. In still other embodiments, the SMO enhances exclusion of exon 5N or enhances inclusion of exon 5A during splicing of a SCN8A pre-mRNA. In another embodiment, the SMO enhances exclusion of exon 18A or enhances inclusion of exon 18A during splicing of a SCN8A pre-mRNA. In still other embodiments, the SMO enhances exclusion of exon 18N or enhances inclusion of exon18A during splicing of a SCN8A pre-mRNA.

The hybridization can be by conventional Watson-Crick base pairing by nucleotide complementarity and/or wobble pairing of U-G nucleic acids to form a stable duplex. Wobble base pairing can also be accomplished with Inosine (I-A, I-U, I-C, I-G), where I is inosine. Hybridization can also occur, for example, in the case of an oligonucleotide which binds to DNA duplexes, through specific interactions in the major groove of the double helix.

Conjugation of an SMO to anthraquinones, acridines, biotin, carbohydrates, chitosans, cholesterol, phospholipids, dendrimers, or other lipid and liposomal moieties, colloidal polymeric particles, coumarins, dyes (such as fluoresceins and rhodamines), folate, peptides, phenanthridine, and phenazines, as well as other means known in the art may be used to deliver the oligonucleotides to a cell. The method of delivery selected will depend at least on the cells to be treated and the location of the cells and will be known to those skilled in the art. Localization can be achieved by liposomes, having specific markers on the surface for directing the liposome, by having injection directly into the tissue containing the target cells, by having depot associated in spatial proximity with the target cells, specific receptor mediated uptake, or the like.

As described elsewhere herein and in the art, oligonucleotides may be delivered using, e.g., methods involving liposome-mediated uptake, lipid conjugates, polylysine-mediated uptake, nanoparticle-mediated uptake, and receptor-mediated endocytosis, as well as additional non-endocytic modes of delivery, such as microinjection, permeabilization (e.g., streptolysin-O permeabilization, anionic peptide permeabilization), electroporation, and various non-invasive non-endocytic methods of delivery that are known in the art (refer to Dokka and Rojanasakul, Advanced Drug Delivery Reviews 44, 35-49, incorporated in its entirety herein by reference). Methods of delivery may also include the following.

Cationic Lipids: Naked nucleic acids (e.g., DNA/RNA) can be introduced into cells in vivo by complexing the nucleic acid with cationic lipids or encapsulating the nucleic acid in cationic liposomes. Examples of suitable cationic lipid formulations include N-[-1-(2,3-dioleoyloxy)propyl]N, N,N-triethylammonium chloride (DOTMA) and a 1:1 molar ratio of 1,2-dimyristyloxy-propyl-3-dimethylhydroxyethyl-ammonium bromide (DMRIE) and dioleoyl phosphatidylethanolamine (DOPE) (see e.g., Logan, J. J. et al. (1995) Gene Therapy 2:38-49; San, H. et al. (1993) Human Gene Therapy 4:781-788).

Receptor-Mediated DNA Uptake: Naked nucleic acids can also be introduced into cells in vivo by complexing the nucleic acid to a cation, such as polylysine, which is coupled to a ligand for a cell-surface receptor (see for example Wu, G. and Wu, C. H. (1988) J. Biol. Chem. 263:14621; Wilson et al. (1992) J. Biol. Chem. 267:963-967; and U.S. Pat. No. 5,166,320). Binding of the nucleic acid-ligand complex to the receptor facilitates uptake of the nucleic acid by receptor-mediated endocytosis. A nucleic acid-ligand complex linked to adenovirus capsids which naturally disrupt endosomes, thereby releasing material into the cytoplasm can be used to avoid degradation of the complex by intracellular lysosomes (see for example Curiel et al. (1991) Proc. Natl. Acad. Sci. USA 88:8850; Cristiano et al. (1993) Proc. Natl. Acad. Sci. USA 90:2122-2126). Carrier mediated SMO delivery may also involve the use of lipid-based compounds which are not liposomes. For example, lipofectins and cytofectins are lipid-based positive ions that bind to negatively charged nucleic acids and form a complex that can ferry the nucleic acid across a cell membrane. Another method of carrier mediated transfer involves receptor-based endocytosis. In this method, a ligand (specific to a cell surface receptor) is made to form a complex with a nucleic acid or SMO of interest and then delivered to the bodyTarget cells that have the cell surface receptor will specifically bind the ligand and transport the ligand-DNA complex into the cell.

Oligonucleotides may be directly introduced into the cell (i.e., intracellularly); or introduced extracellularly into a cavity, interstitial space, into the circulation of an organism, introduced orally, or may be introduced by bathing a cell or organism in a solution containing the RNA using methods known in the art for introducing nucleic acid (e.g., DNA) into cells in vivo. Vascular or extravascular circulation, the blood or lymph system, and the cerebrospinal fluid are sites where the RNA may be introduced.

The oligonucleotides of the invention can be delivered to a subject by any art-recognized method. For example, peripheral blood injection of the oligonucleotides of the invention can be used to deliver the reagents via diffusive and/or active means. Alternatively, the oligonucleotides of the invention can be modified to promote crossing of the blood-brain-barrier (BBB) to achieve delivery of said reagents to neuronal cells of the central nervous system (CNS). Specific recent advancements in oligonucleotide technology and delivery strategies have broadened the scope of oligonucleotide usage for neuronal disorders (Forte, A., et al. 2005. Curr. Drug Targets 6:21-29; Jaeger, L. B., and W. A. Banks. 2005. Methods MoI. Med. 106:237-251; Vinogradov, S. V., et al. 2004. Bioconjug. Chem. 5:50-60; the preceding are incorporated herein in their entirety by reference).

In certain inventive embodiments, the oligonucleotides of the invention can be delivered by transdermal methods (e.g., via incorporation of the oligonucleotide reagent(s) of the invention into, e.g., emulsions, with such oligonucleotides optionally packaged into liposomes). Such transdermal and emulsion/liposome-mediated methods of delivery are described for delivery of antisense oligonucleotides in the art, e.g., in U.S. Pat. No. 6,965,025, the contents of which are incorporated in their entirety by reference herein.

The oligonucleotides of the invention may also be delivered via an implantable device (e.g., an infusion pump or other such implantable device). Design of such a device is an art-recognized process.

In another embodiment the SMO is delivered parenterally, for example by intravenous or subcutaneous injections.

In one embodiment, an SMO is delivered directly into the cerebral spinal fluid (CSF) of a subject. Delivery of an SMO into the CSF of a subject may be accomplished by any means known in the art, including, but not limited to, epidural injection or intrathecal injection or intrathecal injection using an infusion pump, or direct brain delivery with a pump or other device.

In one embodiment, SMOs are conjugated to a peptide to facilitate delivery of the SMO across the blood brain barrier (BBB) following parenteral administration to a subject. The SMO may be either directly conjugated to the peptide or indirectly conjugated to the peptide via a linker molecule such as a poly amino acid linker, or by electrostatic interaction. Peptides useful in delivering SMOs across the BBB include, but are not limited to, peptides derived from the rabies virus glycoprotein (RVG) that specifically bind to the nicotinic acetylcholine receptor (AchR) present on neurons and the vascular endothelium of the BBB thereby allowing transvascular delivery, probably by receptor-mediated transcytosis (Kumar et al., 2007, Nature 448:39-43, encompassed by reference in its entirety); Kunitz domain-derived peptides called angiopeps (Demeule et al., 2008, J. Neurochem. 106: 1534-1544; Demeule et al., 2008, J. Pharmacol. Exp. Ther. 324: 1064-1072). Recombinant methods known in the art can also be used to achieve oligonucleotide reagent-induced modulation of splicing in a target nucleic acid. For example, vectors containing oligonucleotides can be employed to express, e.g., an antisense oligonucleotide to modulate splicing of an exon of a targeted pre-mRNA.

For oligonucleotide reagent-mediated modulation of an RNA in a cell line or whole organism, gene expression may be assayed by use of a reporter or drug resistance gene whose protein product is easily assayed. Such reporter genes include acetohydroxyacid synthase (AHAS), alkaline phosphatase (AP), beta galactosidase (LacZ), beta glucuronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin. Depending on the assay, quantitation of the amount of gene expression allows one to determine a degree of modulation which is greater than 10%, 33%, 50%, 90%, 95% or 99% as compared to a cell not treated according to the present invention. Lower doses of injected material and longer times after administration of oligonucleotides may result in modulation in a smaller fraction of cells (e.g., at least 10%, 20%, 50%, 75%, 90%, or 95% of targeted cells). Quantitation of gene expression in a cell may show similar amounts of modulation at the level of accumulation of target mRNA or translation of target protein. As an example, the efficiency of modulation may be determined by assessing the amount of gene product in the cell; pre-mRNA or mRNA may be detected with a hybridization probe having a nucleotide sequence outside the region used for the oligonucleotide reagent, or translated polypeptide may be detected with an antibody raised against the polypeptide sequence of that region.

Pharmaceutical Compositions and Therapies

An SMO of the invention may be administered to a subject in a pharmaceutical composition. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Pharmaceutical compositions can be prepared as described below. Depending on the particular target SCN8A RNA sequence and the dose of oligonucleotide material delivered, this process may modulate SCN8A splicing and the expression or function of resulting SCN8A protein. In one embodiment of the instant invention, exon 5N-containing SCN8A protein production is enhanced in a treated cell, cell extract, organism or patient, with an enhancement of exon 5N-containing SCN8A protein levels of at least about 1.1-, 1.2-, 1.5-, 2-, 3-, 4-, 5-, 7-, 10-, 20-, 100-fold and higher values being exemplary. In another embodiment of the invention, exon 18N-containing SCN8A protein production is enhanced in a treated cell, cell extract, organism or patient, with an enhancement of exon 18N-containing SCN8A protein levels of at least about 1.1-, 1.2-, 1.5-, 2-, 3-, 4-, 5-, 7-, 10-, 20-, 100-fold and higher values being exemplary. Enhancement of gene expression refers to the presence (or observable increase) in the level of protein and/or mRNA product from a target RNA. Specificity refers to the ability to act on the target RNA without manifest effects on other genes of the cell. The consequences of modulation of the target RNA can be confirmed by examination of the outward properties of the cell or organism (see, e.g., Example 1) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS).

The oligonucleotide, i.e. the SMO, may be introduced in an amount which allows delivery of at least one copy per cell. Higher doses (e.g., at least 5, 10, 100, 500 or 1000 copies per cell) of material may yield more effective modulation; lower doses may also be useful for specific applications.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, oral, parenteral, intranasal, buccal, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition including a predetermined amount of the active ingredient. The amount of the active ingredient is generally equal to the dosage of the active ingredient which would be administered to a subject or a convenient fraction of such a dosage such as, for example, one-half or one-third of such a dosage. The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may include between 0.1% and 100% (w/w) active ingredient.

In addition to the active ingredient, a pharmaceutical composition of the invention may further include one or more additional pharmaceutically active agents.

Controlled- or sustained-release formulations of a pharmaceutical composition of the invention may be made using conventional technology. As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intrasternal injection, intratumoral, and kidney dialytic infusion techniques. Formulations of a pharmaceutical composition suitable for parenteral administration include the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further include one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may include, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which include the active ingredient in microcrystalline form, in a liposomal preparation, or as a component of a biodegradable polymer systems. Compositions for sustained release or implantation may include pharmaceutically acceptable polymeric or hydrophobic materials such as an emulsion, an ion exchange resin, a sparingly soluble polymer, or a sparingly soluble salt.

Formulations suitable for nasal administration may, for example, include from about as little as 0.1% (w/w) and as much as 100% (w/w) of the active ingredient, and may further include one or more of the additional ingredients described herein. A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance including an orally dissolvable or degradable composition and, optionally, one or more of the additional ingredients described herein. Alternately, formulations suitable for buccal administration may include a powder or an aerosolized or atomized solution or suspension including the active ingredient. Such powdered, aerosolized, or aerosolized formulations, when dispersed, preferably have an average particle or droplet size in the range from about 0.1 to about 200 nanometers, and may further include one or more of the additional ingredients described herein. As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

The therapeutic and prophylactic methods of the invention thus encompass the use of pharmaceutical compositions including a splice modifying oligonucleotide of the invention to practice the methods of the invention. The precise dosage administered will vary depending upon any number of factors, including but not limited to, the type of animal and type of disease state being treated, the age of the animal and the route of administration.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Kits

Kits for practicing the methods of the invention are further provided. By "kit" is intended any manufacture (e.g., a package or a container) including at least one reagent, e.g., at least one SMO for specifically enhancing inclusion of exon 5N in SCN8A protein (i.e., for enhancing the exclusion of exon 5A), for the treatment of a disease, disorder or condition, e.g., a Dravet Spectrum Epilepsy. In one embodiment of the invention, the kit includes at least one SMO for specifically enhancing the inclusion of exon 18N in SCN8A protein (i.e., for enhancing the exclusion of exon 18A), for the treatment of a disease, disorder or condition, e.g., a Dravet Spectrum Epilepsy. The kit may be promoted, distributed, or sold as a unit for performing the methods of the present invention. Additionally, the kits may contain a package insert describing the kit and including instructional material for its use.

Positive, negative, and/or comparator controls may be included in the kits to validate the activity and correct usage of reagents employed in accordance with the invention. Controls may include samples, such as tissue sections, cells fixed on glass slides, etc., known to be either positive or negative for the presence of the biomarker of interest. The design and use of controls is standard and well within the routine capabilities of those of ordinary skill in the art.

General Terminology

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are well known and commonly employed in the art.

Standard techniques are used for nucleic acid and peptide synthesis. The techniques and procedures are generally performed according to conventional methods in the art and various general references (e.g., Sambrook and Russell, 2001, Molecular Cloning, A Laboratory Approach, Cold Spring Harbor Press, Cold Spring Harbor, N.Y., and Ausubel et al., 2002, Current Protocols in Molecular Biology, John Wiley & Sons, N.Y.), which are provided throughout this document.

The nomenclature used herein and the laboratory procedures used in analytical chemistry and organic syntheses described below are well known and commonly employed in the art. Standard techniques or modifications thereof, are used for chemical syntheses and chemical analyses.

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent on the context in which it is used.

"Antisense activity" means any detectable or measurable activity attributable to the hybridization of an antisense compound to its target nucleic acid. In certain embodiments, antisense activity is a change in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, SMOs, antisense oligonucleotides, siRNAs, shRNAs, ssRNAs, and occupancy-based compounds. Antisense mechanisms include, without limitation, RNase H mediated antisense; RNAi mechanisms, which utilize the RISC pathway and include, without limitation, siRNA, ssRNA and microRNA mechanisms; and occupancy/steric block based mechanisms, including, without limitation uniform modified oligonucleotides. Certain antisense compounds may act through more than one such mechanism and/or through additional mechanisms.

"Antisense oligonucleotide" means a single-stranded oligonucleotide having a nucleobase sequence that permits hybridization to a corresponding segment of a target nucleic acid.

A "disease" is a state of health of subject wherein the subject cannot maintain homeostasis, and wherein if the disease is not ameliorated then the subject's health continues to deteriorate. In contrast, a "disorder" in an subject is a state of health in which the subject is able to maintain homeostasis, but in which the subject's state of health is less favorable than it would be in the absence of the disorder. Left untreated, a disorder does not necessarily cause a further decrease in the subject's state of health. In preferred embodiments, the subject is an animal. In more preferred embodiments, the subject is a mammal. In most preferred embodiments, the subject is a human.

A disease or disorder is "alleviated" if the severity of a symptom of the disease or disorder, or the frequency with which such a symptom is experienced by a subject, or both, is reduced.

The terms "effective amount" and "pharmaceutically effective amount" refer to a nontoxic but sufficient amount of an agent to provide the desired biological result. That result can be reduction and/or alleviation of the signs, symptoms, or causes of a disease or disorder, or any other desired alteration of a biological system. An appropriate effective amount in any individual case may be determined by one of ordinary skill in the art using routine experimentation.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence. The term "exonic regulatory elements" as used herein refers to sequences present on pre-mRNA that enhance or suppress splicing of an exon. An exonic regulatory element that enhances splicing of an exon is an exonic splicing enhancer (ESE). An exonic regulatory element that suppresses splicing of an exon is an exonic splicing suppressor (ESS). An intronic regulatory element that enhances splicing of an exon is an intronic splicing enhancer (ISE). An intronic regulatory element that suppresses splicing of an exon is called an intronic splicing suppressor (ISS).

"Instructional material," as that term is used herein, includes a publication, a recording, a diagram, or any other medium of expression which can be used to communicate the usefulness of the composition and/or compound of the invention in a kit. The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term also includes other modified nucleic acids as described herein. The term nucleic acid also specifically includes nucleic acids composed of bases other than the five biologically occurring bases (adenine, guanine, thymine, cytosine and uracil). The term "nucleic acid" typically refers to large polynucleotides.

Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers.

The terms "nucleic acid," "nucleic acid molecule," "nucleic acid fragment," "nucleic acid sequence or segment," or "polynucleotide" may also be used interchangeably with gene, cDNA, DNA and RNA encoded by a gene, e.g., genomic DNA, and even synthetic DNA sequences. The term also includes sequences that include any of the known base analogs of DNA and RNA.

"Messenger RNA" or "mRNA" is any RNA that specifies the order of amino acids in a protein. It is produced by transcription of DNA by RNA polymerase. In eukaryotes, the initial RNA product (primary transcript, including introns and exons) undergoes processing to yield a functional mRNA (i.e., a mature mRNA), which is then transported to the cytoplasm for translation. "Precursor mRNA" or "pre-mRNA" includes the primary transcript and RNA processing intermediates; the spliceosome assembles on a pre-mRNA and carries out RNA splicing.

By "fragment" or "portion" is meant a full length or less than full length of the nucleotide sequence.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. The terms splice variant and splice isoform may be used interchangeably to denote different mRNAs which are a product of which may or may not encode the same protein, but are a result of differential splicing from the same initial pre-mRNA sequence. Specifically SCN8A exon 18A inclusion generates the SCN8A 18A mRNA transcript variant, while SCN8A exon 18N inclusion generates the SCN8A 18N mRNA transcript variant. Similarly, SCN8A exon 5A inclusion generates the SCN8A 5A mRNA transcript variant, while SCN8A exon 5N inclusion generates the SCN8A 5N mRNA transcript variant. Generally, nucleotide sequence variants of the invention will have in at least one embodiment 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

The terms "isolated and/or purified" refer to in vitro isolation of a nucleic acid, e.g., a DNA or RNA molecule from its natural cellular environment, and from association with other components of the cell or test solution (e.g. RNA pool), such as nucleic acid or polypeptide, so that it can be sequenced, replicated, and/or expressed. Thus, the RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

Nucleic acid molecules having base substitutions (i.e., variants) are prepared by a variety of methods known in the art. These methods include, but are not limited to, isolation from a natural source (in the case of naturally occurring sequence variants) or preparation by oligonucleotide-mediated (or site-directed) mutagenesis, PCR mutagenesis, and cassette mutagenesis of an earlier prepared variant or a non-variant version of the nucleic acid molecule.

"As used herein, the term "derived" or "directed to" with respect to a nucleotide molecule means that the molecule has complementary sequence identity to a particular molecule of interest.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The terms "protein," "peptide" and "polypeptide" are used interchangeably herein.

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may results form, for example, genetic polymorphism or from human manipulation. Methods for such manipulations are generally known in the art.

"Polypeptide" refers to a polymer composed of amino acid residues, related naturally occurring structural variants, and synthetic non-naturally occurring analogs thereof linked via peptide bonds. Synthetic polypeptides can be synthesized, for example, using an automated polypeptide synthesizer. The term "protein" typically refers to large polypeptides.

The term "peptide" typically refers to short polypeptides. Conventional notation is used herein to portray polypeptide sequences: the left-hand end of a polypeptide sequence is the amino-terminus; the right-hand end of a polypeptide sequence is the carboxyl-terminus. A "polynucleotide" means a single strand or parallel and anti-parallel strands of a nucleic acid. Thus, a polynucleotide may be either a single-stranded or a double-stranded nucleic acid. In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T." The term "recombinant DNA" as used herein is defined as DNA produced by joining pieces of DNA from different sources.

The term "recombinant polypeptide" as used herein is defined as a polypeptide produced by using recombinant DNA methods.

By the term "specifically binds," as used herein, is meant a molecule, such as an SMO, which recognizes and binds to another molecule or feature (i.e., the target pre-mRNA), but does not substantially recognize or bind other molecules or features in a sample (i.e., other non-target pre-mRNAs). Two nucleic acids substantially recognize or bind to each other when at least about 50%, preferably at least about 60% and more preferably at least about 80% of corresponding positions in each of the molecules are occupied by nucleotides which normally base pair with each other (e.g., A:T, A:U and G:C nucleotide pairs). Most preferably, two nucleic acids substantially recognize or bind to each other when at least about 90%-100% of corresponding positions in each of the molecules are occupied by nucleotides which normally base pair with each other (e.g., A:T, A:U and G:C nucleotide pairs). In another embodiment, the molecule may be an antibody. Chemical modification of the nucleic acid in part determines hybridization energy and thus how many base pairs are required for specific binding of the SMO nucleic acid sequence and a target nucleic acid sequences. Such calculations are well within the ability of those skilled in the art.

By the term "splice defect of a protein", as used herein, is meant a defective protein resulting from a defect in the splicing of an RNA encoding a protein.

The term "treatment," as used herein, refers to reversing, alleviating, delaying the onset of, inhibiting the progress of and/or preventing a disease or disorder, or one or more symptoms thereof, to which the term is applied in a subject. In some embodiments, treatment may be applied after one or more symptoms have developed. In other embodiments, treatment may be administered in the absence of symptoms. For example, treatment may be administered prior to symptoms (e.g., in light of a history of symptoms and/or one or more other susceptibility factors), or after symptoms have resolved, for example to prevent or delay their reoccurrence.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual and partial numbers within that range, for example, 1, 2, 3, 4, 5, 5.5 and 6. This applies regardless of the breadth of the range.

The invention will now be illustrated by the following non-limiting Example(s).

Example 1

As described herein, novel SMOs were designed to specifically and potently skip selected alternatively spliced exons in SCN8A and the efficacy of these SMOs was subsequently validated in mouse models of epilepsy.

Previously, novel SMOs were developed to modulate alternative splicing of the flip/flop cassette exons of AMPA receptor (AMPA-R) subunits GluA1 and GluA3 as drug candidates for treating intractable epilepsies and amyotrophic lateral sclerosis (ALS). AMPA-Rs are the major excitatory neurotransmitter receptors in the CNS. The well-validated mechanism for reducing network hyperexcitability and excitotoxicity is that reducing GluA-flip exon expression produce AMPA-Rs with much lower sensitivity to glutamate, greatly increased desensitization, and reduced $Ca^{2+}$ permeability. Using the SMO design strategy outlined below, two novel phosphorothioate 2'-O-methyl SMOs, LSP-GR1 and LSP-GR3 (GR1 and GR3) were developed, which potently and very specifically reduced expression of GluA1-flip and GluA3-flip, respectively. The efficacy and specificity of these SMOs was determined by real-time PCR (QPCR) after ICV bolus delivery in neonatal mice. Both GR1 and GR3 showed extraordinary specificity and potency in reducing the expression of their targeted GluA-flip isoforms, without significantly altering other closely related GluA-flip or GluA-flop isoforms (FIG. 1A).

Figure 1B:
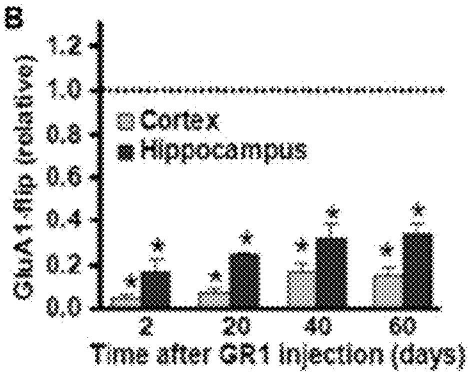
FIG. 1B. A single bilateral ICV injection of LSP-GR1 in 10 d old mice (2 μg per ventricle) produced a 60-80% reduction in GluA1-flip transcripts that was sustained for 2 months after the injection (n=4-5 mice per group; $p<0.001$). For each subset, the bar representing the cortex is shown on the left as a light grey bar and the bar representing the hippocampus is shown on the right as a dark grey bar.

Extraordinary longevity of SMO activity was shown after one bilateral ICV bolus injection of the GR1 at P10 (FIG. 1B). Potent reduction of GluA1-flip expression was observed in the brains of mice 60 d after a single ICV injection. Importantly, mice tested 20 days after P10 injection (at P30), showed no motor deficits or impairment in the Y-maze, a GluA1-dependent working memory task (Sanderson et. al., 2008)(not shown). Remarkably, GR1 activity was demonstrated out to 24 weeks after a single 50 μg spinal intrathecal injection (not shown). Thus drug dosing in humans should be much less frequent than for short-lived small molecules. LSP-GR1 effects on seizure thresholds were examined and it was found that GR1-treated neonatal mice exhibited significantly less severe seizures in response to the convulsant kainate (KA), and none of the GR1-treated mice progressed to status epilepticus (SE) (FIG. 1D). Mice treated with GR1 required 77% more KA to reach SE at P10 (not shown). Injection of GR1 90 min post-seizure at P10 prevented the SE-induced reduction in seizure thresholds at P12 whereas naïve and GR1-treated mice required significantly more KA respectively to reach SE than saline control SE-experienced mice (FIG. 1E). Whole-cell patch-clamp studies confirmed that GR1 greatly reduced AMPA excitatory post-synaptic currents (aEPSCs) (FIG. 1F). Thus GR1 is a highly potent, specific, and long lasting modulator of GluA1 alternative splicing that provides robust neonatal anti-seizure activity.

SMOs for Targeting SCN8A

Figure 1C:
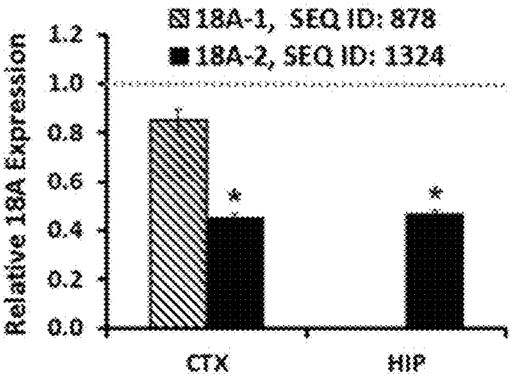
FIG. 1C. Initial evaluation of 2 candidate SCN8A-18A targeting SMOs: E18A-1 (5' g uuu cca cug gca ugc aga agg 3': SEQ ID #878 with n=3 cortex only (dark grey bar); and E18A-2 (5' AGGGUCUCAAAGCUCUUAGGGUC 3': SEQ ID #1324), cortex and hippocampus, n=6 (light grey bars) in P10 pups after P3, P5, and P7 ICV injection (4 μg/ventricle) showed significant reduction in 18A isoform levels. (* denotes $p<0.05$).
Figure 1D:
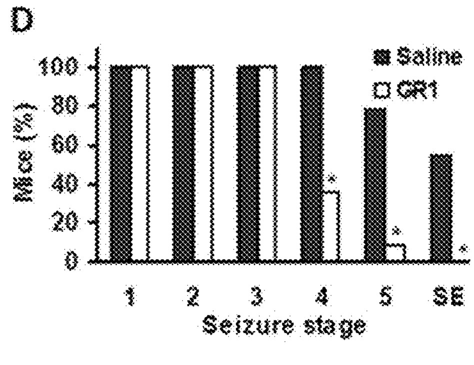
FIGS. 1D-F. ICV injection of LSP-GR1 (GR1) protected neonatal mice from KA-induced seizures, and prevented status epilepticus (SE)-induced increase in AMPA-R (a)EPSCs.
Figure 1E:
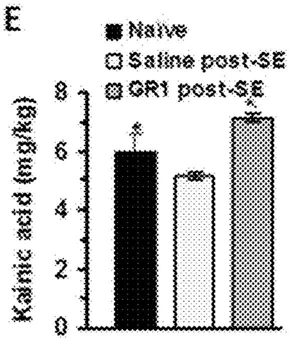
Figure 1F:
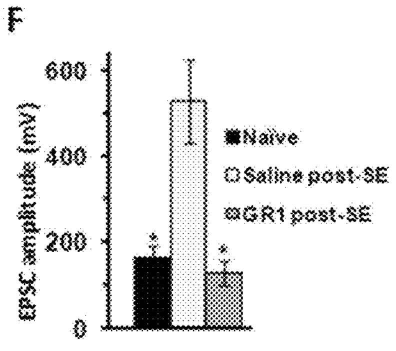

Preliminary in vivo analysis of two candidate SMOs for targeting SCN8A exon 18A, showed that ICV injection of the 18A-2 SMO achieved ~55% exon 18A skipping which is already greater than the 50% reduction expected to be therapeutic (FIG. 1C). SMOs have a significant therapeutic advantage over traditional small molecule inhibitors in that they can precisely target SCN8A splicing, allowing for a highly specific mechanism of action. The strategy of specifically reducing only the Na+ channel that counterbalances SCN1A input (SCN8A) should be a far more effective strategy and cause fewer adverse effects than using sodium channel blockers which antagonize multiple VGS channels. Further, by regulating alternative splicing, an SMO directed against exon 5A specifically reduces excitatory channel properties, rather than simply downregulating overall expression. Additionally, splice regulation of 18A is known to be differentially controlled in non-neuronal cells, thus SMO that escapes from the CNS in active form during normal metabolism is unlikely to affect splicing, or have on-target effects outside of the CNS (Zubovic et. al., 2012). In contrast to classic antisense compounds and siRNAs, SMOs do not recruit degradation enzymes (RNAseH, dicer) and therefore do not cause off-target degradation of transcripts. SMOs bind to their targets with exceptional potency, specificity, and negligible off-target effects (Eckstein 2007). Two SMOs are showing great promise in clinical trials for treating Duchene muscular dystrophy and Spinal muscular atrophy (Disterer et. al., 2014; Porensky and Burghes 2013)

Currently, there are no drugs in clinical use that specifically modulate SCN8 channel/SCN8A subunit properties or expression. The SMOs described herein can be used to treat, e.g., Dravet spectrum epilepsies refractory to current therapies. SMOs are designed for complete selectivity in targeting SCN8A isoform expression without affecting any other highly related VGS channel subunits. Moreover, the SCN8A gene is nearly 100% conserved between mouse and human surrounding the SMO target sites, such that SMOs validated in the mouse model is directly applicable to humans. It has been clearly documented that SMOs are widely distributed and biologically active throughout the CNS after direct delivery to CSF without the necessity of a carrier (Smith et. al., 2006; Williams et. al., 2009) (also see FIG. 1B). However, SMOs alone do not cross the blood-brain barrier when taken orally or parenterally. Clinically, SMOs are administered intrathecally, intracerebroventricularly (ICV), or potentially intranasally (via aerosolized nose spray). Intrathecal osmotic pumps are currently used in over 500,000 patients to treat chronic pain and spasticity, and are well-tolerated. SMOs delivered via spinal intrathecal injections have been shown to reach the brain in rodents and non-human primates (Hua et. al., 2010; Kordasiewicz et. al., 2012; Smith et. al., 2006; Williams et. al., 2009) and have been shown to be well-tolerated in clinical trials in infants and children with SMA. Additionally, implantation of the Omaya reservoir for direct brain/CNS delivery has been used in children as young as 9 months of age (Stephan et. al., 1992). Thus, no further formulation of SMOs is necessary to enable their clinical usage. The highly negative prognosis of uncontrolled seizures in SMEI patients warrants the more invasive delivery system currently necessary for SMO therapy. However, brain delivery of SMOs and other antisense technologies via non-invasive intranasal administration is preferential (Hashizume et. al., 2008; Lee et. al., 2012).

The studies described herein provide the first evidence that SMO-mediated direction of alternative splicing of SCN8A is therapeutic for pediatric seizure disorders, specifically Dravet and related syndromes, in addition to other forms of epilepsy.

Novel drug candidates called Splice Modulating Oligonucleotides (SMOs) will specifically and potently decrease splicing of 1) the SCN8A 18A isoform, resulting in less fully-functional SCN8A and 2) the 5A isoform, modulating channel kinetics to reduce sodium currents. SMOs are developed that decrease expression of SCN8A 5A and 18A isoforms. Also, the dose-response profiles of the top 5A and 18AN SMOs will be determined for increasing seizure threshold to flurothyl in 5-6 week old wild type mice. Further, the efficacy of the top 5A and 18AN SMOs will be evaluated in decreasing susceptibility to febrile seizures and increasing survival in a mutant SCN1A mouse model. Together, these experiments are expected to establish 5A and/or an 18AN SMO as potential drugs for the treatment of children with Dravet Spectrum epilepsies for which there is a significant unmet need. An SMO is currently in clinical trials to treat spinal muscular atrophy (SMA), a devastating neurological disorder of infancy, and thus far, is showing efficacy, safety, and tolerability when delivered by intrathecal injection directly into the CNS (Disterer et. al., 2014).

Design of Splice Modulating Oligonucleotides (SMOs)

[Splice modulating oligonucleotides (SMOs) are designed and validated that specifically and potently modulate SCN8A pre-mRNA splicing to decrease expression of the 18A and 5A isoforms and determine the dose-response profile of the top 2 SMOs (one each for 18A and 5A skipping) in normal mice. Candidate SMOs are developed that target splicing of both human and mouse SCN8A pre-mRNA to reduce expression of the 18A and 5A isoforms. A proven set of molecular engineering tools are used to identify ranked panels of SMOs that decrease the expression of the SCN8 exon 18A and 5A isoforms. The process is refined iteratively to select the most potent SMO candidates for further testing.

SMOs are developed to facilitate specific skipping of exons 5A and 18A, resulting in significantly reduced excitatory function of SCN8 channels. 2'OMe steric block oligomers modulate pre-mRNA splicing through high affinity binding to complementary sequences containing specific splicing elements, resulting in potent and efficient skipping of the targeted exon (Aartsma-Rus et. al., 2005; Aartsma-Rus et. al., 2006; Buvoli et. al., 2007; Wheeler et. al., 2007) (see, FIG. 1C). Pre-mRNA splicing is controlled by the spliceosome, a large ribonucleoprotein (RNP) complex with many auxiliary proteins and small non-coding RNAs. These factors bind to specific splice enhancer and suppressor sequences (motifs) on pre-mRNAs near intron-exon boundaries and coordinate the splicing of pre-mRNA to mRNA. Exons 18A/18N and exons 5A/5N are mutually exclusive cassette exons. Steric blocking of intronic/exonic splice enhancers (ISE/ESEs) and/or 3' and 5' splice sites, while avoiding intronic/exonic splice silencer (ISS/ESS) motifs, prevents spliceosomal recognition of the exon. Thus, when critical splice recognition sequences of an exon are masked by an SMO, the entire intron-exon-intron sequence is treated as a single intron, and the targeted exon is excluded from the resultant mRNA.

To minimize the number of SCN1A knock-in mice needed, the dosing strategy is optimized in normal mice. C57/BL6 mice are used as they are the background strain of the SCN1A mutant GEFS+ mice to be tested below. While complete SCN8A KO causes a severe phenotype in mice including motor system degeneration and early lethality (Martin et. al., 2007; Meisler et. al., 2004) and haplosinsufficient SCN8A mice exhibit spike wave discharges characteristic of absence seizures (Papale et. al., 2009), similar mutations have been found in humans with only mild impact on cognition (Trudeau et. al., 2006). SCN8A haploinsufficiency is adequate to modify the Dravet's phenotype of SCN1A mutant mice, without causing an adverse phenotype (Hawkins et. al., 2011; Martin et. al., 2007; Meisler et. al., 2010), however adverse effects may limit SMO dosing in WT mice. All mice are monitored daily for gross signs of toxicity including weight loss, paralysis, and tremor. For all studies described herein, groups are weight, sex, and litter-matched to reduce phenotypic variability.

Design of Phosphorothioate 2'-O-Methyl Modified SMOs which Targets Splicing of Both Human and Mouse SCN8A Pre-mRNA to Reduce Expression of the 18A and 5A Isoforms.

This process first requires in silico prediction of critical splicing motifs, which encompasses the use of the most advanced RNA and oligo analysis tools. SMOs targeting SCN8A alternative splicing is designed to target either the 3' or 5' splice sites and/or sequences corresponding to predicted ESE/ISE clusters near the splice junctions of exons 5A and 18A. The following summarizes the SMO design process:

Step 1. Identification of Conservation Between Human and Mouse SCN8A Sequences.

Alignments of the highly conserved SCN1-11A gene sequences have been performed to ensure specificity of SMO sites targeting SCN8A splicing, and complete conservation between mouse and human. Thus, SMOs developed and tested in mice can be translated directly to human use.

Step 2 Identification of ESE/ESS/ISE Motifs Surrounding the 3' and 5' Splice Sites of Alternatively Spliced Exons in SCN8A Pre-mRNA.

Splice modulation sites for SCN8A exons 5A and 18A have completely conserved regulatory motifs between mouse and human. ESE motifs were defined using ESE Finder (Cartegni et. al., 2003) RESCUE-ESE (Dravet et. al., 2011; Fairbrother et. al., 2002) and PESX (Zhang and Chasin 2004). ESS elements were predicted by PESX, and the two hexamer data set analysis by FAS-ESS (Wang et. al., 2004) tool. Finally, ISE motifs are predicted using the ACESCAN2 application (Yeo et. al., 2005; Yeo et. al., 2007).

Step 3. RNA Structure and Thermodynamics of SCN8A Target Sequences. The RNA Structure program (Mathews et. al., 2004) predicts secondary structure of target sequences and thermodynamic properties of all potential SMOs targeting SCN8A. Additionally, sequence motifs and structures known or predicted to cause immune stimulation or other toxicities, are screened for, and avoided.

Step 4. BLAST Analysis of Potential Off-Target Hybridization.

All candidate SMOs are screened using BLASTN analysis for potential hybridization to off-target sites in the human/mouse genomes. SMOs with greater than 85% off-target hybridization to any other known gene product are not considered.

Step 5. Prioritization of SMOs Based on Combined Properties.

Thermodynamic properties between SMOs and their target, and self-self binding energies of SMOs, splice site strength, and splicing motifs are combined to establish top candidate SMOs for empirical evaluation of splicing specificity and efficiency. These parameters used to predict top candidate SMOs are all contained in the above referenced oligonucleotide and RNA structure predictive software.

In Vivo Splicing Efficacy

In vivo splicing efficacy of top candidate SMOs are tested in neonatal pups. Splicing efficacy of the top ranked SMOs determined above are validated using well-established in vivo screening protocol in neonatal mice by ICV delivery, and measuring transcript levels with real-time PCR. This testing determines the most effective SMOs (one each targeting SCN8A 5A and 18A exons). Dose-response and dose-timing profile of lead SMOs in reducing SCN8A 5A and 18A expression, respectively, are performed in normal mice and examined at P15, and P42 (6 weeks of age). Dose-response measures both mRNA expression by QPCR and protein expression by Western blot.

Test of In Vivo Splicing Efficacy of Top Candidate SMOs in Neonatal Pups. The in silico splice prediction technology allows bypassing costly and time consuming high throughput oligonucleotide screening. SMO development requires an iterative process of SMO evaluation and optimization, where splicing efficacy of the top 2 ranked SMOs is evaluated, and the results used to strategically select the next top candidate SMOs. For example, 10 SMOs may be used to fully optimize splicing efficiency (see, e.g., Table 1).

TABLE 1

Testing candidate SMOs

| Groups | Treatment | Dose (μg) |
|---|---|---|
| 1-10 | 18A SMOs #1-10 | 4 μg bilateral |
| 11 | Saline | N/A |
| 2-21 | 5A SMOs #1-10 | 4 μg bilateral |
| 22 | Saline | N/A |

Although complete reduction of 18A expression is not desirable, increased SMO potency increases the therapeutic index. Specificity of SMOs that pass the initial screen for potency are confirmed against other highly conserved SCN subunits using QPCR (as done for GR1; FIG. 1A). For all in vivo studies, treated and control animals are litter-matched to reduce variability. FVBs are the preferred strain for SMO screening because of their large litter size, and good maternal care. FVB neonatal mice are given free-hand bilateral injections of SMO on post-natal (P)1, P3, and P5 into the lateral ventricles and brain tissues are harvested at P10 as previously described (Williams et. al., 2009). Cortex and hippocampus are rapidly dissected; RNA isolated, converted cDNA using Multiscribe with random hexamer primers. Custom TaqMan QPCR assays have been designed to specifically detect 5A and 18A isoforms and validated for efficiency over 5 logs of cDNA concentration (not shown). Expression of 5A and 18A transcripts are evaluated by the ΔΔCT method (Livak and Schmittgen 2001) relative to endogenous control (β-Actin). Saline mice are used as controls for multiple SMOs within litter (n=3 mice per SMO; up to 30 SMO-treated or saline mice for 18A and 5A).

We designed and validated splice modulating oligonucleotides (SMOs) that specifically and potently modulate SCN8A pre-mRNA splicing to decrease expression of either the 18A and 5A isoforms. Ten candidate SMO sequences selected by iterative in silico analysis were tested in vivo with bilateral ICV injection in neonatal mouse pups for the ability to direct skipping of SCN8A exon 18A at various doses and dose frequencies. Based on this initial screening, change in splicing for the highest dose tested for each candidate SMO are shown (FIG. 2A) The most potent candidate SMOs after a single 4 μg/bilateral ICV dose were compared to LSP-GR1 for relative efficacy at directing targeted exon skipping (FIG. 2B). Preliminary CNS distribution and assessment of the adverse effects profile of the top 4 SMOs (SCN8A-18A-5—SEQ ID: 1306, 18A-8—SEQ ID: 1307, 18A-9—SEQ ID: 1422, and 18A-10—SEQ ID: 1541) at a maximal intrathecal (IT) dose of 50 μg/5 μL/3 min in adult mice was used to further screen the candidate SMOs the top candidate SMOs (FIG. 2C). SCN8A-18A-9 (18A-9—SEQ ID: 1422) was initially selected for additional testing.

Figure 2E:
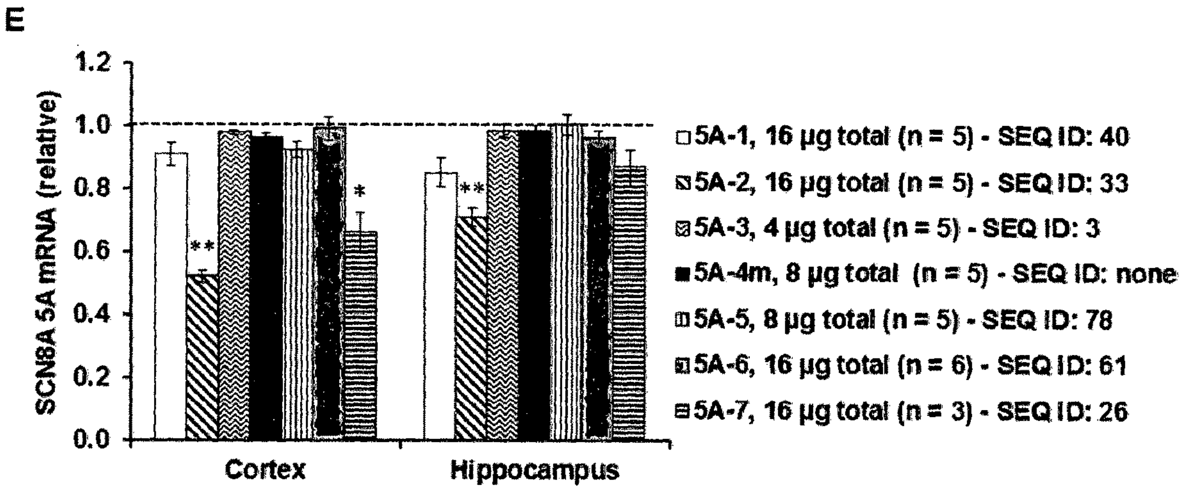
FIGS. 2E-F. Comparison of candidate SCN8A exon 5A skipping SMOs.
Figure 2F:
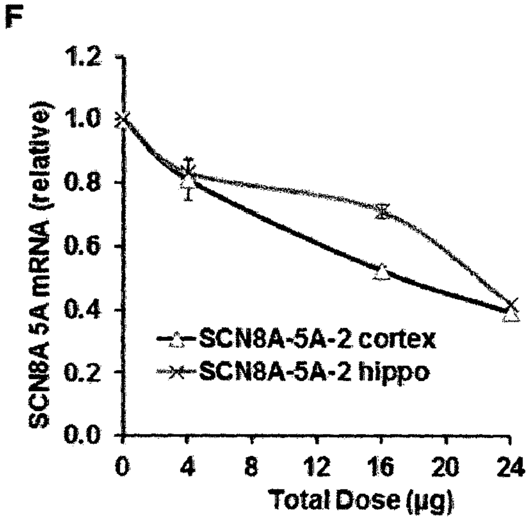

Seven candidate SMO sequences selected by iterative in silico analysis were tested in vivo with bilateral ICV injection in neonatal mouse pups for the ability to direct skipping of SCN8A exon 5A at various doses and dose frequencies. Based on this initial screening, change in splicing for the highest dose tested for each candidate SMO are shown (FIG. 2E). However, SCN8A-5A-2 (5A-2—SEQ ID: 33) produced the most potent splicing response thus far, an effect which is statistically significant at all measures and dose-responsive, such that exon 5A skipping continues to increase with increasing total SMO dose from 4-24 μg (FIG. 2F).

Dose-Response and Timing Profile

Dose-Response and Timing Profile of Two Lead SMOs in Reducing SCN8A 5A and 18A Expression.

A similar injection regimen and QPCR analysis protocol as described above are used, with harvest at two time points, P15 and P42 (6 weeks), to find dosing paradigms that give 25, 50, and 75% knockdown at P15 and last out to 6 weeks. These paradigms are used test lead 5A and 18A SMOs in normal and SCN1A$^{RH/RH}$ mice seizure and longevity studies. Based on the real-time PCR results SMO-mediated reduction of the 18A and 5A isoforms as our index of splicing efficacy is calculated at the various doses. Additionally for 18A SMO treatment, western blot is used to determine correlation between mRNA production and protein expression, as described previously (Martin et. al., 2010). Antibodies are not available to distinguish between SCN8A 5A and 5N isoforms. The experimental groups are defined in Table 2.

TABLE 2

Dose-response profile of lead SMOs

| Groups | Treatment | Dose (μg) | Total mice |
|---|---|---|---|
| 1 | 18A SMO | 6, 4, 2 | 60 |
| 2 | 5A SMO | 6, 4, 2 | 60 |
| 3 | saline | N/A | Up to 60 |

Freehand ICV injections may be performed as frequently as every other day from P1-P12, however based on previous experiments, only 1-2 doses are likely necessary to achieve optimal splicing efficacy (see, FIG. 1B). As expected, a single 4 μg 18A-9 (SEQ ID: 1422) SMO dose in neonatal (P3-5) C57BL/6 mice produced lasting exon 18A skipping out to P28 without any decrement in splicing activity (FIG. 2A). Although significant SCN8A exon 18A splicing remains at P42, the effect is not as robust as seen at earlier time points, suggesting multiple doses or a different dosing timing may be necessary to maintain effect out to 6 weeks (see, FIG. 2D).

Determination of Efficacy of SMOs

The threshold to flurothyl-induced seizures in normal mice after optimized dosing of the SMOs is determined, as SCN8A loss-of-function mutations increase seizure thresholds to flurothyl (Martin et. al., 2007). Also, the efficacy of SMOs is determined (skipping SCN8A 5A and 18A exons) at extending lifespan and reducing spontaneous seizures in a mouse model of GEFS+(SCN1A R1648H).

The effect of SMO treatment on seizure threshold in normal mice is determined. Based on the dose-response data determined above, three SMO doses (25, 50, 75% splicing) are selected for testing in P15 and 5-6 week old mice to examine seizure threshold responses to flurothyl induced seizures. SMO potency and efficacy determines dosing for further experimentation.

The two top SMOs (18A and 5A) are assessed for efficacy in reducing the number of spontaneous seizures in SCN1 $A^{RH/RH}$ mice (Martin et. al., 2010), as a correlative measure to survival.

The efficacy of the two top SMOs (18A and 5A) are evaluated for ability to extend lifespan in SCN1$A^{RH/RH}$ mice, which die by P16-26 without treatment (Martin et. al., 2010).

Directing splicing of SCN8A to skip the 18A or 5A exon (favoring production of the 18N or 5N containing isoforms) diminishes SCN8A-mediated excitation and ameliorates the effects of SCN1A mutations, as when SCN1A and SCN8A loss-of-function mutations occur together (Hawkins et. al., 2011; Martin et. al., 2007; Meisler et. al., 2010).

To accomplish this novel targeting strategy, alternative splicing of the SCN8A channel is directed in order to control channel properties by developing compounds called splice modulating oligonucleotides (SMOs). SMOs are a class of synthetic RNA based compounds that bind directly to a complementary sequence on pre-mRNA and function by sterically blocking or weakening interactions between elements of the splice machinery and the pre-mRNA. The 18A and 18N exons are mutually exclusive cassette exons such that when one exon is excluded the other exon is included. Thus, directing splicing to exclude (skip) the SCN8A exon 18A results in inclusion of exon 18N (truncated isoform) and thereby effectively reduces expression of the full length functional 18A isoform. Similarly, the 5A/5N exons are also mutually exclusive cassette exons, and directing splicing to skip SCN8A exon 5A result in inclusion of exon 5N (decreased gain isoform) and to reduce expression of the undesirable increased gain 5A isoform.

Mice with the SCN8$A^{med/+}$ mutation (resulting in partial SCN8A loss of function) exhibit resistance to flurothyl induced seizure by 5-6 weeks of age (Martin et. al., 2007). The SMO-mediated reduction of SCN8A 18A or 5A isoform expression modulates SCN8A-mediated sodium current in a similar manner to the SCN8A "med" mutation. Thus, the optimal injection frequency as determined above to maintain effect from P15 to 6 weeks in WT mice is used for testing a range of SMO doses in increasing flurothyl seizure threshold in P15 and 5-6 week old WT mice, as physiological validation of our SMO strategy. The most effective dose and injection paradigm that causes seizure resistance in normal mice is used to determine if reducing SCN8A 18A or 5A isoforms can increase lifespan and ameliorate seizure susceptibility in SCN1A R1648H knock-in mice. Similar to SCN1A KO mice, homozygous R1648H (SCN1$A^{RH/RH}$) mice exhibit weight loss, spontaneous seizures, and susceptibility to febrile seizures starting at P14-16 and lethality by P16-26 (Martin et. al., 2010). However, heterozygous SCN1$A^{RH/+}$ mutant mice show a less severe phenotype than SCN1$A^{+/-}$ knockout mice with only ~15% exhibiting spontaneous seizures in adulthood, but do have increased susceptibility to flurothyl and hyperthermia induced seizures by 5-6 weeks of age (Martin et. al., 2010). SCN1A R1648H mutant mice are raised in-house on a C57BL/6 background with care, husbandry, and genotyping performed as described previously (Martin et. al., 2010).

Effect of SMO Treatment on Seizure Threshold in Normal Mice.

The effect of optimized SMO treatment on flurothyl-induced seizure threshold is determined first in P15 and then in 5-6 week old WT mice. The dose-response data (Table 2) is used to select 3 doses with ~25, 50, and 75% efficacy at reducing 18A and 5A expression for functional studies at each time point. C57/BL6 mice are given ICV injection with SMO or saline (Table 3, 18A SMO or 5A SMO for both the P15 and 5-6 week time points).

TABLE 3

Pre-seizure treatment with two lead SMOs

| Group | Treatment | SMO Doses (μg) | Total Mice |
|---|---|---|---|
| 1 | 18A SMO | TBD* 25, 50, 75% | 24 |
| 2 | 5A SMO | TBD* 25, 50, 75% | 24 |
| 3 | Saline | N/A | 48 |

Injection schedule is modified to achieve the indicated level of splicing. 8 mice/group.

Flurothyl seizures are performed as previously described, and outcome measures include latency to initial myoclonic jerk (MJ) and generalized tonic-clonic seizure (GTCS) (Martin et. al., 2007).

SMO Efficacy in Reducing in Spontaneous Seizures in SCN1$A^{RH/RH}$ Mice.

Starting at P15, SCN1$A^{RH/RH}$ mice are evaluated for 4 hrs daily on 3 consecutive days with number of observed behavioral seizures recorded. Efficacy of the two top SMOs (18A and 5A SMOs) are determined by reduction in number of spontaneous seizures in the SCN1$A^{RH/RH}$ mice (Martin et. al., 2010) as compared to saline littermate controls (Table 4).

TABLE 4

SCN1A mutant mouse seizure studies

| Group | Treatment | SMO Dose (μg) | Total Mice |
|---|---|---|---|
| 1 | 18A SMO | TBD* | 12 |
| 2 | 5A SMO | TBD* | 12 |
| 3 | Saline Control | N/A | 12 |

*TBD: dose which showed maximal efficacy and overt tolerability in normal mice in Aim 1 Experiment 3. 12 mice/dose/group, each for Aim 2 Experiments 2 and 3.

This assesses whether any increased in survival seen with SMO treatment is mediated by decreasing seizure activity.

Efficacy of Treatment with the Two Top SMOs (18A and 5A) is Evaluated by Survival in SCN1$A^{RH/RH}$ Mice.

SCN1$A^{RH/RH}$ mice exhibit weight-loss starting at ~P15 corresponding to the onset of spontaneous seizures, and die at ~P18.5 without treatment (Martin et. al., 2010). The SCN1A$^{RH/RH}$ mice treated with 18A or 5A SMO are also assessed daily for righting reflex, body weight, and survival compared to litter matched saline controls (Table 4).

Reduction of full length functional SCN8A (18A SMO) or reduction of "high gain" SCN8A (5A SMO) produces increased resistance to fluorothyl-induced seizures in P15 and 5-6 week old normal mice.

Reduction of sodium current through SCN8 channels, either by reducing full length functional channels (18A SMO) or by altering channel kinetics to a lower gain (5A SMO), reduces seizure frequency and increases survival in mutant SCN1A$^{RH/RH}$ mice. The SCN1A$^{RH/RH}$ mouse model was chosen in this application, rather than SCN1A mouse model, due to lack of success in transferring the highly fragile SCN1A knockout breeders from their home colony. Although SCN1A$^{RH/+}$ mice are a model of GEFS+, a less severe Dravet spectrum epilepsy, homozygous SCN1 A$^{RH/RH}$ mice present a severe, Dravet-like phenotype.

Statistical Analysis:

General statistical measures are performed using GraphPad or StatistiXL. Overall seizure scoring and real-time PCR results are evaluated by student's t-test with Bonferoni correction for multiple comparisons when appropriate. Longevity is analyzed using the Kaplan-Meier survival test. For all data analysis, statistical significance is set at ($p<0.05$).

REFERENCE LIST

Aartsma-Rus, A. et. al., "Functional analysis of 114 exon-internal AONs for targeted DMD exon skipping: indication for steric hindrance of SR protein binding sites", Oligonucleotides., 15 (4), 284-297 (2005).

Aartsma-Rus, A. et. al., "Therapeutic modulation of DMD splicing by blocking exonic splicing enhancer sites with antisense oligonucleotides", Ann. N.Y. Acad. Sci., 1082 74-76 (2006).

Antzelevitch, C. et. al., "Electrophysiologic basis for the antiarrhythmic actions of ranolazine", Heart Rhythm., 8 (8), 1281-1290 (2011).

Bender, A. C. et. al., "SCN1A mutations in Dravet syndrome: Impact of interneuron dysfunction on neural networks and cognitive outcome", Epilepsy Behav., (2012).

Black, J. A. and Waxman, S. G. "Sodium channels and microglial function", Exp. Neurol., 234 (2), 302-315 (2012).

Buvoli, M. et. al., "Interplay between exonic splicing enhancers, mRNA processing, and mRNA surveillance in the dystrophic Mdx mouse", PLoS. ONE., 2 (5), e427-(2007).

Carrithers, M. D. et. al., "Regulation of podosome formation in macrophages by a splice variant of the sodium channel SCN8A", J. Biol. Chem., 284 (12), 8114-8126 (2009).

Cartegni, L. et. al., "ESEfinder: A web resource to identify exonic splicing enhancers", Nucleic Acids Res., 31 (13), 3568-3571 (2003).

Catterall, W. A. et. al., "NaV1.1 channels and epilepsy", J. Physiol, 588 (Pt 11), 1849-1859 (2010).

Chen, Y. et. al., "Functional properties and differential neuromodulation of Na(v)1.6 channels", Mol. Cell Neurosci., 38 (4), 607-615 (2008).

Claes, L. et. al., "De novo mutations in the sodium-channel gene SCN1A cause severe myoclonic epilepsy of infancy", Am. J. Hum. Genet., 68 (6), 1327-1332 (2001).

De, Jonghe P. "Molecular genetics of Dravet syndrome", Dev. Med. Child Neurol., 53 Suppl 2 7-10 (2011).

Disterer, P. et. al., "Development of therapeutic splice-switching oligonucleotides", Hum. Gene Ther., 25 (7), 587-598 (2014).

Dravet, C. et. al., "Severe myoclonic epilepsy in infancy (Dravet syndrome) 30 years later", Epilepsia, 52 Suppl 2 1-2 (2011).

Dravet, C. et. al., "Severe myoclonic epilepsy in infancy: Dravet syndrome", Adv. Neurol., 95 71-102 (2005).

Eckstein, F. "The versatility of oligonucleotides as potential therapeutics", Expert. Opin. Biol. Ther., 7 (7), 1021-1034 (2007).

Estacion, M. et. al., "A novel de novo mutation of SCN8A (Nav1.6) with enhanced channel activation in a child with epileptic encephalopathy", Neurobiol. Dis., 69 117-123 (2014).

Fairbrother, W. G. et. al., "Predictive identification of exonic splicing enhancers in human genes", Science, 297 (5583), 1007-1013 (2002).

Fernandes, A. et. al., "Microglia and inflammation: conspiracy, controversy or control?", Cell Mol. Life Sci., (2014).

Fletcher, E. V. et. al., "Alternative splicing modulates inactivation of type 1 voltage-gated sodium channels by toggling an amino acid in the first S3-S4 linker", J. Biol. Chem., 286 (42), 36700-36708 (2011).

Gargus, J. J. and Tournay, A. "Novel mutation confirms seizure locus SCN1A is also familial hemiplegic migraine locus FHM3", Pediatr. Neurol., 37 (6), 407-410 (2007).

Garry, E. M. et. al., "Varicella zoster virus induces neuropathic changes in rat dorsal root ganglia and behavioral reflex sensitisation that is attenuated by gabapentin or sodium channel blocking drugs", Pain, 118 (1-2), 97-111 (2005).

Gazina, E. V. et. al., "Differential expression of exon 5 splice variants of sodium channel alpha subunit mRNAs in the developing mouse brain", Neuroscience, 166 (1), 195-200 (2010).

Han, S. et. al., "Autistic-like behaviour in Scn1a+/− mice and rescue by enhanced GABA-mediated neurotransmission", Nature, 489 (7416), 385-390 (2012).

Hashizume, R. et. al., "New therapeutic approach for brain tumors: Intranasal delivery of telomerase inhibitor GRN163", Neuro. Oncol., 10 (2), 112-120 (2008).

Hawkins, N. A. et. al., "Neuronal voltage-gated ion channels are genetic modifiers of generalized epilepsy with febrile seizures plus", Neurobiol. Dis., 41 (3), 655-660 (2011).

Heinzen, E. L. et. al., "Nova2 interacts with a cis-acting polymorphism to influence the proportions of drug-responsive splice variants of SCN1A", Am. J. Hum. Genet., 80 (5), 876-883 (2007).

Hua, Y. et. al., "Antisense correction of SMN2 splicing in the CNS rescues necrosis in a type III SMA mouse model", Genes Dev., 24 (15), 1634-1644 (2010).

Kennedy, P. G. et. al., "Varicella-zoster viruses associated with post-herpetic neuralgia induce sodium current density increases in the ND7-23 Nav-1.8 neuroblastoma cell line", PLoS. ONE., 8 (1), e51570-(2013).

Kordasiewicz, H. B. et. al., "Sustained therapeutic reversal of Huntington's disease by transient repression of huntingtin synthesis", Neuron, 74 (6), 1031-1044 (2012).

Kuwabara, S. et. al., "Latent addition in human motor and sensory axons: different site-dependent changes across the carpal tunnel related to persistent Na+ currents", Clin. Neurophysiol., 117 (4), 810-814 (2006).

Lee, S. T. et. al., "miR-206 regulates brain-derived neurotrophic factor in Alzheimer disease model", Ann. Neurol., 72 (2), 269-277 (2012).

Licatalosi, D. D. et. al., "HITS-CLIP yields genome-wide insights into brain alternative RNA processing", Nature, 456 (7221), 464-469 (2008).
Livak, K. J. and Schmittgen, T. D. "Analysis of relative gene expression data using real-time quantitative PCR and the 2-[Delta][Delta] CT method", Methods, 25 402-408 (2001).
Makinson, C. D. et. al., "Role of the hippocampus in Nav1.6 (Scn8a) mediated seizure resistance", Neurobiol. Dis., 68 16-25 (2014).
Mao, Q. et. al., "The up-regulation of voltage-gated sodium channel Nav1.6 expression following fluid percussion traumatic brain injury in rats", Neurosurgery, 66 (6), 1134-1139 (2010).
Martin, M. S. et. al., "Altered function of the SCN1A voltage-gated sodium channel leads to gamma-aminobutyric acid-ergic (GABAergic) interneuron abnormalities", J. Biol. Chem., 285 (13), 9823-9834 (2010).
Martin, M. S. et. al., "The voltage-gated sodium channel Scn8a is a genetic modifier of severe myoclonic epilepsy of infancy", Hum. Mol. Genet., 16 (23), 2892-2899 (2007).
Mathews, D. H. et. al., "Incorporating chemical modification constraints into a dynamic programming algorithm for prediction of RNA secondary structure", Proc. Natl. Acad. Sci. U.S.A, 101 (19), 7287-7292 (2004).
Meisler, M. H. and Kearney, J. A. "Sodium channel mutations in epilepsy and other neurological disorders", J. Clin. Invest, 115 (8), 2010-2017 (2005).
Meisler, M. H. et. al., "Sodium channel gene family: epilepsy mutations, gene interactions and modifier effects", J. Physiol, 588 (Pt 11), 1841-1848 (2010).
Meisler, M. H. et. al., "Allelic mutations of the sodium channel SCN8A reveal multiple cellular and physiological functions", Genetica, 122 (1), 37-45 (2004).
Norden, D. M. and Godbout, I P. "Review: microglia of the aged brain: primed to be activated and resistant to regulation", Neuropathol. Appl. Neurobiol., 39 (1), 19-34 (2013).
Nutini, M. et. al., "Increased expression of the beta3 subunit of voltage-gated Na+ channels in the spinal cord of the SOD1G93A mouse", Mol. Cell Neurosci., 47 (2), 108-118 (2011).
O'Roak, B. J. et. al., "Exome sequencing in sporadic autism spectrum disorders identifies severe de novo mutations", Nat. Genet., 43 (6), 585-589 (2011).
O'Roak, B. J. et. al., "Sporadic autism exomes reveal a highly interconnected protein network of de novo mutations", Nature, 485 (7397), 246-250 (2012).
Oakley, J. C. et. al., "Temperature- and age-dependent seizures in a mouse model of severe myoclonic epilepsy in infancy", Proc. Natl. Acad. Sci. U.S.A, 106 (10), 3994-3999 (2009).
Ogiwara, I. et. al., "Nav1.1 localizes to axons of parvalbumin-positive inhibitory interneurons: a circuit basis for epileptic seizures in mice carrying an Scn1a gene mutation", J. Neurosci., 27 (22), 5903-5914 (2007).
Ohba, C. et. al., "Early onset epileptic encephalopathy caused by de novo SCN8A mutations", Epilepsia, 55 (7), 994-1000 (2014).
Oliva, M. et. al., "Sodium channels and the neurobiology of epilepsy", Epilepsia, 53 (11), 1849-1859 (2012).
Papale, L. A. et. al., "Heterozygous mutations of the voltage-gated sodium channel SCN8A are associated with spike-wave discharges and absence epilepsy in mice", Hum. Mol. Genet., 18 (9), 1633-1641 (2009).
Plummer, N. W. et. al., "Alternative splicing of the sodium channel SCN8A predicts a truncated two-domain protein in fetal brain and non-neuronal cells", J. Biol. Chem., 272 (38), 24008-24015 (1997).
Porensky, P. N. and Burghes, A. H. "Antisense oligonucleotides for the treatment of spinal muscular atrophy", Hum. Gene Ther., 24 (5), 489-498 (2013).
Raman, I. M. et. al., "Altered subthreshold sodium currents and disrupted firing patterns in Purkinje neurons of Scn8a mutant mice", Neuron, 19 (4), 881-891 (1997).
Raymond, C. K. et. al., "Expression of alternatively spliced sodium channel alpha-subunit genes. Unique splicing patterns are observed in dorsal root ganglia", J. Biol. Chem., 279 (44), 46234-46241 (2004).
Sanderson, D. J. et. al., "The role of the GluR-A (GluR1) AMPA receptor subunit in learning and memory", Prog. Brain Res., 169 159-178 (2008).
Schlachter, K. et. al., "A splice site variant in the sodium channel gene SCN1A confers risk of febrile seizures", Neurology, 72 (11), 974-978 (2009).
Sierra, Bello O. et. al., "In silico docking reveals possible Riluzole binding sites on Nav1.6 sodium channel: implications for amyotrophic lateral sclerosis therapy", J. Theor. Biol., 315 53-63 (2012).
Silberstein, S. D. and Dodick, D. W. "Migraine genetics: Part II", Headache, 53 (8), 1218-1229 (2013).
Singh, R. et. al., "Generalized epilepsy with febrile seizures plus: a common childhood-onset genetic epilepsy syndrome", Ann. Neurol., 45 (1), 75-81 (1999).
Smith, R. A. et. al., "Antisense oligonucleotide therapy for neurodegenerative disease", J. Clin. Invest, 116 (8), 2290-2296 (2006).
Stephan, J. L. et. al., "Treatment of central nervous system B lymphoproliferative syndrome by local infusion of a B cell-specific monoclonal antibody", Transplantation, 54 (2), 246-249 (1992).
Tang, B. et. al., "A BAC transgenic mouse model reveals neuron subtype-specific effects of a Generalized Epilepsy with Febrile Seizures Plus (GEFS+) mutation", Neurobiol. Dis., 35 (1), 91-102 (2009).
Trudeau, M. M. et. al., "Heterozygosity for a protein truncation mutation of sodium channel SCN8A in a patient with cerebellar atrophy, ataxia, and mental retardation", J. Med. Genet., 43 (6), 527-530 (2006).
Vaher, U. et. al., "De Novo SCN8A Mutation Identified by Whole-Exome Sequencing in a Boy With Neonatal Epileptic Encephalopathy, Multiple Congenital Anomalies, and Movement Disorders", J. Child Neurol., (2013).
Veeramah, K. R. et. al., "De Novo Pathogenic SCN8A Mutation Identified by Whole-Genome Sequencing of a Family Quartet Affected by Infantile Epileptic Encephalopathy and SUDEP", Am. J. Hum. Genet., 90 (3), 502-510 (2012).
Verret, L. et. al., "Inhibitory interneuron deficit links altered network activity and cognitive dysfunction in Alzheimer model", Cell, 149 (3), 708-721 (2012).
Wang, W. et. al., "The developmental changes of Na(v)1.1 and Na(v)1.2 expression in the human hippocampus and temporal lobe", Brain Res., 1389 61-70 (2011).
Wang, Z. et. al., "Systematic identification and analysis of exonic splicing silencers", Cell, 119 (6), 831-845 (2004).
Waxman, S. G. "Axonal conduction and injury in multiple sclerosis: the role of sodium channels", Nat. Rev. Neurosci., 7 (12), 932-941 (2006).
Weiss, S. et. al., "Riluzole protects against cardiac ischaemia and reperfusion damage via block of the persistent sodium current", Br. J. Pharmacol., 160 (5), 1072-1082 (2010).

Wheeler, T. M. et. al., "Correction of ClC-1 splicing eliminates chloride channelopathy and myotonia in mouse models of myotonic dystrophy", J. Clin. Invest, 117 (12), 3952-3957 (2007).

Williams, J. H. et. al., "Oligonucleotide-mediated survival of motor neuron protein expression in CNS improves phenotype in a mouse model of spinal muscular atrophy", J. Neurosci., 29 (24), 7633-7638 (2009).

Wilson, J. R. and Fehlings, M. G. "Riluzole for acute traumatic spinal cord injury: a promising neuroprotective treatment strategy", World Neurosurg., 81 (5-6), 825-829 (2014).

Xu, R. et. al., "A childhood epilepsy mutation reveals a role for developmentally regulated splicing of a sodium channel", Mol. Cell Neurosci., 35 (2), 292-301 (2007).

Yeo, G. W. et. al., "Discovery and analysis of evolutionarily conserved intronic splicing regulatory elements", PLoS. Genet., 3 (5), e85-(2007).

Yeo, G. W. et. al., "Identification and analysis of alternative splicing events conserved in human and mouse", Proc. Natl. Acad. Sci. U.S.A, 102 (8), 2850-2855 (2005).

Yu, F. H. et. al., "Reduced sodium current in GABAergic interneurons in a mouse model of severe myoclonic epilepsy in infancy", Nat. Neurosci., 9 (9), 1142-1149 (2006).

Zhang, X. H. and Chasin, L. A. "Computational definition of sequence motifs governing constitutive exon splicing", Genes Dev., 18 (11), 1241-1250 (2004).

Zubovic, L. et. al., "Mutually exclusive splicing regulates the Nav 1.6 sodium channel function through a combinatorial mechanism that involves three distinct splicing regulatory elements and their ligands", Nucleic Acids Res., 40 (13), 6255-6269 (2012).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "including," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A composition comprising:

a splice modulating oligonucleotide (SMO), wherein: the nucleotide sequence of the SMO consists of 15 to 26 nucleotides, is at least 90% identical to an equal length fragment of SEQ ID NO: 1253 that comprises SEQ ID NO: 1855, and comprises at least one modified nucleotide; and a carrier or diluent.

2. The composition of claim 1 wherein the SMO comprises one of SEQ ID Nos.: 1855, 1306, 1307, 1364, 1422, 1423, 1424, 1481, 1541, 1308, 1309, 1363, 1365, 1366, 1421, 1480, 1482, 1483, 1540, 1542, 1543, 1601, 1602, 1603, 1604, 1663, 1664, 1665, 1666, 1726, 1727, 1728, 1790, or 1791.

3. The composition of claim 1, wherein at least one nucleotide in said SMO contains a non-naturally occurring modification comprising at least one of a chemical composition of phosphorothioate 2'-O-methyl, phosphorothioate 2'-MOE, locked nucleic acid (LNA) peptide nucleic acid (PNA), phosphorodiamidate morpholino, cholesterol or any combination thereof.

4. The composition of claim 1, wherein at least one of the nucleotides of the SMO is a phosphorothioate 2'-O-methyl modified nucleotide or is a constrained ethyl nucleic acid (cEt).

5. The composition of claim 1, wherein the SMO comprises or consists of SEQ ID NO: 1855.

6. The composition of claim 1, wherein the SMO comprises or consists of a sequence selected from the group consisting of SEQ ID NOs: 1306-1309, 1363-1366, 1421-1424, 1480-1483, 1540-1543, 1601-1604, 1663-1666, 1726-1728, 1790-1791, 1855, 1861-1866, 1889-1893, 1917-1920, 1945-1945, 1973-1974, and 2001, or a variant thereof that is at least 90% identical to the selected sequence.

7. The composition of claim 1, wherein the SMO comprises or consists of a sequence selected from the group consisting of SEQ ID NOs: 1306-1309, 1363-1366, 1421-1424, 1480-1483, 1540-1543, 1601-1604, 1663-1666, 1726-1728, 1790-1791, 1855, 1861-1866, 1889-1893, 1917-1920, 1945-1945, 1973-1974, and 2001, or a variant thereof that is at least 95% identical to the selected sequence.

8. The composition of claim 1, wherein the SMO comprises or consists of a sequence selected from the group consisting of SEQ ID NOs: 1306-1309, 1363-1366, 1421-1424, 1480-1483, 1540-1543, 1601-1604, 1663-1666, 1726-1728, 1790-1791, 1855, 1861-1866, 1889-1893, 1917-1920, 1945-1945, 1973-1974, and 2001.

9. The composition of claim 1, wherein the SMO comprises or consists of a sequence selected from the group consisting of SEQ ID NOs: 1306, 1307, 1364, 1422, 1423, 1424, 1481, 1541, and 1855, or a variant thereof that is at least 90% identical to a sequence selected from the group consisting of SEQ ID NOs: 1306, 1307, 1364, 1422, 1423, 1424, 1481, and 1541.

10. The composition of claim 1, wherein the SMO comprises or consists of a sequence selected from the group consisting of SEQ ID NOs: 1306, 1307, 1364, 1422, 1423, 1424, 1481, 1541, and 1855, or a variant thereof that is at least 95% identical to a sequence selected from the group consisting of SEQ ID NOs: 1306, 1307, 1364, 1422, 1423, 1424, 1481, and 1541.

11. The composition of claim 1, wherein the SMO comprises or consists of a sequence selected from the group consisting of SEQ ID NOs: 1306, 1307, 1364, 1422, 1423, 1424, 1481, 1541, and 1855.

12. The composition of claim 1, wherein the SMO consists of a sequence selected from the group consisting of SEQ ID NOs: 1306, 1307, 1364, 1422, 1423, 1424, 1481, 1541, and 1855.

13. The composition of claim 1, wherein the SMO comprises or consists of a sequence is at least 90% identical to SEQ ID NO: 1855.

14. The composition of claim 1, wherein all of the nucleotides of the SMO are modified nucleotides.

15. The composition of claim 1, wherein the SMO comprises or consists of a sequence that is at least 95% identical to SEQ ID NO: 1855.

16. An SMO, wherein the nucleotide sequence of the SMO consists of 15 to 26 nucleotides, wherein:

(i) the nucleotide sequence of the SMO comprises a sequence that is at least 90% identical to a fragment of SEQ ID NO: 1253, wherein the fragment of SEQ ID NO: 1253:

(a) is of a length identical to that of the SMO, and (b) comprises SEQ ID NO: 1855, and (ii) at least one nucleotide in the SMO is a modified nucleotide.

17. A method of modulating splicing of an SCN8A pre-mRNA comprising:

contacting a plurality of cells with the splice modulating oligonucleotide (SMO) of claim 16 that specifically binds a complementary sequence of the SCN8A pre-mRNA that undergoes splicing to form an mRNA encoding the voltage gated sodium channel subunit SCN8A, wherein the SMO of claim 16 directs exclusion of exon 18A in the SCN8A pre-mRNA in the plurality of cells expressing SCN8A pre-mRNA.

* * * * *

```
                    SEQUENCE LISTING

<160> NUMBER OF SEQ ID NOS: 2143

<210> SEQ ID NO 1
<211> LENGTH: 104
<212> TYPE: DNA
<213> ORGANISM: Homo sapiens

<400> SEQUENCE: 1

actacagata tgtgacagag tttgtggacc tgggcaatgt ctcagcgctg agaacattca     60

gggttctccg agctttgaaa actatctctg taattccagg tgag                     104


<210> SEQ ID NO 2
<211> LENGTH: 104
<212> TYPE: RNA
<213> ORGANISM: Homo sapiens

<400> SEQUENCE: 2

cucaccugga auuacagaga uaguuuucaa agcucggaga acccugaaug uucucagcgc     60

ugagacauug cccaggucca caaacucugu cacauaucug uagu                     104


<210> SEQ ID NO 3
<211> LENGTH: 24
```

<212> TYPE: RNA
<213> ORGANISM: Artificial Sequence
<220> FEATURE:
<223> OTHER INFORMATION: Synthetic Construct

<400> SEQUENCE: 3
cucaccugga auuacagaga uagu 24

<210> SEQ ID NO 4
<211> LENGTH: 24
<212> TYPE: RNA
<213> ORGANISM: Artificial Sequence
<220> FEATURE:
<223> OTHER INFORMATION: Synthetic Construct

<400> SEQUENCE: 4
ucaccuggaa uuacagagau aguu 24

<210> SEQ ID NO 5
<211> LENGTH: 24
<212> TYPE: RNA
<213> ORGANISM: Artificial Sequence
<220> FEATURE:
<223> OTHER INFORMATION: Synthetic Construct

<400> SEQUENCE: 5
caccuggaau uacagagaua guuu 24

<210> SEQ ID NO 6
<211> LENGTH: 24
<212> TYPE: RNA
<213> ORGANISM: Artificial Sequence
<220> FEATURE:
<223> OTHER INFORMATION: Synthetic Construct

<400> SEQUENCE: 6
accuggaauu acagagauag uuuu 24

<210> SEQ ID NO 7
<211> LENGTH: 24
<212> TYPE: RNA
<213> ORGANISM: Artificial Sequence
<220> FEATURE:
<223> OTHER INFORMATION: Synthetic Construct

<400> SEQUENCE: 7
ccuggaauua cagagauagu uuuc 24

<210> SEQ ID NO 8
<211> LENGTH: 24
<212> TYPE: RNA
<213> ORGANISM: Artificial Sequence
<220> FEATURE:
<223> OTHER INFORMATION: Synthetic Construct

<400> SEQUENCE: 8
cuggaauuac agagauaguu uuca 24

<210> SEQ ID NO 9
<211> LENGTH: 24
<212> TYPE: RNA
<213> ORGANISM: Artificial Sequence
<220> FEATURE:
<223> OTHER INFORMATION: Synthetic Construct

<400> SEQUENCE: 9
uggaauuaca gagauaguuu ucaa 24

<210> SEQ ID NO 10
<211> LENGTH: 24
<212> TYPE: RNA
<213> ORGANISM: Artificial Sequence
<220> FEATURE:
<223> OTHER INFORMATION: Synthetic Construct

<400> SEQUENCE: 10
ggaauuacag agauaguuuu caaa 24

<210> SEQ ID NO 11
<211> LENGTH: 24
<212> TYPE: RNA
<213> ORGANISM: Artificial Sequence
<220> FEATURE:
<223> OTHER INFORMATION: Synthetic Construct

<400> SEQUENCE: 11
gaauuacaga gauaguuuuc aaag 24

<210> SEQ ID NO 12
<211> LENGTH: 24
<212> TYPE: RNA
<213> ORGANISM: Artificial Sequence
<220> FEATURE:
<223> OTHER INFORMATION: Synthetic Construct

<400> SEQUENCE: 12
aauuacagag auaguuuuca aagc 24

<210> SEQ ID NO 13
<211> LENGTH: 24
<212> TYPE: RNA
<213> ORGANISM: Artificial Sequence
<220> FEATURE:
<223> OTHER INFORMATION: Synthetic Construct

<400> SEQUENCE: 13
auuacagaga uaguuuucaa agcu 24

<210> SEQ ID NO 14
<211> LENGTH: 24
<212> TYPE: RNA
<213> ORGANISM: Artificial Sequence
<220> FEATURE:
<223> OTHER INFORMATION: Synthetic Construct

<400> SEQUENCE: 14
uuacagagau aguuuucaaa gcuc 24

<210> SEQ ID NO 15
<211> LENGTH: 24
<212> TYPE: RNA
<213> ORGANISM: Artificial Sequence
<220> FEATURE:
<223> OTHER INFORMATION: Synthetic Construct

<400> SEQUENCE: 15
uacagagaua guuuucaaag cucg 24

<210> SEQ ID NO 16
<211> LENGTH: 24
<212> TYPE: RNA
<213> ORGANISM: Artificial Sequence
<220> FEATURE:
<223> OTHER INFORMATION: Synthetic Construct

<400> SEQUENCE: 16
acagagauag uuuucaaagc ucgg 24

<210> SEQ ID NO 17
<211> LENGTH: 24
<212> TYPE: RNA
<213> ORGANISM: Artificial Sequence
<220> FEATURE:
<223> OTHER INFORMATION: Synthetic Construct

<400> SEQUENCE: 17
cagagauagu uuucaaagcu cgga 24

<210> SEQ ID NO 18
<211> LENGTH: 24
<212> TYPE: RNA
<213> ORGANISM: Artificial Sequence
<220> FEATURE:
<223> OTHER INFORMATION: Synthetic Construct

<400> SEQUENCE: 18
agagauaguu uucaaagcuc ggag 24

<210> SEQ ID NO 19
<211> LENGTH: 24
<212> TYPE: RNA
<213> ORGANISM: Artificial Sequence
<220> FEATURE:
<223> OTHER INFORMATION: Synthetic Construct

<400> SEQUENCE: 19
gagauaguuu ucaaagcucg gaga 24

<210> SEQ ID NO 20
<211> LENGTH: 24
<212> TYPE: RNA
<213> ORGANISM: Artificial Sequence
<220> FEATURE:
<223> OTHER INFORMATION: Synthetic Construct

<400> SEQUENCE: 20
agauaguuuu caaagcucgg agaa 24

<210> SEQ ID NO 21
<211> LENGTH: 24
<212> TYPE: RNA
<213> ORGANISM: Artificial Sequence
<220> FEATURE:
<223> OTHER INFORMATION: Synthetic Construct

<400> SEQUENCE: 21
gauaguuuuc aaagcucgga gaac 24

<210> SEQ ID NO 22
<211> LENGTH: 24
<212> TYPE: RNA
<213> ORGANISM: Artificial Sequence
<220> FEATURE:
<223> OTHER INFORMATION: Synthetic Construct

<400> SEQUENCE: 22
auaguuuuca aagcucggag aacc 24

<210> SEQ ID NO 23
<211> LENGTH: 24
<212> TYPE: RNA
<213> ORGANISM: Artificial Sequence
<220> FEATURE:
<223> OTHER INFORMATION: Synthetic Construct

<400> SEQUENCE: 23
uaguuuucaa agcucggaga accc 24

<210> SEQ ID NO 24
<211> LENGTH: 24
<212> TYPE: RNA
<213> ORGANISM: Artificial Sequence
<220> FEATURE:
<223> OTHER INFORMATION: Synthetic Construct

<400> SEQUENCE: 24
aguuuucaaa gcucggagaa cccu 24

<210> SEQ ID NO 25
<211> LENGTH: 24
<212> TYPE: RNA
<213> ORGANISM: Artificial Sequence
<220> FEATURE:
<223> OTHER INFORMATION: Synthetic Construct

<400> SEQUENCE: 25
guuuucaaag cucggagaac ccug 24

<210> SEQ ID NO 26
<211> LENGTH: 24
<212> TYPE: RNA
<213> ORGANISM: Artificial Sequence
<220> FEATURE:
<223> OTHER INFORMATION: Synthetic Construct

<400> SEQUENCE: 26
uuuucaaagc ucggagaacc cuga 24

<210> SEQ ID NO 27
<211> LENGTH: 24
<212> TYPE: RNA
<213> ORGANISM: Artificial Sequence
<220> FEATURE:
<223> OTHER INFORMATION: Synthetic Construct

<400> SEQUENCE: 27
uuucaaagcu cggagaaccc ugaa 24

<210> SEQ ID NO 28
<211> LENGTH: 24
<212> TYPE: RNA
<213> ORGANISM: Artificial Sequence
<220> FEATURE:
<223> OTHER INFORMATION: Synthetic Construct

<400> SEQUENCE: 28
uucaaagcuc ggagaacccu gaau 24

<210> SEQ ID NO 29
<211> LENGTH: 24
<212> TYPE: RNA
<213> ORGANISM: Artificial Sequence
<220> FEATURE:
<223> OTHER INFORMATION: Synthetic Construct

<400> SEQUENCE: 29
ucaaagcucg gagaacccug aaug 24

<210> SEQ ID NO 30
<211> LENGTH: 24
<212> TYPE: RNA
<213> ORGANISM: Artificial Sequence
<220> FEATURE:
<223> OTHER INFORMATION: Synthetic Construct

<400> SEQUENCE: 30
caaagcucgg agaacccuga augu 24

<210> SEQ ID NO 31
<211> LENGTH: 24
<212> TYPE: RNA
<213> ORGANISM: Artificial Sequence
<220> FEATURE:
<223> OTHER INFORMATION: Synthetic Construct

<400> SEQUENCE: 31
aaagcucgga gaacccugaa uguu 24

<210> SEQ ID NO 32
<211> LENGTH: 24
<212> TYPE: RNA
<213> ORGANISM: Artificial Sequence
<220> FEATURE:
<223> OTHER INFORMATION: Synthetic Construct

<400> SEQUENCE: 32
aagcucggag aacccugaau guuc 24

<210> SEQ ID NO 33
<211> LENGTH: 24
<212> TYPE: RNA
<213> ORGANISM: Artificial Sequence
<220> FEATURE:
<223> OTHER INFORMATION: Synthetic Construct

<400> SEQUENCE: 33
agcucggaga acccugaaug uucu 24

<210> SEQ ID NO 34
<211> LENGTH: 24
<212> TYPE: RNA
<213> ORGANISM: Artificial Sequence
<220> FEATURE:
<223> OTHER INFORMATION: Synthetic Construct

<400> SEQUENCE: 34
gcucggagaa cccugaaugu ucuc 24

<210> SEQ ID NO 35
<211> LENGTH: 24
<212> TYPE: RNA
<213> ORGANISM: Artificial Sequence
<220> FEATURE:
<223> OTHER INFORMATION: Synthetic Construct

<400> SEQUENCE: 35
cucggagaac ccugaauguu cuca 24

<210> SEQ ID NO 36

<211> LENGTH: 24
<212> TYPE: RNA
<213> ORGANISM: Artificial Sequence
<220> FEATURE:
<223> OTHER INFORMATION: Synthetic Construct

<400> SEQUENCE: 36
ucggagaacc cugaauguuc ucag 24

<210> SEQ ID NO 37
<211> LENGTH: 24
<212> TYPE: RNA
<213> ORGANISM: Artificial Sequence
<220> FEATURE:
<223> OTHER INFORMATION: Synthetic Construct

<400> SEQUENCE: 37
cggagaaccc ugaauguucu cagc 24

<210> SEQ ID NO 38
<211> LENGTH: 24
<212> TYPE: RNA
<213> ORGANISM: Artificial Sequence
<220> FEATURE:
<223> OTHER INFORMATION: Synthetic Construct

<400> SEQUENCE: 38
ggagaacccu gaauguucuc agcg 24

<210> SEQ ID NO 39
<211> LENGTH: 24
<212> TYPE: RNA
<213> ORGANISM: Artificial Sequence
<220> FEATURE:
<223> OTHER INFORMATION: Synthetic Construct

<400> SEQUENCE: 39
gagaacccug aauguucuca gcgc 24

<210> SEQ ID NO 40
<211> LENGTH: 24
<212> TYPE: RNA
<213> ORGANISM: Artificial Sequence
<220> FEATURE:
<223> OTHER INFORMATION: Synthetic Construct

<400> SEQUENCE: 40
agaacccuga auguucucag cgcu 24

<210> SEQ ID NO 41
<211> LENGTH: 24
<212> TYPE: RNA
<213> ORGANISM: Artificial Sequence
<220> FEATURE:
<223> OTHER INFORMATION: Synthetic Construct

<400> SEQUENCE: 41
gaacccugaa uguucucagc gcug 24

<210> SEQ ID NO 42
<211> LENGTH: 24
<212> TYPE: RNA
<213> ORGANISM: Artificial Sequence
<220> FEATURE:
<223> OTHER INFORMATION: Synthetic Construct

<400> SEQUENCE: 42
aacccugaau guucucagcg cuga 24

<210> SEQ ID NO 43
<211> LENGTH: 24
<212> TYPE: RNA
<213> ORGANISM: Artificial Sequence
<220> FEATURE:
<223> OTHER INFORMATION: Synthetic Construct

<400> SEQUENCE: 43
acccugaaug uucucagcgc ugag 24

<210> SEQ ID NO 44
<211> LENGTH: 24
<212> TYPE: RNA
<213> ORGANISM: Artificial Sequence
<220> FEATURE:
<223> OTHER INFORMATION: Synthetic Construct

<400> SEQUENCE: 44
cccugaaugu ucucagcgcu gaga 24

<210> SEQ ID NO 45
<211> LENGTH: 24
<212> TYPE: RNA
<213> ORGANISM: Artificial Sequence
<220> FEATURE:
<223> OTHER INFORMATION: Synthetic Construct

<400> SEQUENCE: 45
ccugaauguu cucagcgcug agac 24

<210> SEQ ID NO 46
<211> LENGTH: 24
<212> TYPE: RNA
<213> ORGANISM: Artificial Sequence
<220> FEATURE:
<223> OTHER INFORMATION: Synthetic Construct

<400> SEQUENCE: 46
cugaauguuc ucagcgcuga gaca 24

<210> SEQ ID NO 47
<211> LENGTH: 24
<212> TYPE: RNA
<213> ORGANISM: Artificial Sequence
<220> FEATURE:
<223> OTHER INFORMATION: Synthetic Construct

<400> SEQUENCE: 47
ugaauguucu cagcgcugag acau 24

<210> SEQ ID NO 48
<211> LENGTH: 24
<212> TYPE: RNA
<213> ORGANISM: Artificial Sequence
<220> FEATURE:
<223> OTHER INFORMATION: Synthetic Construct

<400> SEQUENCE: 48
gaauguucuc agcgcugaga cauu 24

<210> SEQ ID NO 49
<211> LENGTH: 24
<212> TYPE: RNA

<213> ORGANISM: Artificial Sequence
<220> FEATURE:
<223> OTHER INFORMATION: Synthetic Construct

<400> SEQUENCE: 49
aauguucuca gcgcugagac auug 24

<210> SEQ ID NO 50
<211> LENGTH: 24
<212> TYPE: RNA
<213> ORGANISM: Artificial Sequence
<220> FEATURE:
<223> OTHER INFORMATION: Synthetic Construct

<400> SEQUENCE: 50
auguucucag cgcugagaca uugc 24

<210> SEQ ID NO 51
<211> LENGTH: 24
<212> TYPE: RNA
<213> ORGANISM: Artificial Sequence
<220> FEATURE:
<223> OTHER INFORMATION: Synthetic Construct

<400> SEQUENCE: 51
uguucucagc gcugagacau ugcc 24

<210> SEQ ID NO 52
<211> LENGTH: 24
<212> TYPE: RNA
<213> ORGANISM: Artificial Sequence
<220> FEATURE:
<223> OTHER INFORMATION: Synthetic Construct

<400> SEQUENCE: 52
guucucagcg cugagacauu gccc 24

<210> SEQ ID NO 53
<211> LENGTH: 24
<212> TYPE: RNA
<213> ORGANISM: Artificial Sequence
<220> FEATURE:
<223> OTHER INFORMATION: Synthetic Construct

<400> SEQUENCE: 53
uucucagcgc ugagacauug ccca 24

<210> SEQ ID NO 54
<211> LENGTH: 24
<212> TYPE: RNA
<213> ORGANISM: Artificial Sequence
<220> FEATURE:
<223> OTHER INFORMATION: Synthetic Construct

<400> SEQUENCE: 54
ucucagcgcu gagacauugc ccag 24

<210> SEQ ID NO 55
<211> LENGTH: 24
<212> TYPE: RNA
<213> ORGANISM: Artificial Sequence
<220> FEATURE:
<223> OTHER INFORMATION: Synthetic Construct

<400> SEQUENCE: 55
cucagcgcug agacauugcc cagg 24

<210> SEQ ID NO 56
<211> LENGTH: 24
<212> TYPE: RNA
<213> ORGANISM: Artificial Sequence
<220> FEATURE:
<223> OTHER INFORMATION: Synthetic Construct

<400> SEQUENCE: 56
ucagcgcuga gacauugccc aggu 24

<210> SEQ ID NO 57
<211> LENGTH: 24
<212> TYPE: RNA
<213> ORGANISM: Artificial Sequence
<220> FEATURE:
<223> OTHER INFORMATION: Synthetic Construct

<400> SEQUENCE: 57
cagcgcugag acauugccca gguc 24

<210> SEQ ID NO 58
<211> LENGTH: 24
<212> TYPE: RNA
<213> ORGANISM: Artificial Sequence
<220> FEATURE:
<223> OTHER INFORMATION: Synthetic Construct

<400> SEQUENCE: 58
agcgcugaga cauugcccag gucc 24

<210> SEQ ID NO 59
<211> LENGTH: 24
<212> TYPE: RNA
<213> ORGANISM: Artificial Sequence
<220> FEATURE:
<223> OTHER INFORMATION: Synthetic Construct

<400> SEQUENCE: 59
gcgcugagac auugcccagg ucca 24

<210> SEQ ID NO 60
<211> LENGTH: 24
<212> TYPE: RNA
<213> ORGANISM: Artificial Sequence
<220> FEATURE:
<223> OTHER INFORMATION: Synthetic Construct

<400> SEQUENCE: 60
cgcugagaca uugcccaggu ccac 24

<210> SEQ ID NO 61
<211> LENGTH: 24
<212> TYPE: RNA
<213> ORGANISM: Artificial Sequence
<220> FEATURE:
<223> OTHER INFORMATION: Synthetic Construct

<400> SEQUENCE: 61
gcugagacau ugcccagguc caca 24

<210> SEQ ID NO 62
<211> LENGTH: 24
<212> TYPE: RNA
<213> ORGANISM: Artificial Sequence
<220> FEATURE:

-continued

<223> OTHER INFORMATION: Synthetic Construct

<400> SEQUENCE: 62
cugagacauu gcccaggucc acaa 24

<210> SEQ ID NO 63
<211> LENGTH: 24
<212> TYPE: RNA
<213> ORGANISM: Artificial Sequence
<220> FEATURE:
<223> OTHER INFORMATION: Synthetic Construct

<400> SEQUENCE: 63
ugagacauug cccaggucca caaa 24

<210> SEQ ID NO 64
<211> LENGTH: 24
<212> TYPE: RNA
<213> ORGANISM: Artificial Sequence
<220> FEATURE:
<223> OTHER INFORMATION: Synthetic Construct

<400> SEQUENCE: 64
gagacauugc ccagguccac aaac 24

<210> SEQ ID NO 65
<211> LENGTH: 24
<212> TYPE: RNA
<213> ORGANISM: Artificial Sequence
<220> FEATURE:
<223> OTHER INFORMATION: Synthetic Construct

<400> SEQUENCE: 65
agacauugcc cagguccaca aacu 24

<210> SEQ ID NO 66
<211> LENGTH: 24
<212> TYPE: RNA
<213> ORGANISM: Artificial Sequence
<220> FEATURE:
<223> OTHER INFORMATION: Synthetic Construct

<400> SEQUENCE: 66
gacauugccc agguccacaa acuc 24

<210> SEQ ID NO 67
<211> LENGTH: 24
<212> TYPE: RNA
<213> ORGANISM: Artificial Sequence
<220> FEATURE:
<223> OTHER INFORMATION: Synthetic Construct

<400> SEQUENCE: 67
acauugccca gguccacaaa cucu 24

<210> SEQ ID NO 68
<211> LENGTH: 24
<212> TYPE: RNA
<213> ORGANISM: Artificial Sequence
<220> FEATURE:
<223> OTHER INFORMATION: Synthetic Construct

<400> SEQUENCE: 68
cauugcccag guccacaaac ucug 24

<210> SEQ ID NO 69
<211> LENGTH: 24
<212> TYPE: RNA
<213> ORGANISM: Artificial Sequence
<220> FEATURE:
<223> OTHER INFORMATION: Synthetic Construct

<400> SEQUENCE: 69
auugcccagg uccacaaacu cugu 24

<210> SEQ ID NO 70
<211> LENGTH: 24
<212> TYPE: RNA
<213> ORGANISM: Artificial Sequence
<220> FEATURE:
<223> OTHER INFORMATION: Synthetic Construct

<400> SEQUENCE: 70
uugcccaggu ccacaaacuc uguc 24

<210> SEQ ID NO 71
<211> LENGTH: 24
<212> TYPE: RNA
<213> ORGANISM: Artificial Sequence
<220> FEATURE:
<223> OTHER INFORMATION: Synthetic Construct

<400> SEQUENCE: 71
ugcccagguc cacaaacucu guca 24

<210> SEQ ID NO 72
<211> LENGTH: 24
<212> TYPE: RNA
<213> ORGANISM: Artificial Sequence
<220> FEATURE:
<223> OTHER INFORMATION: Synthetic Construct

<400> SEQUENCE: 72
gcccaggucc acaaacucug ucac 24

<210> SEQ ID NO 73
<211> LENGTH: 24
<212> TYPE: RNA
<213> ORGANISM: Artificial Sequence
<220> FEATURE:
<223> OTHER INFORMATION: Synthetic Construct

<400> SEQUENCE: 73
cccaggucca caaacucugu caca 24

<210> SEQ ID NO 74
<211> LENGTH: 24
<212> TYPE: RNA
<213> ORGANISM: Artificial Sequence
<220> FEATURE:
<223> OTHER INFORMATION: Synthetic Construct

<400> SEQUENCE: 74
ccagguccac aaacucuguc acau 24

<210> SEQ ID NO 75
<211> LENGTH: 24
<212> TYPE: RNA
<213> ORGANISM: Artificial Sequence
<220> FEATURE:
<223> OTHER INFORMATION: Synthetic Construct

```
<400> SEQUENCE: 75

cagguccaca aacucuguca caua                                          24


<210> SEQ ID NO 76
<211> LENGTH: 24
<212> TYPE: RNA
<213> ORGANISM: Artificial Sequence
<220> FEATURE:
<223> OTHER INFORMATION: Synthetic Construct

<400> SEQUENCE: 76

agguccacaa acucugucac auau                                          24


<210> SEQ ID NO 77
<211> LENGTH: 24
<212> TYPE: RNA
<213> ORGANISM: Artificial Sequence
<220> FEATURE:
<223> OTHER INFORMATION: Synthetic Construct

<400> SEQUENCE: 77

gguccacaaa cucugucaca uauc                                          24


<210> SEQ ID NO 78
<211> LENGTH: 24
<212> TYPE: RNA
<213> ORGANISM: Artificial Sequence
<220> FEATURE:
<223> OTHER INFORMATION: Synthetic Construct

<400> SEQUENCE: 78

guccacaaac ucugucacau aucu                                          24


<210> SEQ ID NO 79
<211> LENGTH: 24
<212> TYPE: RNA
<213> ORGANISM: Artificial Sequence
<220> FEATURE:
<223> OTHER INFORMATION: Synthetic Construct

<400> SEQUENCE: 79

uccacaaacu cugucacaua ucug                                          24


<210> SEQ ID NO 80
<211> LENGTH: 24
<212> TYPE: RNA
<213> ORGANISM: Artificial Sequence
<220> FEATURE:
<223> OTHER INFORMATION: Synthetic Construct

<400> SEQUENCE: 80

ccacaaacuc ugucacauau cugu                                          24


<210> SEQ ID NO 81
<211> LENGTH: 24
<212> TYPE: RNA
<213> ORGANISM: Artificial Sequence
<220> FEATURE:
<223> OTHER INFORMATION: Synthetic Construct

<400> SEQUENCE: 81

cacaaacucu gucacauauc ugua                                          24


<210> SEQ ID NO 82
<211> LENGTH: 24
```

<212> TYPE: RNA
<213> ORGANISM: Artificial Sequence
<220> FEATURE:
<223> OTHER INFORMATION: Synthetic Construct

<400> SEQUENCE: 82
acaaacucug ucacauaucu guag 24

<210> SEQ ID NO 83
<211> LENGTH: 24
<212> TYPE: RNA
<213> ORGANISM: Artificial Sequence
<220> FEATURE:
<223> OTHER INFORMATION: Synthetic Construct

<400> SEQUENCE: 83
caaacucugu cacauaucug uagu 24

<210> SEQ ID NO 84
<211> LENGTH: 23
<212> TYPE: RNA
<213> ORGANISM: Artificial Sequence
<220> FEATURE:
<223> OTHER INFORMATION: Synthetic Construct

<400> SEQUENCE: 84
cucaccugga auuacagaga uag 23

<210> SEQ ID NO 85
<211> LENGTH: 23
<212> TYPE: RNA
<213> ORGANISM: Artificial Sequence
<220> FEATURE:
<223> OTHER INFORMATION: Synthetic Construct

<400> SEQUENCE: 85
ucaccuggaa uuacagagau agu 23

<210> SEQ ID NO 86
<211> LENGTH: 23
<212> TYPE: RNA
<213> ORGANISM: Artificial Sequence
<220> FEATURE:
<223> OTHER INFORMATION: Synthetic Construct

<400> SEQUENCE: 86
caccuggaau uacagagaua guu 23

<210> SEQ ID NO 87
<211> LENGTH: 23
<212> TYPE: RNA
<213> ORGANISM: Artificial Sequence
<220> FEATURE:
<223> OTHER INFORMATION: Synthetic Construct

<400> SEQUENCE: 87
accuggaauu acagagauag uuu 23

<210> SEQ ID NO 88
<211> LENGTH: 23
<212> TYPE: RNA
<213> ORGANISM: Artificial Sequence
<220> FEATURE:
<223> OTHER INFORMATION: Synthetic Construct

<400> SEQUENCE: 88
ccuggaauua cagagauagu uuu 23

<210> SEQ ID NO 89
<211> LENGTH: 23
<212> TYPE: RNA
<213> ORGANISM: Artificial Sequence
<220> FEATURE:
<223> OTHER INFORMATION: Synthetic Construct

<400> SEQUENCE: 89
cuggaauuac agagauaguu uuc 23

<210> SEQ ID NO 90
<211> LENGTH: 23
<212> TYPE: RNA
<213> ORGANISM: Artificial Sequence
<220> FEATURE:
<223> OTHER INFORMATION: Synthetic Construct

<400> SEQUENCE: 90
uggaauuaca gagauaguuu uca 23

<210> SEQ ID NO 91
<211> LENGTH: 23
<212> TYPE: RNA
<213> ORGANISM: Artificial Sequence
<220> FEATURE:
<223> OTHER INFORMATION: Synthetic Construct

<400> SEQUENCE: 91
ggaauuacag agauaguuuu caa 23

<210> SEQ ID NO 92
<211> LENGTH: 23
<212> TYPE: RNA
<213> ORGANISM: Artificial Sequence
<220> FEATURE:
<223> OTHER INFORMATION: Synthetic Construct

<400> SEQUENCE: 92
gaauuacaga gauaguuuuc aaa 23

<210> SEQ ID NO 93
<211> LENGTH: 23
<212> TYPE: RNA
<213> ORGANISM: Artificial Sequence
<220> FEATURE:
<223> OTHER INFORMATION: Synthetic Construct

<400> SEQUENCE: 93
aauuacagag auaguuuuca aag 23

<210> SEQ ID NO 94
<211> LENGTH: 23
<212> TYPE: RNA
<213> ORGANISM: Artificial Sequence
<220> FEATURE:
<223> OTHER INFORMATION: Synthetic Construct

<400> SEQUENCE: 94
auuacagaga uaguuuucaa agc 23

<210> SEQ ID NO 95
<211> LENGTH: 23
<212> TYPE: RNA
<213> ORGANISM: Artificial Sequence
<220> FEATURE:
<223> OTHER INFORMATION: Synthetic Construct

<400> SEQUENCE: 95
uuacagagau aguuuucaaa gcu 23

<210> SEQ ID NO 96
<211> LENGTH: 23
<212> TYPE: RNA
<213> ORGANISM: Artificial Sequence
<220> FEATURE:
<223> OTHER INFORMATION: Synthetic Construct

<400> SEQUENCE: 96
uacagagaua guuuucaaag cuc 23

<210> SEQ ID NO 97
<211> LENGTH: 23
<212> TYPE: RNA
<213> ORGANISM: Artificial Sequence
<220> FEATURE:
<223> OTHER INFORMATION: Synthetic Construct

<400> SEQUENCE: 97
acagagauag uuuucaaagc ucg 23

<210> SEQ ID NO 98
<211> LENGTH: 23
<212> TYPE: RNA
<213> ORGANISM: Artificial Sequence
<220> FEATURE:
<223> OTHER INFORMATION: Synthetic Construct

<400> SEQUENCE: 98
cagagauagu uuucaaagcu cgg 23

<210> SEQ ID NO 99
<211> LENGTH: 23
<212> TYPE: RNA
<213> ORGANISM: Artificial Sequence
<220> FEATURE:
<223> OTHER INFORMATION: Synthetic Construct

<400> SEQUENCE: 99
agagauaguu uucaaagcuc gga 23

<210> SEQ ID NO 100
<211> LENGTH: 23
<212> TYPE: RNA
<213> ORGANISM: Artificial Sequence
<220> FEATURE:
<223> OTHER INFORMATION: Synthetic Construct

<400> SEQUENCE: 100
gagauaguuu ucaaagcucg gag 23

<210> SEQ ID NO 101
<211> LENGTH: 23
<212> TYPE: RNA
<213> ORGANISM: Artificial Sequence
<220> FEATURE:
<223> OTHER INFORMATION: Synthetic Construct

<400> SEQUENCE: 101
agauaguuuu caaagcucgg aga 23

<210> SEQ ID NO 102
<211> LENGTH: 23
<212> TYPE: RNA
<213> ORGANISM: Artificial Sequence
<220> FEATURE:
<223> OTHER INFORMATION: Synthetic Construct

<400> SEQUENCE: 102
gauaguuuuc aaagcucgga gaa 23

<210> SEQ ID NO 103
<211> LENGTH: 23
<212> TYPE: RNA
<213> ORGANISM: Artificial Sequence
<220> FEATURE:
<223> OTHER INFORMATION: Synthetic Construct

<400> SEQUENCE: 103
auaguuuuca aagcucggag aac 23

<210> SEQ ID NO 104
<211> LENGTH: 23
<212> TYPE: RNA
<213> ORGANISM: Artificial Sequence
<220> FEATURE:
<223> OTHER INFORMATION: Synthetic Construct

<400> SEQUENCE: 104
uaguuuucaa agcucggaga acc 23

<210> SEQ ID NO 105
<211> LENGTH: 23
<212> TYPE: RNA
<213> ORGANISM: Artificial Sequence
<220> FEATURE:
<223> OTHER INFORMATION: Synthetic Construct

<400> SEQUENCE: 105
aguuuucaaa gcucggagaa ccc 23

<210> SEQ ID NO 106
<211> LENGTH: 23
<212> TYPE: RNA
<213> ORGANISM: Artificial Sequence
<220> FEATURE:
<223> OTHER INFORMATION: Synthetic Construct

<400> SEQUENCE: 106
guuuucaaag cucggagaac ccu 23

<210> SEQ ID NO 107
<211> LENGTH: 23
<212> TYPE: RNA
<213> ORGANISM: Artificial Sequence
<220> FEATURE:
<223> OTHER INFORMATION: Synthetic Construct

<400> SEQUENCE: 107
uuuucaaagc ucggagaacc cug 23

<210> SEQ ID NO 108
<211> LENGTH: 23
<212> TYPE: RNA
<213> ORGANISM: Artificial Sequence
<220> FEATURE:
<223> OTHER INFORMATION: Synthetic Construct

<400> SEQUENCE: 108
uuucaaagcu cggagaaccc uga 23

<210> SEQ ID NO 109
<211> LENGTH: 23
<212> TYPE: RNA
<213> ORGANISM: Artificial Sequence
<220> FEATURE:
<223> OTHER INFORMATION: Synthetic Construct

<400> SEQUENCE: 109
uucaaagcuc ggagaacccu gaa 23

<210> SEQ ID NO 110
<211> LENGTH: 23
<212> TYPE: RNA
<213> ORGANISM: Artificial Sequence
<220> FEATURE:
<223> OTHER INFORMATION: Synthetic Construct

<400> SEQUENCE: 110
ucaaagcucg gagaacccug aau 23

<210> SEQ ID NO 111
<211> LENGTH: 23
<212> TYPE: RNA
<213> ORGANISM: Artificial Sequence
<220> FEATURE:
<223> OTHER INFORMATION: Synthetic Construct

<400> SEQUENCE: 111
caaagcucgg agaacccuga aug 23

<210> SEQ ID NO 112
<211> LENGTH: 23
<212> TYPE: RNA
<213> ORGANISM: Artificial Sequence
<220> FEATURE:
<223> OTHER INFORMATION: Synthetic Construct

<400> SEQUENCE: 112
aaagcucgga gaacccugaa ugu 23

<210> SEQ ID NO 113
<211> LENGTH: 23
<212> TYPE: RNA
<213> ORGANISM: Artificial Sequence
<220> FEATURE:
<223> OTHER INFORMATION: Synthetic Construct

<400> SEQUENCE: 113
aagcucggag aacccugaau guu 23

<210> SEQ ID NO 114
<211> LENGTH: 23
<212> TYPE: RNA
<213> ORGANISM: Artificial Sequence
<220> FEATURE:
<223> OTHER INFORMATION: Synthetic Construct

<400> SEQUENCE: 114
agcucggaga acccugaaug uuc 23

<210> SEQ ID NO 115

<211> LENGTH: 23
<212> TYPE: RNA
<213> ORGANISM: Artificial Sequence
<220> FEATURE:
<223> OTHER INFORMATION: Synthetic Construct

<400> SEQUENCE: 115
gcucggagaa cccugaaugu ucu 23

<210> SEQ ID NO 116
<211> LENGTH: 23
<212> TYPE: RNA
<213> ORGANISM: Artificial Sequence
<220> FEATURE:
<223> OTHER INFORMATION: Synthetic Construct

<400> SEQUENCE: 116
cucggagaac ccugaauguu cuc 23

<210> SEQ ID NO 117
<211> LENGTH: 23
<212> TYPE: RNA
<213> ORGANISM: Artificial Sequence
<220> FEATURE:
<223> OTHER INFORMATION: Synthetic Construct

<400> SEQUENCE: 117
ucggagaacc cugaauguuc uca 23

<210> SEQ ID NO 118
<211> LENGTH: 23
<212> TYPE: RNA
<213> ORGANISM: Artificial Sequence
<220> FEATURE:
<223> OTHER INFORMATION: Synthetic Construct

<400> SEQUENCE: 118
cggagaaccc ugaauguucu cag 23

<210> SEQ ID NO 119
<211> LENGTH: 23
<212> TYPE: RNA
<213> ORGANISM: Artificial Sequence
<220> FEATURE:
<223> OTHER INFORMATION: Synthetic Construct

<400> SEQUENCE: 119
ggagaacccu gaauguucuc agc 23

<210> SEQ ID NO 120
<211> LENGTH: 23
<212> TYPE: RNA
<213> ORGANISM: Artificial Sequence
<220> FEATURE:
<223> OTHER INFORMATION: Synthetic Construct

<400> SEQUENCE: 120
gagaacccug aauguucuca gcg 23

<210> SEQ ID NO 121
<211> LENGTH: 23
<212> TYPE: RNA
<213> ORGANISM: Artificial Sequence
<220> FEATURE:
<223> OTHER INFORMATION: Synthetic Construct

<400> SEQUENCE: 121
agaacccuga auguucucag cgc 23

<210> SEQ ID NO 122
<211> LENGTH: 23
<212> TYPE: RNA
<213> ORGANISM: Artificial Sequence
<220> FEATURE:
<223> OTHER INFORMATION: Synthetic Construct

<400> SEQUENCE: 122
gaacccugaa uguucucagc gcu 23

<210> SEQ ID NO 123
<211> LENGTH: 23
<212> TYPE: RNA
<213> ORGANISM: Artificial Sequence
<220> FEATURE:
<223> OTHER INFORMATION: Synthetic Construct

<400> SEQUENCE: 123
aacccugaau guucucagcg cug 23

<210> SEQ ID NO 124
<211> LENGTH: 23
<212> TYPE: RNA
<213> ORGANISM: Artificial Sequence
<220> FEATURE:
<223> OTHER INFORMATION: Synthetic Construct

<400> SEQUENCE: 124
acccugaaug uucucagcgc uga 23

<210> SEQ ID NO 125
<211> LENGTH: 23
<212> TYPE: RNA
<213> ORGANISM: Artificial Sequence
<220> FEATURE:
<223> OTHER INFORMATION: Synthetic Construct

<400> SEQUENCE: 125
cccugaaugu ucucagcgcu gag 23

<210> SEQ ID NO 126
<211> LENGTH: 23
<212> TYPE: RNA
<213> ORGANISM: Artificial Sequence
<220> FEATURE:
<223> OTHER INFORMATION: Synthetic Construct

<400> SEQUENCE: 126
ccugaauguu cucagcgcug aga 23

<210> SEQ ID NO 127
<211> LENGTH: 23
<212> TYPE: RNA
<213> ORGANISM: Artificial Sequence
<220> FEATURE:
<223> OTHER INFORMATION: Synthetic Construct

<400> SEQUENCE: 127
cugaauguuc ucagcgcuga gac 23

<210> SEQ ID NO 128
<211> LENGTH: 23
<212> TYPE: RNA

<213> ORGANISM: Artificial Sequence
<220> FEATURE:
<223> OTHER INFORMATION: Synthetic Construct

<400> SEQUENCE: 128
ugaauguucu cagcgcugag aca 23

<210> SEQ ID NO 129
<211> LENGTH: 23
<212> TYPE: RNA
<213> ORGANISM: Artificial Sequence
<220> FEATURE:
<223> OTHER INFORMATION: Synthetic Construct

<400> SEQUENCE: 129
gaauguucuc agcgcugaga cau 23

<210> SEQ ID NO 130
<211> LENGTH: 23
<212> TYPE: RNA
<213> ORGANISM: Artificial Sequence
<220> FEATURE:
<223> OTHER INFORMATION: Synthetic Construct

<400> SEQUENCE: 130
aauguucuca gcgcugagac auu 23

<210> SEQ ID NO 131
<211> LENGTH: 23
<212> TYPE: RNA
<213> ORGANISM: Artificial Sequence
<220> FEATURE:
<223> OTHER INFORMATION: Synthetic Construct

<400> SEQUENCE: 131
auguucucag cgcugagaca uug 23

<210> SEQ ID NO 132
<211> LENGTH: 23
<212> TYPE: RNA
<213> ORGANISM: Artificial Sequence
<220> FEATURE:
<223> OTHER INFORMATION: Synthetic Construct

<400> SEQUENCE: 132
uguucucagc gcugagacau ugc 23

<210> SEQ ID NO 133
<211> LENGTH: 23
<212> TYPE: RNA
<213> ORGANISM: Artificial Sequence
<220> FEATURE:
<223> OTHER INFORMATION: Synthetic Construct

<400> SEQUENCE: 133
guucucagcg cugagacauu gcc 23

<210> SEQ ID NO 134
<211> LENGTH: 23
<212> TYPE: RNA
<213> ORGANISM: Artificial Sequence
<220> FEATURE:
<223> OTHER INFORMATION: Synthetic Construct

<400> SEQUENCE: 134
uucucagcgc ugagacauug ccc 23

<210> SEQ ID NO 135
<211> LENGTH: 23
<212> TYPE: RNA
<213> ORGANISM: Artificial Sequence
<220> FEATURE:
<223> OTHER INFORMATION: Synthetic Construct

<400> SEQUENCE: 135
ucucagcgcu gagacauugc cca 23

<210> SEQ ID NO 136
<211> LENGTH: 23
<212> TYPE: RNA
<213> ORGANISM: Artificial Sequence
<220> FEATURE:
<223> OTHER INFORMATION: Synthetic Construct

<400> SEQUENCE: 136
cucagcgcug agacauugcc cag 23

<210> SEQ ID NO 137
<211> LENGTH: 23
<212> TYPE: RNA
<213> ORGANISM: Artificial Sequence
<220> FEATURE:
<223> OTHER INFORMATION: Synthetic Construct

<400> SEQUENCE: 137
ucagcgcuga gacauugccc agg 23

<210> SEQ ID NO 138
<211> LENGTH: 23
<212> TYPE: RNA
<213> ORGANISM: Artificial Sequence
<220> FEATURE:
<223> OTHER INFORMATION: Synthetic Construct

<400> SEQUENCE: 138
cagcgcugag acauugccca ggu 23

<210> SEQ ID NO 139
<211> LENGTH: 23
<212> TYPE: RNA
<213> ORGANISM: Artificial Sequence
<220> FEATURE:
<223> OTHER INFORMATION: Synthetic Construct

<400> SEQUENCE: 139
agcgcugaga cauugcccag guc 23

<210> SEQ ID NO 140
<211> LENGTH: 23
<212> TYPE: RNA
<213> ORGANISM: Artificial Sequence
<220> FEATURE:
<223> OTHER INFORMATION: Synthetic Construct

<400> SEQUENCE: 140
gcgcugagac auugcccagg ucc 23

<210> SEQ ID NO 141
<211> LENGTH: 23
<212> TYPE: RNA
<213> ORGANISM: Artificial Sequence
<220> FEATURE:

<223> OTHER INFORMATION: Synthetic Construct

<400> SEQUENCE: 141
cgcugagaca uugcccaggu cca                                           23

<210> SEQ ID NO 142
<211> LENGTH: 23
<212> TYPE: RNA
<213> ORGANISM: Artificial Sequence
<220> FEATURE:
<223> OTHER INFORMATION: Synthetic Construct

<400> SEQUENCE: 142
gcugagacau ugcccagguc cac                                           23

<210> SEQ ID NO 143
<211> LENGTH: 23
<212> TYPE: RNA
<213> ORGANISM: Artificial Sequence
<220> FEATURE:
<223> OTHER INFORMATION: Synthetic Construct

<400> SEQUENCE: 143
cugagacauu gcccaggucc aca                                           23

<210> SEQ ID NO 144
<211> LENGTH: 23
<212> TYPE: RNA
<213> ORGANISM: Artificial Sequence
<220> FEATURE:
<223> OTHER INFORMATION: Synthetic Construct

<400> SEQUENCE: 144
ugagacauug cccaggucca caa                                           23

<210> SEQ ID NO 145
<211> LENGTH: 23
<212> TYPE: RNA
<213> ORGANISM: Artificial Sequence
<220> FEATURE:
<223> OTHER INFORMATION: Synthetic Construct

<400> SEQUENCE: 145
gagacauugc ccagguccac aaa                                           23

<210> SEQ ID NO 146
<211> LENGTH: 23
<212> TYPE: RNA
<213> ORGANISM: Artificial Sequence
<220> FEATURE:
<223> OTHER INFORMATION: Synthetic Construct

<400> SEQUENCE: 146
agacauugcc cagguccaca aac                                           23

<210> SEQ ID NO 147
<211> LENGTH: 23
<212> TYPE: RNA
<213> ORGANISM: Artificial Sequence
<220> FEATURE:
<223> OTHER INFORMATION: Synthetic Construct

<400> SEQUENCE: 147
gacauugccc agguccacaa acu                                           23

-continued

<210> SEQ ID NO 148
<211> LENGTH: 23
<212> TYPE: RNA
<213> ORGANISM: Artificial Sequence
<220> FEATURE:
<223> OTHER INFORMATION: Synthetic Construct

<400> SEQUENCE: 148
acauugccca gguccacaaa cuc 23

<210> SEQ ID NO 149
<211> LENGTH: 23
<212> TYPE: RNA
<213> ORGANISM: Artificial Sequence
<220> FEATURE:
<223> OTHER INFORMATION: Synthetic Construct

<400> SEQUENCE: 149
cauugcccag guccacaaac ucu 23

<210> SEQ ID NO 150
<211> LENGTH: 23
<212> TYPE: RNA
<213> ORGANISM: Artificial Sequence
<220> FEATURE:
<223> OTHER INFORMATION: Synthetic Construct

<400> SEQUENCE: 150
auugcccagg uccacaaacu cug 23

<210> SEQ ID NO 151
<211> LENGTH: 23
<212> TYPE: RNA
<213> ORGANISM: Artificial Sequence
<220> FEATURE:
<223> OTHER INFORMATION: Synthetic Construct

<400> SEQUENCE: 151
uugcccaggu ccacaaacuc ugu 23

<210> SEQ ID NO 152
<211> LENGTH: 23
<212> TYPE: RNA
<213> ORGANISM: Artificial Sequence
<220> FEATURE:
<223> OTHER INFORMATION: Synthetic Construct

<400> SEQUENCE: 152
ugcccagguc cacaaacucu guc 23

<210> SEQ ID NO 153
<211> LENGTH: 23
<212> TYPE: RNA
<213> ORGANISM: Artificial Sequence
<220> FEATURE:
<223> OTHER INFORMATION: Synthetic Construct

<400> SEQUENCE: 153
gcccaggucc acaaacucug uca 23

<210> SEQ ID NO 154
<211> LENGTH: 23
<212> TYPE: RNA
<213> ORGANISM: Artificial Sequence
<220> FEATURE:
<223> OTHER INFORMATION: Synthetic Construct

<400> SEQUENCE: 154
cccaggucca caaacucugu cac 23

<210> SEQ ID NO 155
<211> LENGTH: 23
<212> TYPE: RNA
<213> ORGANISM: Artificial Sequence
<220> FEATURE:
<223> OTHER INFORMATION: Synthetic Construct

<400> SEQUENCE: 155
ccagguccac aaacucuguc aca 23

<210> SEQ ID NO 156
<211> LENGTH: 23
<212> TYPE: RNA
<213> ORGANISM: Artificial Sequence
<220> FEATURE:
<223> OTHER INFORMATION: Synthetic Construct

<400> SEQUENCE: 156
cagguccaca aacucuguca cau 23

<210> SEQ ID NO 157
<211> LENGTH: 23
<212> TYPE: RNA
<213> ORGANISM: Artificial Sequence
<220> FEATURE:
<223> OTHER INFORMATION: Synthetic Construct

<400> SEQUENCE: 157
agguccacaa acucugucac aua 23

<210> SEQ ID NO 158
<211> LENGTH: 23
<212> TYPE: RNA
<213> ORGANISM: Artificial Sequence
<220> FEATURE:
<223> OTHER INFORMATION: Synthetic Construct

<400> SEQUENCE: 158
gguccacaaa cucugucaca uau 23

<210> SEQ ID NO 159
<211> LENGTH: 23
<212> TYPE: RNA
<213> ORGANISM: Artificial Sequence
<220> FEATURE:
<223> OTHER INFORMATION: Synthetic Construct

<400> SEQUENCE: 159
guccacaaac ucugucacau auc 23

<210> SEQ ID NO 160
<211> LENGTH: 23
<212> TYPE: RNA
<213> ORGANISM: Artificial Sequence
<220> FEATURE:
<223> OTHER INFORMATION: Synthetic Construct

<400> SEQUENCE: 160
uccacaaacu cugucacaua ucu 23

<210> SEQ ID NO 161
<211> LENGTH: 23

<212> TYPE: RNA
<213> ORGANISM: Artificial Sequence
<220> FEATURE:
<223> OTHER INFORMATION: Synthetic Construct

<400> SEQUENCE: 161
ccacaaacuc ugucacauau cug 23

<210> SEQ ID NO 162
<211> LENGTH: 23
<212> TYPE: RNA
<213> ORGANISM: Artificial Sequence
<220> FEATURE:
<223> OTHER INFORMATION: Synthetic Construct

<400> SEQUENCE: 162
cacaaacucu gucacauauc ugu 23

<210> SEQ ID NO 163
<211> LENGTH: 23
<212> TYPE: RNA
<213> ORGANISM: Artificial Sequence
<220> FEATURE:
<223> OTHER INFORMATION: Synthetic Construct

<400> SEQUENCE: 163
acaaacucug ucacauaucu gua 23

<210> SEQ ID NO 164
<211> LENGTH: 23
<212> TYPE: RNA
<213> ORGANISM: Artificial Sequence
<220> FEATURE:
<223> OTHER INFORMATION: Synthetic Construct

<400> SEQUENCE: 164
caaacucugu cacauaucug uag 23

<210> SEQ ID NO 165
<211> LENGTH: 23
<212> TYPE: RNA
<213> ORGANISM: Artificial Sequence
<220> FEATURE:
<223> OTHER INFORMATION: Synthetic Construct

<400> SEQUENCE: 165
aaacucuguc acauaucugu agu 23

<210> SEQ ID NO 166
<211> LENGTH: 22
<212> TYPE: RNA
<213> ORGANISM: Artificial Sequence
<220> FEATURE:
<223> OTHER INFORMATION: Synthetic Construct

<400> SEQUENCE: 166
cucaccugga auuacagaga ua 22

<210> SEQ ID NO 167
<211> LENGTH: 22
<212> TYPE: RNA
<213> ORGANISM: Artificial Sequence
<220> FEATURE:
<223> OTHER INFORMATION: Synthetic Construct

<400> SEQUENCE: 167
ucaccuggaa uuacagagau ag 22

<210> SEQ ID NO 168
<211> LENGTH: 22
<212> TYPE: RNA
<213> ORGANISM: Artificial Sequence
<220> FEATURE:
<223> OTHER INFORMATION: Synthetic Construct

<400> SEQUENCE: 168
caccuggaau uacagagaua gu 22

<210> SEQ ID NO 169
<211> LENGTH: 22
<212> TYPE: RNA
<213> ORGANISM: Artificial Sequence
<220> FEATURE:
<223> OTHER INFORMATION: Synthetic Construct

<400> SEQUENCE: 169
accuggaauu acagagauag uu 22

<210> SEQ ID NO 170
<211> LENGTH: 22
<212> TYPE: RNA
<213> ORGANISM: Artificial Sequence
<220> FEATURE:
<223> OTHER INFORMATION: Synthetic Construct

<400> SEQUENCE: 170
ccuggaauua cagagauagu uu 22

<210> SEQ ID NO 171
<211> LENGTH: 22
<212> TYPE: RNA
<213> ORGANISM: Artificial Sequence
<220> FEATURE:
<223> OTHER INFORMATION: Synthetic Construct

<400> SEQUENCE: 171
cuggaauuac agagauaguu uu 22

<210> SEQ ID NO 172
<211> LENGTH: 22
<212> TYPE: RNA
<213> ORGANISM: Artificial Sequence
<220> FEATURE:
<223> OTHER INFORMATION: Synthetic Construct

<400> SEQUENCE: 172
uggaauuaca gagauaguuu uc 22

<210> SEQ ID NO 173
<211> LENGTH: 22
<212> TYPE: RNA
<213> ORGANISM: Artificial Sequence
<220> FEATURE:
<223> OTHER INFORMATION: Synthetic Construct

<400> SEQUENCE: 173
ggaauuacag agauaguuuu ca 22

<210> SEQ ID NO 174
<211> LENGTH: 22
<212> TYPE: RNA
<213> ORGANISM: Artificial Sequence -continued
<220> FEATURE:
<223> OTHER INFORMATION: Synthetic Construct

<400> SEQUENCE: 174
gaauuacaga gauaguuuuc aa 22

<210> SEQ ID NO 175
<211> LENGTH: 22
<212> TYPE: RNA
<213> ORGANISM: Artificial Sequence
<220> FEATURE:
<223> OTHER INFORMATION: Synthetic Construct

<400> SEQUENCE: 175
aauuacagag auaguuuuca aa 22

<210> SEQ ID NO 176
<211> LENGTH: 22
<212> TYPE: RNA
<213> ORGANISM: Artificial Sequence
<220> FEATURE:
<223> OTHER INFORMATION: Synthetic Construct

<400> SEQUENCE: 176
auuacagaga uaguuuucaa ag 22

<210> SEQ ID NO 177
<211> LENGTH: 22
<212> TYPE: RNA
<213> ORGANISM: Artificial Sequence
<220> FEATURE:
<223> OTHER INFORMATION: Synthetic Construct

<400> SEQUENCE: 177
uuacagagau aguuuucaaa gc 22

<210> SEQ ID NO 178
<211> LENGTH: 22
<212> TYPE: RNA
<213> ORGANISM: Artificial Sequence
<220> FEATURE:
<223> OTHER INFORMATION: Synthetic Construct

<400> SEQUENCE: 178
uacagagaua guuuucaaag cu 22

<210> SEQ ID NO 179
<211> LENGTH: 22
<212> TYPE: RNA
<213> ORGANISM: Artificial Sequence
<220> FEATURE:
<223> OTHER INFORMATION: Synthetic Construct

<400> SEQUENCE: 179
acagagauag uuuucaaagc uc 22

<210> SEQ ID NO 180
<211> LENGTH: 22
<212> TYPE: RNA
<213> ORGANISM: Artificial Sequence
<220> FEATURE:
<223> OTHER INFORMATION: Synthetic Construct

<400> SEQUENCE: 180
cagagauagu uuucaaagcu cg 22

-continued

<210> SEQ ID NO 181
<211> LENGTH: 22
<212> TYPE: RNA
<213> ORGANISM: Artificial Sequence
<220> FEATURE:
<223> OTHER INFORMATION: Synthetic Construct

<400> SEQUENCE: 181
agagauaguu uucaaagcuc gg 22

<210> SEQ ID NO 182
<211> LENGTH: 22
<212> TYPE: RNA
<213> ORGANISM: Artificial Sequence
<220> FEATURE:
<223> OTHER INFORMATION: Synthetic Construct

<400> SEQUENCE: 182
gagauaguuu ucaaagcucg ga 22

<210> SEQ ID NO 183
<211> LENGTH: 22
<212> TYPE: RNA
<213> ORGANISM: Artificial Sequence
<220> FEATURE:
<223> OTHER INFORMATION: Synthetic Construct

<400> SEQUENCE: 183
agauaguuuu caaagcucgg ag 22

<210> SEQ ID NO 184
<211> LENGTH: 22
<212> TYPE: RNA
<213> ORGANISM: Artificial Sequence
<220> FEATURE:
<223> OTHER INFORMATION: Synthetic Construct

<400> SEQUENCE: 184
gauaguuuuc aaagcucgga ga 22

<210> SEQ ID NO 185
<211> LENGTH: 22
<212> TYPE: RNA
<213> ORGANISM: Artificial Sequence
<220> FEATURE:
<223> OTHER INFORMATION: Synthetic Construct

<400> SEQUENCE: 185
auaguuuuca aagcucggag aa 22

<210> SEQ ID NO 186
<211> LENGTH: 22
<212> TYPE: RNA
<213> ORGANISM: Artificial Sequence
<220> FEATURE:
<223> OTHER INFORMATION: Synthetic Construct

<400> SEQUENCE: 186
uaguuuucaa agcucggaga ac 22

<210> SEQ ID NO 187
<211> LENGTH: 22
<212> TYPE: RNA
<213> ORGANISM: Artificial Sequence
<220> FEATURE:
<223> OTHER INFORMATION: Synthetic Construct

<400> SEQUENCE: 187
aguuuucaaa gcucggagaa cc 22

<210> SEQ ID NO 188
<211> LENGTH: 22
<212> TYPE: RNA
<213> ORGANISM: Artificial Sequence
<220> FEATURE:
<223> OTHER INFORMATION: Synthetic Construct

<400> SEQUENCE: 188
guuuucaaag cucggagaac cc 22

<210> SEQ ID NO 189
<211> LENGTH: 22
<212> TYPE: RNA
<213> ORGANISM: Artificial Sequence
<220> FEATURE:
<223> OTHER INFORMATION: Synthetic Construct

<400> SEQUENCE: 189
uuuucaaagc ucggagaacc cu 22

<210> SEQ ID NO 190
<211> LENGTH: 22
<212> TYPE: RNA
<213> ORGANISM: Artificial Sequence
<220> FEATURE:
<223> OTHER INFORMATION: Synthetic Construct

<400> SEQUENCE: 190
uuucaaagcu cggagaaccc ug 22

<210> SEQ ID NO 191
<211> LENGTH: 22
<212> TYPE: RNA
<213> ORGANISM: Artificial Sequence
<220> FEATURE:
<223> OTHER INFORMATION: Synthetic Construct

<400> SEQUENCE: 191
uucaaagcuc ggagaacccu ga 22

<210> SEQ ID NO 192
<211> LENGTH: 22
<212> TYPE: RNA
<213> ORGANISM: Artificial Sequence
<220> FEATURE:
<223> OTHER INFORMATION: Synthetic Construct

<400> SEQUENCE: 192
ucaaagcucg gagaacccug aa 22

<210> SEQ ID NO 193
<211> LENGTH: 22
<212> TYPE: RNA
<213> ORGANISM: Artificial Sequence
<220> FEATURE:
<223> OTHER INFORMATION: Synthetic Construct

<400> SEQUENCE: 193
caaagcucgg agaacccuga au 22

<210> SEQ ID NO 194

<211> LENGTH: 22
<212> TYPE: RNA
<213> ORGANISM: Artificial Sequence
<220> FEATURE:
<223> OTHER INFORMATION: Synthetic Construct

<400> SEQUENCE: 194
aaagcucgga gaacccugaa ug 22

<210> SEQ ID NO 195
<211> LENGTH: 22
<212> TYPE: RNA
<213> ORGANISM: Artificial Sequence
<220> FEATURE:
<223> OTHER INFORMATION: Synthetic Construct

<400> SEQUENCE: 195
aagcucggag aacccugaau gu 22

<210> SEQ ID NO 196
<211> LENGTH: 22
<212> TYPE: RNA
<213> ORGANISM: Artificial Sequence
<220> FEATURE:
<223> OTHER INFORMATION: Synthetic Construct

<400> SEQUENCE: 196
agcucggaga acccugaaug uu 22

<210> SEQ ID NO 197
<211> LENGTH: 22
<212> TYPE: RNA
<213> ORGANISM: Artificial Sequence
<220> FEATURE:
<223> OTHER INFORMATION: Synthetic Construct

<400> SEQUENCE: 197
gcucggagaa cccugaaugu uc 22

<210> SEQ ID NO 198
<211> LENGTH: 22
<212> TYPE: RNA
<213> ORGANISM: Artificial Sequence
<220> FEATURE:
<223> OTHER INFORMATION: Synthetic Construct

<400> SEQUENCE: 198
cucggagaac ccugaauguu cu 22

<210> SEQ ID NO 199
<211> LENGTH: 22
<212> TYPE: RNA
<213> ORGANISM: Artificial Sequence
<220> FEATURE:
<223> OTHER INFORMATION: Synthetic Construct

<400> SEQUENCE: 199
ucggagaacc cugaauguuc uc 22

<210> SEQ ID NO 200
<211> LENGTH: 22
<212> TYPE: RNA
<213> ORGANISM: Artificial Sequence
<220> FEATURE:
<223> OTHER INFORMATION: Synthetic Construct

<400> SEQUENCE: 200
cggagaaccc ugaauguucu ca 22

<210> SEQ ID NO 201
<211> LENGTH: 22
<212> TYPE: RNA
<213> ORGANISM: Artificial Sequence
<220> FEATURE:
<223> OTHER INFORMATION: Synthetic Construct

<400> SEQUENCE: 201
ggagaacccu gaauguucuc ag 22

<210> SEQ ID NO 202
<211> LENGTH: 22
<212> TYPE: RNA
<213> ORGANISM: Artificial Sequence
<220> FEATURE:
<223> OTHER INFORMATION: Synthetic Construct

<400> SEQUENCE: 202
gagaacccug aauguucuca gc 22

<210> SEQ ID NO 203
<211> LENGTH: 22
<212> TYPE: RNA
<213> ORGANISM: Artificial Sequence
<220> FEATURE:
<223> OTHER INFORMATION: Synthetic Construct

<400> SEQUENCE: 203
agaacccuga auguucucag cg 22

<210> SEQ ID NO 204
<211> LENGTH: 22
<212> TYPE: RNA
<213> ORGANISM: Artificial Sequence
<220> FEATURE:
<223> OTHER INFORMATION: Synthetic Construct

<400> SEQUENCE: 204
gaacccugaa uguucucagc gc 22

<210> SEQ ID NO 205
<211> LENGTH: 22
<212> TYPE: RNA
<213> ORGANISM: Artificial Sequence
<220> FEATURE:
<223> OTHER INFORMATION: Synthetic Construct

<400> SEQUENCE: 205
aacccugaau guucucagcg cu 22

<210> SEQ ID NO 206
<211> LENGTH: 22
<212> TYPE: RNA
<213> ORGANISM: Artificial Sequence
<220> FEATURE:
<223> OTHER INFORMATION: Synthetic Construct

<400> SEQUENCE: 206
acccugaaug uucucagcgc ug 22

<210> SEQ ID NO 207
<211> LENGTH: 22
<212> TYPE: RNA

<213> ORGANISM: Artificial Sequence
<220> FEATURE:
<223> OTHER INFORMATION: Synthetic Construct

<400> SEQUENCE: 207
cccugaaugu ucucagcgcu ga 22

<210> SEQ ID NO 208
<211> LENGTH: 22
<212> TYPE: RNA
<213> ORGANISM: Artificial Sequence
<220> FEATURE:
<223> OTHER INFORMATION: Synthetic Construct

<400> SEQUENCE: 208
ccugaauguu cucagcgcug ag 22

<210> SEQ ID NO 209
<211> LENGTH: 22
<212> TYPE: RNA
<213> ORGANISM: Artificial Sequence
<220> FEATURE:
<223> OTHER INFORMATION: Synthetic Construct

<400> SEQUENCE: 209
cugaauguuc ucagcgcuga ga 22

<210> SEQ ID NO 210
<211> LENGTH: 22
<212> TYPE: RNA
<213> ORGANISM: Artificial Sequence
<220> FEATURE:
<223> OTHER INFORMATION: Synthetic Construct

<400> SEQUENCE: 210
ugaauguucu cagcgcugag ac 22

<210> SEQ ID NO 211
<211> LENGTH: 22
<212> TYPE: RNA
<213> ORGANISM: Artificial Sequence
<220> FEATURE:
<223> OTHER INFORMATION: Synthetic Construct

<400> SEQUENCE: 211
gaauguucuc agcgcugaga ca 22

<210> SEQ ID NO 212
<211> LENGTH: 22
<212> TYPE: RNA
<213> ORGANISM: Artificial Sequence
<220> FEATURE:
<223> OTHER INFORMATION: Synthetic Construct

<400> SEQUENCE: 212
aauguucuca gcgcugagac au 22

<210> SEQ ID NO 213
<211> LENGTH: 22
<212> TYPE: RNA
<213> ORGANISM: Artificial Sequence
<220> FEATURE:
<223> OTHER INFORMATION: Synthetic Construct

<400> SEQUENCE: 213
auguucucag cgcugagaca uu 22

<210> SEQ ID NO 214
<211> LENGTH: 22
<212> TYPE: RNA
<213> ORGANISM: Artificial Sequence
<220> FEATURE:
<223> OTHER INFORMATION: Synthetic Construct

<400> SEQUENCE: 214
uguucucagc gcugagacau ug 22

<210> SEQ ID NO 215
<211> LENGTH: 22
<212> TYPE: RNA
<213> ORGANISM: Artificial Sequence
<220> FEATURE:
<223> OTHER INFORMATION: Synthetic Construct

<400> SEQUENCE: 215
guucucagcg cugagacauu gc 22

<210> SEQ ID NO 216
<211> LENGTH: 22
<212> TYPE: RNA
<213> ORGANISM: Artificial Sequence
<220> FEATURE:
<223> OTHER INFORMATION: Synthetic Construct

<400> SEQUENCE: 216
uucucagcgc ugagacauug cc 22

<210> SEQ ID NO 217
<211> LENGTH: 22
<212> TYPE: RNA
<213> ORGANISM: Artificial Sequence
<220> FEATURE:
<223> OTHER INFORMATION: Synthetic Construct

<400> SEQUENCE: 217
ucucagcgcu gagacauugc cc 22

<210> SEQ ID NO 218
<211> LENGTH: 22
<212> TYPE: RNA
<213> ORGANISM: Artificial Sequence
<220> FEATURE:
<223> OTHER INFORMATION: Synthetic Construct

<400> SEQUENCE: 218
cucagcgcug agacauugcc ca 22

<210> SEQ ID NO 219
<211> LENGTH: 22
<212> TYPE: RNA
<213> ORGANISM: Artificial Sequence
<220> FEATURE:
<223> OTHER INFORMATION: Synthetic Construct

<400> SEQUENCE: 219
ucagcgcuga gacauugccc ag 22

<210> SEQ ID NO 220
<211> LENGTH: 22
<212> TYPE: RNA
<213> ORGANISM: Artificial Sequence
<220> FEATURE:

<223> OTHER INFORMATION: Synthetic Construct

<400> SEQUENCE: 220
cagcgcugag acauugccca gg 22

<210> SEQ ID NO 221
<211> LENGTH: 22
<212> TYPE: RNA
<213> ORGANISM: Artificial Sequence
<220> FEATURE:
<223> OTHER INFORMATION: Synthetic Construct

<400> SEQUENCE: 221
agcgcugaga cauugcccag gu 22

<210> SEQ ID NO 222
<211> LENGTH: 22
<212> TYPE: RNA
<213> ORGANISM: Artificial Sequence
<220> FEATURE:
<223> OTHER INFORMATION: Synthetic Construct

<400> SEQUENCE: 222
gcgcugagac auugcccagg uc 22

<210> SEQ ID NO 223
<211> LENGTH: 22
<212> TYPE: RNA
<213> ORGANISM: Artificial Sequence
<220> FEATURE:
<223> OTHER INFORMATION: Synthetic Construct

<400> SEQUENCE: 223
cgcugagaca uugcccaggu cc 22

<210> SEQ ID NO 224
<211> LENGTH: 22
<212> TYPE: RNA
<213> ORGANISM: Artificial Sequence
<220> FEATURE:
<223> OTHER INFORMATION: Synthetic Construct

<400> SEQUENCE: 224
gcugagacau ugcccagguc ca 22

<210> SEQ ID NO 225
<211> LENGTH: 22
<212> TYPE: RNA
<213> ORGANISM: Artificial Sequence
<220> FEATURE:
<223> OTHER INFORMATION: Synthetic Construct

<400> SEQUENCE: 225
cugagacauu gcccaggucc ac 22

<210> SEQ ID NO 226
<211> LENGTH: 22
<212> TYPE: RNA
<213> ORGANISM: Artificial Sequence
<220> FEATURE:
<223> OTHER INFORMATION: Synthetic Construct

<400> SEQUENCE: 226
ugagacauug cccaggucca ca 22

-continued

<210> SEQ ID NO 227
<211> LENGTH: 22
<212> TYPE: RNA
<213> ORGANISM: Artificial Sequence
<220> FEATURE:
<223> OTHER INFORMATION: Synthetic Construct

<400> SEQUENCE: 227
gagacauugc ccagguccac aa 22

<210> SEQ ID NO 228
<211> LENGTH: 22
<212> TYPE: RNA
<213> ORGANISM: Artificial Sequence
<220> FEATURE:
<223> OTHER INFORMATION: Synthetic Construct

<400> SEQUENCE: 228
agacauugcc cagguccaca aa 22

<210> SEQ ID NO 229
<211> LENGTH: 22
<212> TYPE: RNA
<213> ORGANISM: Artificial Sequence
<220> FEATURE:
<223> OTHER INFORMATION: Synthetic Construct

<400> SEQUENCE: 229
gacauugccc agguccacaa ac 22

<210> SEQ ID NO 230
<211> LENGTH: 22
<212> TYPE: RNA
<213> ORGANISM: Artificial Sequence
<220> FEATURE:
<223> OTHER INFORMATION: Synthetic Construct

<400> SEQUENCE: 230
acauugccca gguccacaaa cu 22

<210> SEQ ID NO 231
<211> LENGTH: 22
<212> TYPE: RNA
<213> ORGANISM: Artificial Sequence
<220> FEATURE:
<223> OTHER INFORMATION: Synthetic Construct

<400> SEQUENCE: 231
cauugcccag guccacaaac uc 22

<210> SEQ ID NO 232
<211> LENGTH: 22
<212> TYPE: RNA
<213> ORGANISM: Artificial Sequence
<220> FEATURE:
<223> OTHER INFORMATION: Synthetic Construct

<400> SEQUENCE: 232
auugcccagg uccacaaacu cu 22

<210> SEQ ID NO 233
<211> LENGTH: 22
<212> TYPE: RNA
<213> ORGANISM: Artificial Sequence
<220> FEATURE:
<223> OTHER INFORMATION: Synthetic Construct

<400> SEQUENCE: 233
uugcccaggu ccacaaacuc ug 22

<210> SEQ ID NO 234
<211> LENGTH: 22
<212> TYPE: RNA
<213> ORGANISM: Artificial Sequence
<220> FEATURE:
<223> OTHER INFORMATION: Synthetic Construct

<400> SEQUENCE: 234
ugcccagguc cacaaacucu gu 22

<210> SEQ ID NO 235
<211> LENGTH: 22
<212> TYPE: RNA
<213> ORGANISM: Artificial Sequence
<220> FEATURE:
<223> OTHER INFORMATION: Synthetic Construct

<400> SEQUENCE: 235
gcccaggucc acaaacucug uc 22

<210> SEQ ID NO 236
<211> LENGTH: 22
<212> TYPE: RNA
<213> ORGANISM: Artificial Sequence
<220> FEATURE:
<223> OTHER INFORMATION: Synthetic Construct

<400> SEQUENCE: 236
cccaggucca caaacucugu ca 22

<210> SEQ ID NO 237
<211> LENGTH: 22
<212> TYPE: RNA
<213> ORGANISM: Artificial Sequence
<220> FEATURE:
<223> OTHER INFORMATION: Synthetic Construct

<400> SEQUENCE: 237
ccagguccac aaacucuguc ac 22

<210> SEQ ID NO 238
<211> LENGTH: 22
<212> TYPE: RNA
<213> ORGANISM: Artificial Sequence
<220> FEATURE:
<223> OTHER INFORMATION: Synthetic Construct

<400> SEQUENCE: 238
cagguccaca aacucuguca ca 22

<210> SEQ ID NO 239
<211> LENGTH: 22
<212> TYPE: RNA
<213> ORGANISM: Artificial Sequence
<220> FEATURE:
<223> OTHER INFORMATION: Synthetic Construct

<400> SEQUENCE: 239
agguccacaa acucugucac au 22

<210> SEQ ID NO 240
<211> LENGTH: 22

<212> TYPE: RNA
<213> ORGANISM: Artificial Sequence
<220> FEATURE:
<223> OTHER INFORMATION: Synthetic Construct

<400> SEQUENCE: 240
gguccacaaa cucugucaca ua 22

<210> SEQ ID NO 241
<211> LENGTH: 22
<212> TYPE: RNA
<213> ORGANISM: Artificial Sequence
<220> FEATURE:
<223> OTHER INFORMATION: Synthetic Construct

<400> SEQUENCE: 241
guccacaaac ucugucacau au 22

<210> SEQ ID NO 242
<211> LENGTH: 22
<212> TYPE: RNA
<213> ORGANISM: Artificial Sequence
<220> FEATURE:
<223> OTHER INFORMATION: Synthetic Construct

<400> SEQUENCE: 242
uccacaaacu cugucacaua uc 22

<210> SEQ ID NO 243
<211> LENGTH: 22
<212> TYPE: RNA
<213> ORGANISM: Artificial Sequence
<220> FEATURE:
<223> OTHER INFORMATION: Synthetic Construct

<400> SEQUENCE: 243
ccacaaacuc ugucacauau cu 22

<210> SEQ ID NO 244
<211> LENGTH: 22
<212> TYPE: RNA
<213> ORGANISM: Artificial Sequence
<220> FEATURE:
<223> OTHER INFORMATION: Synthetic Construct

<400> SEQUENCE: 244
cacaaacucu gucacauauc ug 22

<210> SEQ ID NO 245
<211> LENGTH: 22
<212> TYPE: RNA
<213> ORGANISM: Artificial Sequence
<220> FEATURE:
<223> OTHER INFORMATION: Synthetic Construct

<400> SEQUENCE: 245
acaaacucug ucacauaucu gu 22

<210> SEQ ID NO 246
<211> LENGTH: 22
<212> TYPE: RNA
<213> ORGANISM: Artificial Sequence
<220> FEATURE:
<223> OTHER INFORMATION: Synthetic Construct

<400> SEQUENCE: 246
caaacucugu cacauaucug ua 22

<210> SEQ ID NO 247
<211> LENGTH: 22
<212> TYPE: RNA
<213> ORGANISM: Artificial Sequence
<220> FEATURE:
<223> OTHER INFORMATION: Synthetic Construct

<400> SEQUENCE: 247
aaacucuguc acauaucugu ag 22

<210> SEQ ID NO 248
<211> LENGTH: 22
<212> TYPE: RNA
<213> ORGANISM: Artificial Sequence
<220> FEATURE:
<223> OTHER INFORMATION: Synthetic Construct

<400> SEQUENCE: 248
aacucuguca cauaucugua gu 22

<210> SEQ ID NO 249
<211> LENGTH: 21
<212> TYPE: RNA
<213> ORGANISM: Artificial Sequence
<220> FEATURE:
<223> OTHER INFORMATION: Synthetic Construct

<400> SEQUENCE: 249
cucaccugga auuacagaga u 21

<210> SEQ ID NO 250
<211> LENGTH: 21
<212> TYPE: RNA
<213> ORGANISM: Artificial Sequence
<220> FEATURE:
<223> OTHER INFORMATION: Synthetic Construct

<400> SEQUENCE: 250
ucaccuggaa uuacagagau a 21

<210> SEQ ID NO 251
<211> LENGTH: 21
<212> TYPE: RNA
<213> ORGANISM: Artificial Sequence
<220> FEATURE:
<223> OTHER INFORMATION: Synthetic Construct

<400> SEQUENCE: 251
caccuggaau uacagagaua g 21

<210> SEQ ID NO 252
<211> LENGTH: 21
<212> TYPE: RNA
<213> ORGANISM: Artificial Sequence
<220> FEATURE:
<223> OTHER INFORMATION: Synthetic Construct

<400> SEQUENCE: 252
accuggaauu acagagauag u 21

<210> SEQ ID NO 253
<211> LENGTH: 21
<212> TYPE: RNA
<213> ORGANISM: Artificial Sequence
<220> FEATURE:
<223> OTHER INFORMATION: Synthetic Construct

<400> SEQUENCE: 253
ccuggaauua cagagauagu u 21

<210> SEQ ID NO 254
<211> LENGTH: 21
<212> TYPE: RNA
<213> ORGANISM: Artificial Sequence
<220> FEATURE:
<223> OTHER INFORMATION: Synthetic Construct

<400> SEQUENCE: 254
cuggaauuac agagauaguu u 21

<210> SEQ ID NO 255
<211> LENGTH: 21
<212> TYPE: RNA
<213> ORGANISM: Artificial Sequence
<220> FEATURE:
<223> OTHER INFORMATION: Synthetic Construct

<400> SEQUENCE: 255
uggaauuaca gagauaguuu u 21

<210> SEQ ID NO 256
<211> LENGTH: 21
<212> TYPE: RNA
<213> ORGANISM: Artificial Sequence
<220> FEATURE:
<223> OTHER INFORMATION: Synthetic Construct

<400> SEQUENCE: 256
ggaauuacag agauaguuuu c 21

<210> SEQ ID NO 257
<211> LENGTH: 21
<212> TYPE: RNA
<213> ORGANISM: Artificial Sequence
<220> FEATURE:
<223> OTHER INFORMATION: Synthetic Construct

<400> SEQUENCE: 257
gaauuacaga gauaguuuuc a 21

<210> SEQ ID NO 258
<211> LENGTH: 21
<212> TYPE: RNA
<213> ORGANISM: Artificial Sequence
<220> FEATURE:
<223> OTHER INFORMATION: Synthetic Construct

<400> SEQUENCE: 258
aauuacagag auaguuuuca a 21

<210> SEQ ID NO 259
<211> LENGTH: 21
<212> TYPE: RNA
<213> ORGANISM: Artificial Sequence
<220> FEATURE:
<223> OTHER INFORMATION: Synthetic Construct

<400> SEQUENCE: 259
auuacagaga uaguuuucaa a 21

<210> SEQ ID NO 260
<211> LENGTH: 21
<212> TYPE: RNA
<213> ORGANISM: Artificial Sequence
<220> FEATURE:
<223> OTHER INFORMATION: Synthetic Construct

<400> SEQUENCE: 260
uuacagagau aguuuucaaa g 21

<210> SEQ ID NO 261
<211> LENGTH: 21
<212> TYPE: RNA
<213> ORGANISM: Artificial Sequence
<220> FEATURE:
<223> OTHER INFORMATION: Synthetic Construct

<400> SEQUENCE: 261
uacagagaua guuuucaaag c 21

<210> SEQ ID NO 262
<211> LENGTH: 21
<212> TYPE: RNA
<213> ORGANISM: Artificial Sequence
<220> FEATURE:
<223> OTHER INFORMATION: Synthetic Construct

<400> SEQUENCE: 262
acagagauag uuuucaaagc u 21

<210> SEQ ID NO 263
<211> LENGTH: 21
<212> TYPE: RNA
<213> ORGANISM: Artificial Sequence
<220> FEATURE:
<223> OTHER INFORMATION: Synthetic Construct

<400> SEQUENCE: 263
cagagauagu uuucaaagcu c 21

<210> SEQ ID NO 264
<211> LENGTH: 21
<212> TYPE: RNA
<213> ORGANISM: Artificial Sequence
<220> FEATURE:
<223> OTHER INFORMATION: Synthetic Construct

<400> SEQUENCE: 264
agagauaguu uucaaagcuc g 21

<210> SEQ ID NO 265
<211> LENGTH: 21
<212> TYPE: RNA
<213> ORGANISM: Artificial Sequence
<220> FEATURE:
<223> OTHER INFORMATION: Synthetic Construct

<400> SEQUENCE: 265
gagauaguuu ucaaagcucg g 21

<210> SEQ ID NO 266
<211> LENGTH: 21
<212> TYPE: RNA
<213> ORGANISM: Artificial Sequence
<220> FEATURE:
<223> OTHER INFORMATION: Synthetic Construct

<400> SEQUENCE: 266
agauaguuuu caaagcucgg a 21

<210> SEQ ID NO 267
<211> LENGTH: 21
<212> TYPE: RNA
<213> ORGANISM: Artificial Sequence
<220> FEATURE:
<223> OTHER INFORMATION: Synthetic Construct

<400> SEQUENCE: 267
gauaguuuuc aaagcucgga g 21

<210> SEQ ID NO 268
<211> LENGTH: 21
<212> TYPE: RNA
<213> ORGANISM: Artificial Sequence
<220> FEATURE:
<223> OTHER INFORMATION: Synthetic Construct

<400> SEQUENCE: 268
auaguuuuca aagcucggag a 21

<210> SEQ ID NO 269
<211> LENGTH: 21
<212> TYPE: RNA
<213> ORGANISM: Artificial Sequence
<220> FEATURE:
<223> OTHER INFORMATION: Synthetic Construct

<400> SEQUENCE: 269
uaguuuucaa agcucggaga a 21

<210> SEQ ID NO 270
<211> LENGTH: 21
<212> TYPE: RNA
<213> ORGANISM: Artificial Sequence
<220> FEATURE:
<223> OTHER INFORMATION: Synthetic Construct

<400> SEQUENCE: 270
aguuuucaaa gcucggagaa c 21

<210> SEQ ID NO 271
<211> LENGTH: 21
<212> TYPE: RNA
<213> ORGANISM: Artificial Sequence
<220> FEATURE:
<223> OTHER INFORMATION: Synthetic Construct

<400> SEQUENCE: 271
guuuucaaag cucggagaac c 21

<210> SEQ ID NO 272
<211> LENGTH: 21
<212> TYPE: RNA
<213> ORGANISM: Artificial Sequence
<220> FEATURE:
<223> OTHER INFORMATION: Synthetic Construct

<400> SEQUENCE: 272
uuuucaaagc ucggagaacc c 21

<210> SEQ ID NO 273

<211> LENGTH: 21
<212> TYPE: RNA
<213> ORGANISM: Artificial Sequence
<220> FEATURE:
<223> OTHER INFORMATION: Synthetic Construct

<400> SEQUENCE: 273
uuucaaagcu cggagaaccc u 21

<210> SEQ ID NO 274
<211> LENGTH: 21
<212> TYPE: RNA
<213> ORGANISM: Artificial Sequence
<220> FEATURE:
<223> OTHER INFORMATION: Synthetic Construct

<400> SEQUENCE: 274
uucaaagcuc ggagaacccu g 21

<210> SEQ ID NO 275
<211> LENGTH: 21
<212> TYPE: RNA
<213> ORGANISM: Artificial Sequence
<220> FEATURE:
<223> OTHER INFORMATION: Synthetic Construct

<400> SEQUENCE: 275
ucaaagcucg gagaacccug a 21

<210> SEQ ID NO 276
<211> LENGTH: 21
<212> TYPE: RNA
<213> ORGANISM: Artificial Sequence
<220> FEATURE:
<223> OTHER INFORMATION: Synthetic Construct

<400> SEQUENCE: 276
caaagcucgg agaacccuga a 21

<210> SEQ ID NO 277
<211> LENGTH: 21
<212> TYPE: RNA
<213> ORGANISM: Artificial Sequence
<220> FEATURE:
<223> OTHER INFORMATION: Synthetic Construct

<400> SEQUENCE: 277
aaagcucgga gaacccugaa u 21

<210> SEQ ID NO 278
<211> LENGTH: 21
<212> TYPE: RNA
<213> ORGANISM: Artificial Sequence
<220> FEATURE:
<223> OTHER INFORMATION: Synthetic Construct

<400> SEQUENCE: 278
aagcucggag aacccugaau g 21

<210> SEQ ID NO 279
<211> LENGTH: 21
<212> TYPE: RNA
<213> ORGANISM: Artificial Sequence
<220> FEATURE:
<223> OTHER INFORMATION: Synthetic Construct

<400> SEQUENCE: 279
agcucggaga acccugaaug u 21

<210> SEQ ID NO 280
<211> LENGTH: 21
<212> TYPE: RNA
<213> ORGANISM: Artificial Sequence
<220> FEATURE:
<223> OTHER INFORMATION: Synthetic Construct

<400> SEQUENCE: 280
gcucggagaa cccugaaugu u 21

<210> SEQ ID NO 281
<211> LENGTH: 21
<212> TYPE: RNA
<213> ORGANISM: Artificial Sequence
<220> FEATURE:
<223> OTHER INFORMATION: Synthetic Construct

<400> SEQUENCE: 281
cucggagaac ccugaauguu c 21

<210> SEQ ID NO 282
<211> LENGTH: 21
<212> TYPE: RNA
<213> ORGANISM: Artificial Sequence
<220> FEATURE:
<223> OTHER INFORMATION: Synthetic Construct

<400> SEQUENCE: 282
ucggagaacc cugaauguuc u 21

<210> SEQ ID NO 283
<211> LENGTH: 21
<212> TYPE: RNA
<213> ORGANISM: Artificial Sequence
<220> FEATURE:
<223> OTHER INFORMATION: Synthetic Construct

<400> SEQUENCE: 283
cggagaaccc ugaauguucu c 21

<210> SEQ ID NO 284
<211> LENGTH: 21
<212> TYPE: RNA
<213> ORGANISM: Artificial Sequence
<220> FEATURE:
<223> OTHER INFORMATION: Synthetic Construct

<400> SEQUENCE: 284
ggagaacccu gaauguucuc a 21

<210> SEQ ID NO 285
<211> LENGTH: 21
<212> TYPE: RNA
<213> ORGANISM: Artificial Sequence
<220> FEATURE:
<223> OTHER INFORMATION: Synthetic Construct

<400> SEQUENCE: 285
gagaacccug aauguucuca g 21

<210> SEQ ID NO 286
<211> LENGTH: 21
<212> TYPE: RNA

-continued

<213> ORGANISM: Artificial Sequence
<220> FEATURE:
<223> OTHER INFORMATION: Synthetic Construct

<400> SEQUENCE: 286
agaacccuga auguucucag c 21

<210> SEQ ID NO 287
<211> LENGTH: 21
<212> TYPE: RNA
<213> ORGANISM: Artificial Sequence
<220> FEATURE:
<223> OTHER INFORMATION: Synthetic Construct

<400> SEQUENCE: 287
gaacccugaa uguucucagc g 21

<210> SEQ ID NO 288
<211> LENGTH: 21
<212> TYPE: RNA
<213> ORGANISM: Artificial Sequence
<220> FEATURE:
<223> OTHER INFORMATION: Synthetic Construct

<400> SEQUENCE: 288
aacccugaau guucucagcg c 21

<210> SEQ ID NO 289
<211> LENGTH: 21
<212> TYPE: RNA
<213> ORGANISM: Artificial Sequence
<220> FEATURE:
<223> OTHER INFORMATION: Synthetic Construct

<400> SEQUENCE: 289
acccugaaug uucucagcgc u 21

<210> SEQ ID NO 290
<211> LENGTH: 21
<212> TYPE: RNA
<213> ORGANISM: Artificial Sequence
<220> FEATURE:
<223> OTHER INFORMATION: Synthetic Construct

<400> SEQUENCE: 290
cccugaaugu ucucagcgcu g 21

<210> SEQ ID NO 291
<211> LENGTH: 21
<212> TYPE: RNA
<213> ORGANISM: Artificial Sequence
<220> FEATURE:
<223> OTHER INFORMATION: Synthetic Construct

<400> SEQUENCE: 291
ccugaauguu cucagcgcug a 21

<210> SEQ ID NO 292
<211> LENGTH: 21
<212> TYPE: RNA
<213> ORGANISM: Artificial Sequence
<220> FEATURE:
<223> OTHER INFORMATION: Synthetic Construct

<400> SEQUENCE: 292
cugaauguuc ucagcgcuga g 21

<210> SEQ ID NO 293
<211> LENGTH: 21
<212> TYPE: RNA
<213> ORGANISM: Artificial Sequence
<220> FEATURE:
<223> OTHER INFORMATION: Synthetic Construct

<400> SEQUENCE: 293
ugaauguucu cagcgcugag a 21

<210> SEQ ID NO 294
<211> LENGTH: 21
<212> TYPE: RNA
<213> ORGANISM: Artificial Sequence
<220> FEATURE:
<223> OTHER INFORMATION: Synthetic Construct

<400> SEQUENCE: 294
gaauguucuc agcgcugaga c 21

<210> SEQ ID NO 295
<211> LENGTH: 21
<212> TYPE: RNA
<213> ORGANISM: Artificial Sequence
<220> FEATURE:
<223> OTHER INFORMATION: Synthetic Construct

<400> SEQUENCE: 295
aauguucuca gcgcugagac a 21

<210> SEQ ID NO 296
<211> LENGTH: 21
<212> TYPE: RNA
<213> ORGANISM: Artificial Sequence
<220> FEATURE:
<223> OTHER INFORMATION: Synthetic Construct

<400> SEQUENCE: 296
auguucucag cgcugagaca u 21

<210> SEQ ID NO 297
<211> LENGTH: 21
<212> TYPE: RNA
<213> ORGANISM: Artificial Sequence
<220> FEATURE:
<223> OTHER INFORMATION: Synthetic Construct

<400> SEQUENCE: 297
uguucucagc gcugagacau u 21

<210> SEQ ID NO 298
<211> LENGTH: 21
<212> TYPE: RNA
<213> ORGANISM: Artificial Sequence
<220> FEATURE:
<223> OTHER INFORMATION: Synthetic Construct

<400> SEQUENCE: 298
guucucagcg cugagacauu g 21

<210> SEQ ID NO 299
<211> LENGTH: 21
<212> TYPE: RNA
<213> ORGANISM: Artificial Sequence
<220> FEATURE:

<223> OTHER INFORMATION: Synthetic Construct

<400> SEQUENCE: 299
uucucagcgc ugagacauug c 21

<210> SEQ ID NO 300
<211> LENGTH: 21
<212> TYPE: RNA
<213> ORGANISM: Artificial Sequence
<220> FEATURE:
<223> OTHER INFORMATION: Synthetic Construct

<400> SEQUENCE: 300
ucucagcgcu gagacauugc c 21

<210> SEQ ID NO 301
<211> LENGTH: 21
<212> TYPE: RNA
<213> ORGANISM: Artificial Sequence
<220> FEATURE:
<223> OTHER INFORMATION: Synthetic Construct

<400> SEQUENCE: 301
cucagcgcug agacauugcc c 21

<210> SEQ ID NO 302
<211> LENGTH: 21
<212> TYPE: RNA
<213> ORGANISM: Artificial Sequence
<220> FEATURE:
<223> OTHER INFORMATION: Synthetic Construct

<400> SEQUENCE: 302
ucagcgcuga gacauugccc a 21

<210> SEQ ID NO 303
<211> LENGTH: 21
<212> TYPE: RNA
<213> ORGANISM: Artificial Sequence
<220> FEATURE:
<223> OTHER INFORMATION: Synthetic Construct

<400> SEQUENCE: 303
cagcgcugag acauugccca g 21

<210> SEQ ID NO 304
<211> LENGTH: 21
<212> TYPE: RNA
<213> ORGANISM: Artificial Sequence
<220> FEATURE:
<223> OTHER INFORMATION: Synthetic Construct

<400> SEQUENCE: 304
agcgcugaga cauugcccag g 21

<210> SEQ ID NO 305
<211> LENGTH: 21
<212> TYPE: RNA
<213> ORGANISM: Artificial Sequence
<220> FEATURE:
<223> OTHER INFORMATION: Synthetic Construct

<400> SEQUENCE: 305
gcgcugagac auugcccagg u 21

<210> SEQ ID NO 306
<211> LENGTH: 21
<212> TYPE: RNA
<213> ORGANISM: Artificial Sequence
<220> FEATURE:
<223> OTHER INFORMATION: Synthetic Construct

<400> SEQUENCE: 306
cgcugagaca uugcccaggu c 21

<210> SEQ ID NO 307
<211> LENGTH: 21
<212> TYPE: RNA
<213> ORGANISM: Artificial Sequence
<220> FEATURE:
<223> OTHER INFORMATION: Synthetic Construct

<400> SEQUENCE: 307
gcugagacau ugcccagguc c 21

<210> SEQ ID NO 308
<211> LENGTH: 21
<212> TYPE: RNA
<213> ORGANISM: Artificial Sequence
<220> FEATURE:
<223> OTHER INFORMATION: Synthetic Construct

<400> SEQUENCE: 308
cugagacauu gcccaggucc a 21

<210> SEQ ID NO 309
<211> LENGTH: 21
<212> TYPE: RNA
<213> ORGANISM: Artificial Sequence
<220> FEATURE:
<223> OTHER INFORMATION: Synthetic Construct

<400> SEQUENCE: 309
ugagacauug cccaggucca c 21

<210> SEQ ID NO 310
<211> LENGTH: 21
<212> TYPE: RNA
<213> ORGANISM: Artificial Sequence
<220> FEATURE:
<223> OTHER INFORMATION: Synthetic Construct

<400> SEQUENCE: 310
gagacauugc ccagguccac a 21

<210> SEQ ID NO 311
<211> LENGTH: 21
<212> TYPE: RNA
<213> ORGANISM: Artificial Sequence
<220> FEATURE:
<223> OTHER INFORMATION: Synthetic Construct

<400> SEQUENCE: 311
agacauugcc cagguccaca a 21

<210> SEQ ID NO 312
<211> LENGTH: 21
<212> TYPE: RNA
<213> ORGANISM: Artificial Sequence
<220> FEATURE:
<223> OTHER INFORMATION: Synthetic Construct

<400> SEQUENCE: 312
gacauugccc agguccacaa a 21

<210> SEQ ID NO 313
<211> LENGTH: 21
<212> TYPE: RNA
<213> ORGANISM: Artificial Sequence
<220> FEATURE:
<223> OTHER INFORMATION: Synthetic Construct

<400> SEQUENCE: 313
acauugccca gguccacaaa c 21

<210> SEQ ID NO 314
<211> LENGTH: 21
<212> TYPE: RNA
<213> ORGANISM: Artificial Sequence
<220> FEATURE:
<223> OTHER INFORMATION: Synthetic Construct

<400> SEQUENCE: 314
cauugcccag guccacaaac u 21

<210> SEQ ID NO 315
<211> LENGTH: 21
<212> TYPE: RNA
<213> ORGANISM: Artificial Sequence
<220> FEATURE:
<223> OTHER INFORMATION: Synthetic Construct

<400> SEQUENCE: 315
auugcccagg uccacaaacu c 21

<210> SEQ ID NO 316
<211> LENGTH: 21
<212> TYPE: RNA
<213> ORGANISM: Artificial Sequence
<220> FEATURE:
<223> OTHER INFORMATION: Synthetic Construct

<400> SEQUENCE: 316
uugcccaggu ccacaaacuc u 21

<210> SEQ ID NO 317
<211> LENGTH: 21
<212> TYPE: RNA
<213> ORGANISM: Artificial Sequence
<220> FEATURE:
<223> OTHER INFORMATION: Synthetic Construct

<400> SEQUENCE: 317
ugcccagguc cacaaacucu g 21

<210> SEQ ID NO 318
<211> LENGTH: 21
<212> TYPE: RNA
<213> ORGANISM: Artificial Sequence
<220> FEATURE:
<223> OTHER INFORMATION: Synthetic Construct

<400> SEQUENCE: 318
gcccaggucc acaaacucug u 21

<210> SEQ ID NO 319
<211> LENGTH: 21

<212> TYPE: RNA
<213> ORGANISM: Artificial Sequence
<220> FEATURE:
<223> OTHER INFORMATION: Synthetic Construct

<400> SEQUENCE: 319
cccaggucca caaacucugu c 21

<210> SEQ ID NO 320
<211> LENGTH: 21
<212> TYPE: RNA
<213> ORGANISM: Artificial Sequence
<220> FEATURE:
<223> OTHER INFORMATION: Synthetic Construct

<400> SEQUENCE: 320
ccagguccac aaacucuguc a 21

<210> SEQ ID NO 321
<211> LENGTH: 21
<212> TYPE: RNA
<213> ORGANISM: Artificial Sequence
<220> FEATURE:
<223> OTHER INFORMATION: Synthetic Construct

<400> SEQUENCE: 321
cagguccaca aacucuguca c 21

<210> SEQ ID NO 322
<211> LENGTH: 21
<212> TYPE: RNA
<213> ORGANISM: Artificial Sequence
<220> FEATURE:
<223> OTHER INFORMATION: Synthetic Construct

<400> SEQUENCE: 322
agguccacaa acucugucac a 21

<210> SEQ ID NO 323
<211> LENGTH: 21
<212> TYPE: RNA
<213> ORGANISM: Artificial Sequence
<220> FEATURE:
<223> OTHER INFORMATION: Synthetic Construct

<400> SEQUENCE: 323
gguccacaaa cucugucaca u 21

<210> SEQ ID NO 324
<211> LENGTH: 21
<212> TYPE: RNA
<213> ORGANISM: Artificial Sequence
<220> FEATURE:
<223> OTHER INFORMATION: Synthetic Construct

<400> SEQUENCE: 324
guccacaaac ucugucacau a 21

<210> SEQ ID NO 325
<211> LENGTH: 21
<212> TYPE: RNA
<213> ORGANISM: Artificial Sequence
<220> FEATURE:
<223> OTHER INFORMATION: Synthetic Construct

<400> SEQUENCE: 325
uccacaaacu cugucacaua u 21

<210> SEQ ID NO 326
<211> LENGTH: 21
<212> TYPE: RNA
<213> ORGANISM: Artificial Sequence
<220> FEATURE:
<223> OTHER INFORMATION: Synthetic Construct

<400> SEQUENCE: 326
ccacaaacuc ugucacauau c 21

<210> SEQ ID NO 327
<211> LENGTH: 21
<212> TYPE: RNA
<213> ORGANISM: Artificial Sequence
<220> FEATURE:
<223> OTHER INFORMATION: Synthetic Construct

<400> SEQUENCE: 327
cacaaacucu gucacauauc u 21

<210> SEQ ID NO 328
<211> LENGTH: 21
<212> TYPE: RNA
<213> ORGANISM: Artificial Sequence
<220> FEATURE:
<223> OTHER INFORMATION: Synthetic Construct

<400> SEQUENCE: 328
acaaacucug ucacauaucu g 21

<210> SEQ ID NO 329
<211> LENGTH: 21
<212> TYPE: RNA
<213> ORGANISM: Artificial Sequence
<220> FEATURE:
<223> OTHER INFORMATION: Synthetic Construct

<400> SEQUENCE: 329
caaacucugu cacauaucug u 21

<210> SEQ ID NO 330
<211> LENGTH: 21
<212> TYPE: RNA
<213> ORGANISM: Artificial Sequence
<220> FEATURE:
<223> OTHER INFORMATION: Synthetic Construct

<400> SEQUENCE: 330
aaacucuguc acauaucugu a 21

<210> SEQ ID NO 331
<211> LENGTH: 21
<212> TYPE: RNA
<213> ORGANISM: Artificial Sequence
<220> FEATURE:
<223> OTHER INFORMATION: Synthetic Construct

<400> SEQUENCE: 331
aacucuguca cauaucugua g 21

<210> SEQ ID NO 332
<211> LENGTH: 21
<212> TYPE: RNA
<213> ORGANISM: Artificial Sequence
<220> FEATURE:
<223> OTHER INFORMATION: Synthetic Construct

<400> SEQUENCE: 332
acucugucac auaucuguag u 21

<210> SEQ ID NO 333
<211> LENGTH: 20
<212> TYPE: RNA
<213> ORGANISM: Artificial Sequence
<220> FEATURE:
<223> OTHER INFORMATION: Synthetic Construct

<400> SEQUENCE: 333
cucaccugga auuacagaga 20

<210> SEQ ID NO 334
<211> LENGTH: 20
<212> TYPE: RNA
<213> ORGANISM: Artificial Sequence
<220> FEATURE:
<223> OTHER INFORMATION: Synthetic Construct

<400> SEQUENCE: 334
ucaccuggaa uuacagagau 20

<210> SEQ ID NO 335
<211> LENGTH: 20
<212> TYPE: RNA
<213> ORGANISM: Artificial Sequence
<220> FEATURE:
<223> OTHER INFORMATION: Synthetic Construct

<400> SEQUENCE: 335
caccuggaau uacagagaua 20

<210> SEQ ID NO 336
<211> LENGTH: 20
<212> TYPE: RNA
<213> ORGANISM: Artificial Sequence
<220> FEATURE:
<223> OTHER INFORMATION: Synthetic Construct

<400> SEQUENCE: 336
accuggaauu acagagauag 20

<210> SEQ ID NO 337
<211> LENGTH: 20
<212> TYPE: RNA
<213> ORGANISM: Artificial Sequence
<220> FEATURE:
<223> OTHER INFORMATION: Synthetic Construct

<400> SEQUENCE: 337
ccuggaauua cagagauagu 20

<210> SEQ ID NO 338
<211> LENGTH: 20
<212> TYPE: RNA
<213> ORGANISM: Artificial Sequence
<220> FEATURE:
<223> OTHER INFORMATION: Synthetic Construct

<400> SEQUENCE: 338
cuggaauuac agagauaguu 20

<210> SEQ ID NO 339
<211> LENGTH: 20
<212> TYPE: RNA
<213> ORGANISM: Artificial Sequence
<220> FEATURE:
<223> OTHER INFORMATION: Synthetic Construct

<400> SEQUENCE: 339
uggaauuaca gagauaguuu 20

<210> SEQ ID NO 340
<211> LENGTH: 20
<212> TYPE: RNA
<213> ORGANISM: Artificial Sequence
<220> FEATURE:
<223> OTHER INFORMATION: Synthetic Construct

<400> SEQUENCE: 340
ggaauuacag agauaguuuu 20

<210> SEQ ID NO 341
<211> LENGTH: 20
<212> TYPE: RNA
<213> ORGANISM: Artificial Sequence
<220> FEATURE:
<223> OTHER INFORMATION: Synthetic Construct

<400> SEQUENCE: 341
gaauuacaga gauaguuuuc 20

<210> SEQ ID NO 342
<211> LENGTH: 20
<212> TYPE: RNA
<213> ORGANISM: Artificial Sequence
<220> FEATURE:
<223> OTHER INFORMATION: Synthetic Construct

<400> SEQUENCE: 342
aauuacagag auaguuuuca 20

<210> SEQ ID NO 343
<211> LENGTH: 20
<212> TYPE: RNA
<213> ORGANISM: Artificial Sequence
<220> FEATURE:
<223> OTHER INFORMATION: Synthetic Construct

<400> SEQUENCE: 343
auuacagaga uaguuuucaa 20

<210> SEQ ID NO 344
<211> LENGTH: 20
<212> TYPE: RNA
<213> ORGANISM: Artificial Sequence
<220> FEATURE:
<223> OTHER INFORMATION: Synthetic Construct

<400> SEQUENCE: 344
uuacagagau aguuuucaaa 20

<210> SEQ ID NO 345
<211> LENGTH: 20
<212> TYPE: RNA
<213> ORGANISM: Artificial Sequence
<220> FEATURE:
<223> OTHER INFORMATION: Synthetic Construct

<400> SEQUENCE: 345
uacagagaua guuuucaaag 20

<210> SEQ ID NO 346
<211> LENGTH: 20
<212> TYPE: RNA
<213> ORGANISM: Artificial Sequence
<220> FEATURE:
<223> OTHER INFORMATION: Synthetic Construct

<400> SEQUENCE: 346
acagagauag uuuucaaagc 20

<210> SEQ ID NO 347
<211> LENGTH: 20
<212> TYPE: RNA
<213> ORGANISM: Artificial Sequence
<220> FEATURE:
<223> OTHER INFORMATION: Synthetic Construct

<400> SEQUENCE: 347
cagagauagu uuucaaagcu 20

<210> SEQ ID NO 348
<211> LENGTH: 20
<212> TYPE: RNA
<213> ORGANISM: Artificial Sequence
<220> FEATURE:
<223> OTHER INFORMATION: Synthetic Construct

<400> SEQUENCE: 348
agagauaguu uucaaagcuc 20

<210> SEQ ID NO 349
<211> LENGTH: 20
<212> TYPE: RNA
<213> ORGANISM: Artificial Sequence
<220> FEATURE:
<223> OTHER INFORMATION: Synthetic Construct

<400> SEQUENCE: 349
gagauaguuu ucaaagcucg 20

<210> SEQ ID NO 350
<211> LENGTH: 20
<212> TYPE: RNA
<213> ORGANISM: Artificial Sequence
<220> FEATURE:
<223> OTHER INFORMATION: Synthetic Construct

<400> SEQUENCE: 350
agauaguuuu caaagcucgg 20

<210> SEQ ID NO 351
<211> LENGTH: 20
<212> TYPE: RNA
<213> ORGANISM: Artificial Sequence
<220> FEATURE:
<223> OTHER INFORMATION: Synthetic Construct

<400> SEQUENCE: 351
gauaguuuuc aaagcucgga 20

<210> SEQ ID NO 352

<211> LENGTH: 20
<212> TYPE: RNA
<213> ORGANISM: Artificial Sequence
<220> FEATURE:
<223> OTHER INFORMATION: Synthetic Construct

<400> SEQUENCE: 352
auaguuuuca aagcucggag 20

<210> SEQ ID NO 353
<211> LENGTH: 20
<212> TYPE: RNA
<213> ORGANISM: Artificial Sequence
<220> FEATURE:
<223> OTHER INFORMATION: Synthetic Construct

<400> SEQUENCE: 353
uaguuuucaa agcucggaga 20

<210> SEQ ID NO 354
<211> LENGTH: 20
<212> TYPE: RNA
<213> ORGANISM: Artificial Sequence
<220> FEATURE:
<223> OTHER INFORMATION: Synthetic Construct

<400> SEQUENCE: 354
aguuuucaaa gcucggagaa 20

<210> SEQ ID NO 355
<211> LENGTH: 20
<212> TYPE: RNA
<213> ORGANISM: Artificial Sequence
<220> FEATURE:
<223> OTHER INFORMATION: Synthetic Construct

<400> SEQUENCE: 355
guuuucaaag cucggagaac 20

<210> SEQ ID NO 356
<211> LENGTH: 20
<212> TYPE: RNA
<213> ORGANISM: Artificial Sequence
<220> FEATURE:
<223> OTHER INFORMATION: Synthetic Construct

<400> SEQUENCE: 356
uuuucaaagc ucggagaacc 20

<210> SEQ ID NO 357
<211> LENGTH: 20
<212> TYPE: RNA
<213> ORGANISM: Artificial Sequence
<220> FEATURE:
<223> OTHER INFORMATION: Synthetic Construct

<400> SEQUENCE: 357
uuucaaagcu cggagaaccc 20

<210> SEQ ID NO 358
<211> LENGTH: 20
<212> TYPE: RNA
<213> ORGANISM: Artificial Sequence
<220> FEATURE:
<223> OTHER INFORMATION: Synthetic Construct

<400> SEQUENCE: 358
uucaaagcuc ggagaacccu 20

<210> SEQ ID NO 359
<211> LENGTH: 20
<212> TYPE: RNA
<213> ORGANISM: Artificial Sequence
<220> FEATURE:
<223> OTHER INFORMATION: Synthetic Construct

<400> SEQUENCE: 359
ucaaagcucg gagaacccug 20

<210> SEQ ID NO 360
<211> LENGTH: 20
<212> TYPE: RNA
<213> ORGANISM: Artificial Sequence
<220> FEATURE:
<223> OTHER INFORMATION: Synthetic Construct

<400> SEQUENCE: 360
caaagcucgg agaacccuga 20

<210> SEQ ID NO 361
<211> LENGTH: 20
<212> TYPE: RNA
<213> ORGANISM: Artificial Sequence
<220> FEATURE:
<223> OTHER INFORMATION: Synthetic Construct

<400> SEQUENCE: 361
aaagcucgga gaacccugaa 20

<210> SEQ ID NO 362
<211> LENGTH: 20
<212> TYPE: RNA
<213> ORGANISM: Artificial Sequence
<220> FEATURE:
<223> OTHER INFORMATION: Synthetic Construct

<400> SEQUENCE: 362
aagcucggag aacccugaau 20

<210> SEQ ID NO 363
<211> LENGTH: 20
<212> TYPE: RNA
<213> ORGANISM: Artificial Sequence
<220> FEATURE:
<223> OTHER INFORMATION: Synthetic Construct

<400> SEQUENCE: 363
agcucggaga acccugaaug 20

<210> SEQ ID NO 364
<211> LENGTH: 20
<212> TYPE: RNA
<213> ORGANISM: Artificial Sequence
<220> FEATURE:
<223> OTHER INFORMATION: Synthetic Construct

<400> SEQUENCE: 364
gcucggagaa cccugaaugu 20

<210> SEQ ID NO 365
<211> LENGTH: 20
<212> TYPE: RNA

<213> ORGANISM: Artificial Sequence
<220> FEATURE:
<223> OTHER INFORMATION: Synthetic Construct

<400> SEQUENCE: 365
cucggagaac ccugaauguu 20

<210> SEQ ID NO 366
<211> LENGTH: 20
<212> TYPE: RNA
<213> ORGANISM: Artificial Sequence
<220> FEATURE:
<223> OTHER INFORMATION: Synthetic Construct

<400> SEQUENCE: 366
ucggagaacc cugaauguuc 20

<210> SEQ ID NO 367
<211> LENGTH: 20
<212> TYPE: RNA
<213> ORGANISM: Artificial Sequence
<220> FEATURE:
<223> OTHER INFORMATION: Synthetic Construct

<400> SEQUENCE: 367
cggagaaccc ugaauguucu 20

<210> SEQ ID NO 368
<211> LENGTH: 20
<212> TYPE: RNA
<213> ORGANISM: Artificial Sequence
<220> FEATURE:
<223> OTHER INFORMATION: Synthetic Construct

<400> SEQUENCE: 368
ggagaacccu gaauguucuc 20

<210> SEQ ID NO 369
<211> LENGTH: 20
<212> TYPE: RNA
<213> ORGANISM: Artificial Sequence
<220> FEATURE:
<223> OTHER INFORMATION: Synthetic Construct

<400> SEQUENCE: 369
gagaacccug aauguucuca 20

<210> SEQ ID NO 370
<211> LENGTH: 20
<212> TYPE: RNA
<213> ORGANISM: Artificial Sequence
<220> FEATURE:
<223> OTHER INFORMATION: Synthetic Construct

<400> SEQUENCE: 370
agaacccuga auguucucag 20

<210> SEQ ID NO 371
<211> LENGTH: 20
<212> TYPE: RNA
<213> ORGANISM: Artificial Sequence
<220> FEATURE:
<223> OTHER INFORMATION: Synthetic Construct

<400> SEQUENCE: 371
gaacccugaa uguucucagc 20

<210> SEQ ID NO 372
<211> LENGTH: 20
<212> TYPE: RNA
<213> ORGANISM: Artificial Sequence
<220> FEATURE:
<223> OTHER INFORMATION: Synthetic Construct

<400> SEQUENCE: 372
aacccugaau guucucagcg 20

<210> SEQ ID NO 373
<211> LENGTH: 20
<212> TYPE: RNA
<213> ORGANISM: Artificial Sequence
<220> FEATURE:
<223> OTHER INFORMATION: Synthetic Construct

<400> SEQUENCE: 373
acccugaaug uucucagcgc 20

<210> SEQ ID NO 374
<211> LENGTH: 20
<212> TYPE: RNA
<213> ORGANISM: Artificial Sequence
<220> FEATURE:
<223> OTHER INFORMATION: Synthetic Construct

<400> SEQUENCE: 374
cccugaaugu ucucagcgcu 20

<210> SEQ ID NO 375
<211> LENGTH: 20
<212> TYPE: RNA
<213> ORGANISM: Artificial Sequence
<220> FEATURE:
<223> OTHER INFORMATION: Synthetic Construct

<400> SEQUENCE: 375
ccugaauguu cucagcgcug 20

<210> SEQ ID NO 376
<211> LENGTH: 20
<212> TYPE: RNA
<213> ORGANISM: Artificial Sequence
<220> FEATURE:
<223> OTHER INFORMATION: Synthetic Construct

<400> SEQUENCE: 376
cugaauguuc ucagcgcuga 20

<210> SEQ ID NO 377
<211> LENGTH: 20
<212> TYPE: RNA
<213> ORGANISM: Artificial Sequence
<220> FEATURE:
<223> OTHER INFORMATION: Synthetic Construct

<400> SEQUENCE: 377
ugaauguucu cagcgcugag 20

<210> SEQ ID NO 378
<211> LENGTH: 20
<212> TYPE: RNA
<213> ORGANISM: Artificial Sequence
<220> FEATURE:

<223> OTHER INFORMATION: Synthetic Construct

<400> SEQUENCE: 378
gaauguucuc agcgcugaga 20

<210> SEQ ID NO 379
<211> LENGTH: 20
<212> TYPE: RNA
<213> ORGANISM: Artificial Sequence
<220> FEATURE:
<223> OTHER INFORMATION: Synthetic Construct

<400> SEQUENCE: 379
aauguucuca gcgcugagac 20

<210> SEQ ID NO 380
<211> LENGTH: 20
<212> TYPE: RNA
<213> ORGANISM: Artificial Sequence
<220> FEATURE:
<223> OTHER INFORMATION: Synthetic Construct

<400> SEQUENCE: 380
auguucucag cgcugagaca 20

<210> SEQ ID NO 381
<211> LENGTH: 20
<212> TYPE: RNA
<213> ORGANISM: Artificial Sequence
<220> FEATURE:
<223> OTHER INFORMATION: Synthetic Construct

<400> SEQUENCE: 381
uguucucagc gcugagacau 20

<210> SEQ ID NO 382
<211> LENGTH: 20
<212> TYPE: RNA
<213> ORGANISM: Artificial Sequence
<220> FEATURE:
<223> OTHER INFORMATION: Synthetic Construct

<400> SEQUENCE: 382
guucucagcg cugagacauu 20

<210> SEQ ID NO 383
<211> LENGTH: 20
<212> TYPE: RNA
<213> ORGANISM: Artificial Sequence
<220> FEATURE:
<223> OTHER INFORMATION: Synthetic Construct

<400> SEQUENCE: 383
uucucagcgc ugagacauug 20

<210> SEQ ID NO 384
<211> LENGTH: 20
<212> TYPE: RNA
<213> ORGANISM: Artificial Sequence
<220> FEATURE:
<223> OTHER INFORMATION: Synthetic Construct

<400> SEQUENCE: 384
ucucagcgcu gagacauugc 20

<210> SEQ ID NO 385
<211> LENGTH: 20
<212> TYPE: RNA
<213> ORGANISM: Artificial Sequence
<220> FEATURE:
<223> OTHER INFORMATION: Synthetic Construct

<400> SEQUENCE: 385
cucagcgcug agacauugcc 20

<210> SEQ ID NO 386
<211> LENGTH: 20
<212> TYPE: RNA
<213> ORGANISM: Artificial Sequence
<220> FEATURE:
<223> OTHER INFORMATION: Synthetic Construct

<400> SEQUENCE: 386
ucagcgcuga gacauugccc 20

<210> SEQ ID NO 387
<211> LENGTH: 20
<212> TYPE: RNA
<213> ORGANISM: Artificial Sequence
<220> FEATURE:
<223> OTHER INFORMATION: Synthetic Construct

<400> SEQUENCE: 387
cagcgcugag acauugccca 20

<210> SEQ ID NO 388
<211> LENGTH: 20
<212> TYPE: RNA
<213> ORGANISM: Artificial Sequence
<220> FEATURE:
<223> OTHER INFORMATION: Synthetic Construct

<400> SEQUENCE: 388
agcgcugaga cauugcccag 20

<210> SEQ ID NO 389
<211> LENGTH: 20
<212> TYPE: RNA
<213> ORGANISM: Artificial Sequence
<220> FEATURE:
<223> OTHER INFORMATION: Synthetic Construct

<400> SEQUENCE: 389
gcgcugagac auugcccagg 20

<210> SEQ ID NO 390
<211> LENGTH: 20
<212> TYPE: RNA
<213> ORGANISM: Artificial Sequence
<220> FEATURE:
<223> OTHER INFORMATION: Synthetic Construct

<400> SEQUENCE: 390
cgcugagaca uugcccaggu 20

<210> SEQ ID NO 391
<211> LENGTH: 20
<212> TYPE: RNA
<213> ORGANISM: Artificial Sequence
<220> FEATURE:
<223> OTHER INFORMATION: Synthetic Construct

<400> SEQUENCE: 391
gcugagacau ugcccagguc 20

<210> SEQ ID NO 392
<211> LENGTH: 20
<212> TYPE: RNA
<213> ORGANISM: Artificial Sequence
<220> FEATURE:
<223> OTHER INFORMATION: Synthetic Construct

<400> SEQUENCE: 392
cugagacauu gcccaggucc 20

<210> SEQ ID NO 393
<211> LENGTH: 20
<212> TYPE: RNA
<213> ORGANISM: Artificial Sequence
<220> FEATURE:
<223> OTHER INFORMATION: Synthetic Construct

<400> SEQUENCE: 393
ugagacauug cccaggucca 20

<210> SEQ ID NO 394
<211> LENGTH: 20
<212> TYPE: RNA
<213> ORGANISM: Artificial Sequence
<220> FEATURE:
<223> OTHER INFORMATION: Synthetic Construct

<400> SEQUENCE: 394
gagacauugc ccagguccac 20

<210> SEQ ID NO 395
<211> LENGTH: 20
<212> TYPE: RNA
<213> ORGANISM: Artificial Sequence
<220> FEATURE:
<223> OTHER INFORMATION: Synthetic Construct

<400> SEQUENCE: 395
agacauugcc cagguccaca 20

<210> SEQ ID NO 396
<211> LENGTH: 20
<212> TYPE: RNA
<213> ORGANISM: Artificial Sequence
<220> FEATURE:
<223> OTHER INFORMATION: Synthetic Construct

<400> SEQUENCE: 396
gacauugccc agguccacaa 20

<210> SEQ ID NO 397
<211> LENGTH: 20
<212> TYPE: RNA
<213> ORGANISM: Artificial Sequence
<220> FEATURE:
<223> OTHER INFORMATION: Synthetic Construct

<400> SEQUENCE: 397
acauugccca gguccacaaa 20

<210> SEQ ID NO 398
<211> LENGTH: 20

<212> TYPE: RNA
<213> ORGANISM: Artificial Sequence
<220> FEATURE:
<223> OTHER INFORMATION: Synthetic Construct

<400> SEQUENCE: 398
cauugcccag guccacaaac 20

<210> SEQ ID NO 399
<211> LENGTH: 20
<212> TYPE: RNA
<213> ORGANISM: Artificial Sequence
<220> FEATURE:
<223> OTHER INFORMATION: Synthetic Construct

<400> SEQUENCE: 399
auugcccagg uccacaaacu 20

<210> SEQ ID NO 400
<211> LENGTH: 20
<212> TYPE: RNA
<213> ORGANISM: Artificial Sequence
<220> FEATURE:
<223> OTHER INFORMATION: Synthetic Construct

<400> SEQUENCE: 400
uugcccaggu ccacaaacuc 20

<210> SEQ ID NO 401
<211> LENGTH: 20
<212> TYPE: RNA
<213> ORGANISM: Artificial Sequence
<220> FEATURE:
<223> OTHER INFORMATION: Synthetic Construct

<400> SEQUENCE: 401
ugcccagguc cacaaacucu 20

<210> SEQ ID NO 402
<211> LENGTH: 20
<212> TYPE: RNA
<213> ORGANISM: Artificial Sequence
<220> FEATURE:
<223> OTHER INFORMATION: Synthetic Construct

<400> SEQUENCE: 402
gcccaggucc acaaacucug 20

<210> SEQ ID NO 403
<211> LENGTH: 20
<212> TYPE: RNA
<213> ORGANISM: Artificial Sequence
<220> FEATURE:
<223> OTHER INFORMATION: Synthetic Construct

<400> SEQUENCE: 403
cccaggucca caaacucugu 20

<210> SEQ ID NO 404
<211> LENGTH: 20
<212> TYPE: RNA
<213> ORGANISM: Artificial Sequence
<220> FEATURE:
<223> OTHER INFORMATION: Synthetic Construct

<400> SEQUENCE: 404

-continued ccagguccac aaacucuguc 20

<210> SEQ ID NO 405
<211> LENGTH: 20
<212> TYPE: RNA
<213> ORGANISM: Artificial Sequence
<220> FEATURE:
<223> OTHER INFORMATION: Synthetic Construct

<400> SEQUENCE: 405
cagguccaca aacucuguca 20

<210> SEQ ID NO 406
<211> LENGTH: 20
<212> TYPE: RNA
<213> ORGANISM: Artificial Sequence
<220> FEATURE:
<223> OTHER INFORMATION: Synthetic Construct

<400> SEQUENCE: 406
agguccacaa acucugucac 20

<210> SEQ ID NO 407
<211> LENGTH: 20
<212> TYPE: RNA
<213> ORGANISM: Artificial Sequence
<220> FEATURE:
<223> OTHER INFORMATION: Synthetic Construct

<400> SEQUENCE: 407
gguccacaaa cucugucaca 20

<210> SEQ ID NO 408
<211> LENGTH: 20
<212> TYPE: RNA
<213> ORGANISM: Artificial Sequence
<220> FEATURE:
<223> OTHER INFORMATION: Synthetic Construct

<400> SEQUENCE: 408
guccacaaac ucugucacau 20

<210> SEQ ID NO 409
<211> LENGTH: 20
<212> TYPE: RNA
<213> ORGANISM: Artificial Sequence
<220> FEATURE:
<223> OTHER INFORMATION: Synthetic Construct

<400> SEQUENCE: 409
uccacaaacu cugucacaua 20

<210> SEQ ID NO 410
<211> LENGTH: 20
<212> TYPE: RNA
<213> ORGANISM: Artificial Sequence
<220> FEATURE:
<223> OTHER INFORMATION: Synthetic Construct

<400> SEQUENCE: 410
ccacaaacuc ugucacauau 20

<210> SEQ ID NO 411
<211> LENGTH: 20
<212> TYPE: RNA
<213> ORGANISM: Artificial Sequence
<220> FEATURE:
<223> OTHER INFORMATION: Synthetic Construct

<400> SEQUENCE: 411
cacaaacucu gucacauauc 20

<210> SEQ ID NO 412
<211> LENGTH: 20
<212> TYPE: RNA
<213> ORGANISM: Artificial Sequence
<220> FEATURE:
<223> OTHER INFORMATION: Synthetic Construct

<400> SEQUENCE: 412
acaaacucug ucacauaucu 20

<210> SEQ ID NO 413
<211> LENGTH: 20
<212> TYPE: RNA
<213> ORGANISM: Artificial Sequence
<220> FEATURE:
<223> OTHER INFORMATION: Synthetic Construct

<400> SEQUENCE: 413
caaacucugu cacauaucug 20

<210> SEQ ID NO 414
<211> LENGTH: 20
<212> TYPE: RNA
<213> ORGANISM: Artificial Sequence
<220> FEATURE:
<223> OTHER INFORMATION: Synthetic Construct

<400> SEQUENCE: 414
aaacucuguc acauaucugu 20

<210> SEQ ID NO 415
<211> LENGTH: 20
<212> TYPE: RNA
<213> ORGANISM: Artificial Sequence
<220> FEATURE:
<223> OTHER INFORMATION: Synthetic Construct

<400> SEQUENCE: 415
aacucuguca cauaucugua 20

<210> SEQ ID NO 416
<211> LENGTH: 20
<212> TYPE: RNA
<213> ORGANISM: Artificial Sequence
<220> FEATURE:
<223> OTHER INFORMATION: Synthetic Construct

<400> SEQUENCE: 416
acucugucac auaucuguag 20

<210> SEQ ID NO 417
<211> LENGTH: 20
<212> TYPE: RNA
<213> ORGANISM: Artificial Sequence
<220> FEATURE:
<223> OTHER INFORMATION: Synthetic Construct

<400> SEQUENCE: 417
cucugucaca uaucuguagu 20

<210> SEQ ID NO 418
<211> LENGTH: 19
<212> TYPE: RNA
<213> ORGANISM: Artificial Sequence
<220> FEATURE:
<223> OTHER INFORMATION: Synthetic Construct

<400> SEQUENCE: 418
cucaccugga auuacagag 19

<210> SEQ ID NO 419
<211> LENGTH: 19
<212> TYPE: RNA
<213> ORGANISM: Artificial Sequence
<220> FEATURE:
<223> OTHER INFORMATION: Synthetic Construct

<400> SEQUENCE: 419
ucaccuggaa uuacagaga 19

<210> SEQ ID NO 420
<211> LENGTH: 19
<212> TYPE: RNA
<213> ORGANISM: Artificial Sequence
<220> FEATURE:
<223> OTHER INFORMATION: Synthetic Construct

<400> SEQUENCE: 420
caccuggaau uacagagau 19

<210> SEQ ID NO 421
<211> LENGTH: 19
<212> TYPE: RNA
<213> ORGANISM: Artificial Sequence
<220> FEATURE:
<223> OTHER INFORMATION: Synthetic Construct

<400> SEQUENCE: 421
accuggaauu acagagaua 19

<210> SEQ ID NO 422
<211> LENGTH: 19
<212> TYPE: RNA
<213> ORGANISM: Artificial Sequence
<220> FEATURE:
<223> OTHER INFORMATION: Synthetic Construct

<400> SEQUENCE: 422
ccuggaauua cagagauag 19

<210> SEQ ID NO 423
<211> LENGTH: 19
<212> TYPE: RNA
<213> ORGANISM: Artificial Sequence
<220> FEATURE:
<223> OTHER INFORMATION: Synthetic Construct

<400> SEQUENCE: 423
cuggaauuac agagauagu 19

<210> SEQ ID NO 424
<211> LENGTH: 19
<212> TYPE: RNA
<213> ORGANISM: Artificial Sequence
<220> FEATURE:
<223> OTHER INFORMATION: Synthetic Construct

<400> SEQUENCE: 424
uggaauuaca gagauaguu 19

<210> SEQ ID NO 425
<211> LENGTH: 19
<212> TYPE: RNA
<213> ORGANISM: Artificial Sequence
<220> FEATURE:
<223> OTHER INFORMATION: Synthetic Construct

<400> SEQUENCE: 425
ggaauuacag agauaguuu 19

<210> SEQ ID NO 426
<211> LENGTH: 19
<212> TYPE: RNA
<213> ORGANISM: Artificial Sequence
<220> FEATURE:
<223> OTHER INFORMATION: Synthetic Construct

<400> SEQUENCE: 426
gaauuacaga gauaguuuu 19

<210> SEQ ID NO 427
<211> LENGTH: 19
<212> TYPE: RNA
<213> ORGANISM: Artificial Sequence
<220> FEATURE:
<223> OTHER INFORMATION: Synthetic Construct

<400> SEQUENCE: 427
aauuacagag auaguuuuc 19

<210> SEQ ID NO 428
<211> LENGTH: 19
<212> TYPE: RNA
<213> ORGANISM: Artificial Sequence
<220> FEATURE:
<223> OTHER INFORMATION: Synthetic Construct

<400> SEQUENCE: 428
auuacagaga uaguuuuca 19

<210> SEQ ID NO 429
<211> LENGTH: 19
<212> TYPE: RNA
<213> ORGANISM: Artificial Sequence
<220> FEATURE:
<223> OTHER INFORMATION: Synthetic Construct

<400> SEQUENCE: 429
uuacagagau aguuuucaa 19

<210> SEQ ID NO 430
<211> LENGTH: 19
<212> TYPE: RNA
<213> ORGANISM: Artificial Sequence
<220> FEATURE:
<223> OTHER INFORMATION: Synthetic Construct

<400> SEQUENCE: 430
uacagagaua guuuucaaa 19

<210> SEQ ID NO 431

<211> LENGTH: 19
<212> TYPE: RNA
<213> ORGANISM: Artificial Sequence
<220> FEATURE:
<223> OTHER INFORMATION: Synthetic Construct

<400> SEQUENCE: 431
acagagauag uuuucaaag 19

<210> SEQ ID NO 432
<211> LENGTH: 19
<212> TYPE: RNA
<213> ORGANISM: Artificial Sequence
<220> FEATURE:
<223> OTHER INFORMATION: Synthetic Construct

<400> SEQUENCE: 432
cagagauagu uuucaaagc 19

<210> SEQ ID NO 433
<211> LENGTH: 19
<212> TYPE: RNA
<213> ORGANISM: Artificial Sequence
<220> FEATURE:
<223> OTHER INFORMATION: Synthetic Construct

<400> SEQUENCE: 433
agagauaguu uucaaagcu 19

<210> SEQ ID NO 434
<211> LENGTH: 19
<212> TYPE: RNA
<213> ORGANISM: Artificial Sequence
<220> FEATURE:
<223> OTHER INFORMATION: Synthetic Construct

<400> SEQUENCE: 434
gagauaguuu ucaaagcuc 19

<210> SEQ ID NO 435
<211> LENGTH: 19
<212> TYPE: RNA
<213> ORGANISM: Artificial Sequence
<220> FEATURE:
<223> OTHER INFORMATION: Synthetic Construct

<400> SEQUENCE: 435
agauaguuuu caaagcucg 19

<210> SEQ ID NO 436
<211> LENGTH: 19
<212> TYPE: RNA
<213> ORGANISM: Artificial Sequence
<220> FEATURE:
<223> OTHER INFORMATION: Synthetic Construct

<400> SEQUENCE: 436
gauaguuuuc aaagcucgg 19

<210> SEQ ID NO 437
<211> LENGTH: 19
<212> TYPE: RNA
<213> ORGANISM: Artificial Sequence
<220> FEATURE:
<223> OTHER INFORMATION: Synthetic Construct

<400> SEQUENCE: 437
auaguuuuca aagcucgga 19

<210> SEQ ID NO 438
<211> LENGTH: 19
<212> TYPE: RNA
<213> ORGANISM: Artificial Sequence
<220> FEATURE:
<223> OTHER INFORMATION: Synthetic Construct

<400> SEQUENCE: 438
uaguuuucaa agcucggag 19

<210> SEQ ID NO 439
<211> LENGTH: 19
<212> TYPE: RNA
<213> ORGANISM: Artificial Sequence
<220> FEATURE:
<223> OTHER INFORMATION: Synthetic Construct

<400> SEQUENCE: 439
aguuuucaaa gcucggaga 19

<210> SEQ ID NO 440
<211> LENGTH: 19
<212> TYPE: RNA
<213> ORGANISM: Artificial Sequence
<220> FEATURE:
<223> OTHER INFORMATION: Synthetic Construct

<400> SEQUENCE: 440
guuuucaaag cucggagaa 19

<210> SEQ ID NO 441
<211> LENGTH: 19
<212> TYPE: RNA
<213> ORGANISM: Artificial Sequence
<220> FEATURE:
<223> OTHER INFORMATION: Synthetic Construct

<400> SEQUENCE: 441
uuuucaaagc ucggagaac 19

<210> SEQ ID NO 442
<211> LENGTH: 19
<212> TYPE: RNA
<213> ORGANISM: Artificial Sequence
<220> FEATURE:
<223> OTHER INFORMATION: Synthetic Construct

<400> SEQUENCE: 442
uuucaaagcu cggagaacc 19

<210> SEQ ID NO 443
<211> LENGTH: 19
<212> TYPE: RNA
<213> ORGANISM: Artificial Sequence
<220> FEATURE:
<223> OTHER INFORMATION: Synthetic Construct

<400> SEQUENCE: 443
uucaaagcuc ggagaaccc 19

<210> SEQ ID NO 444
<211> LENGTH: 19
<212> TYPE: RNA

<213> ORGANISM: Artificial Sequence
<220> FEATURE:
<223> OTHER INFORMATION: Synthetic Construct

<400> SEQUENCE: 444
ucaaagcucg gagaacccu 19

<210> SEQ ID NO 445
<211> LENGTH: 19
<212> TYPE: RNA
<213> ORGANISM: Artificial Sequence
<220> FEATURE:
<223> OTHER INFORMATION: Synthetic Construct

<400> SEQUENCE: 445
caaagcucgg agaacccug 19

<210> SEQ ID NO 446
<211> LENGTH: 19
<212> TYPE: RNA
<213> ORGANISM: Artificial Sequence
<220> FEATURE:
<223> OTHER INFORMATION: Synthetic Construct

<400> SEQUENCE: 446
aaagcucgga gaacccuga 19

<210> SEQ ID NO 447
<211> LENGTH: 19
<212> TYPE: RNA
<213> ORGANISM: Artificial Sequence
<220> FEATURE:
<223> OTHER INFORMATION: Synthetic Construct

<400> SEQUENCE: 447
aagcucggag aacccugaa 19

<210> SEQ ID NO 448
<211> LENGTH: 19
<212> TYPE: RNA
<213> ORGANISM: Artificial Sequence
<220> FEATURE:
<223> OTHER INFORMATION: Synthetic Construct

<400> SEQUENCE: 448
agcucggaga acccugaau 19

<210> SEQ ID NO 449
<211> LENGTH: 19
<212> TYPE: RNA
<213> ORGANISM: Artificial Sequence
<220> FEATURE:
<223> OTHER INFORMATION: Synthetic Construct

<400> SEQUENCE: 449
gcucggagaa cccugaaug 19

<210> SEQ ID NO 450
<211> LENGTH: 19
<212> TYPE: RNA
<213> ORGANISM: Artificial Sequence
<220> FEATURE:
<223> OTHER INFORMATION: Synthetic Construct

<400> SEQUENCE: 450
cucggagaac ccugaaugu 19

<210> SEQ ID NO 451
<211> LENGTH: 19
<212> TYPE: RNA
<213> ORGANISM: Artificial Sequence
<220> FEATURE:
<223> OTHER INFORMATION: Synthetic Construct

<400> SEQUENCE: 451
ucggagaacc cugaauguu 19

<210> SEQ ID NO 452
<211> LENGTH: 19
<212> TYPE: RNA
<213> ORGANISM: Artificial Sequence
<220> FEATURE:
<223> OTHER INFORMATION: Synthetic Construct

<400> SEQUENCE: 452
cggagaaccc ugaauguuc 19

<210> SEQ ID NO 453
<211> LENGTH: 19
<212> TYPE: RNA
<213> ORGANISM: Artificial Sequence
<220> FEATURE:
<223> OTHER INFORMATION: Synthetic Construct

<400> SEQUENCE: 453
ggagaacccu gaauguucu 19

<210> SEQ ID NO 454
<211> LENGTH: 19
<212> TYPE: RNA
<213> ORGANISM: Artificial Sequence
<220> FEATURE:
<223> OTHER INFORMATION: Synthetic Construct

<400> SEQUENCE: 454
gagaacccug aauguucuc 19

<210> SEQ ID NO 455
<211> LENGTH: 19
<212> TYPE: RNA
<213> ORGANISM: Artificial Sequence
<220> FEATURE:
<223> OTHER INFORMATION: Synthetic Construct

<400> SEQUENCE: 455
agaacccuga auguucuca 19

<210> SEQ ID NO 456
<211> LENGTH: 19
<212> TYPE: RNA
<213> ORGANISM: Artificial Sequence
<220> FEATURE:
<223> OTHER INFORMATION: Synthetic Construct

<400> SEQUENCE: 456
gaacccugaa uguucucag 19

<210> SEQ ID NO 457
<211> LENGTH: 19
<212> TYPE: RNA
<213> ORGANISM: Artificial Sequence
<220> FEATURE:

<223> OTHER INFORMATION: Synthetic Construct

<400> SEQUENCE: 457
aacccugaau guucucagc 19

<210> SEQ ID NO 458
<211> LENGTH: 19
<212> TYPE: RNA
<213> ORGANISM: Artificial Sequence
<220> FEATURE:
<223> OTHER INFORMATION: Synthetic Construct

<400> SEQUENCE: 458
acccugaaug uucucagcg 19

<210> SEQ ID NO 459
<211> LENGTH: 19
<212> TYPE: RNA
<213> ORGANISM: Artificial Sequence
<220> FEATURE:
<223> OTHER INFORMATION: Synthetic Construct

<400> SEQUENCE: 459
cccugaaugu ucucagcgc 19

<210> SEQ ID NO 460
<211> LENGTH: 19
<212> TYPE: RNA
<213> ORGANISM: Artificial Sequence
<220> FEATURE:
<223> OTHER INFORMATION: Synthetic Construct

<400> SEQUENCE: 460
ccugaauguu cucagcgcu 19

<210> SEQ ID NO 461
<211> LENGTH: 19
<212> TYPE: RNA
<213> ORGANISM: Artificial Sequence
<220> FEATURE:
<223> OTHER INFORMATION: Synthetic Construct

<400> SEQUENCE: 461
cugaauguuc ucagcgcug 19

<210> SEQ ID NO 462
<211> LENGTH: 19
<212> TYPE: RNA
<213> ORGANISM: Artificial Sequence
<220> FEATURE:
<223> OTHER INFORMATION: Synthetic Construct

<400> SEQUENCE: 462
ugaauguucu cagcgcuga 19

<210> SEQ ID NO 463
<211> LENGTH: 19
<212> TYPE: RNA
<213> ORGANISM: Artificial Sequence
<220> FEATURE:
<223> OTHER INFORMATION: Synthetic Construct

<400> SEQUENCE: 463
gaauguucuc agcgcugag 19

<210> SEQ ID NO 464
<211> LENGTH: 19
<212> TYPE: RNA
<213> ORGANISM: Artificial Sequence
<220> FEATURE:
<223> OTHER INFORMATION: Synthetic Construct

<400> SEQUENCE: 464
aauguucuca gcgcugaga 19

<210> SEQ ID NO 465
<211> LENGTH: 19
<212> TYPE: RNA
<213> ORGANISM: Artificial Sequence
<220> FEATURE:
<223> OTHER INFORMATION: Synthetic Construct

<400> SEQUENCE: 465
auguucucag cgcugagac 19

<210> SEQ ID NO 466
<211> LENGTH: 19
<212> TYPE: RNA
<213> ORGANISM: Artificial Sequence
<220> FEATURE:
<223> OTHER INFORMATION: Synthetic Construct

<400> SEQUENCE: 466
uguucucagc gcugagaca 19

<210> SEQ ID NO 467
<211> LENGTH: 19
<212> TYPE: RNA
<213> ORGANISM: Artificial Sequence
<220> FEATURE:
<223> OTHER INFORMATION: Synthetic Construct

<400> SEQUENCE: 467
guucucagcg cugagacau 19

<210> SEQ ID NO 468
<211> LENGTH: 19
<212> TYPE: RNA
<213> ORGANISM: Artificial Sequence
<220> FEATURE:
<223> OTHER INFORMATION: Synthetic Construct

<400> SEQUENCE: 468
uucucagcgc ugagacauu 19

<210> SEQ ID NO 469
<211> LENGTH: 19
<212> TYPE: RNA
<213> ORGANISM: Artificial Sequence
<220> FEATURE:
<223> OTHER INFORMATION: Synthetic Construct

<400> SEQUENCE: 469
ucucagcgcu gagacauug 19

<210> SEQ ID NO 470
<211> LENGTH: 19
<212> TYPE: RNA
<213> ORGANISM: Artificial Sequence
<220> FEATURE:
<223> OTHER INFORMATION: Synthetic Construct

<400> SEQUENCE: 470
cucagcgcug agacauugc 19

<210> SEQ ID NO 471
<211> LENGTH: 19
<212> TYPE: RNA
<213> ORGANISM: Artificial Sequence
<220> FEATURE:
<223> OTHER INFORMATION: Synthetic Construct

<400> SEQUENCE: 471
ucagcgcuga gacauugcc 19

<210> SEQ ID NO 472
<211> LENGTH: 19
<212> TYPE: RNA
<213> ORGANISM: Artificial Sequence
<220> FEATURE:
<223> OTHER INFORMATION: Synthetic Construct

<400> SEQUENCE: 472
cagcgcugag acauugccc 19

<210> SEQ ID NO 473
<211> LENGTH: 19
<212> TYPE: RNA
<213> ORGANISM: Artificial Sequence
<220> FEATURE:
<223> OTHER INFORMATION: Synthetic Construct

<400> SEQUENCE: 473
agcgcugaga cauugccca 19

<210> SEQ ID NO 474
<211> LENGTH: 19
<212> TYPE: RNA
<213> ORGANISM: Artificial Sequence
<220> FEATURE:
<223> OTHER INFORMATION: Synthetic Construct

<400> SEQUENCE: 474
gcgcugagac auugcccag 19

<210> SEQ ID NO 475
<211> LENGTH: 19
<212> TYPE: RNA
<213> ORGANISM: Artificial Sequence
<220> FEATURE:
<223> OTHER INFORMATION: Synthetic Construct

<400> SEQUENCE: 475
cgcugagaca uugcccagg 19

<210> SEQ ID NO 476
<211> LENGTH: 19
<212> TYPE: RNA
<213> ORGANISM: Artificial Sequence
<220> FEATURE:
<223> OTHER INFORMATION: Synthetic Construct

<400> SEQUENCE: 476
gcugagacau ugcccaggu 19

<210> SEQ ID NO 477
<211> LENGTH: 19

<212> TYPE: RNA
<213> ORGANISM: Artificial Sequence
<220> FEATURE:
<223> OTHER INFORMATION: Synthetic Construct

<400> SEQUENCE: 477
cugagacauu gcccagguc 19

<210> SEQ ID NO 478
<211> LENGTH: 19
<212> TYPE: RNA
<213> ORGANISM: Artificial Sequence
<220> FEATURE:
<223> OTHER INFORMATION: Synthetic Construct

<400> SEQUENCE: 478
ugagacauug cccaggucc 19

<210> SEQ ID NO 479
<211> LENGTH: 19
<212> TYPE: RNA
<213> ORGANISM: Artificial Sequence
<220> FEATURE:
<223> OTHER INFORMATION: Synthetic Construct

<400> SEQUENCE: 479
gagacauugc ccaggucca 19

<210> SEQ ID NO 480
<211> LENGTH: 19
<212> TYPE: RNA
<213> ORGANISM: Artificial Sequence
<220> FEATURE:
<223> OTHER INFORMATION: Synthetic Construct

<400> SEQUENCE: 480
agacauugcc cagguccac 19

<210> SEQ ID NO 481
<211> LENGTH: 19
<212> TYPE: RNA
<213> ORGANISM: Artificial Sequence
<220> FEATURE:
<223> OTHER INFORMATION: Synthetic Construct

<400> SEQUENCE: 481
gacauugccc agguccaca 19

<210> SEQ ID NO 482
<211> LENGTH: 19
<212> TYPE: RNA
<213> ORGANISM: Artificial Sequence
<220> FEATURE:
<223> OTHER INFORMATION: Synthetic Construct

<400> SEQUENCE: 482
acauugccca gguccacaa 19

<210> SEQ ID NO 483
<211> LENGTH: 19
<212> TYPE: RNA
<213> ORGANISM: Artificial Sequence
<220> FEATURE:
<223> OTHER INFORMATION: Synthetic Construct

<400> SEQUENCE: 483
cauugcccag guccacaaa 19

<210> SEQ ID NO 484
<211> LENGTH: 19
<212> TYPE: RNA
<213> ORGANISM: Artificial Sequence
<220> FEATURE:
<223> OTHER INFORMATION: Synthetic Construct

<400> SEQUENCE: 484
auugcccagg uccacaaac 19

<210> SEQ ID NO 485
<211> LENGTH: 19
<212> TYPE: RNA
<213> ORGANISM: Artificial Sequence
<220> FEATURE:
<223> OTHER INFORMATION: Synthetic Construct

<400> SEQUENCE: 485
uugcccaggu ccacaaacu 19

<210> SEQ ID NO 486
<211> LENGTH: 19
<212> TYPE: RNA
<213> ORGANISM: Artificial Sequence
<220> FEATURE:
<223> OTHER INFORMATION: Synthetic Construct

<400> SEQUENCE: 486
ugcccagguc cacaaacuc 19

<210> SEQ ID NO 487
<211> LENGTH: 19
<212> TYPE: RNA
<213> ORGANISM: Artificial Sequence
<220> FEATURE:
<223> OTHER INFORMATION: Synthetic Construct

<400> SEQUENCE: 487
gcccaggucc acaaacucu 19

<210> SEQ ID NO 488
<211> LENGTH: 19
<212> TYPE: RNA
<213> ORGANISM: Artificial Sequence
<220> FEATURE:
<223> OTHER INFORMATION: Synthetic Construct

<400> SEQUENCE: 488
cccaggucca caaacucug 19

<210> SEQ ID NO 489
<211> LENGTH: 19
<212> TYPE: RNA
<213> ORGANISM: Artificial Sequence
<220> FEATURE:
<223> OTHER INFORMATION: Synthetic Construct

<400> SEQUENCE: 489
ccagguccac aaacucugu 19

<210> SEQ ID NO 490
<211> LENGTH: 19
<212> TYPE: RNA
<213> ORGANISM: Artificial Sequence

```
<220> FEATURE:
<223> OTHER INFORMATION: Synthetic Construct

<400> SEQUENCE: 490

cagguccaca aacucuguc                                                      19

<210> SEQ ID NO 491
<211> LENGTH: 19
<212> TYPE: RNA
<213> ORGANISM: Artificial Sequence
<220> FEATURE:
<223> OTHER INFORMATION: Synthetic Construct

<400> SEQUENCE: 491

agguccacaa acucuguca                                                      19

<210> SEQ ID NO 492
<211> LENGTH: 19
<212> TYPE: RNA
<213> ORGANISM: Artificial Sequence
<220> FEATURE:
<223> OTHER INFORMATION: Synthetic Construct

<400> SEQUENCE: 492

gguccacaaa cucugucac                                                      19

<210> SEQ ID NO 493
<211> LENGTH: 19
<212> TYPE: RNA
<213> ORGANISM: Artificial Sequence
<220> FEATURE:
<223> OTHER INFORMATION: Synthetic Construct

<400> SEQUENCE: 493

guccacaaac ucugucaca                                                      19

<210> SEQ ID NO 494
<211> LENGTH: 19
<212> TYPE: RNA
<213> ORGANISM: Artificial Sequence
<220> FEATURE:
<223> OTHER INFORMATION: Synthetic Construct

<400> SEQUENCE: 494

uccacaaacu cugucacau                                                      19

<210> SEQ ID NO 495
<211> LENGTH: 19
<212> TYPE: RNA
<213> ORGANISM: Artificial Sequence
<220> FEATURE:
<223> OTHER INFORMATION: Synthetic Construct

<400> SEQUENCE: 495

ccacaaacuc ugucacaua                                                      19

<210> SEQ ID NO 496
<211> LENGTH: 19
<212> TYPE: RNA
<213> ORGANISM: Artificial Sequence
<220> FEATURE:
<223> OTHER INFORMATION: Synthetic Construct

<400> SEQUENCE: 496

cacaaacucu gucacauau                                                      19
```

<210> SEQ ID NO 497
<211> LENGTH: 19
<212> TYPE: RNA
<213> ORGANISM: Artificial Sequence
<220> FEATURE:
<223> OTHER INFORMATION: Synthetic Construct

<400> SEQUENCE: 497
acaaacucug ucacauauc 19

<210> SEQ ID NO 498
<211> LENGTH: 19
<212> TYPE: RNA
<213> ORGANISM: Artificial Sequence
<220> FEATURE:
<223> OTHER INFORMATION: Synthetic Construct

<400> SEQUENCE: 498
caaacucugu cacauaucu 19

<210> SEQ ID NO 499
<211> LENGTH: 19
<212> TYPE: RNA
<213> ORGANISM: Artificial Sequence
<220> FEATURE:
<223> OTHER INFORMATION: Synthetic Construct

<400> SEQUENCE: 499
aaacucuguc acauaucug 19

<210> SEQ ID NO 500
<211> LENGTH: 19
<212> TYPE: RNA
<213> ORGANISM: Artificial Sequence
<220> FEATURE:
<223> OTHER INFORMATION: Synthetic Construct

<400> SEQUENCE: 500
aacucuguca cauaucugu 19

<210> SEQ ID NO 501
<211> LENGTH: 19
<212> TYPE: RNA
<213> ORGANISM: Artificial Sequence
<220> FEATURE:
<223> OTHER INFORMATION: Synthetic Construct

<400> SEQUENCE: 501
acucugucac auaucugua 19

<210> SEQ ID NO 502
<211> LENGTH: 19
<212> TYPE: RNA
<213> ORGANISM: Artificial Sequence
<220> FEATURE:
<223> OTHER INFORMATION: Synthetic Construct

<400> SEQUENCE: 502
cucugucaca uaucuguag 19

<210> SEQ ID NO 503
<211> LENGTH: 19
<212> TYPE: RNA
<213> ORGANISM: Artificial Sequence
<220> FEATURE:
<223> OTHER INFORMATION: Synthetic Construct

<400> SEQUENCE: 503
ucugucacau aucuguagu 19

<210> SEQ ID NO 504
<211> LENGTH: 18
<212> TYPE: RNA
<213> ORGANISM: Artificial Sequence
<220> FEATURE:
<223> OTHER INFORMATION: Synthetic Construct

<400> SEQUENCE: 504
cucaccugga auuacaga 18

<210> SEQ ID NO 505
<211> LENGTH: 18
<212> TYPE: RNA
<213> ORGANISM: Artificial Sequence
<220> FEATURE:
<223> OTHER INFORMATION: Synthetic Construct

<400> SEQUENCE: 505
ucaccuggaa uuacagag 18

<210> SEQ ID NO 506
<211> LENGTH: 18
<212> TYPE: RNA
<213> ORGANISM: Artificial Sequence
<220> FEATURE:
<223> OTHER INFORMATION: Synthetic Construct

<400> SEQUENCE: 506
caccuggaau uacagaga 18

<210> SEQ ID NO 507
<211> LENGTH: 18
<212> TYPE: RNA
<213> ORGANISM: Artificial Sequence
<220> FEATURE:
<223> OTHER INFORMATION: Synthetic Construct

<400> SEQUENCE: 507
accuggaauu acagagau 18

<210> SEQ ID NO 508
<211> LENGTH: 18
<212> TYPE: RNA
<213> ORGANISM: Artificial Sequence
<220> FEATURE:
<223> OTHER INFORMATION: Synthetic Construct

<400> SEQUENCE: 508
ccuggaauua cagagaua 18

<210> SEQ ID NO 509
<211> LENGTH: 18
<212> TYPE: RNA
<213> ORGANISM: Artificial Sequence
<220> FEATURE:
<223> OTHER INFORMATION: Synthetic Construct

<400> SEQUENCE: 509
cuggaauuac agagauag 18

<210> SEQ ID NO 510

<211> LENGTH: 18
<212> TYPE: RNA
<213> ORGANISM: Artificial Sequence
<220> FEATURE:
<223> OTHER INFORMATION: Synthetic Construct

<400> SEQUENCE: 510
uggaauuaca gagauagu 18

<210> SEQ ID NO 511
<211> LENGTH: 18
<212> TYPE: RNA
<213> ORGANISM: Artificial Sequence
<220> FEATURE:
<223> OTHER INFORMATION: Synthetic Construct

<400> SEQUENCE: 511
ggaauuacag agauaguu 18

<210> SEQ ID NO 512
<211> LENGTH: 18
<212> TYPE: RNA
<213> ORGANISM: Artificial Sequence
<220> FEATURE:
<223> OTHER INFORMATION: Synthetic Construct

<400> SEQUENCE: 512
gaauuacaga gauaguuu 18

<210> SEQ ID NO 513
<211> LENGTH: 18
<212> TYPE: RNA
<213> ORGANISM: Artificial Sequence
<220> FEATURE:
<223> OTHER INFORMATION: Synthetic Construct

<400> SEQUENCE: 513
aauuacagag auaguuuu 18

<210> SEQ ID NO 514
<211> LENGTH: 18
<212> TYPE: RNA
<213> ORGANISM: Artificial Sequence
<220> FEATURE:
<223> OTHER INFORMATION: Synthetic Construct

<400> SEQUENCE: 514
auuacagaga uaguuuuc 18

<210> SEQ ID NO 515
<211> LENGTH: 18
<212> TYPE: RNA
<213> ORGANISM: Artificial Sequence
<220> FEATURE:
<223> OTHER INFORMATION: Synthetic Construct

<400> SEQUENCE: 515
uuacagagau aguuuuca 18

<210> SEQ ID NO 516
<211> LENGTH: 18
<212> TYPE: RNA
<213> ORGANISM: Artificial Sequence
<220> FEATURE:
<223> OTHER INFORMATION: Synthetic Construct

<400> SEQUENCE: 516
uacagagaua guuuucaa 18

<210> SEQ ID NO 517
<211> LENGTH: 18
<212> TYPE: RNA
<213> ORGANISM: Artificial Sequence
<220> FEATURE:
<223> OTHER INFORMATION: Synthetic Construct

<400> SEQUENCE: 517
acagagauag uuuucaaa 18

<210> SEQ ID NO 518
<211> LENGTH: 18
<212> TYPE: RNA
<213> ORGANISM: Artificial Sequence
<220> FEATURE:
<223> OTHER INFORMATION: Synthetic Construct

<400> SEQUENCE: 518
cagagauagu uuucaaag 18

<210> SEQ ID NO 519
<211> LENGTH: 18
<212> TYPE: RNA
<213> ORGANISM: Artificial Sequence
<220> FEATURE:
<223> OTHER INFORMATION: Synthetic Construct

<400> SEQUENCE: 519
agagauaguu uucaaagc 18

<210> SEQ ID NO 520
<211> LENGTH: 18
<212> TYPE: RNA
<213> ORGANISM: Artificial Sequence
<220> FEATURE:
<223> OTHER INFORMATION: Synthetic Construct

<400> SEQUENCE: 520
gagauaguuu ucaaagcu 18

<210> SEQ ID NO 521
<211> LENGTH: 18
<212> TYPE: RNA
<213> ORGANISM: Artificial Sequence
<220> FEATURE:
<223> OTHER INFORMATION: Synthetic Construct

<400> SEQUENCE: 521
agauaguuuu caaagcuc 18

<210> SEQ ID NO 522
<211> LENGTH: 18
<212> TYPE: RNA
<213> ORGANISM: Artificial Sequence
<220> FEATURE:
<223> OTHER INFORMATION: Synthetic Construct

<400> SEQUENCE: 522
gauaguuuuc aaagcucg 18

<210> SEQ ID NO 523
<211> LENGTH: 18
<212> TYPE: RNA

<213> ORGANISM: Artificial Sequence
<220> FEATURE:
<223> OTHER INFORMATION: Synthetic Construct

<400> SEQUENCE: 523
auaguuuuca aagcucgg 18

<210> SEQ ID NO 524
<211> LENGTH: 18
<212> TYPE: RNA
<213> ORGANISM: Artificial Sequence
<220> FEATURE:
<223> OTHER INFORMATION: Synthetic Construct

<400> SEQUENCE: 524
uaguuuucaa agcucgga 18

<210> SEQ ID NO 525
<211> LENGTH: 18
<212> TYPE: RNA
<213> ORGANISM: Artificial Sequence
<220> FEATURE:
<223> OTHER INFORMATION: Synthetic Construct

<400> SEQUENCE: 525
aguuuucaaa gcucggag 18

<210> SEQ ID NO 526
<211> LENGTH: 18
<212> TYPE: RNA
<213> ORGANISM: Artificial Sequence
<220> FEATURE:
<223> OTHER INFORMATION: Synthetic Construct

<400> SEQUENCE: 526
guuuucaaag cucggaga 18

<210> SEQ ID NO 527
<211> LENGTH: 18
<212> TYPE: RNA
<213> ORGANISM: Artificial Sequence
<220> FEATURE:
<223> OTHER INFORMATION: Synthetic Construct

<400> SEQUENCE: 527
uuuucaaagc ucggagaa 18

<210> SEQ ID NO 528
<211> LENGTH: 18
<212> TYPE: RNA
<213> ORGANISM: Artificial Sequence
<220> FEATURE:
<223> OTHER INFORMATION: Synthetic Construct

<400> SEQUENCE: 528
uuucaaagcu cggagaac 18

<210> SEQ ID NO 529
<211> LENGTH: 18
<212> TYPE: RNA
<213> ORGANISM: Artificial Sequence
<220> FEATURE:
<223> OTHER INFORMATION: Synthetic Construct

<400> SEQUENCE: 529
uucaaagcuc ggagaacc 18

<210> SEQ ID NO 530
<211> LENGTH: 18
<212> TYPE: RNA
<213> ORGANISM: Artificial Sequence
<220> FEATURE:
<223> OTHER INFORMATION: Synthetic Construct

<400> SEQUENCE: 530
ucaaagcucg gagaaccc 18

<210> SEQ ID NO 531
<211> LENGTH: 18
<212> TYPE: RNA
<213> ORGANISM: Artificial Sequence
<220> FEATURE:
<223> OTHER INFORMATION: Synthetic Construct

<400> SEQUENCE: 531
caaagcucgg agaacccu 18

<210> SEQ ID NO 532
<211> LENGTH: 18
<212> TYPE: RNA
<213> ORGANISM: Artificial Sequence
<220> FEATURE:
<223> OTHER INFORMATION: Synthetic Construct

<400> SEQUENCE: 532
aaagcucgga gaacccug 18

<210> SEQ ID NO 533
<211> LENGTH: 18
<212> TYPE: RNA
<213> ORGANISM: Artificial Sequence
<220> FEATURE:
<223> OTHER INFORMATION: Synthetic Construct

<400> SEQUENCE: 533
aagcucggag aacccuga 18

<210> SEQ ID NO 534
<211> LENGTH: 18
<212> TYPE: RNA
<213> ORGANISM: Artificial Sequence
<220> FEATURE:
<223> OTHER INFORMATION: Synthetic Construct

<400> SEQUENCE: 534
agcucggaga acccugaa 18

<210> SEQ ID NO 535
<211> LENGTH: 18
<212> TYPE: RNA
<213> ORGANISM: Artificial Sequence
<220> FEATURE:
<223> OTHER INFORMATION: Synthetic Construct

<400> SEQUENCE: 535
gcucggagaa cccugaau 18

<210> SEQ ID NO 536
<211> LENGTH: 18
<212> TYPE: RNA
<213> ORGANISM: Artificial Sequence
<220> FEATURE:

<223> OTHER INFORMATION: Synthetic Construct

<400> SEQUENCE: 536
cucggagaac ccugaaug 18

<210> SEQ ID NO 537
<211> LENGTH: 18
<212> TYPE: RNA
<213> ORGANISM: Artificial Sequence
<220> FEATURE:
<223> OTHER INFORMATION: Synthetic Construct

<400> SEQUENCE: 537
ucggagaacc cugaaugu 18

<210> SEQ ID NO 538
<211> LENGTH: 18
<212> TYPE: RNA
<213> ORGANISM: Artificial Sequence
<220> FEATURE:
<223> OTHER INFORMATION: Synthetic Construct

<400> SEQUENCE: 538
cggagaaccc ugaauguu 18

<210> SEQ ID NO 539
<211> LENGTH: 18
<212> TYPE: RNA
<213> ORGANISM: Artificial Sequence
<220> FEATURE:
<223> OTHER INFORMATION: Synthetic Construct

<400> SEQUENCE: 539
ggagaacccu gaauguuc 18

<210> SEQ ID NO 540
<211> LENGTH: 18
<212> TYPE: RNA
<213> ORGANISM: Artificial Sequence
<220> FEATURE:
<223> OTHER INFORMATION: Synthetic Construct

<400> SEQUENCE: 540
gagaacccug aauguucu 18

<210> SEQ ID NO 541
<211> LENGTH: 18
<212> TYPE: RNA
<213> ORGANISM: Artificial Sequence
<220> FEATURE:
<223> OTHER INFORMATION: Synthetic Construct

<400> SEQUENCE: 541
agaacccuga auguucuc 18

<210> SEQ ID NO 542
<211> LENGTH: 18
<212> TYPE: RNA
<213> ORGANISM: Artificial Sequence
<220> FEATURE:
<223> OTHER INFORMATION: Synthetic Construct

<400> SEQUENCE: 542
gaacccugaa uguucuca 18

<210> SEQ ID NO 543
<211> LENGTH: 18
<212> TYPE: RNA
<213> ORGANISM: Artificial Sequence
<220> FEATURE:
<223> OTHER INFORMATION: Synthetic Construct

<400> SEQUENCE: 543
aacccugaau guucucag 18

<210> SEQ ID NO 544
<211> LENGTH: 18
<212> TYPE: RNA
<213> ORGANISM: Artificial Sequence
<220> FEATURE:
<223> OTHER INFORMATION: Synthetic Construct

<400> SEQUENCE: 544
acccugaaug uucucagc 18

<210> SEQ ID NO 545
<211> LENGTH: 18
<212> TYPE: RNA
<213> ORGANISM: Artificial Sequence
<220> FEATURE:
<223> OTHER INFORMATION: Synthetic Construct

<400> SEQUENCE: 545
cccugaaugu ucucagcg 18

<210> SEQ ID NO 546
<211> LENGTH: 18
<212> TYPE: RNA
<213> ORGANISM: Artificial Sequence
<220> FEATURE:
<223> OTHER INFORMATION: Synthetic Construct

<400> SEQUENCE: 546
ccugaauguu cucagcgc 18

<210> SEQ ID NO 547
<211> LENGTH: 18
<212> TYPE: RNA
<213> ORGANISM: Artificial Sequence
<220> FEATURE:
<223> OTHER INFORMATION: Synthetic Construct

<400> SEQUENCE: 547
cugaauguuc ucagcgcu 18

<210> SEQ ID NO 548
<211> LENGTH: 18
<212> TYPE: RNA
<213> ORGANISM: Artificial Sequence
<220> FEATURE:
<223> OTHER INFORMATION: Synthetic Construct

<400> SEQUENCE: 548
ugaauguucu cagcgcug 18

<210> SEQ ID NO 549
<211> LENGTH: 18
<212> TYPE: RNA
<213> ORGANISM: Artificial Sequence
<220> FEATURE:
<223> OTHER INFORMATION: Synthetic Construct

<400> SEQUENCE: 549
gaauguucuc agcgcuga 18

<210> SEQ ID NO 550
<211> LENGTH: 18
<212> TYPE: RNA
<213> ORGANISM: Artificial Sequence
<220> FEATURE:
<223> OTHER INFORMATION: Synthetic Construct

<400> SEQUENCE: 550
aauguucuca gcgcugag 18

<210> SEQ ID NO 551
<211> LENGTH: 18
<212> TYPE: RNA
<213> ORGANISM: Artificial Sequence
<220> FEATURE:
<223> OTHER INFORMATION: Synthetic Construct

<400> SEQUENCE: 551
auguucucag cgcugaga 18

<210> SEQ ID NO 552
<211> LENGTH: 18
<212> TYPE: RNA
<213> ORGANISM: Artificial Sequence
<220> FEATURE:
<223> OTHER INFORMATION: Synthetic Construct

<400> SEQUENCE: 552
uguucucagc gcugagac 18

<210> SEQ ID NO 553
<211> LENGTH: 18
<212> TYPE: RNA
<213> ORGANISM: Artificial Sequence
<220> FEATURE:
<223> OTHER INFORMATION: Synthetic Construct

<400> SEQUENCE: 553
guucucagcg cugagaca 18

<210> SEQ ID NO 554
<211> LENGTH: 18
<212> TYPE: RNA
<213> ORGANISM: Artificial Sequence
<220> FEATURE:
<223> OTHER INFORMATION: Synthetic Construct

<400> SEQUENCE: 554
uucucagcgc ugagacau 18

<210> SEQ ID NO 555
<211> LENGTH: 18
<212> TYPE: RNA
<213> ORGANISM: Artificial Sequence
<220> FEATURE:
<223> OTHER INFORMATION: Synthetic Construct

<400> SEQUENCE: 555
ucucagcgcu gagacauu 18

<210> SEQ ID NO 556
<211> LENGTH: 18

<212> TYPE: RNA
<213> ORGANISM: Artificial Sequence
<220> FEATURE:
<223> OTHER INFORMATION: Synthetic Construct

<400> SEQUENCE: 556
cucagcgcug agacauug 18

<210> SEQ ID NO 557
<211> LENGTH: 18
<212> TYPE: RNA
<213> ORGANISM: Artificial Sequence
<220> FEATURE:
<223> OTHER INFORMATION: Synthetic Construct

<400> SEQUENCE: 557
ucagcgcuga gacauugc 18

<210> SEQ ID NO 558
<211> LENGTH: 18
<212> TYPE: RNA
<213> ORGANISM: Artificial Sequence
<220> FEATURE:
<223> OTHER INFORMATION: Synthetic Construct

<400> SEQUENCE: 558
cagcgcugag acauugcc 18

<210> SEQ ID NO 559
<211> LENGTH: 18
<212> TYPE: RNA
<213> ORGANISM: Artificial Sequence
<220> FEATURE:
<223> OTHER INFORMATION: Synthetic Construct

<400> SEQUENCE: 559
agcgcugaga cauugccc 18

<210> SEQ ID NO 560
<211> LENGTH: 18
<212> TYPE: RNA
<213> ORGANISM: Artificial Sequence
<220> FEATURE:
<223> OTHER INFORMATION: Synthetic Construct

<400> SEQUENCE: 560
gcgcugagac auugccca 18

<210> SEQ ID NO 561
<211> LENGTH: 18
<212> TYPE: RNA
<213> ORGANISM: Artificial Sequence
<220> FEATURE:
<223> OTHER INFORMATION: Synthetic Construct

<400> SEQUENCE: 561
cgcugagaca uugcccag 18

<210> SEQ ID NO 562
<211> LENGTH: 18
<212> TYPE: RNA
<213> ORGANISM: Artificial Sequence
<220> FEATURE:
<223> OTHER INFORMATION: Synthetic Construct

<400> SEQUENCE: 562
gcugagacau ugcccagg 18

<210> SEQ ID NO 563
<211> LENGTH: 18
<212> TYPE: RNA
<213> ORGANISM: Artificial Sequence
<220> FEATURE:
<223> OTHER INFORMATION: Synthetic Construct

<400> SEQUENCE: 563
cugagacauu gcccaggu 18

<210> SEQ ID NO 564
<211> LENGTH: 18
<212> TYPE: RNA
<213> ORGANISM: Artificial Sequence
<220> FEATURE:
<223> OTHER INFORMATION: Synthetic Construct

<400> SEQUENCE: 564
ugagacauug cccagguc 18

<210> SEQ ID NO 565
<211> LENGTH: 18
<212> TYPE: RNA
<213> ORGANISM: Artificial Sequence
<220> FEATURE:
<223> OTHER INFORMATION: Synthetic Construct

<400> SEQUENCE: 565
gagacauugc ccaggucc 18

<210> SEQ ID NO 566
<211> LENGTH: 18
<212> TYPE: RNA
<213> ORGANISM: Artificial Sequence
<220> FEATURE:
<223> OTHER INFORMATION: Synthetic Construct

<400> SEQUENCE: 566
agacauugcc caggucca 18

<210> SEQ ID NO 567
<211> LENGTH: 18
<212> TYPE: RNA
<213> ORGANISM: Artificial Sequence
<220> FEATURE:
<223> OTHER INFORMATION: Synthetic Construct

<400> SEQUENCE: 567
gacauugccc agguccac 18

<210> SEQ ID NO 568
<211> LENGTH: 18
<212> TYPE: RNA
<213> ORGANISM: Artificial Sequence
<220> FEATURE:
<223> OTHER INFORMATION: Synthetic Construct

<400> SEQUENCE: 568
acauugccca gguccaca 18

<210> SEQ ID NO 569
<211> LENGTH: 18
<212> TYPE: RNA
<213> ORGANISM: Artificial Sequence
<220> FEATURE:
<223> OTHER INFORMATION: Synthetic Construct

<400> SEQUENCE: 569
cauugcccag guccacaa 18

<210> SEQ ID NO 570
<211> LENGTH: 18
<212> TYPE: RNA
<213> ORGANISM: Artificial Sequence
<220> FEATURE:
<223> OTHER INFORMATION: Synthetic Construct

<400> SEQUENCE: 570
auugcccagg uccacaaa 18

<210> SEQ ID NO 571
<211> LENGTH: 18
<212> TYPE: RNA
<213> ORGANISM: Artificial Sequence
<220> FEATURE:
<223> OTHER INFORMATION: Synthetic Construct

<400> SEQUENCE: 571
uugcccaggu ccacaaac 18

<210> SEQ ID NO 572
<211> LENGTH: 18
<212> TYPE: RNA
<213> ORGANISM: Artificial Sequence
<220> FEATURE:
<223> OTHER INFORMATION: Synthetic Construct

<400> SEQUENCE: 572
ugcccagguc cacaaacu 18

<210> SEQ ID NO 573
<211> LENGTH: 18
<212> TYPE: RNA
<213> ORGANISM: Artificial Sequence
<220> FEATURE:
<223> OTHER INFORMATION: Synthetic Construct

<400> SEQUENCE: 573
gcccaggucc acaaacuc 18

<210> SEQ ID NO 574
<211> LENGTH: 18
<212> TYPE: RNA
<213> ORGANISM: Artificial Sequence
<220> FEATURE:
<223> OTHER INFORMATION: Synthetic Construct

<400> SEQUENCE: 574
cccaggucca caaacucu 18

<210> SEQ ID NO 575
<211> LENGTH: 18
<212> TYPE: RNA
<213> ORGANISM: Artificial Sequence
<220> FEATURE:
<223> OTHER INFORMATION: Synthetic Construct

<400> SEQUENCE: 575
ccagguccac aaacucug 18

```
<210> SEQ ID NO 576
<211> LENGTH: 18
<212> TYPE: RNA
<213> ORGANISM: Artificial Sequence
<220> FEATURE:
<223> OTHER INFORMATION: Synthetic Construct

<400> SEQUENCE: 576

cagguccaca aacucugu                                                 18

<210> SEQ ID NO 577
<211> LENGTH: 18
<212> TYPE: RNA
<213> ORGANISM: Artificial Sequence
<220> FEATURE:
<223> OTHER INFORMATION: Synthetic Construct

<400> SEQUENCE: 577

agguccacaa acucuguc                                                 18

<210> SEQ ID NO 578
<211> LENGTH: 18
<212> TYPE: RNA
<213> ORGANISM: Artificial Sequence
<220> FEATURE:
<223> OTHER INFORMATION: Synthetic Construct

<400> SEQUENCE: 578

gguccacaaa cucuguca                                                 18

<210> SEQ ID NO 579
<211> LENGTH: 18
<212> TYPE: RNA
<213> ORGANISM: Artificial Sequence
<220> FEATURE:
<223> OTHER INFORMATION: Synthetic Construct

<400> SEQUENCE: 579

guccacaaac ucugucac                                                 18

<210> SEQ ID NO 580
<211> LENGTH: 18
<212> TYPE: RNA
<213> ORGANISM: Artificial Sequence
<220> FEATURE:
<223> OTHER INFORMATION: Synthetic Construct

<400> SEQUENCE: 580

uccacaaacu cugucaca                                                 18

<210> SEQ ID NO 581
<211> LENGTH: 18
<212> TYPE: RNA
<213> ORGANISM: Artificial Sequence
<220> FEATURE:
<223> OTHER INFORMATION: Synthetic Construct

<400> SEQUENCE: 581

ccacaaacuc ugucacau                                                 18

<210> SEQ ID NO 582
<211> LENGTH: 18
<212> TYPE: RNA
<213> ORGANISM: Artificial Sequence
<220> FEATURE:
<223> OTHER INFORMATION: Synthetic Construct
```

<400> SEQUENCE: 582
cacaaacucu gucacaua 18

<210> SEQ ID NO 583
<211> LENGTH: 18
<212> TYPE: RNA
<213> ORGANISM: Artificial Sequence
<220> FEATURE:
<223> OTHER INFORMATION: Synthetic Construct

<400> SEQUENCE: 583
acaaacucug ucacauau 18

<210> SEQ ID NO 584
<211> LENGTH: 18
<212> TYPE: RNA
<213> ORGANISM: Artificial Sequence
<220> FEATURE:
<223> OTHER INFORMATION: Synthetic Construct

<400> SEQUENCE: 584
caaacucugu cacauauc 18

<210> SEQ ID NO 585
<211> LENGTH: 18
<212> TYPE: RNA
<213> ORGANISM: Artificial Sequence
<220> FEATURE:
<223> OTHER INFORMATION: Synthetic Construct

<400> SEQUENCE: 585
aaacucuguc acauaucu 18

<210> SEQ ID NO 586
<211> LENGTH: 18
<212> TYPE: RNA
<213> ORGANISM: Artificial Sequence
<220> FEATURE:
<223> OTHER INFORMATION: Synthetic Construct

<400> SEQUENCE: 586
aacucuguca cauaucug 18

<210> SEQ ID NO 587
<211> LENGTH: 18
<212> TYPE: RNA
<213> ORGANISM: Artificial Sequence
<220> FEATURE:
<223> OTHER INFORMATION: Synthetic Construct

<400> SEQUENCE: 587
acucugucac auaucugu 18

<210> SEQ ID NO 588
<211> LENGTH: 18
<212> TYPE: RNA
<213> ORGANISM: Artificial Sequence
<220> FEATURE:
<223> OTHER INFORMATION: Synthetic Construct

<400> SEQUENCE: 588
cucugucaca uaucugua 18

<210> SEQ ID NO 589

<211> LENGTH: 18
<212> TYPE: RNA
<213> ORGANISM: Artificial Sequence
<220> FEATURE:
<223> OTHER INFORMATION: Synthetic Construct

<400> SEQUENCE: 589
ucugucacau aucuguag 18

<210> SEQ ID NO 590
<211> LENGTH: 18
<212> TYPE: RNA
<213> ORGANISM: Artificial Sequence
<220> FEATURE:
<223> OTHER INFORMATION: Synthetic Construct

<400> SEQUENCE: 590
cugucacaua ucuguagu 18

<210> SEQ ID NO 591
<211> LENGTH: 17
<212> TYPE: RNA
<213> ORGANISM: Artificial Sequence
<220> FEATURE:
<223> OTHER INFORMATION: Synthetic Construct

<400> SEQUENCE: 591
cucaccugga auuacag 17

<210> SEQ ID NO 592
<211> LENGTH: 17
<212> TYPE: RNA
<213> ORGANISM: Artificial Sequence
<220> FEATURE:
<223> OTHER INFORMATION: Synthetic Construct

<400> SEQUENCE: 592
ucaccuggaa uuacaga 17

<210> SEQ ID NO 593
<211> LENGTH: 17
<212> TYPE: RNA
<213> ORGANISM: Artificial Sequence
<220> FEATURE:
<223> OTHER INFORMATION: Synthetic Construct

<400> SEQUENCE: 593
caccuggaau uacagag 17

<210> SEQ ID NO 594
<211> LENGTH: 17
<212> TYPE: RNA
<213> ORGANISM: Artificial Sequence
<220> FEATURE:
<223> OTHER INFORMATION: Synthetic Construct

<400> SEQUENCE: 594
accuggaauu acagaga 17

<210> SEQ ID NO 595
<211> LENGTH: 17
<212> TYPE: RNA
<213> ORGANISM: Artificial Sequence
<220> FEATURE:
<223> OTHER INFORMATION: Synthetic Construct

<400> SEQUENCE: 595
ccuggaauua cagagau 17

<210> SEQ ID NO 596
<211> LENGTH: 17
<212> TYPE: RNA
<213> ORGANISM: Artificial Sequence
<220> FEATURE:
<223> OTHER INFORMATION: Synthetic Construct

<400> SEQUENCE: 596
cuggaauuac agagaua 17

<210> SEQ ID NO 597
<211> LENGTH: 17
<212> TYPE: RNA
<213> ORGANISM: Artificial Sequence
<220> FEATURE:
<223> OTHER INFORMATION: Synthetic Construct

<400> SEQUENCE: 597
uggaauuaca gagauag 17

<210> SEQ ID NO 598
<211> LENGTH: 17
<212> TYPE: RNA
<213> ORGANISM: Artificial Sequence
<220> FEATURE:
<223> OTHER INFORMATION: Synthetic Construct

<400> SEQUENCE: 598
ggaauuacag agauagu 17

<210> SEQ ID NO 599
<211> LENGTH: 17
<212> TYPE: RNA
<213> ORGANISM: Artificial Sequence
<220> FEATURE:
<223> OTHER INFORMATION: Synthetic Construct

<400> SEQUENCE: 599
gaauuacaga gauaguu 17

<210> SEQ ID NO 600
<211> LENGTH: 17
<212> TYPE: RNA
<213> ORGANISM: Artificial Sequence
<220> FEATURE:
<223> OTHER INFORMATION: Synthetic Construct

<400> SEQUENCE: 600
aauuacagag auaguuu 17

<210> SEQ ID NO 601
<211> LENGTH: 17
<212> TYPE: RNA
<213> ORGANISM: Artificial Sequence
<220> FEATURE:
<223> OTHER INFORMATION: Synthetic Construct

<400> SEQUENCE: 601
auuacagaga uaguuuu 17

<210> SEQ ID NO 602
<211> LENGTH: 17
<212> TYPE: RNA

<213> ORGANISM: Artificial Sequence
<220> FEATURE:
<223> OTHER INFORMATION: Synthetic Construct

<400> SEQUENCE: 602
uuacagagau aguuuuc 17

<210> SEQ ID NO 603
<211> LENGTH: 17
<212> TYPE: RNA
<213> ORGANISM: Artificial Sequence
<220> FEATURE:
<223> OTHER INFORMATION: Synthetic Construct

<400> SEQUENCE: 603
uacagagaua guuuuca 17

<210> SEQ ID NO 604
<211> LENGTH: 17
<212> TYPE: RNA
<213> ORGANISM: Artificial Sequence
<220> FEATURE:
<223> OTHER INFORMATION: Synthetic Construct

<400> SEQUENCE: 604
acagagauag uuuucaa 17

<210> SEQ ID NO 605
<211> LENGTH: 17
<212> TYPE: RNA
<213> ORGANISM: Artificial Sequence
<220> FEATURE:
<223> OTHER INFORMATION: Synthetic Construct

<400> SEQUENCE: 605
cagagauagu uuucaaa 17

<210> SEQ ID NO 606
<211> LENGTH: 17
<212> TYPE: RNA
<213> ORGANISM: Artificial Sequence
<220> FEATURE:
<223> OTHER INFORMATION: Synthetic Construct

<400> SEQUENCE: 606
agagauaguu uucaaag 17

<210> SEQ ID NO 607
<211> LENGTH: 17
<212> TYPE: RNA
<213> ORGANISM: Artificial Sequence
<220> FEATURE:
<223> OTHER INFORMATION: Synthetic Construct

<400> SEQUENCE: 607
gagauaguuu ucaaagc 17

<210> SEQ ID NO 608
<211> LENGTH: 17
<212> TYPE: RNA
<213> ORGANISM: Artificial Sequence
<220> FEATURE:
<223> OTHER INFORMATION: Synthetic Construct

<400> SEQUENCE: 608
agauaguuuu caaagcu 17

<210> SEQ ID NO 609
<211> LENGTH: 17
<212> TYPE: RNA
<213> ORGANISM: Artificial Sequence
<220> FEATURE:
<223> OTHER INFORMATION: Synthetic Construct

<400> SEQUENCE: 609
gauaguuuuc aaagcuc 17

<210> SEQ ID NO 610
<211> LENGTH: 17
<212> TYPE: RNA
<213> ORGANISM: Artificial Sequence
<220> FEATURE:
<223> OTHER INFORMATION: Synthetic Construct

<400> SEQUENCE: 610
auaguuuuca aagcucg 17

<210> SEQ ID NO 611
<211> LENGTH: 17
<212> TYPE: RNA
<213> ORGANISM: Artificial Sequence
<220> FEATURE:
<223> OTHER INFORMATION: Synthetic Construct

<400> SEQUENCE: 611
uaguuuucaa agcucgg 17

<210> SEQ ID NO 612
<211> LENGTH: 17
<212> TYPE: RNA
<213> ORGANISM: Artificial Sequence
<220> FEATURE:
<223> OTHER INFORMATION: Synthetic Construct

<400> SEQUENCE: 612
aguuuucaaa gcucgga 17

<210> SEQ ID NO 613
<211> LENGTH: 17
<212> TYPE: RNA
<213> ORGANISM: Artificial Sequence
<220> FEATURE:
<223> OTHER INFORMATION: Synthetic Construct

<400> SEQUENCE: 613
guuuucaaag cucggag 17

<210> SEQ ID NO 614
<211> LENGTH: 17
<212> TYPE: RNA
<213> ORGANISM: Artificial Sequence
<220> FEATURE:
<223> OTHER INFORMATION: Synthetic Construct

<400> SEQUENCE: 614
uuuucaaagc ucggaga 17

<210> SEQ ID NO 615
<211> LENGTH: 17
<212> TYPE: RNA
<213> ORGANISM: Artificial Sequence
<220> FEATURE:

<223> OTHER INFORMATION: Synthetic Construct

<400> SEQUENCE: 615
uuucaaagcu cggagaa 17

<210> SEQ ID NO 616
<211> LENGTH: 17
<212> TYPE: RNA
<213> ORGANISM: Artificial Sequence
<220> FEATURE:
<223> OTHER INFORMATION: Synthetic Construct

<400> SEQUENCE: 616
uucaaagcuc ggagaac 17

<210> SEQ ID NO 617
<211> LENGTH: 17
<212> TYPE: RNA
<213> ORGANISM: Artificial Sequence
<220> FEATURE:
<223> OTHER INFORMATION: Synthetic Construct

<400> SEQUENCE: 617
ucaaagcucg gagaacc 17

<210> SEQ ID NO 618
<211> LENGTH: 17
<212> TYPE: RNA
<213> ORGANISM: Artificial Sequence
<220> FEATURE:
<223> OTHER INFORMATION: Synthetic Construct

<400> SEQUENCE: 618
caaagcucgg agaaccc 17

<210> SEQ ID NO 619
<211> LENGTH: 17
<212> TYPE: RNA
<213> ORGANISM: Artificial Sequence
<220> FEATURE:
<223> OTHER INFORMATION: Synthetic Construct

<400> SEQUENCE: 619
aaagcucgga gaacccu 17

<210> SEQ ID NO 620
<211> LENGTH: 17
<212> TYPE: RNA
<213> ORGANISM: Artificial Sequence
<220> FEATURE:
<223> OTHER INFORMATION: Synthetic Construct

<400> SEQUENCE: 620
aagcucggag aacccug 17

<210> SEQ ID NO 621
<211> LENGTH: 17
<212> TYPE: RNA
<213> ORGANISM: Artificial Sequence
<220> FEATURE:
<223> OTHER INFORMATION: Synthetic Construct

<400> SEQUENCE: 621
agcucggaga acccuga 17

-continued

<210> SEQ ID NO 622
<211> LENGTH: 17
<212> TYPE: RNA
<213> ORGANISM: Artificial Sequence
<220> FEATURE:
<223> OTHER INFORMATION: Synthetic Construct

<400> SEQUENCE: 622
gcucggagaa cccugaa 17

<210> SEQ ID NO 623
<211> LENGTH: 17
<212> TYPE: RNA
<213> ORGANISM: Artificial Sequence
<220> FEATURE:
<223> OTHER INFORMATION: Synthetic Construct

<400> SEQUENCE: 623
cucggagaac ccugaau 17

<210> SEQ ID NO 624
<211> LENGTH: 17
<212> TYPE: RNA
<213> ORGANISM: Artificial Sequence
<220> FEATURE:
<223> OTHER INFORMATION: Synthetic Construct

<400> SEQUENCE: 624
ucggagaacc cugaaug 17

<210> SEQ ID NO 625
<211> LENGTH: 17
<212> TYPE: RNA
<213> ORGANISM: Artificial Sequence
<220> FEATURE:
<223> OTHER INFORMATION: Synthetic Construct

<400> SEQUENCE: 625
cggagaaccc ugaaugu 17

<210> SEQ ID NO 626
<211> LENGTH: 17
<212> TYPE: RNA
<213> ORGANISM: Artificial Sequence
<220> FEATURE:
<223> OTHER INFORMATION: Synthetic Construct

<400> SEQUENCE: 626
ggagaacccu gaauguu 17

<210> SEQ ID NO 627
<211> LENGTH: 17
<212> TYPE: RNA
<213> ORGANISM: Artificial Sequence
<220> FEATURE:
<223> OTHER INFORMATION: Synthetic Construct

<400> SEQUENCE: 627
gagaacccug aauguuc 17

<210> SEQ ID NO 628
<211> LENGTH: 17
<212> TYPE: RNA
<213> ORGANISM: Artificial Sequence
<220> FEATURE:
<223> OTHER INFORMATION: Synthetic Construct

<400> SEQUENCE: 628
agaacccuga auguucu 17

<210> SEQ ID NO 629
<211> LENGTH: 17
<212> TYPE: RNA
<213> ORGANISM: Artificial Sequence
<220> FEATURE:
<223> OTHER INFORMATION: Synthetic Construct

<400> SEQUENCE: 629
gaacccugaa uguucuc 17

<210> SEQ ID NO 630
<211> LENGTH: 17
<212> TYPE: RNA
<213> ORGANISM: Artificial Sequence
<220> FEATURE:
<223> OTHER INFORMATION: Synthetic Construct

<400> SEQUENCE: 630
aacccugaau guucuca 17

<210> SEQ ID NO 631
<211> LENGTH: 17
<212> TYPE: RNA
<213> ORGANISM: Artificial Sequence
<220> FEATURE:
<223> OTHER INFORMATION: Synthetic Construct

<400> SEQUENCE: 631
acccugaaug uucucag 17

<210> SEQ ID NO 632
<211> LENGTH: 17
<212> TYPE: RNA
<213> ORGANISM: Artificial Sequence
<220> FEATURE:
<223> OTHER INFORMATION: Synthetic Construct

<400> SEQUENCE: 632
cccugaaugu ucucagc 17

<210> SEQ ID NO 633
<211> LENGTH: 17
<212> TYPE: RNA
<213> ORGANISM: Artificial Sequence
<220> FEATURE:
<223> OTHER INFORMATION: Synthetic Construct

<400> SEQUENCE: 633
ccugaauguu cucagcg 17

<210> SEQ ID NO 634
<211> LENGTH: 17
<212> TYPE: RNA
<213> ORGANISM: Artificial Sequence
<220> FEATURE:
<223> OTHER INFORMATION: Synthetic Construct

<400> SEQUENCE: 634
cugaauguuc ucagcgc 17

<210> SEQ ID NO 635
<211> LENGTH: 17

<212> TYPE: RNA
<213> ORGANISM: Artificial Sequence
<220> FEATURE:
<223> OTHER INFORMATION: Synthetic Construct

<400> SEQUENCE: 635
ugaauguucu cagcgcu 17

<210> SEQ ID NO 636
<211> LENGTH: 17
<212> TYPE: RNA
<213> ORGANISM: Artificial Sequence
<220> FEATURE:
<223> OTHER INFORMATION: Synthetic Construct

<400> SEQUENCE: 636
gaauguucuc agcgcug 17

<210> SEQ ID NO 637
<211> LENGTH: 17
<212> TYPE: RNA
<213> ORGANISM: Artificial Sequence
<220> FEATURE:
<223> OTHER INFORMATION: Synthetic Construct

<400> SEQUENCE: 637
aauguucuca gcgcuga 17

<210> SEQ ID NO 638
<211> LENGTH: 17
<212> TYPE: RNA
<213> ORGANISM: Artificial Sequence
<220> FEATURE:
<223> OTHER INFORMATION: Synthetic Construct

<400> SEQUENCE: 638
auguucucag cgcugag 17

<210> SEQ ID NO 639
<211> LENGTH: 17
<212> TYPE: RNA
<213> ORGANISM: Artificial Sequence
<220> FEATURE:
<223> OTHER INFORMATION: Synthetic Construct

<400> SEQUENCE: 639
uguucucagc gcugaga 17

<210> SEQ ID NO 640
<211> LENGTH: 17
<212> TYPE: RNA
<213> ORGANISM: Artificial Sequence
<220> FEATURE:
<223> OTHER INFORMATION: Synthetic Construct

<400> SEQUENCE: 640
guucucagcg cugagac 17

<210> SEQ ID NO 641
<211> LENGTH: 17
<212> TYPE: RNA
<213> ORGANISM: Artificial Sequence
<220> FEATURE:
<223> OTHER INFORMATION: Synthetic Construct

<400> SEQUENCE: 641
uucucagcgc ugagaca 17

<210> SEQ ID NO 642
<211> LENGTH: 17
<212> TYPE: RNA
<213> ORGANISM: Artificial Sequence
<220> FEATURE:
<223> OTHER INFORMATION: Synthetic Construct

<400> SEQUENCE: 642
ucucagcgcu gagacau 17

<210> SEQ ID NO 643
<211> LENGTH: 17
<212> TYPE: RNA
<213> ORGANISM: Artificial Sequence
<220> FEATURE:
<223> OTHER INFORMATION: Synthetic Construct

<400> SEQUENCE: 643
cucagcgcug agacauu 17

<210> SEQ ID NO 644
<211> LENGTH: 17
<212> TYPE: RNA
<213> ORGANISM: Artificial Sequence
<220> FEATURE:
<223> OTHER INFORMATION: Synthetic Construct

<400> SEQUENCE: 644
ucagcgcuga gacauug 17

<210> SEQ ID NO 645
<211> LENGTH: 17
<212> TYPE: RNA
<213> ORGANISM: Artificial Sequence
<220> FEATURE:
<223> OTHER INFORMATION: Synthetic Construct

<400> SEQUENCE: 645
cagcgcugag acauugc 17

<210> SEQ ID NO 646
<211> LENGTH: 17
<212> TYPE: RNA
<213> ORGANISM: Artificial Sequence
<220> FEATURE:
<223> OTHER INFORMATION: Synthetic Construct

<400> SEQUENCE: 646
agcgcugaga cauugcc 17

<210> SEQ ID NO 647
<211> LENGTH: 17
<212> TYPE: RNA
<213> ORGANISM: Artificial Sequence
<220> FEATURE:
<223> OTHER INFORMATION: Synthetic Construct

<400> SEQUENCE: 647
gcgcugagac auugccc 17

<210> SEQ ID NO 648
<211> LENGTH: 17
<212> TYPE: RNA
<213> ORGANISM: Artificial Sequence

```
<220> FEATURE:
<223> OTHER INFORMATION: Synthetic Construct

<400> SEQUENCE: 648

cgcugagaca uugccca                                                    17

<210> SEQ ID NO 649
<211> LENGTH: 17
<212> TYPE: RNA
<213> ORGANISM: Artificial Sequence
<220> FEATURE:
<223> OTHER INFORMATION: Synthetic Construct

<400> SEQUENCE: 649

gcugagacau ugcccag                                                    17

<210> SEQ ID NO 650
<211> LENGTH: 17
<212> TYPE: RNA
<213> ORGANISM: Artificial Sequence
<220> FEATURE:
<223> OTHER INFORMATION: Synthetic Construct

<400> SEQUENCE: 650

cugagacauu gcccagg                                                    17

<210> SEQ ID NO 651
<211> LENGTH: 17
<212> TYPE: RNA
<213> ORGANISM: Artificial Sequence
<220> FEATURE:
<223> OTHER INFORMATION: Synthetic Construct

<400> SEQUENCE: 651

ugagacauug cccaggu                                                    17

<210> SEQ ID NO 652
<211> LENGTH: 17
<212> TYPE: RNA
<213> ORGANISM: Artificial Sequence
<220> FEATURE:
<223> OTHER INFORMATION: Synthetic Construct

<400> SEQUENCE: 652

gagacauugc ccagguc                                                    17

<210> SEQ ID NO 653
<211> LENGTH: 17
<212> TYPE: RNA
<213> ORGANISM: Artificial Sequence
<220> FEATURE:
<223> OTHER INFORMATION: Synthetic Construct

<400> SEQUENCE: 653

agacauugcc caggucc                                                    17

<210> SEQ ID NO 654
<211> LENGTH: 17
<212> TYPE: RNA
<213> ORGANISM: Artificial Sequence
<220> FEATURE:
<223> OTHER INFORMATION: Synthetic Construct

<400> SEQUENCE: 654

gacauugccc aggucca                                                    17
```

<210> SEQ ID NO 655
<211> LENGTH: 17
<212> TYPE: RNA
<213> ORGANISM: Artificial Sequence
<220> FEATURE:
<223> OTHER INFORMATION: Synthetic Construct

<400> SEQUENCE: 655
acauugccca gguccac 17

<210> SEQ ID NO 656
<211> LENGTH: 17
<212> TYPE: RNA
<213> ORGANISM: Artificial Sequence
<220> FEATURE:
<223> OTHER INFORMATION: Synthetic Construct

<400> SEQUENCE: 656
cauugcccag guccaca 17

<210> SEQ ID NO 657
<211> LENGTH: 17
<212> TYPE: RNA
<213> ORGANISM: Artificial Sequence
<220> FEATURE:
<223> OTHER INFORMATION: Synthetic Construct

<400> SEQUENCE: 657
auugcccagg uccacaa 17

<210> SEQ ID NO 658
<211> LENGTH: 17
<212> TYPE: RNA
<213> ORGANISM: Artificial Sequence
<220> FEATURE:
<223> OTHER INFORMATION: Synthetic Construct

<400> SEQUENCE: 658
uugcccaggu ccacaaa 17

<210> SEQ ID NO 659
<211> LENGTH: 17
<212> TYPE: RNA
<213> ORGANISM: Artificial Sequence
<220> FEATURE:
<223> OTHER INFORMATION: Synthetic Construct

<400> SEQUENCE: 659
ugcccagguc cacaaac 17

<210> SEQ ID NO 660
<211> LENGTH: 17
<212> TYPE: RNA
<213> ORGANISM: Artificial Sequence
<220> FEATURE:
<223> OTHER INFORMATION: Synthetic Construct

<400> SEQUENCE: 660
gcccaggucc acaaacu 17

<210> SEQ ID NO 661
<211> LENGTH: 17
<212> TYPE: RNA
<213> ORGANISM: Artificial Sequence
<220> FEATURE:
<223> OTHER INFORMATION: Synthetic Construct

<400> SEQUENCE: 661
cccaggucca caaacuc 17

<210> SEQ ID NO 662
<211> LENGTH: 17
<212> TYPE: RNA
<213> ORGANISM: Artificial Sequence
<220> FEATURE:
<223> OTHER INFORMATION: Synthetic Construct

<400> SEQUENCE: 662
ccagguccac aaacucu 17

<210> SEQ ID NO 663
<211> LENGTH: 17
<212> TYPE: RNA
<213> ORGANISM: Artificial Sequence
<220> FEATURE:
<223> OTHER INFORMATION: Synthetic Construct

<400> SEQUENCE: 663
cagguccaca aacucug 17

<210> SEQ ID NO 664
<211> LENGTH: 17
<212> TYPE: RNA
<213> ORGANISM: Artificial Sequence
<220> FEATURE:
<223> OTHER INFORMATION: Synthetic Construct

<400> SEQUENCE: 664
agguccacaa acucugu 17

<210> SEQ ID NO 665
<211> LENGTH: 17
<212> TYPE: RNA
<213> ORGANISM: Artificial Sequence
<220> FEATURE:
<223> OTHER INFORMATION: Synthetic Construct

<400> SEQUENCE: 665
gguccacaaa cucuguc 17

<210> SEQ ID NO 666
<211> LENGTH: 17
<212> TYPE: RNA
<213> ORGANISM: Artificial Sequence
<220> FEATURE:
<223> OTHER INFORMATION: Synthetic Construct

<400> SEQUENCE: 666
guccacaaac ucuguca 17

<210> SEQ ID NO 667
<211> LENGTH: 17
<212> TYPE: RNA
<213> ORGANISM: Artificial Sequence
<220> FEATURE:
<223> OTHER INFORMATION: Synthetic Construct

<400> SEQUENCE: 667
uccacaaacu cugucac 17

<210> SEQ ID NO 668

<211> LENGTH: 17
<212> TYPE: RNA
<213> ORGANISM: Artificial Sequence
<220> FEATURE:
<223> OTHER INFORMATION: Synthetic Construct

<400> SEQUENCE: 668
ccacaaacuc ugucaca 17

<210> SEQ ID NO 669
<211> LENGTH: 17
<212> TYPE: RNA
<213> ORGANISM: Artificial Sequence
<220> FEATURE:
<223> OTHER INFORMATION: Synthetic Construct

<400> SEQUENCE: 669
cacaaacucu gucacau 17

<210> SEQ ID NO 670
<211> LENGTH: 17
<212> TYPE: RNA
<213> ORGANISM: Artificial Sequence
<220> FEATURE:
<223> OTHER INFORMATION: Synthetic Construct

<400> SEQUENCE: 670
acaaacucug ucacaua 17

<210> SEQ ID NO 671
<211> LENGTH: 17
<212> TYPE: RNA
<213> ORGANISM: Artificial Sequence
<220> FEATURE:
<223> OTHER INFORMATION: Synthetic Construct

<400> SEQUENCE: 671
caaacucugu cacauau 17

<210> SEQ ID NO 672
<211> LENGTH: 17
<212> TYPE: RNA
<213> ORGANISM: Artificial Sequence
<220> FEATURE:
<223> OTHER INFORMATION: Synthetic Construct

<400> SEQUENCE: 672
aaacucuguc acauauc 17

<210> SEQ ID NO 673
<211> LENGTH: 17
<212> TYPE: RNA
<213> ORGANISM: Artificial Sequence
<220> FEATURE:
<223> OTHER INFORMATION: Synthetic Construct

<400> SEQUENCE: 673
aacucuguca cauaucu 17

<210> SEQ ID NO 674
<211> LENGTH: 17
<212> TYPE: RNA
<213> ORGANISM: Artificial Sequence
<220> FEATURE:
<223> OTHER INFORMATION: Synthetic Construct

<400> SEQUENCE: 674
acucugucac auaucug 17

<210> SEQ ID NO 675
<211> LENGTH: 17
<212> TYPE: RNA
<213> ORGANISM: Artificial Sequence
<220> FEATURE:
<223> OTHER INFORMATION: Synthetic Construct

<400> SEQUENCE: 675
cucugucaca uaucugu 17

<210> SEQ ID NO 676
<211> LENGTH: 17
<212> TYPE: RNA
<213> ORGANISM: Artificial Sequence
<220> FEATURE:
<223> OTHER INFORMATION: Synthetic Construct

<400> SEQUENCE: 676
ucugucacau aucugua 17

<210> SEQ ID NO 677
<211> LENGTH: 17
<212> TYPE: RNA
<213> ORGANISM: Artificial Sequence
<220> FEATURE:
<223> OTHER INFORMATION: Synthetic Construct

<400> SEQUENCE: 677
cugucacaua ucuguag 17

<210> SEQ ID NO 678
<211> LENGTH: 17
<212> TYPE: RNA
<213> ORGANISM: Artificial Sequence
<220> FEATURE:
<223> OTHER INFORMATION: Synthetic Construct

<400> SEQUENCE: 678
ugucacauau cuguagu 17

<210> SEQ ID NO 679
<211> LENGTH: 16
<212> TYPE: RNA
<213> ORGANISM: Artificial Sequence
<220> FEATURE:
<223> OTHER INFORMATION: Synthetic Construct

<400> SEQUENCE: 679
cucaccugga auuaca 16

<210> SEQ ID NO 680
<211> LENGTH: 16
<212> TYPE: RNA
<213> ORGANISM: Artificial Sequence
<220> FEATURE:
<223> OTHER INFORMATION: Synthetic Construct

<400> SEQUENCE: 680
ucaccuggaa uuacag 16

<210> SEQ ID NO 681
<211> LENGTH: 16
<212> TYPE: RNA

<213> ORGANISM: Artificial Sequence
<220> FEATURE:
<223> OTHER INFORMATION: Synthetic Construct

<400> SEQUENCE: 681
caccuggaau uacaga 16

<210> SEQ ID NO 682
<211> LENGTH: 16
<212> TYPE: RNA
<213> ORGANISM: Artificial Sequence
<220> FEATURE:
<223> OTHER INFORMATION: Synthetic Construct

<400> SEQUENCE: 682
accuggaauu acagag 16

<210> SEQ ID NO 683
<211> LENGTH: 16
<212> TYPE: RNA
<213> ORGANISM: Artificial Sequence
<220> FEATURE:
<223> OTHER INFORMATION: Synthetic Construct

<400> SEQUENCE: 683
ccuggaauua cagaga 16

<210> SEQ ID NO 684
<211> LENGTH: 16
<212> TYPE: RNA
<213> ORGANISM: Artificial Sequence
<220> FEATURE:
<223> OTHER INFORMATION: Synthetic Construct

<400> SEQUENCE: 684
cuggaauuac agagau 16

<210> SEQ ID NO 685
<211> LENGTH: 16
<212> TYPE: RNA
<213> ORGANISM: Artificial Sequence
<220> FEATURE:
<223> OTHER INFORMATION: Synthetic Construct

<400> SEQUENCE: 685
uggaauuaca gagaua 16

<210> SEQ ID NO 686
<211> LENGTH: 16
<212> TYPE: RNA
<213> ORGANISM: Artificial Sequence
<220> FEATURE:
<223> OTHER INFORMATION: Synthetic Construct

<400> SEQUENCE: 686
ggaauuacag agauag 16

<210> SEQ ID NO 687
<211> LENGTH: 16
<212> TYPE: RNA
<213> ORGANISM: Artificial Sequence
<220> FEATURE:
<223> OTHER INFORMATION: Synthetic Construct

<400> SEQUENCE: 687
gaauuacaga gauagu 16

<210> SEQ ID NO 688
<211> LENGTH: 16
<212> TYPE: RNA
<213> ORGANISM: Artificial Sequence
<220> FEATURE:
<223> OTHER INFORMATION: Synthetic Construct

<400> SEQUENCE: 688
aauuacagag auaguu 16

<210> SEQ ID NO 689
<211> LENGTH: 16
<212> TYPE: RNA
<213> ORGANISM: Artificial Sequence
<220> FEATURE:
<223> OTHER INFORMATION: Synthetic Construct

<400> SEQUENCE: 689
auuacagaga uaguuu 16

<210> SEQ ID NO 690
<211> LENGTH: 16
<212> TYPE: RNA
<213> ORGANISM: Artificial Sequence
<220> FEATURE:
<223> OTHER INFORMATION: Synthetic Construct

<400> SEQUENCE: 690
uuacagagau aguuuu 16

<210> SEQ ID NO 691
<211> LENGTH: 16
<212> TYPE: RNA
<213> ORGANISM: Artificial Sequence
<220> FEATURE:
<223> OTHER INFORMATION: Synthetic Construct

<400> SEQUENCE: 691
uacagagaua guuuuc 16

<210> SEQ ID NO 692
<211> LENGTH: 16
<212> TYPE: RNA
<213> ORGANISM: Artificial Sequence
<220> FEATURE:
<223> OTHER INFORMATION: Synthetic Construct

<400> SEQUENCE: 692
acagagauag uuuuca 16

<210> SEQ ID NO 693
<211> LENGTH: 16
<212> TYPE: RNA
<213> ORGANISM: Artificial Sequence
<220> FEATURE:
<223> OTHER INFORMATION: Synthetic Construct

<400> SEQUENCE: 693
cagagauagu uuucaa 16

<210> SEQ ID NO 694
<211> LENGTH: 16
<212> TYPE: RNA
<213> ORGANISM: Artificial Sequence
<220> FEATURE:

<223> OTHER INFORMATION: Synthetic Construct

<400> SEQUENCE: 694
agagauaguu uucaaa 16

<210> SEQ ID NO 695
<211> LENGTH: 16
<212> TYPE: RNA
<213> ORGANISM: Artificial Sequence
<220> FEATURE:
<223> OTHER INFORMATION: Synthetic Construct

<400> SEQUENCE: 695
gagauaguuu ucaaag 16

<210> SEQ ID NO 696
<211> LENGTH: 16
<212> TYPE: RNA
<213> ORGANISM: Artificial Sequence
<220> FEATURE:
<223> OTHER INFORMATION: Synthetic Construct

<400> SEQUENCE: 696
agauaguuuu caaagc 16

<210> SEQ ID NO 697
<211> LENGTH: 16
<212> TYPE: RNA
<213> ORGANISM: Artificial Sequence
<220> FEATURE:
<223> OTHER INFORMATION: Synthetic Construct

<400> SEQUENCE: 697
gauaguuuuc aaagcu 16

<210> SEQ ID NO 698
<211> LENGTH: 16
<212> TYPE: RNA
<213> ORGANISM: Artificial Sequence
<220> FEATURE:
<223> OTHER INFORMATION: Synthetic Construct

<400> SEQUENCE: 698
auaguuuuca aagcuc 16

<210> SEQ ID NO 699
<211> LENGTH: 16
<212> TYPE: RNA
<213> ORGANISM: Artificial Sequence
<220> FEATURE:
<223> OTHER INFORMATION: Synthetic Construct

<400> SEQUENCE: 699
uaguuuucaa agcucg 16

<210> SEQ ID NO 700
<211> LENGTH: 16
<212> TYPE: RNA
<213> ORGANISM: Artificial Sequence
<220> FEATURE:
<223> OTHER INFORMATION: Synthetic Construct

<400> SEQUENCE: 700
aguuuucaaa gcucgg 16

<210> SEQ ID NO 701
<211> LENGTH: 16
<212> TYPE: RNA
<213> ORGANISM: Artificial Sequence
<220> FEATURE:
<223> OTHER INFORMATION: Synthetic Construct

<400> SEQUENCE: 701
guuuucaaag cucgga 16

<210> SEQ ID NO 702
<211> LENGTH: 16
<212> TYPE: RNA
<213> ORGANISM: Artificial Sequence
<220> FEATURE:
<223> OTHER INFORMATION: Synthetic Construct

<400> SEQUENCE: 702
uuuucaaagc ucggag 16

<210> SEQ ID NO 703
<211> LENGTH: 16
<212> TYPE: RNA
<213> ORGANISM: Artificial Sequence
<220> FEATURE:
<223> OTHER INFORMATION: Synthetic Construct

<400> SEQUENCE: 703
uuucaaagcu cggaga 16

<210> SEQ ID NO 704
<211> LENGTH: 16
<212> TYPE: RNA
<213> ORGANISM: Artificial Sequence
<220> FEATURE:
<223> OTHER INFORMATION: Synthetic Construct

<400> SEQUENCE: 704
uucaaagcuc ggagaa 16

<210> SEQ ID NO 705
<211> LENGTH: 16
<212> TYPE: RNA
<213> ORGANISM: Artificial Sequence
<220> FEATURE:
<223> OTHER INFORMATION: Synthetic Construct

<400> SEQUENCE: 705
ucaaagcucg gagaac 16

<210> SEQ ID NO 706
<211> LENGTH: 16
<212> TYPE: RNA
<213> ORGANISM: Artificial Sequence
<220> FEATURE:
<223> OTHER INFORMATION: Synthetic Construct

<400> SEQUENCE: 706
caaagcucgg agaacc 16

<210> SEQ ID NO 707
<211> LENGTH: 16
<212> TYPE: RNA
<213> ORGANISM: Artificial Sequence
<220> FEATURE:
<223> OTHER INFORMATION: Synthetic Construct

<400> SEQUENCE: 707
aaagcucgga gaaccc 16

<210> SEQ ID NO 708
<211> LENGTH: 16
<212> TYPE: RNA
<213> ORGANISM: Artificial Sequence
<220> FEATURE:
<223> OTHER INFORMATION: Synthetic Construct

<400> SEQUENCE: 708
aagcucggag aacccu 16

<210> SEQ ID NO 709
<211> LENGTH: 16
<212> TYPE: RNA
<213> ORGANISM: Artificial Sequence
<220> FEATURE:
<223> OTHER INFORMATION: Synthetic Construct

<400> SEQUENCE: 709
agcucggaga acccug 16

<210> SEQ ID NO 710
<211> LENGTH: 16
<212> TYPE: RNA
<213> ORGANISM: Artificial Sequence
<220> FEATURE:
<223> OTHER INFORMATION: Synthetic Construct

<400> SEQUENCE: 710
gcucggagaa cccuga 16

<210> SEQ ID NO 711
<211> LENGTH: 16
<212> TYPE: RNA
<213> ORGANISM: Artificial Sequence
<220> FEATURE:
<223> OTHER INFORMATION: Synthetic Construct

<400> SEQUENCE: 711
cucggagaac ccugaa 16

<210> SEQ ID NO 712
<211> LENGTH: 16
<212> TYPE: RNA
<213> ORGANISM: Artificial Sequence
<220> FEATURE:
<223> OTHER INFORMATION: Synthetic Construct

<400> SEQUENCE: 712
ucggagaacc cugaau 16

<210> SEQ ID NO 713
<211> LENGTH: 16
<212> TYPE: RNA
<213> ORGANISM: Artificial Sequence
<220> FEATURE:
<223> OTHER INFORMATION: Synthetic Construct

<400> SEQUENCE: 713
cggagaaccc ugaaug 16

<210> SEQ ID NO 714
<211> LENGTH: 16

<212> TYPE: RNA
<213> ORGANISM: Artificial Sequence
<220> FEATURE:
<223> OTHER INFORMATION: Synthetic Construct

<400> SEQUENCE: 714
ggagaacccu gaaugu 16

<210> SEQ ID NO 715
<211> LENGTH: 16
<212> TYPE: RNA
<213> ORGANISM: Artificial Sequence
<220> FEATURE:
<223> OTHER INFORMATION: Synthetic Construct

<400> SEQUENCE: 715
gagaacccug aauguu 16

<210> SEQ ID NO 716
<211> LENGTH: 16
<212> TYPE: RNA
<213> ORGANISM: Artificial Sequence
<220> FEATURE:
<223> OTHER INFORMATION: Synthetic Construct

<400> SEQUENCE: 716
agaacccuga auguuc 16

<210> SEQ ID NO 717
<211> LENGTH: 16
<212> TYPE: RNA
<213> ORGANISM: Artificial Sequence
<220> FEATURE:
<223> OTHER INFORMATION: Synthetic Construct

<400> SEQUENCE: 717
gaacccugaa uguucu 16

<210> SEQ ID NO 718
<211> LENGTH: 16
<212> TYPE: RNA
<213> ORGANISM: Artificial Sequence
<220> FEATURE:
<223> OTHER INFORMATION: Synthetic Construct

<400> SEQUENCE: 718
aacccugaau guucuc 16

<210> SEQ ID NO 719
<211> LENGTH: 16
<212> TYPE: RNA
<213> ORGANISM: Artificial Sequence
<220> FEATURE:
<223> OTHER INFORMATION: Synthetic Construct

<400> SEQUENCE: 719
acccugaaug uucuca 16

<210> SEQ ID NO 720
<211> LENGTH: 16
<212> TYPE: RNA
<213> ORGANISM: Artificial Sequence
<220> FEATURE:
<223> OTHER INFORMATION: Synthetic Construct

<400> SEQUENCE: 720
cccugaaugu ucucag 16

<210> SEQ ID NO 721
<211> LENGTH: 16
<212> TYPE: RNA
<213> ORGANISM: Artificial Sequence
<220> FEATURE:
<223> OTHER INFORMATION: Synthetic Construct

<400> SEQUENCE: 721
ccugaauguu cucagc 16

<210> SEQ ID NO 722
<211> LENGTH: 16
<212> TYPE: RNA
<213> ORGANISM: Artificial Sequence
<220> FEATURE:
<223> OTHER INFORMATION: Synthetic Construct

<400> SEQUENCE: 722
cugaauguuc ucagcg 16

<210> SEQ ID NO 723
<211> LENGTH: 16
<212> TYPE: RNA
<213> ORGANISM: Artificial Sequence
<220> FEATURE:
<223> OTHER INFORMATION: Synthetic Construct

<400> SEQUENCE: 723
ugaauguucu cagcgc 16

<210> SEQ ID NO 724
<211> LENGTH: 16
<212> TYPE: RNA
<213> ORGANISM: Artificial Sequence
<220> FEATURE:
<223> OTHER INFORMATION: Synthetic Construct

<400> SEQUENCE: 724
gaauguucuc agcgcu 16

<210> SEQ ID NO 725
<211> LENGTH: 16
<212> TYPE: RNA
<213> ORGANISM: Artificial Sequence
<220> FEATURE:
<223> OTHER INFORMATION: Synthetic Construct

<400> SEQUENCE: 725
aauguucuca gcgcug 16

<210> SEQ ID NO 726
<211> LENGTH: 16
<212> TYPE: RNA
<213> ORGANISM: Artificial Sequence
<220> FEATURE:
<223> OTHER INFORMATION: Synthetic Construct

<400> SEQUENCE: 726
auguucucag cgcuga 16

<210> SEQ ID NO 727
<211> LENGTH: 16
<212> TYPE: RNA
<213> ORGANISM: Artificial Sequence
<220> FEATURE:
<223> OTHER INFORMATION: Synthetic Construct

<400> SEQUENCE: 727
uguucucagc gcugag 16

<210> SEQ ID NO 728
<211> LENGTH: 16
<212> TYPE: RNA
<213> ORGANISM: Artificial Sequence
<220> FEATURE:
<223> OTHER INFORMATION: Synthetic Construct

<400> SEQUENCE: 728
guucucagcg cugaga 16

<210> SEQ ID NO 729
<211> LENGTH: 16
<212> TYPE: RNA
<213> ORGANISM: Artificial Sequence
<220> FEATURE:
<223> OTHER INFORMATION: Synthetic Construct

<400> SEQUENCE: 729
uucucagcgc ugagac 16

<210> SEQ ID NO 730
<211> LENGTH: 16
<212> TYPE: RNA
<213> ORGANISM: Artificial Sequence
<220> FEATURE:
<223> OTHER INFORMATION: Synthetic Construct

<400> SEQUENCE: 730
ucucagcgcu gagaca 16

<210> SEQ ID NO 731
<211> LENGTH: 16
<212> TYPE: RNA
<213> ORGANISM: Artificial Sequence
<220> FEATURE:
<223> OTHER INFORMATION: Synthetic Construct

<400> SEQUENCE: 731
cucagcgcug agacau 16

<210> SEQ ID NO 732
<211> LENGTH: 16
<212> TYPE: RNA
<213> ORGANISM: Artificial Sequence
<220> FEATURE:
<223> OTHER INFORMATION: Synthetic Construct

<400> SEQUENCE: 732
ucagcgcuga gacauu 16

<210> SEQ ID NO 733
<211> LENGTH: 16
<212> TYPE: RNA
<213> ORGANISM: Artificial Sequence
<220> FEATURE:
<223> OTHER INFORMATION: Synthetic Construct

<400> SEQUENCE: 733
cagcgcugag acauug 16

<210> SEQ ID NO 734
<211> LENGTH: 16
<212> TYPE: RNA
<213> ORGANISM: Artificial Sequence
<220> FEATURE:
<223> OTHER INFORMATION: Synthetic Construct

<400> SEQUENCE: 734
agcgcugaga cauugc 16

<210> SEQ ID NO 735
<211> LENGTH: 16
<212> TYPE: RNA
<213> ORGANISM: Artificial Sequence
<220> FEATURE:
<223> OTHER INFORMATION: Synthetic Construct

<400> SEQUENCE: 735
gcgcugagac auugcc 16

<210> SEQ ID NO 736
<211> LENGTH: 16
<212> TYPE: RNA
<213> ORGANISM: Artificial Sequence
<220> FEATURE:
<223> OTHER INFORMATION: Synthetic Construct

<400> SEQUENCE: 736
cgcugagaca uugccc 16

<210> SEQ ID NO 737
<211> LENGTH: 16
<212> TYPE: RNA
<213> ORGANISM: Artificial Sequence
<220> FEATURE:
<223> OTHER INFORMATION: Synthetic Construct

<400> SEQUENCE: 737
gcugagacau ugccca 16

<210> SEQ ID NO 738
<211> LENGTH: 16
<212> TYPE: RNA
<213> ORGANISM: Artificial Sequence
<220> FEATURE:
<223> OTHER INFORMATION: Synthetic Construct

<400> SEQUENCE: 738
cugagacauu gcccag 16

<210> SEQ ID NO 739
<211> LENGTH: 16
<212> TYPE: RNA
<213> ORGANISM: Artificial Sequence
<220> FEATURE:
<223> OTHER INFORMATION: Synthetic Construct

<400> SEQUENCE: 739
ugagacauug cccagg 16

<210> SEQ ID NO 740
<211> LENGTH: 16
<212> TYPE: RNA
<213> ORGANISM: Artificial Sequence
<220> FEATURE:
<223> OTHER INFORMATION: Synthetic Construct

```
<400> SEQUENCE: 740

gagacauugc ccaggu                                                    16

<210> SEQ ID NO 741
<211> LENGTH: 16
<212> TYPE: RNA
<213> ORGANISM: Artificial Sequence
<220> FEATURE:
<223> OTHER INFORMATION: Synthetic Construct

<400> SEQUENCE: 741

agacauugcc cagguc                                                    16

<210> SEQ ID NO 742
<211> LENGTH: 16
<212> TYPE: RNA
<213> ORGANISM: Artificial Sequence
<220> FEATURE:
<223> OTHER INFORMATION: Synthetic Construct

<400> SEQUENCE: 742

gacauugccc aggucc                                                    16

<210> SEQ ID NO 743
<211> LENGTH: 16
<212> TYPE: RNA
<213> ORGANISM: Artificial Sequence
<220> FEATURE:
<223> OTHER INFORMATION: Synthetic Construct

<400> SEQUENCE: 743

acauugccca ggucca                                                    16

<210> SEQ ID NO 744
<211> LENGTH: 16
<212> TYPE: RNA
<213> ORGANISM: Artificial Sequence
<220> FEATURE:
<223> OTHER INFORMATION: Synthetic Construct

<400> SEQUENCE: 744

cauugcccag guccac                                                    16

<210> SEQ ID NO 745
<211> LENGTH: 16
<212> TYPE: RNA
<213> ORGANISM: Artificial Sequence
<220> FEATURE:
<223> OTHER INFORMATION: Synthetic Construct

<400> SEQUENCE: 745

auugcccagg uccaca                                                    16

<210> SEQ ID NO 746
<211> LENGTH: 16
<212> TYPE: RNA
<213> ORGANISM: Artificial Sequence
<220> FEATURE:
<223> OTHER INFORMATION: Synthetic Construct

<400> SEQUENCE: 746

uugcccaggu ccacaa                                                    16

<210> SEQ ID NO 747
```

<211> LENGTH: 16
<212> TYPE: RNA
<213> ORGANISM: Artificial Sequence
<220> FEATURE:
<223> OTHER INFORMATION: Synthetic Construct

<400> SEQUENCE: 747
ugcccagguc cacaaa 16

<210> SEQ ID NO 748
<211> LENGTH: 16
<212> TYPE: RNA
<213> ORGANISM: Artificial Sequence
<220> FEATURE:
<223> OTHER INFORMATION: Synthetic Construct

<400> SEQUENCE: 748
gcccaggucc acaaac 16

<210> SEQ ID NO 749
<211> LENGTH: 16
<212> TYPE: RNA
<213> ORGANISM: Artificial Sequence
<220> FEATURE:
<223> OTHER INFORMATION: Synthetic Construct

<400> SEQUENCE: 749
cccaggucca caaacu 16

<210> SEQ ID NO 750
<211> LENGTH: 16
<212> TYPE: RNA
<213> ORGANISM: Artificial Sequence
<220> FEATURE:
<223> OTHER INFORMATION: Synthetic Construct

<400> SEQUENCE: 750
ccagguccac aaacuc 16

<210> SEQ ID NO 751
<211> LENGTH: 16
<212> TYPE: RNA
<213> ORGANISM: Artificial Sequence
<220> FEATURE:
<223> OTHER INFORMATION: Synthetic Construct

<400> SEQUENCE: 751
cagguccaca aacucu 16

<210> SEQ ID NO 752
<211> LENGTH: 16
<212> TYPE: RNA
<213> ORGANISM: Artificial Sequence
<220> FEATURE:
<223> OTHER INFORMATION: Synthetic Construct

<400> SEQUENCE: 752
agguccacaa acucug 16

<210> SEQ ID NO 753
<211> LENGTH: 16
<212> TYPE: RNA
<213> ORGANISM: Artificial Sequence
<220> FEATURE:
<223> OTHER INFORMATION: Synthetic Construct

<400> SEQUENCE: 753
gguccacaaa cucugu 16

<210> SEQ ID NO 754
<211> LENGTH: 16
<212> TYPE: RNA
<213> ORGANISM: Artificial Sequence
<220> FEATURE:
<223> OTHER INFORMATION: Synthetic Construct

<400> SEQUENCE: 754
guccacaaac ucuguc 16

<210> SEQ ID NO 755
<211> LENGTH: 16
<212> TYPE: RNA
<213> ORGANISM: Artificial Sequence
<220> FEATURE:
<223> OTHER INFORMATION: Synthetic Construct

<400> SEQUENCE: 755
uccacaaacu cuguca 16

<210> SEQ ID NO 756
<211> LENGTH: 16
<212> TYPE: RNA
<213> ORGANISM: Artificial Sequence
<220> FEATURE:
<223> OTHER INFORMATION: Synthetic Construct

<400> SEQUENCE: 756
ccacaaacuc ugucac 16

<210> SEQ ID NO 757
<211> LENGTH: 16
<212> TYPE: RNA
<213> ORGANISM: Artificial Sequence
<220> FEATURE:
<223> OTHER INFORMATION: Synthetic Construct

<400> SEQUENCE: 757
cacaaacucu gucaca 16

<210> SEQ ID NO 758
<211> LENGTH: 16
<212> TYPE: RNA
<213> ORGANISM: Artificial Sequence
<220> FEATURE:
<223> OTHER INFORMATION: Synthetic Construct

<400> SEQUENCE: 758
acaaacucug ucacau 16

<210> SEQ ID NO 759
<211> LENGTH: 16
<212> TYPE: RNA
<213> ORGANISM: Artificial Sequence
<220> FEATURE:
<223> OTHER INFORMATION: Synthetic Construct

<400> SEQUENCE: 759
caaacucugu cacaua 16

<210> SEQ ID NO 760
<211> LENGTH: 16
<212> TYPE: RNA

<213> ORGANISM: Artificial Sequence
<220> FEATURE:
<223> OTHER INFORMATION: Synthetic Construct

<400> SEQUENCE: 760
aaacucuguc acauau 16

<210> SEQ ID NO 761
<211> LENGTH: 16
<212> TYPE: RNA
<213> ORGANISM: Artificial Sequence
<220> FEATURE:
<223> OTHER INFORMATION: Synthetic Construct

<400> SEQUENCE: 761
aacucuguca cauauc 16

<210> SEQ ID NO 762
<211> LENGTH: 16
<212> TYPE: RNA
<213> ORGANISM: Artificial Sequence
<220> FEATURE:
<223> OTHER INFORMATION: Synthetic Construct

<400> SEQUENCE: 762
acucugucac auaucu 16

<210> SEQ ID NO 763
<211> LENGTH: 16
<212> TYPE: RNA
<213> ORGANISM: Artificial Sequence
<220> FEATURE:
<223> OTHER INFORMATION: Synthetic Construct

<400> SEQUENCE: 763
cucugucaca uaucug 16

<210> SEQ ID NO 764
<211> LENGTH: 16
<212> TYPE: RNA
<213> ORGANISM: Artificial Sequence
<220> FEATURE:
<223> OTHER INFORMATION: Synthetic Construct

<400> SEQUENCE: 764
ucugucacau aucugu 16

<210> SEQ ID NO 765
<211> LENGTH: 16
<212> TYPE: RNA
<213> ORGANISM: Artificial Sequence
<220> FEATURE:
<223> OTHER INFORMATION: Synthetic Construct

<400> SEQUENCE: 765
cugucacaua ucugua 16

<210> SEQ ID NO 766
<211> LENGTH: 16
<212> TYPE: RNA
<213> ORGANISM: Artificial Sequence
<220> FEATURE:
<223> OTHER INFORMATION: Synthetic Construct

<400> SEQUENCE: 766
ugucacauau cuguag 16

<210> SEQ ID NO 767
<211> LENGTH: 16
<212> TYPE: RNA
<213> ORGANISM: Artificial Sequence
<220> FEATURE:
<223> OTHER INFORMATION: Synthetic Construct

<400> SEQUENCE: 767
gucacauauc uguagu 16

<210> SEQ ID NO 768
<211> LENGTH: 15
<212> TYPE: RNA
<213> ORGANISM: Artificial Sequence
<220> FEATURE:
<223> OTHER INFORMATION: Synthetic Construct

<400> SEQUENCE: 768
cucaccugga auuac 15

<210> SEQ ID NO 769
<211> LENGTH: 15
<212> TYPE: RNA
<213> ORGANISM: Artificial Sequence
<220> FEATURE:
<223> OTHER INFORMATION: Synthetic Construct

<400> SEQUENCE: 769
ucaccuggaa uuaca 15

<210> SEQ ID NO 770
<211> LENGTH: 15
<212> TYPE: RNA
<213> ORGANISM: Artificial Sequence
<220> FEATURE:
<223> OTHER INFORMATION: Synthetic Construct

<400> SEQUENCE: 770
caccuggaau uacag 15

<210> SEQ ID NO 771
<211> LENGTH: 15
<212> TYPE: RNA
<213> ORGANISM: Artificial Sequence
<220> FEATURE:
<223> OTHER INFORMATION: Synthetic Construct

<400> SEQUENCE: 771
accuggaauu acaga 15

<210> SEQ ID NO 772
<211> LENGTH: 15
<212> TYPE: RNA
<213> ORGANISM: Artificial Sequence
<220> FEATURE:
<223> OTHER INFORMATION: Synthetic Construct

<400> SEQUENCE: 772
ccuggaauua cagag 15

<210> SEQ ID NO 773
<211> LENGTH: 15
<212> TYPE: RNA
<213> ORGANISM: Artificial Sequence
<220> FEATURE:

<223> OTHER INFORMATION: Synthetic Construct

<400> SEQUENCE: 773
cuggaauuac agaga 15

<210> SEQ ID NO 774
<211> LENGTH: 15
<212> TYPE: RNA
<213> ORGANISM: Artificial Sequence
<220> FEATURE:
<223> OTHER INFORMATION: Synthetic Construct

<400> SEQUENCE: 774
uggaauuaca gagau 15

<210> SEQ ID NO 775
<211> LENGTH: 15
<212> TYPE: RNA
<213> ORGANISM: Artificial Sequence
<220> FEATURE:
<223> OTHER INFORMATION: Synthetic Construct

<400> SEQUENCE: 775
ggaauuacag agaua 15

<210> SEQ ID NO 776
<211> LENGTH: 15
<212> TYPE: RNA
<213> ORGANISM: Artificial Sequence
<220> FEATURE:
<223> OTHER INFORMATION: Synthetic Construct

<400> SEQUENCE: 776
gaauuacaga gauag 15

<210> SEQ ID NO 777
<211> LENGTH: 15
<212> TYPE: RNA
<213> ORGANISM: Artificial Sequence
<220> FEATURE:
<223> OTHER INFORMATION: Synthetic Construct

<400> SEQUENCE: 777
aauuacagag auagu 15

<210> SEQ ID NO 778
<211> LENGTH: 15
<212> TYPE: RNA
<213> ORGANISM: Artificial Sequence
<220> FEATURE:
<223> OTHER INFORMATION: Synthetic Construct

<400> SEQUENCE: 778
auuacagaga uaguu 15

<210> SEQ ID NO 779
<211> LENGTH: 15
<212> TYPE: RNA
<213> ORGANISM: Artificial Sequence
<220> FEATURE:
<223> OTHER INFORMATION: Synthetic Construct

<400> SEQUENCE: 779
uuacagagau aguuu 15

<210> SEQ ID NO 780
<211> LENGTH: 15
<212> TYPE: RNA
<213> ORGANISM: Artificial Sequence
<220> FEATURE:
<223> OTHER INFORMATION: Synthetic Construct

<400> SEQUENCE: 780
uacagagaua guuuu 15

<210> SEQ ID NO 781
<211> LENGTH: 15
<212> TYPE: RNA
<213> ORGANISM: Artificial Sequence
<220> FEATURE:
<223> OTHER INFORMATION: Synthetic Construct

<400> SEQUENCE: 781
acagagauag uuuuc 15

<210> SEQ ID NO 782
<211> LENGTH: 15
<212> TYPE: RNA
<213> ORGANISM: Artificial Sequence
<220> FEATURE:
<223> OTHER INFORMATION: Synthetic Construct

<400> SEQUENCE: 782
cagagauagu uuuca 15

<210> SEQ ID NO 783
<211> LENGTH: 15
<212> TYPE: RNA
<213> ORGANISM: Artificial Sequence
<220> FEATURE:
<223> OTHER INFORMATION: Synthetic Construct

<400> SEQUENCE: 783
agagauaguu uucaa 15

<210> SEQ ID NO 784
<211> LENGTH: 15
<212> TYPE: RNA
<213> ORGANISM: Artificial Sequence
<220> FEATURE:
<223> OTHER INFORMATION: Synthetic Construct

<400> SEQUENCE: 784
gagauaguuu ucaaa 15

<210> SEQ ID NO 785
<211> LENGTH: 15
<212> TYPE: RNA
<213> ORGANISM: Artificial Sequence
<220> FEATURE:
<223> OTHER INFORMATION: Synthetic Construct

<400> SEQUENCE: 785
agauaguuuu caaag 15

<210> SEQ ID NO 786
<211> LENGTH: 15
<212> TYPE: RNA
<213> ORGANISM: Artificial Sequence
<220> FEATURE:
<223> OTHER INFORMATION: Synthetic Construct

<400> SEQUENCE: 786
gauaguuuuc aaagc 15

<210> SEQ ID NO 787
<211> LENGTH: 15
<212> TYPE: RNA
<213> ORGANISM: Artificial Sequence
<220> FEATURE:
<223> OTHER INFORMATION: Synthetic Construct

<400> SEQUENCE: 787
auaguuuuca aagcu 15

<210> SEQ ID NO 788
<211> LENGTH: 15
<212> TYPE: RNA
<213> ORGANISM: Artificial Sequence
<220> FEATURE:
<223> OTHER INFORMATION: Synthetic Construct

<400> SEQUENCE: 788
uaguuuucaa agcuc 15

<210> SEQ ID NO 789
<211> LENGTH: 15
<212> TYPE: RNA
<213> ORGANISM: Artificial Sequence
<220> FEATURE:
<223> OTHER INFORMATION: Synthetic Construct

<400> SEQUENCE: 789
aguuuucaaa gcucg 15

<210> SEQ ID NO 790
<211> LENGTH: 15
<212> TYPE: RNA
<213> ORGANISM: Artificial Sequence
<220> FEATURE:
<223> OTHER INFORMATION: Synthetic Construct

<400> SEQUENCE: 790
guuuucaaag cucgg 15

<210> SEQ ID NO 791
<211> LENGTH: 15
<212> TYPE: RNA
<213> ORGANISM: Artificial Sequence
<220> FEATURE:
<223> OTHER INFORMATION: Synthetic Construct

<400> SEQUENCE: 791
uuuucaaagc ucgga 15

<210> SEQ ID NO 792
<211> LENGTH: 15
<212> TYPE: RNA
<213> ORGANISM: Artificial Sequence
<220> FEATURE:
<223> OTHER INFORMATION: Synthetic Construct

<400> SEQUENCE: 792
uuucaaagcu cggag 15

<210> SEQ ID NO 793
<211> LENGTH: 15

<212> TYPE: RNA
<213> ORGANISM: Artificial Sequence
<220> FEATURE:
<223> OTHER INFORMATION: Synthetic Construct

<400> SEQUENCE: 793
uucaaagcuc ggaga 15

<210> SEQ ID NO 794
<211> LENGTH: 15
<212> TYPE: RNA
<213> ORGANISM: Artificial Sequence
<220> FEATURE:
<223> OTHER INFORMATION: Synthetic Construct

<400> SEQUENCE: 794
ucaaagcucg gagaa 15

<210> SEQ ID NO 795
<211> LENGTH: 15
<212> TYPE: RNA
<213> ORGANISM: Artificial Sequence
<220> FEATURE:
<223> OTHER INFORMATION: Synthetic Construct

<400> SEQUENCE: 795
caaagcucgg agaac 15

<210> SEQ ID NO 796
<211> LENGTH: 15
<212> TYPE: RNA
<213> ORGANISM: Artificial Sequence
<220> FEATURE:
<223> OTHER INFORMATION: Synthetic Construct

<400> SEQUENCE: 796
aaagcucgga gaacc 15

<210> SEQ ID NO 797
<211> LENGTH: 15
<212> TYPE: RNA
<213> ORGANISM: Artificial Sequence
<220> FEATURE:
<223> OTHER INFORMATION: Synthetic Construct

<400> SEQUENCE: 797
aagcucggag aaccc 15

<210> SEQ ID NO 798
<211> LENGTH: 15
<212> TYPE: RNA
<213> ORGANISM: Artificial Sequence
<220> FEATURE:
<223> OTHER INFORMATION: Synthetic Construct

<400> SEQUENCE: 798
agcucggaga acccu 15

<210> SEQ ID NO 799
<211> LENGTH: 15
<212> TYPE: RNA
<213> ORGANISM: Artificial Sequence
<220> FEATURE:
<223> OTHER INFORMATION: Synthetic Construct

<400> SEQUENCE: 799
gcucggagaa cccug 15

<210> SEQ ID NO 800
<211> LENGTH: 15
<212> TYPE: RNA
<213> ORGANISM: Artificial Sequence
<220> FEATURE:
<223> OTHER INFORMATION: Synthetic Construct

<400> SEQUENCE: 800
cucggagaac ccuga 15

<210> SEQ ID NO 801
<211> LENGTH: 15
<212> TYPE: RNA
<213> ORGANISM: Artificial Sequence
<220> FEATURE:
<223> OTHER INFORMATION: Synthetic Construct

<400> SEQUENCE: 801
ucggagaacc cugaa 15

<210> SEQ ID NO 802
<211> LENGTH: 15
<212> TYPE: RNA
<213> ORGANISM: Artificial Sequence
<220> FEATURE:
<223> OTHER INFORMATION: Synthetic Construct

<400> SEQUENCE: 802
cggagaaccc ugaau 15

<210> SEQ ID NO 803
<211> LENGTH: 15
<212> TYPE: RNA
<213> ORGANISM: Artificial Sequence
<220> FEATURE:
<223> OTHER INFORMATION: Synthetic Construct

<400> SEQUENCE: 803
ggagaacccu gaaug 15

<210> SEQ ID NO 804
<211> LENGTH: 15
<212> TYPE: RNA
<213> ORGANISM: Artificial Sequence
<220> FEATURE:
<223> OTHER INFORMATION: Synthetic Construct

<400> SEQUENCE: 804
gagaacccug aaugu 15

<210> SEQ ID NO 805
<211> LENGTH: 15
<212> TYPE: RNA
<213> ORGANISM: Artificial Sequence
<220> FEATURE:
<223> OTHER INFORMATION: Synthetic Construct

<400> SEQUENCE: 805
agaacccuga auguu 15

<210> SEQ ID NO 806
<211> LENGTH: 15
<212> TYPE: RNA
<213> ORGANISM: Artificial Sequence
<220> FEATURE:
<223> OTHER INFORMATION: Synthetic Construct

<400> SEQUENCE: 806
gaacccugaa uguuc 15

<210> SEQ ID NO 807
<211> LENGTH: 15
<212> TYPE: RNA
<213> ORGANISM: Artificial Sequence
<220> FEATURE:
<223> OTHER INFORMATION: Synthetic Construct

<400> SEQUENCE: 807
aacccugaau guucu 15

<210> SEQ ID NO 808
<211> LENGTH: 15
<212> TYPE: RNA
<213> ORGANISM: Artificial Sequence
<220> FEATURE:
<223> OTHER INFORMATION: Synthetic Construct

<400> SEQUENCE: 808
acccugaaug uucuc 15

<210> SEQ ID NO 809
<211> LENGTH: 15
<212> TYPE: RNA
<213> ORGANISM: Artificial Sequence
<220> FEATURE:
<223> OTHER INFORMATION: Synthetic Construct

<400> SEQUENCE: 809
cccugaaugu ucuca 15

<210> SEQ ID NO 810
<211> LENGTH: 15
<212> TYPE: RNA
<213> ORGANISM: Artificial Sequence
<220> FEATURE:
<223> OTHER INFORMATION: Synthetic Construct

<400> SEQUENCE: 810
ccugaauguu cucag 15

<210> SEQ ID NO 811
<211> LENGTH: 15
<212> TYPE: RNA
<213> ORGANISM: Artificial Sequence
<220> FEATURE:
<223> OTHER INFORMATION: Synthetic Construct

<400> SEQUENCE: 811
cugaauguuc ucagc 15

<210> SEQ ID NO 812
<211> LENGTH: 15
<212> TYPE: RNA
<213> ORGANISM: Artificial Sequence
<220> FEATURE:
<223> OTHER INFORMATION: Synthetic Construct

<400> SEQUENCE: 812
ugaauguucu cagcg 15

<210> SEQ ID NO 813
<211> LENGTH: 15
<212> TYPE: RNA
<213> ORGANISM: Artificial Sequence
<220> FEATURE:
<223> OTHER INFORMATION: Synthetic Construct

<400> SEQUENCE: 813
gaauguucuc agcgc 15

<210> SEQ ID NO 814
<211> LENGTH: 15
<212> TYPE: RNA
<213> ORGANISM: Artificial Sequence
<220> FEATURE:
<223> OTHER INFORMATION: Synthetic Construct

<400> SEQUENCE: 814
aauguucuca gcgcu 15

<210> SEQ ID NO 815
<211> LENGTH: 15
<212> TYPE: RNA
<213> ORGANISM: Artificial Sequence
<220> FEATURE:
<223> OTHER INFORMATION: Synthetic Construct

<400> SEQUENCE: 815
auguucucag cgcug 15

<210> SEQ ID NO 816
<211> LENGTH: 15
<212> TYPE: RNA
<213> ORGANISM: Artificial Sequence
<220> FEATURE:
<223> OTHER INFORMATION: Synthetic Construct

<400> SEQUENCE: 816
uguucucagc gcuga 15

<210> SEQ ID NO 817
<211> LENGTH: 15
<212> TYPE: RNA
<213> ORGANISM: Artificial Sequence
<220> FEATURE:
<223> OTHER INFORMATION: Synthetic Construct

<400> SEQUENCE: 817
guucucagcg cugag 15

<210> SEQ ID NO 818
<211> LENGTH: 15
<212> TYPE: RNA
<213> ORGANISM: Artificial Sequence
<220> FEATURE:
<223> OTHER INFORMATION: Synthetic Construct

<400> SEQUENCE: 818
uucucagcgc ugaga 15

<210> SEQ ID NO 819
<211> LENGTH: 15
<212> TYPE: RNA
<213> ORGANISM: Artificial Sequence
<220> FEATURE:
<223> OTHER INFORMATION: Synthetic Construct

<400> SEQUENCE: 819
ucucagcgcu gagac 15

<210> SEQ ID NO 820
<211> LENGTH: 15
<212> TYPE: RNA
<213> ORGANISM: Artificial Sequence
<220> FEATURE:
<223> OTHER INFORMATION: Synthetic Construct

<400> SEQUENCE: 820
cucagcgcug agaca 15

<210> SEQ ID NO 821
<211> LENGTH: 15
<212> TYPE: RNA
<213> ORGANISM: Artificial Sequence
<220> FEATURE:
<223> OTHER INFORMATION: Synthetic Construct

<400> SEQUENCE: 821
ucagcgcuga gacau 15

<210> SEQ ID NO 822
<211> LENGTH: 15
<212> TYPE: RNA
<213> ORGANISM: Artificial Sequence
<220> FEATURE:
<223> OTHER INFORMATION: Synthetic Construct

<400> SEQUENCE: 822
cagcgcugag acauu 15

<210> SEQ ID NO 823
<211> LENGTH: 15
<212> TYPE: RNA
<213> ORGANISM: Artificial Sequence
<220> FEATURE:
<223> OTHER INFORMATION: Synthetic Construct

<400> SEQUENCE: 823
agcgcugaga cauug 15

<210> SEQ ID NO 824
<211> LENGTH: 15
<212> TYPE: RNA
<213> ORGANISM: Artificial Sequence
<220> FEATURE:
<223> OTHER INFORMATION: Synthetic Construct

<400> SEQUENCE: 824
gcgcugagac auugc 15

<210> SEQ ID NO 825
<211> LENGTH: 15
<212> TYPE: RNA
<213> ORGANISM: Artificial Sequence
<220> FEATURE:
<223> OTHER INFORMATION: Synthetic Construct

<400> SEQUENCE: 825
cgcugagaca uugcc 15

<210> SEQ ID NO 826

<211> LENGTH: 15
<212> TYPE: RNA
<213> ORGANISM: Artificial Sequence
<220> FEATURE:
<223> OTHER INFORMATION: Synthetic Construct

<400> SEQUENCE: 826
gcugagacau ugccc 15

<210> SEQ ID NO 827
<211> LENGTH: 15
<212> TYPE: RNA
<213> ORGANISM: Artificial Sequence
<220> FEATURE:
<223> OTHER INFORMATION: Synthetic Construct

<400> SEQUENCE: 827
cugagacauu gccca 15

<210> SEQ ID NO 828
<211> LENGTH: 15
<212> TYPE: RNA
<213> ORGANISM: Artificial Sequence
<220> FEATURE:
<223> OTHER INFORMATION: Synthetic Construct

<400> SEQUENCE: 828
ugagacauug cccag 15

<210> SEQ ID NO 829
<211> LENGTH: 15
<212> TYPE: RNA
<213> ORGANISM: Artificial Sequence
<220> FEATURE:
<223> OTHER INFORMATION: Synthetic Construct

<400> SEQUENCE: 829
gagacauugc ccagg 15

<210> SEQ ID NO 830
<211> LENGTH: 15
<212> TYPE: RNA
<213> ORGANISM: Artificial Sequence
<220> FEATURE:
<223> OTHER INFORMATION: Synthetic Construct

<400> SEQUENCE: 830
agacauugcc caggu 15

<210> SEQ ID NO 831
<211> LENGTH: 15
<212> TYPE: RNA
<213> ORGANISM: Artificial Sequence
<220> FEATURE:
<223> OTHER INFORMATION: Synthetic Construct

<400> SEQUENCE: 831
gacauugccc agguc 15

<210> SEQ ID NO 832
<211> LENGTH: 15
<212> TYPE: RNA
<213> ORGANISM: Artificial Sequence
<220> FEATURE:
<223> OTHER INFORMATION: Synthetic Construct

<400> SEQUENCE: 832
acauugccca ggucc 15

<210> SEQ ID NO 833
<211> LENGTH: 15
<212> TYPE: RNA
<213> ORGANISM: Artificial Sequence
<220> FEATURE:
<223> OTHER INFORMATION: Synthetic Construct

<400> SEQUENCE: 833
cauugcccag gucca 15

<210> SEQ ID NO 834
<211> LENGTH: 15
<212> TYPE: RNA
<213> ORGANISM: Artificial Sequence
<220> FEATURE:
<223> OTHER INFORMATION: Synthetic Construct

<400> SEQUENCE: 834
auugcccagg uccac 15

<210> SEQ ID NO 835
<211> LENGTH: 15
<212> TYPE: RNA
<213> ORGANISM: Artificial Sequence
<220> FEATURE:
<223> OTHER INFORMATION: Synthetic Construct

<400> SEQUENCE: 835
uugcccaggu ccaca 15

<210> SEQ ID NO 836
<211> LENGTH: 15
<212> TYPE: RNA
<213> ORGANISM: Artificial Sequence
<220> FEATURE:
<223> OTHER INFORMATION: Synthetic Construct

<400> SEQUENCE: 836
ugcccagguc cacaa 15

<210> SEQ ID NO 837
<211> LENGTH: 15
<212> TYPE: RNA
<213> ORGANISM: Artificial Sequence
<220> FEATURE:
<223> OTHER INFORMATION: Synthetic Construct

<400> SEQUENCE: 837
gcccaggucc acaaa 15

<210> SEQ ID NO 838
<211> LENGTH: 15
<212> TYPE: RNA
<213> ORGANISM: Artificial Sequence
<220> FEATURE:
<223> OTHER INFORMATION: Synthetic Construct

<400> SEQUENCE: 838
cccaggucca caaac 15

<210> SEQ ID NO 839
<211> LENGTH: 15
<212> TYPE: RNA

```
<213> ORGANISM: Artificial Sequence
<220> FEATURE:
<223> OTHER INFORMATION: Synthetic Construct

<400> SEQUENCE: 839

ccagguccac aaacu                                                    15

<210> SEQ ID NO 840
<211> LENGTH: 15
<212> TYPE: RNA
<213> ORGANISM: Artificial Sequence
<220> FEATURE:
<223> OTHER INFORMATION: Synthetic Construct

<400> SEQUENCE: 840

cagguccaca aacuc                                                    15

<210> SEQ ID NO 841
<211> LENGTH: 15
<212> TYPE: RNA
<213> ORGANISM: Artificial Sequence
<220> FEATURE:
<223> OTHER INFORMATION: Synthetic Construct

<400> SEQUENCE: 841

agguccacaa acucu                                                    15

<210> SEQ ID NO 842
<211> LENGTH: 15
<212> TYPE: RNA
<213> ORGANISM: Artificial Sequence
<220> FEATURE:
<223> OTHER INFORMATION: Synthetic Construct

<400> SEQUENCE: 842

gguccacaaa cucug                                                    15

<210> SEQ ID NO 843
<211> LENGTH: 15
<212> TYPE: RNA
<213> ORGANISM: Artificial Sequence
<220> FEATURE:
<223> OTHER INFORMATION: Synthetic Construct

<400> SEQUENCE: 843

guccacaaac ucugu                                                    15

<210> SEQ ID NO 844
<211> LENGTH: 15
<212> TYPE: RNA
<213> ORGANISM: Artificial Sequence
<220> FEATURE:
<223> OTHER INFORMATION: Synthetic Construct

<400> SEQUENCE: 844

uccacaaacu cuguc                                                    15

<210> SEQ ID NO 845
<211> LENGTH: 15
<212> TYPE: RNA
<213> ORGANISM: Artificial Sequence
<220> FEATURE:
<223> OTHER INFORMATION: Synthetic Construct

<400> SEQUENCE: 845

ccacaaacuc uguca                                                    15
```

<210> SEQ ID NO 846
<211> LENGTH: 15
<212> TYPE: RNA
<213> ORGANISM: Artificial Sequence
<220> FEATURE:
<223> OTHER INFORMATION: Synthetic Construct

<400> SEQUENCE: 846
cacaaacucu gucac 15

<210> SEQ ID NO 847
<211> LENGTH: 15
<212> TYPE: RNA
<213> ORGANISM: Artificial Sequence
<220> FEATURE:
<223> OTHER INFORMATION: Synthetic Construct

<400> SEQUENCE: 847
acaaacucug ucaca 15

<210> SEQ ID NO 848
<211> LENGTH: 15
<212> TYPE: RNA
<213> ORGANISM: Artificial Sequence
<220> FEATURE:
<223> OTHER INFORMATION: Synthetic Construct

<400> SEQUENCE: 848
caaacucugu cacau 15

<210> SEQ ID NO 849
<211> LENGTH: 15
<212> TYPE: RNA
<213> ORGANISM: Artificial Sequence
<220> FEATURE:
<223> OTHER INFORMATION: Synthetic Construct

<400> SEQUENCE: 849
aaacucuguc acaua 15

<210> SEQ ID NO 850
<211> LENGTH: 15
<212> TYPE: RNA
<213> ORGANISM: Artificial Sequence
<220> FEATURE:
<223> OTHER INFORMATION: Synthetic Construct

<400> SEQUENCE: 850
aacucuguca cauau 15

<210> SEQ ID NO 851
<211> LENGTH: 15
<212> TYPE: RNA
<213> ORGANISM: Artificial Sequence
<220> FEATURE:
<223> OTHER INFORMATION: Synthetic Construct

<400> SEQUENCE: 851
acucugucac auauc 15

<210> SEQ ID NO 852
<211> LENGTH: 15
<212> TYPE: RNA
<213> ORGANISM: Artificial Sequence
<220> FEATURE:

<223> OTHER INFORMATION: Synthetic Construct

<400> SEQUENCE: 852
cucugucaca uaucu 15

<210> SEQ ID NO 853
<211> LENGTH: 15
<212> TYPE: RNA
<213> ORGANISM: Artificial Sequence
<220> FEATURE:
<223> OTHER INFORMATION: Synthetic Construct

<400> SEQUENCE: 853
ucugucacau aucug 15

<210> SEQ ID NO 854
<211> LENGTH: 15
<212> TYPE: RNA
<213> ORGANISM: Artificial Sequence
<220> FEATURE:
<223> OTHER INFORMATION: Synthetic Construct

<400> SEQUENCE: 854
cugucacaua ucugu 15

<210> SEQ ID NO 855
<211> LENGTH: 15
<212> TYPE: RNA
<213> ORGANISM: Artificial Sequence
<220> FEATURE:
<223> OTHER INFORMATION: Synthetic Construct

<400> SEQUENCE: 855
ugucacauau cugua 15

<210> SEQ ID NO 856
<211> LENGTH: 15
<212> TYPE: RNA
<213> ORGANISM: Artificial Sequence
<220> FEATURE:
<223> OTHER INFORMATION: Synthetic Construct

<400> SEQUENCE: 856
gucacauauc uguag 15

<210> SEQ ID NO 857
<211> LENGTH: 15
<212> TYPE: RNA
<213> ORGANISM: Artificial Sequence
<220> FEATURE:
<223> OTHER INFORMATION: Synthetic Construct

<400> SEQUENCE: 857
ucacauaucu guagu 15

<210> SEQ ID NO 858
<211> LENGTH: 29
<212> TYPE: DNA
<213> ORGANISM: Homo sapiens

<400> SEQUENCE: 858
gatccttctg catgccagtg gaaactgtt 29

<210> SEQ ID NO 859
<211> LENGTH: 29

<212> TYPE: RNA
<213> ORGANISM: Homo sapiens

<400> SEQUENCE: 859
aacaguuucc acuggcaugc agaaggauc 29

<210> SEQ ID NO 860
<211> LENGTH: 24
<212> TYPE: RNA
<213> ORGANISM: Artificial Sequence
<220> FEATURE:
<223> OTHER INFORMATION: Synthetic Construct

<400> SEQUENCE: 860
aacaguuucc acuggcaugc agaa 24

<210> SEQ ID NO 861
<211> LENGTH: 24
<212> TYPE: RNA
<213> ORGANISM: Artificial Sequence
<220> FEATURE:
<223> OTHER INFORMATION: Synthetic Construct

<400> SEQUENCE: 861
acaguuucca cuggcaugca gaag 24

<210> SEQ ID NO 862
<211> LENGTH: 24
<212> TYPE: RNA
<213> ORGANISM: Artificial Sequence
<220> FEATURE:
<223> OTHER INFORMATION: Synthetic Construct

<400> SEQUENCE: 862
caguuuccac uggcaugcag aagg 24

<210> SEQ ID NO 863
<211> LENGTH: 24
<212> TYPE: RNA
<213> ORGANISM: Artificial Sequence
<220> FEATURE:
<223> OTHER INFORMATION: Synthetic Construct

<400> SEQUENCE: 863
aguuuccacu ggcaugcaga agga 24

<210> SEQ ID NO 864
<211> LENGTH: 24
<212> TYPE: RNA
<213> ORGANISM: Artificial Sequence
<220> FEATURE:
<223> OTHER INFORMATION: Synthetic Construct

<400> SEQUENCE: 864
guuuccacug gcaugcagaa ggau 24

<210> SEQ ID NO 865
<211> LENGTH: 24
<212> TYPE: RNA
<213> ORGANISM: Artificial Sequence
<220> FEATURE:
<223> OTHER INFORMATION: Synthetic Construct

<400> SEQUENCE: 865
uuuccacugg caugcagaag gauc 24

<210> SEQ ID NO 866
<211> LENGTH: 23
<212> TYPE: RNA
<213> ORGANISM: Artificial Sequence
<220> FEATURE:
<223> OTHER INFORMATION: Synthetic Construct

<400> SEQUENCE: 866
aacaguuucc acuggcaugc aga 23

<210> SEQ ID NO 867
<211> LENGTH: 23
<212> TYPE: RNA
<213> ORGANISM: Artificial Sequence
<220> FEATURE:
<223> OTHER INFORMATION: Synthetic Construct

<400> SEQUENCE: 867
acaguuucca cuggcaugca gaa 23

<210> SEQ ID NO 868
<211> LENGTH: 23
<212> TYPE: RNA
<213> ORGANISM: Artificial Sequence
<220> FEATURE:
<223> OTHER INFORMATION: Synthetic Construct

<400> SEQUENCE: 868
caguuuccac uggcaugcag aag 23

<210> SEQ ID NO 869
<211> LENGTH: 23
<212> TYPE: RNA
<213> ORGANISM: Artificial Sequence
<220> FEATURE:
<223> OTHER INFORMATION: Synthetic Construct

<400> SEQUENCE: 869
aguuuccacu ggcaugcaga agg 23

<210> SEQ ID NO 870
<211> LENGTH: 23
<212> TYPE: RNA
<213> ORGANISM: Artificial Sequence
<220> FEATURE:
<223> OTHER INFORMATION: Synthetic Construct

<400> SEQUENCE: 870
guuuccacug gcaugcagaa gga 23

<210> SEQ ID NO 871
<211> LENGTH: 23
<212> TYPE: RNA
<213> ORGANISM: Artificial Sequence
<220> FEATURE:
<223> OTHER INFORMATION: Synthetic Construct

<400> SEQUENCE: 871
uuuccacugg caugcagaag gau 23

<210> SEQ ID NO 872
<211> LENGTH: 23
<212> TYPE: RNA
<213> ORGANISM: Artificial Sequence
<220> FEATURE:
<223> OTHER INFORMATION: Synthetic Construct

<400> SEQUENCE: 872
uuccacuggc augcagaagg auc 23

<210> SEQ ID NO 873
<211> LENGTH: 22
<212> TYPE: RNA
<213> ORGANISM: Artificial Sequence
<220> FEATURE:
<223> OTHER INFORMATION: Synthetic Construct

<400> SEQUENCE: 873
aacaguuucc acuggcaugc ag 22

<210> SEQ ID NO 874
<211> LENGTH: 22
<212> TYPE: RNA
<213> ORGANISM: Artificial Sequence
<220> FEATURE:
<223> OTHER INFORMATION: Synthetic Construct

<400> SEQUENCE: 874
acaguuucca cuggcaugca ga 22

<210> SEQ ID NO 875
<211> LENGTH: 22
<212> TYPE: RNA
<213> ORGANISM: Artificial Sequence
<220> FEATURE:
<223> OTHER INFORMATION: Synthetic Construct

<400> SEQUENCE: 875
caguuuccac uggcaugcag aa 22

<210> SEQ ID NO 876
<211> LENGTH: 22
<212> TYPE: RNA
<213> ORGANISM: Artificial Sequence
<220> FEATURE:
<223> OTHER INFORMATION: Synthetic Construct

<400> SEQUENCE: 876
aguuuccacu ggcaugcaga ag 22

<210> SEQ ID NO 877
<211> LENGTH: 22
<212> TYPE: RNA
<213> ORGANISM: Artificial Sequence
<220> FEATURE:
<223> OTHER INFORMATION: Synthetic Construct

<400> SEQUENCE: 877
aguuuccacu ggcaugcaga ag 22

<210> SEQ ID NO 878
<211> LENGTH: 22
<212> TYPE: RNA
<213> ORGANISM: Artificial Sequence
<220> FEATURE:
<223> OTHER INFORMATION: Synthetic Construct

<400> SEQUENCE: 878
guuuccacug gcaugcagaa gg 22

<210> SEQ ID NO 879

<211> LENGTH: 22
<212> TYPE: RNA
<213> ORGANISM: Artificial Sequence
<220> FEATURE:
<223> OTHER INFORMATION: Synthetic Construct

<400> SEQUENCE: 879
uuccacuggc augcagaagg au 22

<210> SEQ ID NO 880
<211> LENGTH: 22
<212> TYPE: RNA
<213> ORGANISM: Artificial Sequence
<220> FEATURE:
<223> OTHER INFORMATION: Synthetic Construct

<400> SEQUENCE: 880
uccacuggca ugcagaagga uc 22

<210> SEQ ID NO 881
<211> LENGTH: 21
<212> TYPE: RNA
<213> ORGANISM: Artificial Sequence
<220> FEATURE:
<223> OTHER INFORMATION: Synthetic Construct

<400> SEQUENCE: 881
aacaguuucc acuggcaugc a 21

<210> SEQ ID NO 882
<211> LENGTH: 21
<212> TYPE: RNA
<213> ORGANISM: Artificial Sequence
<220> FEATURE:
<223> OTHER INFORMATION: Synthetic Construct

<400> SEQUENCE: 882
acaguuucca cuggcaugca g 21

<210> SEQ ID NO 883
<211> LENGTH: 21
<212> TYPE: RNA
<213> ORGANISM: Artificial Sequence
<220> FEATURE:
<223> OTHER INFORMATION: Synthetic Construct

<400> SEQUENCE: 883
caguuuccac uggcaugcag a 21

<210> SEQ ID NO 884
<211> LENGTH: 21
<212> TYPE: RNA
<213> ORGANISM: Artificial Sequence
<220> FEATURE:
<223> OTHER INFORMATION: Synthetic Construct

<400> SEQUENCE: 884
aguuuccacu ggcaugcaga a 21

<210> SEQ ID NO 885
<211> LENGTH: 21
<212> TYPE: RNA
<213> ORGANISM: Artificial Sequence
<220> FEATURE:
<223> OTHER INFORMATION: Synthetic Construct

<400> SEQUENCE: 885
guuuccacug gcaugcagaa g 21

<210> SEQ ID NO 886
<211> LENGTH: 21
<212> TYPE: RNA
<213> ORGANISM: Artificial Sequence
<220> FEATURE:
<223> OTHER INFORMATION: Synthetic Construct

<400> SEQUENCE: 886
uuuccacugg caugcagaag g 21

<210> SEQ ID NO 887
<211> LENGTH: 21
<212> TYPE: RNA
<213> ORGANISM: Artificial Sequence
<220> FEATURE:
<223> OTHER INFORMATION: Synthetic Construct

<400> SEQUENCE: 887
uuccacuggc augcagaagg a 21

<210> SEQ ID NO 888
<211> LENGTH: 21
<212> TYPE: RNA
<213> ORGANISM: Artificial Sequence
<220> FEATURE:
<223> OTHER INFORMATION: Synthetic Construct

<400> SEQUENCE: 888
uccacuggca ugcagaagga u 21

<210> SEQ ID NO 889
<211> LENGTH: 21
<212> TYPE: RNA
<213> ORGANISM: Artificial Sequence
<220> FEATURE:
<223> OTHER INFORMATION: Synthetic Construct

<400> SEQUENCE: 889
ccacuggcau gcagaaggau c 21

<210> SEQ ID NO 890
<211> LENGTH: 20
<212> TYPE: RNA
<213> ORGANISM: Artificial Sequence
<220> FEATURE:
<223> OTHER INFORMATION: Synthetic Construct

<400> SEQUENCE: 890
aacaguuucc acuggcaugc 20

<210> SEQ ID NO 891
<211> LENGTH: 20
<212> TYPE: RNA
<213> ORGANISM: Artificial Sequence
<220> FEATURE:
<223> OTHER INFORMATION: Synthetic Construct

<400> SEQUENCE: 891
acaguuucca cuggcaugca 20

<210> SEQ ID NO 892
<211> LENGTH: 20
<212> TYPE: RNA

<213> ORGANISM: Artificial Sequence
<220> FEATURE:
<223> OTHER INFORMATION: Synthetic Construct

<400> SEQUENCE: 892
caguuuccac uggcaugcag 20

<210> SEQ ID NO 893
<211> LENGTH: 20
<212> TYPE: RNA
<213> ORGANISM: Artificial Sequence
<220> FEATURE:
<223> OTHER INFORMATION: Synthetic Construct

<400> SEQUENCE: 893
aguuuccacu ggcaugcaga 20

<210> SEQ ID NO 894
<211> LENGTH: 20
<212> TYPE: RNA
<213> ORGANISM: Artificial Sequence
<220> FEATURE:
<223> OTHER INFORMATION: Synthetic Construct

<400> SEQUENCE: 894
guuuccacug gcaugcagaa 20

<210> SEQ ID NO 895
<211> LENGTH: 20
<212> TYPE: RNA
<213> ORGANISM: Artificial Sequence
<220> FEATURE:
<223> OTHER INFORMATION: Synthetic Construct

<400> SEQUENCE: 895
uuuccacugg caugcagaag 20

<210> SEQ ID NO 896
<211> LENGTH: 20
<212> TYPE: RNA
<213> ORGANISM: Artificial Sequence
<220> FEATURE:
<223> OTHER INFORMATION: Synthetic Construct

<400> SEQUENCE: 896
uuccacuggc augcagaagg 20

<210> SEQ ID NO 897
<211> LENGTH: 20
<212> TYPE: RNA
<213> ORGANISM: Artificial Sequence
<220> FEATURE:
<223> OTHER INFORMATION: Synthetic Construct

<400> SEQUENCE: 897
uccacuggca ugcagaagga 20

<210> SEQ ID NO 898
<211> LENGTH: 20
<212> TYPE: RNA
<213> ORGANISM: Artificial Sequence
<220> FEATURE:
<223> OTHER INFORMATION: Synthetic Construct

<400> SEQUENCE: 898
ccacuggcau gcagaaggau 20

<210> SEQ ID NO 899
<211> LENGTH: 20
<212> TYPE: RNA
<213> ORGANISM: Artificial Sequence
<220> FEATURE:
<223> OTHER INFORMATION: Synthetic Construct

<400> SEQUENCE: 899
cacuggcaug cagaaggauc 20

<210> SEQ ID NO 900
<211> LENGTH: 19
<212> TYPE: RNA
<213> ORGANISM: Artificial Sequence
<220> FEATURE:
<223> OTHER INFORMATION: Synthetic Construct

<400> SEQUENCE: 900
aacaguuucc acuggcaug 19

<210> SEQ ID NO 901
<211> LENGTH: 19
<212> TYPE: RNA
<213> ORGANISM: Artificial Sequence
<220> FEATURE:
<223> OTHER INFORMATION: Synthetic Construct

<400> SEQUENCE: 901
acaguuucca cuggcaugc 19

<210> SEQ ID NO 902
<211> LENGTH: 19
<212> TYPE: RNA
<213> ORGANISM: Artificial Sequence
<220> FEATURE:
<223> OTHER INFORMATION: Synthetic Construct

<400> SEQUENCE: 902
caguuuccac uggcaugca 19

<210> SEQ ID NO 903
<211> LENGTH: 19
<212> TYPE: RNA
<213> ORGANISM: Artificial Sequence
<220> FEATURE:
<223> OTHER INFORMATION: Synthetic Construct

<400> SEQUENCE: 903
aguuuccacu ggcaugcag 19

<210> SEQ ID NO 904
<211> LENGTH: 19
<212> TYPE: RNA
<213> ORGANISM: Artificial Sequence
<220> FEATURE:
<223> OTHER INFORMATION: Synthetic Construct

<400> SEQUENCE: 904
guuuccacug gcaugcaga 19

<210> SEQ ID NO 905
<211> LENGTH: 19
<212> TYPE: RNA
<213> ORGANISM: Artificial Sequence
<220> FEATURE:

-continued

<223> OTHER INFORMATION: Synthetic Construct

<400> SEQUENCE: 905
uuuccacugg caugcagaa 19

<210> SEQ ID NO 906
<211> LENGTH: 19
<212> TYPE: RNA
<213> ORGANISM: Artificial Sequence
<220> FEATURE:
<223> OTHER INFORMATION: Synthetic Construct

<400> SEQUENCE: 906
uuccacuggc augcagaag 19

<210> SEQ ID NO 907
<211> LENGTH: 19
<212> TYPE: RNA
<213> ORGANISM: Artificial Sequence
<220> FEATURE:
<223> OTHER INFORMATION: Synthetic Construct

<400> SEQUENCE: 907
uccacuggca ugcagaagg 19

<210> SEQ ID NO 908
<211> LENGTH: 19
<212> TYPE: RNA
<213> ORGANISM: Artificial Sequence
<220> FEATURE:
<223> OTHER INFORMATION: Synthetic Construct

<400> SEQUENCE: 908
ccacuggcau gcagaagga 19

<210> SEQ ID NO 909
<211> LENGTH: 19
<212> TYPE: RNA
<213> ORGANISM: Artificial Sequence
<220> FEATURE:
<223> OTHER INFORMATION: Synthetic Construct

<400> SEQUENCE: 909
cacuggcaug cagaaggau 19

<210> SEQ ID NO 910
<211> LENGTH: 19
<212> TYPE: RNA
<213> ORGANISM: Artificial Sequence
<220> FEATURE:
<223> OTHER INFORMATION: Synthetic Construct

<400> SEQUENCE: 910
acuggcaugc agaaggauc 19

<210> SEQ ID NO 911
<211> LENGTH: 18
<212> TYPE: RNA
<213> ORGANISM: Artificial Sequence
<220> FEATURE:
<223> OTHER INFORMATION: Synthetic Construct

<400> SEQUENCE: 911
aacaguuucc acuggcau 18

-continued

<210> SEQ ID NO 912
<211> LENGTH: 18
<212> TYPE: RNA
<213> ORGANISM: Artificial Sequence
<220> FEATURE:
<223> OTHER INFORMATION: Synthetic Construct

<400> SEQUENCE: 912
acaguuucca cuggcaug 18

<210> SEQ ID NO 913
<211> LENGTH: 18
<212> TYPE: RNA
<213> ORGANISM: Artificial Sequence
<220> FEATURE:
<223> OTHER INFORMATION: Synthetic Construct

<400> SEQUENCE: 913
caguuuccac uggcaugc 18

<210> SEQ ID NO 914
<211> LENGTH: 18
<212> TYPE: RNA
<213> ORGANISM: Artificial Sequence
<220> FEATURE:
<223> OTHER INFORMATION: Synthetic Construct

<400> SEQUENCE: 914
aguuuccacu ggcaugca 18

<210> SEQ ID NO 915
<211> LENGTH: 18
<212> TYPE: RNA
<213> ORGANISM: Artificial Sequence
<220> FEATURE:
<223> OTHER INFORMATION: Synthetic Construct

<400> SEQUENCE: 915
guuuccacug gcaugcag 18

<210> SEQ ID NO 916
<211> LENGTH: 18
<212> TYPE: RNA
<213> ORGANISM: Artificial Sequence
<220> FEATURE:
<223> OTHER INFORMATION: Synthetic Construct

<400> SEQUENCE: 916
uuuccacugg caugcaga 18

<210> SEQ ID NO 917
<211> LENGTH: 18
<212> TYPE: RNA
<213> ORGANISM: Artificial Sequence
<220> FEATURE:
<223> OTHER INFORMATION: Synthetic Construct

<400> SEQUENCE: 917
uuccacuggc augcagaa 18

<210> SEQ ID NO 918
<211> LENGTH: 18
<212> TYPE: RNA
<213> ORGANISM: Artificial Sequence
<220> FEATURE:
<223> OTHER INFORMATION: Synthetic Construct

<400> SEQUENCE: 918
uccacuggca ugcagaag 18

<210> SEQ ID NO 919
<211> LENGTH: 18
<212> TYPE: RNA
<213> ORGANISM: Artificial Sequence
<220> FEATURE:
<223> OTHER INFORMATION: Synthetic Construct

<400> SEQUENCE: 919
ccacuggcau gcagaagg 18

<210> SEQ ID NO 920
<211> LENGTH: 18
<212> TYPE: RNA
<213> ORGANISM: Artificial Sequence
<220> FEATURE:
<223> OTHER INFORMATION: Synthetic Construct

<400> SEQUENCE: 920
cacuggcaug cagaagga 18

<210> SEQ ID NO 921
<211> LENGTH: 18
<212> TYPE: RNA
<213> ORGANISM: Artificial Sequence
<220> FEATURE:
<223> OTHER INFORMATION: Synthetic Construct

<400> SEQUENCE: 921
acuggcaugc agaaggau 18

<210> SEQ ID NO 922
<211> LENGTH: 18
<212> TYPE: RNA
<213> ORGANISM: Artificial Sequence
<220> FEATURE:
<223> OTHER INFORMATION: Synthetic Construct

<400> SEQUENCE: 922
cuggcaugca gaaggauc 18

<210> SEQ ID NO 923
<211> LENGTH: 17
<212> TYPE: RNA
<213> ORGANISM: Artificial Sequence
<220> FEATURE:
<223> OTHER INFORMATION: Synthetic Construct

<400> SEQUENCE: 923
aacaguuucc acuggca 17

<210> SEQ ID NO 924
<211> LENGTH: 17
<212> TYPE: RNA
<213> ORGANISM: Artificial Sequence
<220> FEATURE:
<223> OTHER INFORMATION: Synthetic Construct

<400> SEQUENCE: 924
acaguuucca cuggcau 17

<210> SEQ ID NO 925
<211> LENGTH: 17

<212> TYPE: RNA
<213> ORGANISM: Artificial Sequence
<220> FEATURE:
<223> OTHER INFORMATION: Synthetic Construct

<400> SEQUENCE: 925
caguuuccac uggcaug 17

<210> SEQ ID NO 926
<211> LENGTH: 17
<212> TYPE: RNA
<213> ORGANISM: Artificial Sequence
<220> FEATURE:
<223> OTHER INFORMATION: Synthetic Construct

<400> SEQUENCE: 926
aguuuccacu ggcaugc 17

<210> SEQ ID NO 927
<211> LENGTH: 17
<212> TYPE: RNA
<213> ORGANISM: Artificial Sequence
<220> FEATURE:
<223> OTHER INFORMATION: Synthetic Construct

<400> SEQUENCE: 927
guuuccacug gcaugca 17

<210> SEQ ID NO 928
<211> LENGTH: 17
<212> TYPE: RNA
<213> ORGANISM: Artificial Sequence
<220> FEATURE:
<223> OTHER INFORMATION: Synthetic Construct

<400> SEQUENCE: 928
uuuccacugg caugcag 17

<210> SEQ ID NO 929
<211> LENGTH: 17
<212> TYPE: RNA
<213> ORGANISM: Artificial Sequence
<220> FEATURE:
<223> OTHER INFORMATION: Synthetic Construct

<400> SEQUENCE: 929
uuccacuggc augcaga 17

<210> SEQ ID NO 930
<211> LENGTH: 17
<212> TYPE: RNA
<213> ORGANISM: Artificial Sequence
<220> FEATURE:
<223> OTHER INFORMATION: Synthetic Construct

<400> SEQUENCE: 930
uccacuggca ugcagaa 17

<210> SEQ ID NO 931
<211> LENGTH: 17
<212> TYPE: RNA
<213> ORGANISM: Artificial Sequence
<220> FEATURE:
<223> OTHER INFORMATION: Synthetic Construct

<400> SEQUENCE: 931
ccacuggcau gcagaag 17

<210> SEQ ID NO 932
<211> LENGTH: 17
<212> TYPE: RNA
<213> ORGANISM: Artificial Sequence
<220> FEATURE:
<223> OTHER INFORMATION: Synthetic Construct

<400> SEQUENCE: 932
cacuggcaug cagaagg 17

<210> SEQ ID NO 933
<211> LENGTH: 17
<212> TYPE: RNA
<213> ORGANISM: Artificial Sequence
<220> FEATURE:
<223> OTHER INFORMATION: Synthetic Construct

<400> SEQUENCE: 933
acuggcaugc agaagga 17

<210> SEQ ID NO 934
<211> LENGTH: 17
<212> TYPE: RNA
<213> ORGANISM: Artificial Sequence
<220> FEATURE:
<223> OTHER INFORMATION: Synthetic Construct

<400> SEQUENCE: 934
cuggcaugca gaaggau 17

<210> SEQ ID NO 935
<211> LENGTH: 17
<212> TYPE: RNA
<213> ORGANISM: Artificial Sequence
<220> FEATURE:
<223> OTHER INFORMATION: Synthetic Construct

<400> SEQUENCE: 935
uggcaugcag aaggauc 17

<210> SEQ ID NO 936
<211> LENGTH: 16
<212> TYPE: RNA
<213> ORGANISM: Artificial Sequence
<220> FEATURE:
<223> OTHER INFORMATION: Synthetic Construct

<400> SEQUENCE: 936
aacaguuucc acuggc 16

<210> SEQ ID NO 937
<211> LENGTH: 16
<212> TYPE: RNA
<213> ORGANISM: Artificial Sequence
<220> FEATURE:
<223> OTHER INFORMATION: Synthetic Construct

<400> SEQUENCE: 937
acaguuucca cuggca 16

<210> SEQ ID NO 938
<211> LENGTH: 16
<212> TYPE: RNA
<213> ORGANISM: Artificial Sequence
<220> FEATURE:
<223> OTHER INFORMATION: Synthetic Construct

<400> SEQUENCE: 938
caguuuccac uggcau 16

<210> SEQ ID NO 939
<211> LENGTH: 16
<212> TYPE: RNA
<213> ORGANISM: Artificial Sequence
<220> FEATURE:
<223> OTHER INFORMATION: Synthetic Construct

<400> SEQUENCE: 939
aguuuccacu ggcaug 16

<210> SEQ ID NO 940
<211> LENGTH: 16
<212> TYPE: RNA
<213> ORGANISM: Artificial Sequence
<220> FEATURE:
<223> OTHER INFORMATION: Synthetic Construct

<400> SEQUENCE: 940
guuuccacug gcaugc 16

<210> SEQ ID NO 941
<211> LENGTH: 16
<212> TYPE: RNA
<213> ORGANISM: Artificial Sequence
<220> FEATURE:
<223> OTHER INFORMATION: Synthetic Construct

<400> SEQUENCE: 941
uuuccacugg caugca 16

<210> SEQ ID NO 942
<211> LENGTH: 16
<212> TYPE: RNA
<213> ORGANISM: Artificial Sequence
<220> FEATURE:
<223> OTHER INFORMATION: Synthetic Construct

<400> SEQUENCE: 942
uuccacuggc augcag 16

<210> SEQ ID NO 943
<211> LENGTH: 16
<212> TYPE: RNA
<213> ORGANISM: Artificial Sequence
<220> FEATURE:
<223> OTHER INFORMATION: Synthetic Construct

<400> SEQUENCE: 943
uccacuggca ugcaga 16

<210> SEQ ID NO 944
<211> LENGTH: 16
<212> TYPE: RNA
<213> ORGANISM: Artificial Sequence
<220> FEATURE:
<223> OTHER INFORMATION: Synthetic Construct

<400> SEQUENCE: 944
ccacuggcau gcagaa 16

<210> SEQ ID NO 945
<211> LENGTH: 16
<212> TYPE: RNA
<213> ORGANISM: Artificial Sequence
<220> FEATURE:
<223> OTHER INFORMATION: Synthetic Construct

<400> SEQUENCE: 945
cacuggcaug cagaag 16

<210> SEQ ID NO 946
<211> LENGTH: 16
<212> TYPE: RNA
<213> ORGANISM: Artificial Sequence
<220> FEATURE:
<223> OTHER INFORMATION: Synthetic Construct

<400> SEQUENCE: 946
acuggcaugc agaagg 16

<210> SEQ ID NO 947
<211> LENGTH: 16
<212> TYPE: RNA
<213> ORGANISM: Artificial Sequence
<220> FEATURE:
<223> OTHER INFORMATION: Synthetic Construct

<400> SEQUENCE: 947
cuggcaugca gaagga 16

<210> SEQ ID NO 948
<211> LENGTH: 16
<212> TYPE: RNA
<213> ORGANISM: Artificial Sequence
<220> FEATURE:
<223> OTHER INFORMATION: Synthetic Construct

<400> SEQUENCE: 948
uggcaugcag aaggau 16

<210> SEQ ID NO 949
<211> LENGTH: 16
<212> TYPE: RNA
<213> ORGANISM: Artificial Sequence
<220> FEATURE:
<223> OTHER INFORMATION: Synthetic Construct

<400> SEQUENCE: 949
ggcaugcaga aggauc 16

<210> SEQ ID NO 950
<211> LENGTH: 15
<212> TYPE: RNA
<213> ORGANISM: Artificial Sequence
<220> FEATURE:
<223> OTHER INFORMATION: Synthetic Construct

<400> SEQUENCE: 950
aacaguuucc acugg 15

<210> SEQ ID NO 951
<211> LENGTH: 15
<212> TYPE: RNA
<213> ORGANISM: Artificial Sequence
<220> FEATURE:
<223> OTHER INFORMATION: Synthetic Construct

<400> SEQUENCE: 951
acaguuucca cuggc 15

<210> SEQ ID NO 952
<211> LENGTH: 15
<212> TYPE: RNA
<213> ORGANISM: Artificial Sequence
<220> FEATURE:
<223> OTHER INFORMATION: Synthetic Construct

<400> SEQUENCE: 952
caguuuccac uggca 15

<210> SEQ ID NO 953
<211> LENGTH: 15
<212> TYPE: RNA
<213> ORGANISM: Artificial Sequence
<220> FEATURE:
<223> OTHER INFORMATION: Synthetic Construct

<400> SEQUENCE: 953
aguuuccacu ggcau 15

<210> SEQ ID NO 954
<211> LENGTH: 15
<212> TYPE: RNA
<213> ORGANISM: Artificial Sequence
<220> FEATURE:
<223> OTHER INFORMATION: Synthetic Construct

<400> SEQUENCE: 954
guuuccacug gcaug 15

<210> SEQ ID NO 955
<211> LENGTH: 15
<212> TYPE: RNA
<213> ORGANISM: Artificial Sequence
<220> FEATURE:
<223> OTHER INFORMATION: Synthetic Construct

<400> SEQUENCE: 955
uuuccacugg caugc 15

<210> SEQ ID NO 956
<211> LENGTH: 15
<212> TYPE: RNA
<213> ORGANISM: Artificial Sequence
<220> FEATURE:
<223> OTHER INFORMATION: Synthetic Construct

<400> SEQUENCE: 956
uuccacuggc augca 15

<210> SEQ ID NO 957
<211> LENGTH: 15
<212> TYPE: RNA
<213> ORGANISM: Artificial Sequence
<220> FEATURE:
<223> OTHER INFORMATION: Synthetic Construct

<400> SEQUENCE: 957
uccacuggca ugcag 15

<210> SEQ ID NO 958

<211> LENGTH: 15
<212> TYPE: RNA
<213> ORGANISM: Artificial Sequence
<220> FEATURE:
<223> OTHER INFORMATION: Synthetic Construct

<400> SEQUENCE: 958
ccacuggcau gcaga 15

<210> SEQ ID NO 959
<211> LENGTH: 15
<212> TYPE: RNA
<213> ORGANISM: Artificial Sequence
<220> FEATURE:
<223> OTHER INFORMATION: Synthetic Construct

<400> SEQUENCE: 959
cacuggcaug cagaa 15

<210> SEQ ID NO 960
<211> LENGTH: 15
<212> TYPE: RNA
<213> ORGANISM: Artificial Sequence
<220> FEATURE:
<223> OTHER INFORMATION: Synthetic Construct

<400> SEQUENCE: 960
acuggcaugc agaag 15

<210> SEQ ID NO 961
<211> LENGTH: 15
<212> TYPE: RNA
<213> ORGANISM: Artificial Sequence
<220> FEATURE:
<223> OTHER INFORMATION: Synthetic Construct

<400> SEQUENCE: 961
cuggcaugca gaagg 15

<210> SEQ ID NO 962
<211> LENGTH: 15
<212> TYPE: RNA
<213> ORGANISM: Artificial Sequence
<220> FEATURE:
<223> OTHER INFORMATION: Synthetic Construct

<400> SEQUENCE: 962
uggcaugcag aagga 15

<210> SEQ ID NO 963
<211> LENGTH: 15
<212> TYPE: RNA
<213> ORGANISM: Artificial Sequence
<220> FEATURE:
<223> OTHER INFORMATION: Synthetic Construct

<400> SEQUENCE: 963
ggcaugcaga aggau 15

<210> SEQ ID NO 964
<211> LENGTH: 15
<212> TYPE: RNA
<213> ORGANISM: Artificial Sequence
<220> FEATURE:
<223> OTHER INFORMATION: Synthetic Construct

<400> SEQUENCE: 964
gcaugcagaa ggauc 15

<210> SEQ ID NO 965
<211> LENGTH: 47
<212> TYPE: DNA
<213> ORGANISM: Homo sapiens

<400> SEQUENCE: 965
tgagaccctt aagagcctta tcacgatttg aagggatgag ggtaaga 47

<210> SEQ ID NO 966
<211> LENGTH: 47
<212> TYPE: RNA
<213> ORGANISM: Homo sapiens

<400> SEQUENCE: 966
ucuuacccuc aucccuucaa aucgugauaa ggcucuuaag ggucuca 47

<210> SEQ ID NO 967
<211> LENGTH: 24
<212> TYPE: RNA
<213> ORGANISM: Artificial Sequence
<220> FEATURE:
<223> OTHER INFORMATION: Synthetic Construct

<400> SEQUENCE: 967
ucuuacccuc aucccuucaa aucg 24

<210> SEQ ID NO 968
<211> LENGTH: 24
<212> TYPE: RNA
<213> ORGANISM: Artificial Sequence
<220> FEATURE:
<223> OTHER INFORMATION: Synthetic Construct

<400> SEQUENCE: 968
cuuacccuca ucccuucaaa ucgu 24

<210> SEQ ID NO 969
<211> LENGTH: 24
<212> TYPE: RNA
<213> ORGANISM: Artificial Sequence
<220> FEATURE:
<223> OTHER INFORMATION: Synthetic Construct

<400> SEQUENCE: 969
uuacccucau cccuucaaau cgug 24

<210> SEQ ID NO 970
<211> LENGTH: 24
<212> TYPE: RNA
<213> ORGANISM: Artificial Sequence
<220> FEATURE:
<223> OTHER INFORMATION: Synthetic Construct

<400> SEQUENCE: 970
uacccucauc ccuucaaauc guga 24

<210> SEQ ID NO 971
<211> LENGTH: 24
<212> TYPE: RNA
<213> ORGANISM: Artificial Sequence
<220> FEATURE:
<223> OTHER INFORMATION: Synthetic Construct

<400> SEQUENCE: 971
acccucaucc cuucaaaucg ugau 24

<210> SEQ ID NO 972
<211> LENGTH: 24
<212> TYPE: RNA
<213> ORGANISM: Artificial Sequence
<220> FEATURE:
<223> OTHER INFORMATION: Synthetic Construct

<400> SEQUENCE: 972
cccucauccc uucaaaucgu gaua 24

<210> SEQ ID NO 973
<211> LENGTH: 24
<212> TYPE: RNA
<213> ORGANISM: Artificial Sequence
<220> FEATURE:
<223> OTHER INFORMATION: Synthetic Construct

<400> SEQUENCE: 973
ccucaucccu ucaaaucgug auaa 24

<210> SEQ ID NO 974
<211> LENGTH: 24
<212> TYPE: RNA
<213> ORGANISM: Artificial Sequence
<220> FEATURE:
<223> OTHER INFORMATION: Synthetic Construct

<400> SEQUENCE: 974
cucaucccuu caaaucguga uaag 24

<210> SEQ ID NO 975
<211> LENGTH: 24
<212> TYPE: RNA
<213> ORGANISM: Artificial Sequence
<220> FEATURE:
<223> OTHER INFORMATION: Synthetic Construct

<400> SEQUENCE: 975
ucaucccuuc aaaucgugau aagg 24

<210> SEQ ID NO 976
<211> LENGTH: 24
<212> TYPE: RNA
<213> ORGANISM: Artificial Sequence
<220> FEATURE:
<223> OTHER INFORMATION: Synthetic Construct

<400> SEQUENCE: 976
caucccuuca aaucgugaua aggc 24

<210> SEQ ID NO 977
<211> LENGTH: 24
<212> TYPE: RNA
<213> ORGANISM: Artificial Sequence
<220> FEATURE:
<223> OTHER INFORMATION: Synthetic Construct

<400> SEQUENCE: 977
aucccuucaa aucgugauaa ggcu 24

<210> SEQ ID NO 978
<211> LENGTH: 24

<212> TYPE: RNA
<213> ORGANISM: Artificial Sequence
<220> FEATURE:
<223> OTHER INFORMATION: Synthetic Construct

<400> SEQUENCE: 978
ucccuucaaa ucgugauaag gcuc 24

<210> SEQ ID NO 979
<211> LENGTH: 24
<212> TYPE: RNA
<213> ORGANISM: Artificial Sequence
<220> FEATURE:
<223> OTHER INFORMATION: Synthetic Construct

<400> SEQUENCE: 979
cccuucaaau cgugauaagg cucu 24

<210> SEQ ID NO 980
<211> LENGTH: 24
<212> TYPE: RNA
<213> ORGANISM: Artificial Sequence
<220> FEATURE:
<223> OTHER INFORMATION: Synthetic Construct

<400> SEQUENCE: 980
ccuucaaauc gugauaaggc ucuu 24

<210> SEQ ID NO 981
<211> LENGTH: 24
<212> TYPE: RNA
<213> ORGANISM: Artificial Sequence
<220> FEATURE:
<223> OTHER INFORMATION: Synthetic Construct

<400> SEQUENCE: 981
cuucaaaucg ugauaaggcu cuua 24

<210> SEQ ID NO 982
<211> LENGTH: 24
<212> TYPE: RNA
<213> ORGANISM: Artificial Sequence
<220> FEATURE:
<223> OTHER INFORMATION: Synthetic Construct

<400> SEQUENCE: 982
uucaaaucgu gauaaggcuc uuaa 24

<210> SEQ ID NO 983
<211> LENGTH: 24
<212> TYPE: RNA
<213> ORGANISM: Artificial Sequence
<220> FEATURE:
<223> OTHER INFORMATION: Synthetic Construct

<400> SEQUENCE: 983
ucaaaucgug auaaggcucu uaag 24

<210> SEQ ID NO 984
<211> LENGTH: 24
<212> TYPE: RNA
<213> ORGANISM: Artificial Sequence
<220> FEATURE:
<223> OTHER INFORMATION: Synthetic Construct

<400> SEQUENCE: 984

-continued caaaucguga uaaggcucuu aagg 24

<210> SEQ ID NO 985
<211> LENGTH: 24
<212> TYPE: RNA
<213> ORGANISM: Artificial Sequence
<220> FEATURE:
<223> OTHER INFORMATION: Synthetic Construct

<400> SEQUENCE: 985
aaaucgugau aaggcucuua aggg 24

<210> SEQ ID NO 986
<211> LENGTH: 24
<212> TYPE: RNA
<213> ORGANISM: Artificial Sequence
<220> FEATURE:
<223> OTHER INFORMATION: Synthetic Construct

<400> SEQUENCE: 986
aaucgugaua aggcucuuaa gggu 24

<210> SEQ ID NO 987
<211> LENGTH: 24
<212> TYPE: RNA
<213> ORGANISM: Artificial Sequence
<220> FEATURE:
<223> OTHER INFORMATION: Synthetic Construct

<400> SEQUENCE: 987
aucgugauaa ggcucuuaag gguc 24

<210> SEQ ID NO 988
<211> LENGTH: 24
<212> TYPE: RNA
<213> ORGANISM: Artificial Sequence
<220> FEATURE:
<223> OTHER INFORMATION: Synthetic Construct

<400> SEQUENCE: 988
ucgugauaag gcucuuaagg gucu 24

<210> SEQ ID NO 989
<211> LENGTH: 24
<212> TYPE: RNA
<213> ORGANISM: Artificial Sequence
<220> FEATURE:
<223> OTHER INFORMATION: Synthetic Construct

<400> SEQUENCE: 989
cgugauaagg cucuuaaggg ucuc 24

<210> SEQ ID NO 990
<211> LENGTH: 24
<212> TYPE: RNA
<213> ORGANISM: Artificial Sequence
<220> FEATURE:
<223> OTHER INFORMATION: Synthetic Construct

<400> SEQUENCE: 990
gugauaaggc ucuuaagggu cuca 24

<210> SEQ ID NO 991
<211> LENGTH: 23
<212> TYPE: RNA
<213> ORGANISM: Artificial Sequence
<220> FEATURE:
<223> OTHER INFORMATION: Synthetic Construct

<400> SEQUENCE: 991
ucuuacccuc aucccuucaa auc 23

<210> SEQ ID NO 992
<211> LENGTH: 23
<212> TYPE: RNA
<213> ORGANISM: Artificial Sequence
<220> FEATURE:
<223> OTHER INFORMATION: Synthetic Construct

<400> SEQUENCE: 992
cuuacccuca ucccuucaaa ucg 23

<210> SEQ ID NO 993
<211> LENGTH: 23
<212> TYPE: RNA
<213> ORGANISM: Artificial Sequence
<220> FEATURE:
<223> OTHER INFORMATION: Synthetic Construct

<400> SEQUENCE: 993
uuacccucau cccuucaaau cgu 23

<210> SEQ ID NO 994
<211> LENGTH: 23
<212> TYPE: RNA
<213> ORGANISM: Artificial Sequence
<220> FEATURE:
<223> OTHER INFORMATION: Synthetic Construct

<400> SEQUENCE: 994
uacccucauc ccuucaaauc gug 23

<210> SEQ ID NO 995
<211> LENGTH: 23
<212> TYPE: RNA
<213> ORGANISM: Artificial Sequence
<220> FEATURE:
<223> OTHER INFORMATION: Synthetic Construct

<400> SEQUENCE: 995
acccucaucc cuucaaaucg uga 23

<210> SEQ ID NO 996
<211> LENGTH: 23
<212> TYPE: RNA
<213> ORGANISM: Artificial Sequence
<220> FEATURE:
<223> OTHER INFORMATION: Synthetic Construct

<400> SEQUENCE: 996
cccucauccc uucaaaucgu gau 23

<210> SEQ ID NO 997
<211> LENGTH: 23
<212> TYPE: RNA
<213> ORGANISM: Artificial Sequence
<220> FEATURE:
<223> OTHER INFORMATION: Synthetic Construct

<400> SEQUENCE: 997
ccucaucccu ucaaaucgug aua 23

<210> SEQ ID NO 998
<211> LENGTH: 23
<212> TYPE: RNA
<213> ORGANISM: Artificial Sequence
<220> FEATURE:
<223> OTHER INFORMATION: Synthetic Construct

<400> SEQUENCE: 998
cucaucccuu caaaucguga uaa 23

<210> SEQ ID NO 999
<211> LENGTH: 23
<212> TYPE: RNA
<213> ORGANISM: Artificial Sequence
<220> FEATURE:
<223> OTHER INFORMATION: Synthetic Construct

<400> SEQUENCE: 999
ucaucccuuc aaaucgugau aag 23

<210> SEQ ID NO 1000
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1000
caucccuuca aaucgugaua agg 23

<210> SEQ ID NO 1001
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1001
aucccuucaa aucgugauaa ggc 23

<210> SEQ ID NO 1002
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1002
ucccuucaaa ucgugauaag gcu 23

<210> SEQ ID NO 1003
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1003
cccuucaaau cgugauaagg cuc 23

<210> SEQ ID NO 1004
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1004
ccuucaaauc gugauaaggc ucu 23

<210> SEQ ID NO 1005
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1005
cuucaaaucg ugauaaggcu cuu 23

<210> SEQ ID NO 1006
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1006
uucaaaucgu gauaaggcuc uua 23

<210> SEQ ID NO 1007
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1007
ucaaaucgug auaaggcucu uaa 23

<210> SEQ ID NO 1008
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1008
caaaucguga uaaggcucuu aag 23

<210> SEQ ID NO 1009
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1009
aaaucgugau aaggcucuua agg 23

<210> SEQ ID NO 1010
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1010
aaucgugaua aggcucuuaa ggg 23

<210> SEQ ID NO 1011

<211> LENGTH: 23
<212> TYPE: RNA
<213> ORGANISM: Artificial Sequence
<220> FEATURE:
<223> OTHER INFORMATION: Synthetic Construct

<400> SEQUENCE: 1011
aucgugauaa ggcucuuaag ggu 23

<210> SEQ ID NO 1012
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1012
ucgugauaag gcucuuaagg guc 23

<210> SEQ ID NO 1013
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1013
cgugauaagg cucuuaaggg ucu 23

<210> SEQ ID NO 1014
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1014
gugauaaggc ucuuaagggu cuc 23

<210> SEQ ID NO 1015
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1015
ugauaaggcu cuuaaggguc uca 23

<210> SEQ ID NO 1016
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1016
ucuuacccuc aucccuucaa au 22

<210> SEQ ID NO 1017
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1017
cuuacccuca ucccuucaaa uc 22

<210> SEQ ID NO 1018
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1018
uuacccucau cccuucaaau cg 22

<210> SEQ ID NO 1019
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1019
uacccucauc ccuucaaauc gu 22

<210> SEQ ID NO 1020
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1020
uacccucauc ccuucaaauc gu 22

<210> SEQ ID NO 1021
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1021
acccucaucc cuucaaaucg ug 22

<210> SEQ ID NO 1022
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1022
ccucaucccu ucaaaucgug au 22

<210> SEQ ID NO 1023
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1023
cucaucccuu caaaucguga ua 22

<210> SEQ ID NO 1024
<211> LENGTH: 22
<212> TYPE: RNA

<213> ORGANISM: Artificial Sequence
<220> FEATURE:
<223> OTHER INFORMATION: Synthetic Construct

<400> SEQUENCE: 1024
ucaucccuuc aaaucgugau aa 22

<210> SEQ ID NO 1025
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1025
caucccuuca aaucgugaua ag 22

<210> SEQ ID NO 1026
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1026
aucccuucaa aucgugauaa gg 22

<210> SEQ ID NO 1027
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1027
ucccuucaaa ucgugauaag gc 22

<210> SEQ ID NO 1028
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1028
cccuucaaau cgugauaagg cu 22

<210> SEQ ID NO 1029
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1029
ccuucaaauc gugauaaggc uc 22

<210> SEQ ID NO 1030
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1030
cuucaaaucg ugauaaggcu cu 22

<210> SEQ ID NO 1031
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1031
uucaaaucgu gauaaggcuc uu 22

<210> SEQ ID NO 1032
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1032
ucaaaucgug auaaggcucu ua 22

<210> SEQ ID NO 1033
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1033
caaaucguga uaaggcucuu aa 22

<210> SEQ ID NO 1034
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1034
aaaucgugau aaggcucuua ag 22

<210> SEQ ID NO 1035
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1035
aaucgugaua aggcucuuaa gg 22

<210> SEQ ID NO 1036
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1036
aucgugauaa ggcucuuaag gg 22

<210> SEQ ID NO 1037
<211> LENGTH: 22
<212> TYPE: RNA
<213> ORGANISM: Artificial Sequence
<220> FEATURE:

<223> OTHER INFORMATION: Synthetic Construct

<400> SEQUENCE: 1037
ucgugauaag gcucuuaagg gu 22

<210> SEQ ID NO 1038
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1038
cgugauaagg cucuuaaggg uc 22

<210> SEQ ID NO 1039
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1039
gugauaaggc ucuuaagggu cu 22

<210> SEQ ID NO 1040
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1040
ugauaaggcu cuuaaggguc uc 22

<210> SEQ ID NO 1041
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1041
gauaaggcuc uuaagggucu ca 22

<210> SEQ ID NO 1042
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1042
ucuuacccuc aucccuucaa a 21

<210> SEQ ID NO 1043
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1043
cuuacccuca ucccuucaaa u 21

<210> SEQ ID NO 1044
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1044
uuacccucau cccuucaaau c 21

<210> SEQ ID NO 1045
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1045
uacccucauc ccuucaaauc g 21

<210> SEQ ID NO 1046
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1046
acccucaucc cuucaaaucg u 21

<210> SEQ ID NO 1047
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1047
cccucauccc uucaaaucgu g 21

<210> SEQ ID NO 1048
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1048
ccucaucccu ucaaaucgug a 21

<210> SEQ ID NO 1049
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1049
cucaucccuu caaaucguga u 21

<210> SEQ ID NO 1050
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1050
ucaucccuuc aaaucgugau a 21

<210> SEQ ID NO 1051
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1051
caucccuuca aaucgugaua a 21

<210> SEQ ID NO 1052
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1052
aucccuucaa aucgugauaa g 21

<210> SEQ ID NO 1053
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1053
ucccuucaaa ucgugauaag g 21

<210> SEQ ID NO 1054
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1054
cccuucaaau cgugauaagg c 21

<210> SEQ ID NO 1055
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1055
ccuucaaauc gugauaaggc u 21

<210> SEQ ID NO 1056
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1056
cuucaaaucg ugauaaggcu c 21

<210> SEQ ID NO 1057
<211> LENGTH: 21

<212> TYPE: RNA
<213> ORGANISM: Artificial Sequence
<220> FEATURE:
<223> OTHER INFORMATION: Synthetic Construct

<400> SEQUENCE: 1057
uucaaaucgu gauaaggcuc u 21

<210> SEQ ID NO 1058
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1058
ucaaaucgug auaaggcucu u 21

<210> SEQ ID NO 1059
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1059
caaaucguga uaaggcucuu a 21

<210> SEQ ID NO 1060
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1060
aaaucgugau aaggcucuua a 21

<210> SEQ ID NO 1061
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1061
aaucgugaua aggcucuuaa g 21

<210> SEQ ID NO 1062
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1062
aucgugauaa ggcucuuaag g 21

<210> SEQ ID NO 1063
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1063
ucgugauaag gcucuuaagg g 21

<210> SEQ ID NO 1064
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1064
cgugauaagg cucuuaaggg u 21

<210> SEQ ID NO 1065
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1065
gugauaaggc ucuuaagggu c 21

<210> SEQ ID NO 1066
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1066
ugauaaggcu cuuaaggguc u 21

<210> SEQ ID NO 1067
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1067
gauaaggcuc uuaagggucu c 21

<210> SEQ ID NO 1068
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1068
auaaggcucu uaagggucuc a 21

<210> SEQ ID NO 1069
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1069
ucuuacccuc aucccuucaa 20

<210> SEQ ID NO 1070
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1070
cuuacccuca ucccuucaaa 20

<210> SEQ ID NO 1071
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1071
uuacccucau cccuucaaau 20

<210> SEQ ID NO 1072
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1072
uacccucauc ccuucaaauc 20

<210> SEQ ID NO 1073
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1073
acccucaucc cuucaaaucg 20

<210> SEQ ID NO 1074
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1074
cccucauccc uucaaaucgu 20

<210> SEQ ID NO 1075
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1075
ccucaucccu ucaaaucgug 20

<210> SEQ ID NO 1076
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1076
cucaucccuu caaaucguga 20

<210> SEQ ID NO 1077
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1077
ucaucccuuc aaaucgugau 20

<210> SEQ ID NO 1078
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1078
caucccuuca aaucgugaua 20

<210> SEQ ID NO 1079
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1079
aucccuucaa aucgugauaa 20

<210> SEQ ID NO 1080
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1080
ucccuucaaa ucgugauaag 20

<210> SEQ ID NO 1081
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1081
cccuucaaau cgugauaagg 20

<210> SEQ ID NO 1082
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1082
ccuucaaauc gugauaaggc 20

<210> SEQ ID NO 1083
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1083
cuucaaaucg ugauaaggcu 20

<210> SEQ ID NO 1084
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1084
uucaaaucgu gauaaggcuc 20

<210> SEQ ID NO 1085
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1085
ucaaaucgug auaaggcucu 20

<210> SEQ ID NO 1086
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1086
caaaucguga uaaggcucuu 20

<210> SEQ ID NO 1087
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1087
aaaucgugau aaggcucuua 20

<210> SEQ ID NO 1088
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1088
aaucgugaua aggcucuuaa 20

<210> SEQ ID NO 1089
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1089
aucgugauaa ggcucuuaag 20

<210> SEQ ID NO 1090

<211> LENGTH: 20
<212> TYPE: RNA
<213> ORGANISM: Artificial Sequence
<220> FEATURE:
<223> OTHER INFORMATION: Synthetic Construct

<400> SEQUENCE: 1090
ucgugauaag gcucuuaagg 20

<210> SEQ ID NO 1091
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1091
cgugauaagg cucuuaaggg 20

<210> SEQ ID NO 1092
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1092
gugauaaggc ucuuaagggu 20

<210> SEQ ID NO 1093
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1093
ugauaaggcu cuuaaggguc 20

<210> SEQ ID NO 1094
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1094
gauaaggcuc uuaagggucu 20

<210> SEQ ID NO 1095
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1095
auaaggcucu uaagggucuc 20

<210> SEQ ID NO 1096
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1096
uaaggcucuu aagggucuca 20

<210> SEQ ID NO 1097
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1097
ucuuacccuc aucccuuca 19

<210> SEQ ID NO 1098
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1098
cuuacccuca ucccuucaa 19

<210> SEQ ID NO 1099
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1099
uuacccucau cccuucaaa 19

<210> SEQ ID NO 1100
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1100
uacccucauc ccuucaaau 19

<210> SEQ ID NO 1101
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1101
acccucaucc cuucaaauc 19

<210> SEQ ID NO 1102
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1102
cccucauccc uucaaaucg 19

<210> SEQ ID NO 1103
<211> LENGTH: 19
<212> TYPE: RNA

<213> ORGANISM: Artificial Sequence
<220> FEATURE:
<223> OTHER INFORMATION: Synthetic Construct

<400> SEQUENCE: 1103
ccucaucccu ucaaaucgu 19

<210> SEQ ID NO 1104
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1104
cucaucccuu caaaucgug 19

<210> SEQ ID NO 1105
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1105
ucaucccuuc aaaucguga 19

<210> SEQ ID NO 1106
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1106
caucccuuca aaucgugau 19

<210> SEQ ID NO 1107
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1107
aucccuucaa aucgugaua 19

<210> SEQ ID NO 1108
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1108
ucccuucaaa ucgugauaa 19

<210> SEQ ID NO 1109
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1109
cccuucaaau cgugauaag 19

<210> SEQ ID NO 1110
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1110
ccuucaaauc gugauaagg 19

<210> SEQ ID NO 1111
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1111
cuucaaaucg ugauaaggc 19

<210> SEQ ID NO 1112
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1112
uucaaaucgu gauaaggcu 19

<210> SEQ ID NO 1113
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1113
ucaaaucgug auaaggcuc 19

<210> SEQ ID NO 1114
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1114
caaaucguga uaaggcucu 19

<210> SEQ ID NO 1115
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1115
aaaucgugau aaggcucuu 19

<210> SEQ ID NO 1116
<211> LENGTH: 19
<212> TYPE: RNA
<213> ORGANISM: Artificial Sequence
<220> FEATURE:

<223> OTHER INFORMATION: Synthetic Construct

<400> SEQUENCE: 1116
aaucgugaua aggcucuua 19

<210> SEQ ID NO 1117
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1117
aucgugauaa ggcucuuaa 19

<210> SEQ ID NO 1118
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1118
ucgugauaag gcucuuaag 19

<210> SEQ ID NO 1119
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1119
cgugauaagg cucuuaagg 19

<210> SEQ ID NO 1120
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1120
gugauaaggc ucuuaaggg 19

<210> SEQ ID NO 1121
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1121
ugauaaggcu cuuaagggu 19

<210> SEQ ID NO 1122
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1122
gauaaggcuc uuaaggguc 19

-continued

<210> SEQ ID NO 1123
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1123
auaaggcucu uaagggucu 19

<210> SEQ ID NO 1124
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1124
uaaggcucuu aagggucuc 19

<210> SEQ ID NO 1125
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1125
aaggcucuua agggucuca 19

<210> SEQ ID NO 1126
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1126
ucuuacccuc aucccuuc 18

<210> SEQ ID NO 1127
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1127
cuuacccuca ucccuuca 18

<210> SEQ ID NO 1128
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1128
uuacccucau cccuucaa 18

<210> SEQ ID NO 1129
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1129
uacccucauc ccuucaaa 18

<210> SEQ ID NO 1130
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1130
acccucaucc cuucaaau 18

<210> SEQ ID NO 1131
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1131
cccucauccc uucaaauc 18

<210> SEQ ID NO 1132
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1132
ccucaucccu ucaaaucg 18

<210> SEQ ID NO 1133
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1133
cucaucccuu caaaucgu 18

<210> SEQ ID NO 1134
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1134
ucaucccuuc aaaucgug 18

<210> SEQ ID NO 1135
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1135
caucccuuca aaucguga 18

<210> SEQ ID NO 1136
<211> LENGTH: 18

<212> TYPE: RNA
<213> ORGANISM: Artificial Sequence
<220> FEATURE:
<223> OTHER INFORMATION: Synthetic Construct

<400> SEQUENCE: 1136
aucccuucaa aucgugau 18

<210> SEQ ID NO 1137
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1137
ucccuucaaa ucgugaua 18

<210> SEQ ID NO 1138
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1138
cccuucaaau cgugauaa 18

<210> SEQ ID NO 1139
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1139
ccuucaaauc gugauaag 18

<210> SEQ ID NO 1140
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1140
cuucaaaucg ugauaagg 18

<210> SEQ ID NO 1141
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1141
uucaaaucgu gauaaggc 18

<210> SEQ ID NO 1142
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1142
ucaaaucgug auaaggcu 18

<210> SEQ ID NO 1143
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1143
caaaucguga uaaggcuc 18

<210> SEQ ID NO 1144
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1144
aaaucgugau aaggcucu 18

<210> SEQ ID NO 1145
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1145
aaucgugaua aggcucuu 18

<210> SEQ ID NO 1146
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1146
aucgugauaa ggcucuua 18

<210> SEQ ID NO 1147
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1147
ucgugauaag gcucuuaa 18

<210> SEQ ID NO 1148
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1148
cgugauaagg cucuuaag 18

<210> SEQ ID NO 1149
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1149
gugauaaggc ucuuaagg 18

<210> SEQ ID NO 1150
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1150
ugauaaggcu cuuaaggg 18

<210> SEQ ID NO 1151
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1151
gauaaggcuc uuaagggu 18

<210> SEQ ID NO 1152
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1152
auaaggcucu uaaggguc 18

<210> SEQ ID NO 1153
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1153
uaaggcucuu aagggucu 18

<210> SEQ ID NO 1154
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1154
aaggcucuua agggucuc 18

<210> SEQ ID NO 1155
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1155
aggcucuuaa gggucuca 18

<210> SEQ ID NO 1156
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1156
ucuuacccuc aucccuu 17

<210> SEQ ID NO 1157
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1157
cuuacccuca ucccuuc 17

<210> SEQ ID NO 1158
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1158
uuacccucau cccuuca 17

<210> SEQ ID NO 1159
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1159
uacccucauc ccuucaa 17

<210> SEQ ID NO 1160
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1160
acccucaucc cuucaaa 17

<210> SEQ ID NO 1161
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1161
cccucauccc uucaaau 17

<210> SEQ ID NO 1162
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1162
ccucaucccu ucaaauc 17

<210> SEQ ID NO 1163
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1163
cucaucccuu caaaucg 17

<210> SEQ ID NO 1164
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1164
ucaucccuuc aaaucgu 17

<210> SEQ ID NO 1165
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1165
caucccuuca aaucgug 17

<210> SEQ ID NO 1166
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1166
aucccuucaa aucguga 17

<210> SEQ ID NO 1167
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1167
ucccuucaaa ucgugau 17

<210> SEQ ID NO 1168
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1168
cccuucaaau cgugaua 17

<210> SEQ ID NO 1169

<211> LENGTH: 17
<212> TYPE: RNA
<213> ORGANISM: Artificial Sequence
<220> FEATURE:
<223> OTHER INFORMATION: Synthetic Construct

<400> SEQUENCE: 1169
ccuucaaauc gugauaa 17

<210> SEQ ID NO 1170
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1170
cuucaaaucg ugauaag 17

<210> SEQ ID NO 1171
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1171
uucaaaucgu gauaagg 17

<210> SEQ ID NO 1172
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1172
ucaaaucgug auaaggc 17

<210> SEQ ID NO 1173
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1173
caaaucguga uaaggcu 17

<210> SEQ ID NO 1174
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1174
aaaucgugau aaggcuc 17

<210> SEQ ID NO 1175
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1175
aaucgugaua aggcucu 17

<210> SEQ ID NO 1176
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1176
aucgugauaa ggcucuu 17

<210> SEQ ID NO 1177
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1177
ucgugauaag gcucuua 17

<210> SEQ ID NO 1178
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1178
cgugauaagg cucuuaa 17

<210> SEQ ID NO 1179
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1179
gugauaaggc ucuuaag 17

<210> SEQ ID NO 1180
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1180
ugauaaggcu cuuaagg 17

<210> SEQ ID NO 1181
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1181
gauaaggcuc uuaaggg 17

<210> SEQ ID NO 1182
<211> LENGTH: 17
<212> TYPE: RNA

```
<213> ORGANISM: Artificial Sequence
<220> FEATURE:
<223> OTHER INFORMATION: Synthetic Construct

<400> SEQUENCE: 1182

auaaggcucu uaagggu                                                    17

<210> SEQ ID NO 1183
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1183

uaaggcucuu aaggguc                                                    17

<210> SEQ ID NO 1184
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1184

aaggcucuua agggucu                                                    17

<210> SEQ ID NO 1185
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1185

aggcucuuaa gggucuc                                                    17

<210> SEQ ID NO 1186
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1186

ggcucuuaag ggucuca                                                    17

<210> SEQ ID NO 1187
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1187

ucuuacccuc aucccu                                                     16

<210> SEQ ID NO 1188
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1188

cuuacccuca ucccuu                                                     16
```

<210> SEQ ID NO 1189
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1189
uuacccucau cccuuc 16

<210> SEQ ID NO 1190
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1190
uacccucauc ccuuca 16

<210> SEQ ID NO 1191
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1191
acccucaucc cuucaa 16

<210> SEQ ID NO 1192
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1192
cccucauccc uucaaa 16

<210> SEQ ID NO 1193
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1193
ccucaucccu ucaaau 16

<210> SEQ ID NO 1194
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1194
cucaucccuu caaauc 16

<210> SEQ ID NO 1195
<211> LENGTH: 16
<212> TYPE: RNA
<213> ORGANISM: Artificial Sequence
<220> FEATURE:

<223> OTHER INFORMATION: Synthetic Construct

<400> SEQUENCE: 1195
ucaucccuuc aaaucg 16

<210> SEQ ID NO 1196
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1196
caucccuuca aaucgu 16

<210> SEQ ID NO 1197
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1197
aucccuucaa aucgug 16

<210> SEQ ID NO 1198
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1198
ucccuucaaa ucguga 16

<210> SEQ ID NO 1199
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1199
cccuucaaau cgugau 16

<210> SEQ ID NO 1200
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1200
ccuucaaauc gugaua 16

<210> SEQ ID NO 1201
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1201
cuucaaaucg ugauaa 16

<210> SEQ ID NO 1202
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1202
uucaaaucgu gauaag 16

<210> SEQ ID NO 1203
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1203
ucaaaucgug auaagg 16

<210> SEQ ID NO 1204
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1204
caaaucguga uaaggc 16

<210> SEQ ID NO 1205
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1205
aaaucgugau aaggcu 16

<210> SEQ ID NO 1206
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1206
aaucgugaua aggcuc 16

<210> SEQ ID NO 1207
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1207
aucgugauaa ggcucu 16

<210> SEQ ID NO 1208
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1208
ucgugauaag gcucuu 16

<210> SEQ ID NO 1209
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1209
cgugauaagg cucuua 16

<210> SEQ ID NO 1210
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1210
gugauaaggc ucuuaa 16

<210> SEQ ID NO 1211
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1211
ugauaaggcu cuuaag 16

<210> SEQ ID NO 1212
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1212
gauaaggcuc uuaagg 16

<210> SEQ ID NO 1213
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1213
auaaggcucu uaaggg 16

<210> SEQ ID NO 1214
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1214
uaaggcucuu aagggu 16

<210> SEQ ID NO 1215
<211> LENGTH: 16

<212> TYPE: RNA
<213> ORGANISM: Artificial Sequence
<220> FEATURE:
<223> OTHER INFORMATION: Synthetic Construct

<400> SEQUENCE: 1215
aaggcucuua aggguc 16

<210> SEQ ID NO 1216
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1216
aggcucuuaa gggucu 16

<210> SEQ ID NO 1217
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1217
ggcucuuaag ggucuc 16

<210> SEQ ID NO 1218
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1218
gcucuuaagg gucuca 16

<210> SEQ ID NO 1219
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1219
ucuuacccuc auccc 15

<210> SEQ ID NO 1220
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1220
cuuacccuca ucccu 15

<210> SEQ ID NO 1221
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1221
uuacccucau cccuu 15

<210> SEQ ID NO 1222
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1222
uacccucauc ccuuc 15

<210> SEQ ID NO 1223
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1223
acccucaucc cuuca 15

<210> SEQ ID NO 1224
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1224
cccucauccc uucaa 15

<210> SEQ ID NO 1225
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1225
ccucaucccu ucaaa 15

<210> SEQ ID NO 1226
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1226
cucaucccuu caaau 15

<210> SEQ ID NO 1227
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1227
ucaucccuuc aaauc 15

<210> SEQ ID NO 1228
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1228
caucccuuca aaucg 15

<210> SEQ ID NO 1229
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1229
aucccuucaa aucgu 15

<210> SEQ ID NO 1230
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1230
ucccuucaaa ucgug 15

<210> SEQ ID NO 1231
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1231
cccuucaaau cguga 15

<210> SEQ ID NO 1232
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1232
ccuucaaauc gugau 15

<210> SEQ ID NO 1233
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1233
cuucaaaucg ugaua 15

<210> SEQ ID NO 1234
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1234
uucaaaucgu gauaa 15

<210> SEQ ID NO 1235
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1235
ucaaaucgug auaag 15

<210> SEQ ID NO 1236
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1236
caaaucguga uaagg 15

<210> SEQ ID NO 1237
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1237
aaaucgugau aaggc 15

<210> SEQ ID NO 1238
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1238
aaucgugaua aggcu 15

<210> SEQ ID NO 1239
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1239
aucgugauaa ggcuc 15

<210> SEQ ID NO 1240
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1240
ucgugauaag gcucu 15

<210> SEQ ID NO 1241
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1241
cgugauaagg cucuu 15

<210> SEQ ID NO 1242
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1242
gugauaaggc ucuua 15

<210> SEQ ID NO 1243
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1243
ugauaaggcu cuuaa 15

<210> SEQ ID NO 1244
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1244
gauaaggcuc uuaag 15

<210> SEQ ID NO 1245
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1245
auaaggcucu uaagg 15

<210> SEQ ID NO 1246
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1246
uaaggcucuu aaggg 15

<210> SEQ ID NO 1247
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1247
aaggcucuua agggu 15

<210> SEQ ID NO 1248

<211> LENGTH: 15
<212> TYPE: RNA
<213> ORGANISM: Artificial Sequence
<220> FEATURE:
<223> OTHER INFORMATION: Synthetic Construct

<400> SEQUENCE: 1248
aggcucuuaa ggguc 15

<210> SEQ ID NO 1249
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1249
ggcucuuaag ggucu 15

<210> SEQ ID NO 1250
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1250
gcucuuaagg gucuc 15

<210> SEQ ID NO 1251
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1251
cucuuaaggg ucuca 15

<210> SEQ ID NO 1252
<211> LENGTH: 79
<212> TYPE: DNA
<213> ORGANISM: Homo sapiens

<400> SEQUENCE: 1252
tgccctgggc tactcggaac taggtgccat aaagtccctt aggaccctaa gagctttgag 60
acccttaaga gccttatca 79

<210> SEQ ID NO 1253
<211> LENGTH: 79
<212> TYPE: RNA
<213> ORGANISM: Homo sapiens

<400> SEQUENCE: 1253
ugauaaggcu cuuaagggu c ucaaagcucu uaggguccua agggacuuua uggcaccuag 60
uuccgaguag cccagggca 79

<210> SEQ ID NO 1254
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1254
ugauaaggcu cuuaagggguc ucaa 24

<210> SEQ ID NO 1255
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1255
gauaaggcuc uuaagggucu caaa 24

<210> SEQ ID NO 1256
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1256
auaaggcucu uaagggucuc aaag 24

<210> SEQ ID NO 1257
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1257
uaaggcucuu aagggucuca aagc 24

<210> SEQ ID NO 1258
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1258
aaggcucuua agggucucaa agcu 24

<210> SEQ ID NO 1259
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1259
aggcucuuaa gggucucaaa gcuc 24

<210> SEQ ID NO 1260
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1260
ggcucuuaag ggucucaaag cucu 24

<210> SEQ ID NO 1261
<211> LENGTH: 24
<212> TYPE: RNA

<213> ORGANISM: Artificial Sequence
<220> FEATURE:
<223> OTHER INFORMATION: Synthetic Construct

<400> SEQUENCE: 1261
gcucuuaagg gucucaaagc ucuu 24

<210> SEQ ID NO 1262
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1262
cucuuaaggg ucucaaagcu cuua 24

<210> SEQ ID NO 1263
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1263
ucuuaagggu cucaaagcuc uuag 24

<210> SEQ ID NO 1264
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1264
cuuaaggguc ucaaagcucu uagg 24

<210> SEQ ID NO 1265
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1265
uuaagggucu caaagcucuu aggg 24

<210> SEQ ID NO 1266
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1266
uaagggucuc aaagcucuua gggu 24

<210> SEQ ID NO 1267
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1267
aagggucuca aagcucuuag gguc 24

<210> SEQ ID NO 1268
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1268
agggucucaa agcucuuagg gucc                                            24

<210> SEQ ID NO 1269
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1269
gggucucaaa gcucuuaggg uccu                                            24

<210> SEQ ID NO 1270
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1270
ggucucaaag cucuuagggu ccua                                            24

<210> SEQ ID NO 1271
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1271
gucucaaagc ucuuaggguc cuaa                                            24

<210> SEQ ID NO 1272
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1272
ucucaaagcu cuuagggucc uaag                                            24

<210> SEQ ID NO 1273
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1273
cucaaagcuc uuaggguccu aagg                                            24

<210> SEQ ID NO 1274
<211> LENGTH: 24
<212> TYPE: RNA
<213> ORGANISM: Artificial Sequence
<220> FEATURE:

<223> OTHER INFORMATION: Synthetic Construct

<400> SEQUENCE: 1274
ucaaagcucu uaggguccua aggg 24

<210> SEQ ID NO 1275
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1275
caaagcucuu agggucctaa ggga 24

<210> SEQ ID NO 1276
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1276
aaagcucuua ggguccuaag ggac 24

<210> SEQ ID NO 1277
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1277
aagcucuuag gguccuaagg gacu 24

<210> SEQ ID NO 1278
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1278
agcucuuagg guccuaaggg acuu 24

<210> SEQ ID NO 1279
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1279
gcucuuaggg uccuaaggga cuuu 24

<210> SEQ ID NO 1280
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1280
cucuuagggu ccuaagggac uuua 24

```
<210> SEQ ID NO 1281
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1281

ucuuaggguc cuaagggacu uuau                                              24

<210> SEQ ID NO 1282
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1282

cuuagggucc uaagggacuu uaug                                              24

<210> SEQ ID NO 1283
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1283

uuaggguccu aagggacuuu augg                                              24

<210> SEQ ID NO 1284
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1284

uaggguccua agggacuuua uggc                                              24

<210> SEQ ID NO 1285
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1285

aggguccuaa gggacuuuau ggca                                              24

<210> SEQ ID NO 1286
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1286

ggguccuaag ggacuuuaug gcac                                              24

<210> SEQ ID NO 1287
<211> LENGTH: 24
<212> TYPE: RNA
<213> ORGANISM: Artificial Sequence
<220> FEATURE:
<223> OTHER INFORMATION: Synthetic Construct
```

<400> SEQUENCE: 1287
gguccuaagg gacuuuaugg cacc 24

<210> SEQ ID NO 1288
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1288
guccuaaggg acuuuauggc accu 24

<210> SEQ ID NO 1289
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1289
uccuaaggga cuuuauggca ccua 24

<210> SEQ ID NO 1290
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1290
ccuaagggac uuuauggcac cuag 24

<210> SEQ ID NO 1291
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1291
cuaagggacu uuauggcacc uagu 24

<210> SEQ ID NO 1292
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1292
uaagggacuu uauggcaccu aguu 24

<210> SEQ ID NO 1293
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1293
aagggacuuu auggcaccua guuc 24

<210> SEQ ID NO 1294
<211> LENGTH: 24

<212> TYPE: RNA
<213> ORGANISM: Artificial Sequence
<220> FEATURE:
<223> OTHER INFORMATION: Synthetic Construct

<400> SEQUENCE: 1294
agggacuuua uggcaccuag uucc 24

<210> SEQ ID NO 1295
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1295
gggacuuuau ggcaccuagu uccg 24

<210> SEQ ID NO 1296
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1296
ggacuuuaug gcaccuaguu ccga 24

<210> SEQ ID NO 1297
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1297
gacuuuaugg caccuaguuc cgag 24

<210> SEQ ID NO 1298
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1298
acuuuauggc accuaguucc gagu 24

<210> SEQ ID NO 1299
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1299
cuuuauggca ccuaguuccg agua 24

<210> SEQ ID NO 1300
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1300
uuuauggcac cuaguuccga guag 24

<210> SEQ ID NO 1301
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1301
uuauggcacc uaguuccgag uagc 24

<210> SEQ ID NO 1302
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1302
uauggcaccu aguuccgagu agcc 24

<210> SEQ ID NO 1303
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1303
auggcaccua guuccgagua gccc 24

<210> SEQ ID NO 1304
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1304
uggcaccuag uuccgaguag ccca 24

<210> SEQ ID NO 1305
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1305
ggcaccuagu uccgaguagc ccag 24

<210> SEQ ID NO 1306
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1306
gcaccuaguu ccgaguagcc cagg 24

<210> SEQ ID NO 1307
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1307
caccuaguuc cgaguagccc aggg 24

<210> SEQ ID NO 1308
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1308
accuaguucc gaguagccca gggc 24

<210> SEQ ID NO 1309
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1309
ccuaguuccg aguagcccag ggca 24

<210> SEQ ID NO 1310
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1310
ugauaaggcu cuuaaggguc uca 23

<210> SEQ ID NO 1311
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1311
gauaaggcuc uuaaggqucu caa 23

<210> SEQ ID NO 1312
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1312
auaaggcucu uaagggucuc aaa 23

<210> SEQ ID NO 1313
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1313
uaaggcucuu aagggucuca aag 23

<210> SEQ ID NO 1314
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1314
aaggcucuua agggucucaa agc 23

<210> SEQ ID NO 1315
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1315
aggcucuuaa gggucucaaa gcu 23

<210> SEQ ID NO 1316
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1316
ggcucuuaag ggucucaaag cuc 23

<210> SEQ ID NO 1317
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1317
gcucuuaagg gucucaaagc ucu 23

<210> SEQ ID NO 1318
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1318
cucuuaaggg ucucaaagcu cuu 23

<210> SEQ ID NO 1319
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1319
ucuuaagggu cucaaagcuc uua 23

<210> SEQ ID NO 1320
<211> LENGTH: 23
<212> TYPE: RNA
<213> ORGANISM: Artificial Sequence
<220> FEATURE:
<223> OTHER INFORMATION: Synthetic Construct

```
<400> SEQUENCE: 1320

cuuaaggguc ucaaagcucu uag                                            23

<210> SEQ ID NO 1321
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1321

uuaagggucu caaagcucuu agg                                            23

<210> SEQ ID NO 1322
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1322

uaagggucuc aaagcucuua ggg                                            23

<210> SEQ ID NO 1323
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1323

aagggucuca aagcucuuag ggu                                            23

<210> SEQ ID NO 1324
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1324

agggucucaa agcucuuagg guc                                            23

<210> SEQ ID NO 1325
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1325

gggucucaaa gcucuuaggg ucc                                            23

<210> SEQ ID NO 1326
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1326

ggucucaaag cucuuagggu ccu                                            23

<210> SEQ ID NO 1327
```

```
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1327

gucucaaagc ucuuaggguc cua                                              23

<210> SEQ ID NO 1328
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1328

ucucaaagcu cuuagggucc uaa                                              23

<210> SEQ ID NO 1329
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1329

cucaaagcuc uuaggguccu aag                                              23

<210> SEQ ID NO 1330
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1330

ucaaagcucu uaggguccua agg                                              23

<210> SEQ ID NO 1331
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1331

caaagcucuu aggguccuaa ggg                                              23

<210> SEQ ID NO 1332
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1332

aaagcucuua ggguccuaag gga                                              23

<210> SEQ ID NO 1333
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1333
```

aagcucuuag gguccuaagg gac                                                    23

<210> SEQ ID NO 1334
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1334
agcucuuagg guccuaaggg acu                                                    23

<210> SEQ ID NO 1335
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1335
gcucuuaggg uccuaaggga cuu                                                    23

<210> SEQ ID NO 1336
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1336
cucuuagggu ccuaagggac uuu                                                    23

<210> SEQ ID NO 1337
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1337
ucuuaggguc cuaagggacu uua                                                    23

<210> SEQ ID NO 1338
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1338
cuuagggucc uaagggacuu uau                                                    23

<210> SEQ ID NO 1339
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1339
uuaggguccu aagggacuuu aug                                                    23

<210> SEQ ID NO 1340
<211> LENGTH: 23
<212> TYPE: RNA

```
<213> ORGANISM: Artificial Sequence
<220> FEATURE:
<223> OTHER INFORMATION: Synthetic Construct

<400> SEQUENCE: 1340

uaggguccua agggacuuua ugg                                              23

<210> SEQ ID NO 1341
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1341

aggguccuaa gggacuuuau ggc                                              23

<210> SEQ ID NO 1342
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1342

ggguccuaag ggacuuuaug gca                                              23

<210> SEQ ID NO 1343
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1343

gguccuaagg gacuuuaugg cac                                              23

<210> SEQ ID NO 1344
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1344

guccuaaggg acuuuauggc acc                                              23

<210> SEQ ID NO 1345
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1345

uccuaaggga cuuuauggca ccu                                              23

<210> SEQ ID NO 1346
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1346

ccuaagggac uuuauggcac cua                                              23
```

<210> SEQ ID NO 1347
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1347
cuaagggacu uuauggcacc uag 23

<210> SEQ ID NO 1348
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1348
uaagggacuu uauggcaccu agu 23

<210> SEQ ID NO 1349
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1349
aagggacuuu auggcaccua guu 23

<210> SEQ ID NO 1350
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1350
agggacuuua uggcaccuag uuc 23

<210> SEQ ID NO 1351
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1351
gggacuuuau ggcaccuagu ucc 23

<210> SEQ ID NO 1352
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1352
ggacuuuaug gcaccuaguu ccg 23

<210> SEQ ID NO 1353
<211> LENGTH: 23
<212> TYPE: RNA
<213> ORGANISM: Artificial Sequence
<220> FEATURE:

<223> OTHER INFORMATION: Synthetic Construct

<400> SEQUENCE: 1353
gacuuuaugg caccuaguuc cga 23

<210> SEQ ID NO 1354
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1354
acuuuauggc accuaguucc gag 23

<210> SEQ ID NO 1355
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1355
cuuuauggca ccuaguuccg agu 23

<210> SEQ ID NO 1356
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1356
uuuauggcac cuaguuccga gua 23

<210> SEQ ID NO 1357
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1357
uuauggcacc uaguuccgag uag 23

<210> SEQ ID NO 1358
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1358
uauggcaccu aguuccgagu agc 23

<210> SEQ ID NO 1359
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1359
auggcaccua guuccgagua gcc 23

-continued

<210> SEQ ID NO 1360
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1360
uggcaccuag uuccgaguag ccc 23

<210> SEQ ID NO 1361
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1361
ggcaccuagu uccgaguagc cca 23

<210> SEQ ID NO 1362
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1362
gcaccuaguu ccgaguagcc cag 23

<210> SEQ ID NO 1363
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1363
caccuaguuc cgaguagccc agg 23

<210> SEQ ID NO 1364
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1364
accuaguucc gaguagccca ggg 23

<210> SEQ ID NO 1365
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1365
ccuaguuccg aguagcccag ggc 23

<210> SEQ ID NO 1366
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1366
cuaguuccga guagcccagg gca 23

<210> SEQ ID NO 1367
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1367
ugauaaggcu cuuaaggguc uc 22

<210> SEQ ID NO 1368
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1368
gauaaggcuc uuaagggucu ca 22

<210> SEQ ID NO 1369
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1369
auaaggcucu uaagggucuc aa 22

<210> SEQ ID NO 1370
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1370
uaaggcucuu aagggucuca aa 22

<210> SEQ ID NO 1371
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1371
aaggcucuua agggucucaa ag 22

<210> SEQ ID NO 1372
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1372
aggcucuuaa gggucucaaa gc 22

<210> SEQ ID NO 1373
<211> LENGTH: 22

-continued

<210> SEQ ID NO 1373
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1373
ggcucuuaag ggucucaaag cu                                               22

<210> SEQ ID NO 1374
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1374
gcucuuaagg gucucaaagc uc                                               22

<210> SEQ ID NO 1375
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1375
cucuuaaggg ucucaaagcu cu                                               22

<210> SEQ ID NO 1376
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1376
ucuuaagggu cucaaagcuc uu                                               22

<210> SEQ ID NO 1377
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1377
cuuaaggguc ucaaagcucu ua                                               22

<210> SEQ ID NO 1378
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1378
uuaagggucu caaagcucuu ag                                               22

<210> SEQ ID NO 1379
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1379
uaagggucuc aaagcucuua gg 22

<210> SEQ ID NO 1380
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1380
aagggucuca aagcucuuag gg 22

<210> SEQ ID NO 1381
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1381
agggucucaa agcucuuagg gu 22

<210> SEQ ID NO 1382
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1382
gggucucaaa gcucuuaggg uc 22

<210> SEQ ID NO 1383
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1383
ggucucaaag cucuuagggu cc 22

<210> SEQ ID NO 1384
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1384
gucucaaagc ucuuaggguc cu 22

<210> SEQ ID NO 1385
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1385
ucucaaagcu cuuaggg ucc ua 22

<210> SEQ ID NO 1386
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1386
cucaaagcuc uuagggucuu aa 22

<210> SEQ ID NO 1387
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1387
ucaaagcucu uaggguccua ag 22

<210> SEQ ID NO 1388
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1388
caaagcucuu aggguccuaa gg 22

<210> SEQ ID NO 1389
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1389
aaagcucuua ggguccuaag gg 22

<210> SEQ ID NO 1390
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1390
aagcucuuag gguccuaagg ga 22

<210> SEQ ID NO 1391
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1391
agcucuuagg guccuaaggg ac 22

<210> SEQ ID NO 1392
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1392
gcucuuaggg uccuaaggga cu 22

<210> SEQ ID NO 1393
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1393
cucuuagggu ccuaagggac uu                                            22

<210> SEQ ID NO 1394
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1394
ucuuaggguc cuaagggacu uu                                            22

<210> SEQ ID NO 1395
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1395
cuuagggucc uaagggacuu ua                                            22

<210> SEQ ID NO 1396
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1396
uuaggguccu aagggacuuu au                                            22

<210> SEQ ID NO 1397
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1397
uaggguccua agggacuuua ug                                            22

<210> SEQ ID NO 1398
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1398
aggguccuaa gggacuuuau gg                                            22

<210> SEQ ID NO 1399
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1399
ggguccuaag ggacuuuaug gc                                           22

<210> SEQ ID NO 1400
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1400
gguccuaagg gacuuuaugg ca                                           22

<210> SEQ ID NO 1401
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1401
guccuaaggg acuuuauggc ac                                           22

<210> SEQ ID NO 1402
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1402
uccuaaggga cuuuauggca cc                                           22

<210> SEQ ID NO 1403
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1403
ccuaagggac uuuauggcac cu                                           22

<210> SEQ ID NO 1404
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1404
cuaagggacu uuauggcacc ua                                           22

<210> SEQ ID NO 1405
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1405
uaagggacuu uauggcaccu ag                                           22

<210> SEQ ID NO 1406

<211> LENGTH: 22
<212> TYPE: RNA
<213> ORGANISM: Artificial Sequence
<220> FEATURE:
<223> OTHER INFORMATION: Synthetic Construct

<400> SEQUENCE: 1406
aagggacuuu auggcaccua gu 22

<210> SEQ ID NO 1407
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1407
agggacuuua uggcaccuag uu 22

<210> SEQ ID NO 1408
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1408
gggacuuuau ggcaccuagu uc 22

<210> SEQ ID NO 1409
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1409
ggacuuuaug gcaccuaguu cc 22

<210> SEQ ID NO 1410
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1410
gacuuuaugg caccuaguuc cg 22

<210> SEQ ID NO 1411
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1411
acuuuauggc accuaguucc ga 22

<210> SEQ ID NO 1412
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1412
cuuuauggca ccuaguuccg ag 22

<210> SEQ ID NO 1413
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1413
uuuauggcac cuaguuccga gu 22

<210> SEQ ID NO 1414
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1414
uuauggcacc uaguuccgag ua 22

<210> SEQ ID NO 1415
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1415
uauggcaccu aguuccgagu ag 22

<210> SEQ ID NO 1416
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1416
auggcaccua guuccgagua gc 22

<210> SEQ ID NO 1417
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1417
uggcaccuag uuccgaguag cc 22

<210> SEQ ID NO 1418
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1418
ggcaccuagu uccgaguagc cc 22

<210> SEQ ID NO 1419
<211> LENGTH: 22
<212> TYPE: RNA

<213> ORGANISM: Artificial Sequence
<220> FEATURE:
<223> OTHER INFORMATION: Synthetic Construct

<400> SEQUENCE: 1419
gcaccuaguu ccgaguagcc ca 22

<210> SEQ ID NO 1420
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1420
caccuaguuc cgaguagccc ag 22

<210> SEQ ID NO 1421
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1421
accuaguucc gaguagccca gg 22

<210> SEQ ID NO 1422
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1422
ccuaguuccg aguagcccag gg 22

<210> SEQ ID NO 1423
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1423
cuaguuccga guagcccagg gc 22

<210> SEQ ID NO 1424
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1424
uaguuccgag uagcccaggg ca 22

<210> SEQ ID NO 1425
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1425
ugauaaggcu cuuaaggguc u 21

<210> SEQ ID NO 1426
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1426
gauaaggcuc uuaagggucu c 21

<210> SEQ ID NO 1427
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1427
auaaggcucu uaagggucuc a 21

<210> SEQ ID NO 1428
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1428
uaaggcucuu aagggucuca a 21

<210> SEQ ID NO 1429
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1429
aaggcucuua agggucucaa a 21

<210> SEQ ID NO 1430
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1430
aggcucuuaa gggucucaaa g 21

<210> SEQ ID NO 1431
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1431
ggcucuuaag ggucucaaag c 21

<210> SEQ ID NO 1432
<211> LENGTH: 21
<212> TYPE: RNA
<213> ORGANISM: Artificial Sequence
<220> FEATURE:

<223> OTHER INFORMATION: Synthetic Construct

<400> SEQUENCE: 1432
gcucuuaagg gucucaaagc u 21

<210> SEQ ID NO 1433
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1433
cucuuaaggg ucucaaagcu c 21

<210> SEQ ID NO 1434
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1434
ucuuaagggu cucaaagcuc u 21

<210> SEQ ID NO 1435
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1435
cuuaaggguc ucaaagcucu u 21

<210> SEQ ID NO 1436
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1436
uuaagggucu caaagcucuu a 21

<210> SEQ ID NO 1437
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1437
uaagggucuc aaagcucuua g 21

<210> SEQ ID NO 1438
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1438
aagggucuca aagcucuuag g 21

```
<210> SEQ ID NO 1439
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1439

agggucucaa agcucuuagg g                                              21

<210> SEQ ID NO 1440
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1440

gggucucaaa gcucuuaggg u                                              21

<210> SEQ ID NO 1441
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1441

ggucucaaag cucuuagggu c                                              21

<210> SEQ ID NO 1442
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1442

gucucaaagc ucuuaggguc c                                              21

<210> SEQ ID NO 1443
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1443

ucucaaagcu cuuagggucc u                                              21

<210> SEQ ID NO 1444
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1444

cucaaagcuc uuaggguccu a                                              21

<210> SEQ ID NO 1445
<211> LENGTH: 21
<212> TYPE: RNA
<213> ORGANISM: Artificial Sequence
<220> FEATURE:
<223> OTHER INFORMATION: Synthetic Construct
```

```
<400> SEQUENCE: 1445

ucaaagcucu uaggguccua a                                              21

<210> SEQ ID NO 1446
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1446

caaagcucuu aggguccuaa g                                              21

<210> SEQ ID NO 1447
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1447

aaagcucuua ggguccuaag g                                              21

<210> SEQ ID NO 1448
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1448

aagcucuuag gguccuaagg g                                              21

<210> SEQ ID NO 1449
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1449

agcucuuagg guccuaaggg a                                              21

<210> SEQ ID NO 1450
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1450

gcucuuaggg uccuaaggga c                                              21

<210> SEQ ID NO 1451
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1451

cucuuagggu ccuaagggac u                                              21

<210> SEQ ID NO 1452
<211> LENGTH: 21
```

<212> TYPE: RNA
<213> ORGANISM: Artificial Sequence
<220> FEATURE:
<223> OTHER INFORMATION: Synthetic Construct

<400> SEQUENCE: 1452 ucuuagggucc cuaagggacu u 21

<210> SEQ ID NO 1453
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1453
cuuagggucc uaagggacuu u 21

<210> SEQ ID NO 1454
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1454
uuaggguccu aagggacuuu a 21

<210> SEQ ID NO 1455
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1455
uaggguccua agggacuuua u 21

<210> SEQ ID NO 1456
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1456
aggguccuaa gggacuuuau g 21

<210> SEQ ID NO 1457
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1457
ggguccuaag ggacuuuaug g 21

<210> SEQ ID NO 1458
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1458
gguccuaagg gacuuuaugg c 21

<210> SEQ ID NO 1459
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1459
guccuaaggg acuuuauggc a 21

<210> SEQ ID NO 1460
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1460
uccuaaggga cuuuauggca c 21

<210> SEQ ID NO 1461
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1461
ccuaagggac uuuauggcac c 21

<210> SEQ ID NO 1462
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1462
cuaagggacu uuauggcacc u 21

<210> SEQ ID NO 1463
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1463
uaagggacuu uauggcaccu a 21

<210> SEQ ID NO 1464
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1464
aagggacuuu auggcaccua g 21

<210> SEQ ID NO 1465
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1465
agggacuuua uggcaccuag u 21

<210> SEQ ID NO 1466
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1466
gggacuuuau ggcaccuagu u 21

<210> SEQ ID NO 1467
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1467
ggacuuuaug gcaccuaguu c 21

<210> SEQ ID NO 1468
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1468
gacuuuaugg caccuaguuc c 21

<210> SEQ ID NO 1469
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1469
acuuuauggc accuaguucc g 21

<210> SEQ ID NO 1470
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1470
cuuuauggca ccuaguuccg a 21

<210> SEQ ID NO 1471
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1471
uuuauggcac cuaguuccga g 21

<210> SEQ ID NO 1472
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1472
uuauggcacc uaguuccgag u 21

<210> SEQ ID NO 1473
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1473
uauggcaccu aguuccgagu a 21

<210> SEQ ID NO 1474
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1474
auggcaccua guuccgagua g 21

<210> SEQ ID NO 1475
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1475
uggcaccuag uuccgaguag c 21

<210> SEQ ID NO 1476
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1476
ggcaccuagu uccgaguagc c 21

<210> SEQ ID NO 1477
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1477
gcaccuaguu ccgaguagcc c 21

<210> SEQ ID NO 1478
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1478
caccuaguuc cgaguagccc a 21

<210> SEQ ID NO 1479
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1479
accuaguucc gaguagccca g 21

<210> SEQ ID NO 1480
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1480
ccuaguuccg aguagcccag g 21

<210> SEQ ID NO 1481
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1481
cuaguuccga guagcccagg g 21

<210> SEQ ID NO 1482
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1482
uaguuccgag uagcccaggg c 21

<210> SEQ ID NO 1483
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1483
aguuccgagu agcccagggc a 21

<210> SEQ ID NO 1484
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1484
ugauaaggcu cuuaaggguc 20

<210> SEQ ID NO 1485

<211> LENGTH: 20
<212> TYPE: RNA
<213> ORGANISM: Artificial Sequence
<220> FEATURE:
<223> OTHER INFORMATION: Synthetic Construct

<400> SEQUENCE: 1485
gauaaggcuc uuaagggucu 20

<210> SEQ ID NO 1486
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1486
auaaggcucu uaagggucuc 20

<210> SEQ ID NO 1487
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1487
uaaggcucuu aagggucuca 20

<210> SEQ ID NO 1488
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1488
aaggcucuua agggucucaa 20

<210> SEQ ID NO 1489
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1489
aggcucuuaa gggucucaaa 20

<210> SEQ ID NO 1490
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1490
ggcucuuaag ggucucaaag 20

<210> SEQ ID NO 1491
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1491
gcucuuaagg gucucaaagc 20

<210> SEQ ID NO 1492
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1492
cucuuaaggg ucucaaagcu 20

<210> SEQ ID NO 1493
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1493
ucuuaagggu cucaaagcuc 20

<210> SEQ ID NO 1494
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1494
cuuaaggguc ucaaagcucu 20

<210> SEQ ID NO 1495
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1495
uuaagggucu caaagcucuu 20

<210> SEQ ID NO 1496
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1496
uaagggucuc aaagcucuua 20

<210> SEQ ID NO 1497
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1497
aagggucuca aagcucuuag 20

<210> SEQ ID NO 1498
<211> LENGTH: 20
<212> TYPE: RNA

```
<213> ORGANISM: Artificial Sequence
<220> FEATURE:
<223> OTHER INFORMATION: Synthetic Construct

<400> SEQUENCE: 1498

agggucucaa agcucuuagg                                                    20

<210> SEQ ID NO 1499
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1499

gggucucaaa gcucuuaggg                                                    20

<210> SEQ ID NO 1500
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1500

ggucucaaag cucuuagggu                                                    20

<210> SEQ ID NO 1501
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1501

gucucaaagc ucuuaggguc                                                    20

<210> SEQ ID NO 1502
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1502

ucucaaagcu cuuagggucc                                                    20

<210> SEQ ID NO 1503
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1503

cucaaagcuc uuaggguccu                                                    20

<210> SEQ ID NO 1504
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1504

ucaaagcucu uaggguccua                                                    20
```

<210> SEQ ID NO 1505
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1505
caaagcucuu agggucuaa 20

<210> SEQ ID NO 1506
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1506
aaagcucuua ggguccuaag 20

<210> SEQ ID NO 1507
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1507
aagcucuuag gguccuaagg 20

<210> SEQ ID NO 1508
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1508
agcucuuagg guccuaaggg 20

<210> SEQ ID NO 1509
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1509
gcucuuaggg uccuaaggga 20

<210> SEQ ID NO 1510
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1510
cucuuagggu ccuaagggac 20

<210> SEQ ID NO 1511
<211> LENGTH: 20
<212> TYPE: RNA
<213> ORGANISM: Artificial Sequence
<220> FEATURE:

```
<223> OTHER INFORMATION: Synthetic Construct

<400> SEQUENCE: 1511

ucuuaggguc cuaagggacu                                        20

<210> SEQ ID NO 1512
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1512

cuuagggucc uaagggacuu                                        20

<210> SEQ ID NO 1513
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1513

uuaggguccu aagggacuuu                                        20

<210> SEQ ID NO 1514
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1514

uaggguccua agggacuuua                                        20

<210> SEQ ID NO 1515
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1515

aggguccuaa gggacuuuau                                        20

<210> SEQ ID NO 1516
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1516

ggguccuaag ggacuuuaug                                        20

<210> SEQ ID NO 1517
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1517

gguccuaagg gacuuuaugg                                        20
```

<210> SEQ ID NO 1518
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1518
guccuaaggg acuuuauggc 20

<210> SEQ ID NO 1519
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1519
uccuaaggga cuuuauggca 20

<210> SEQ ID NO 1520
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1520
ccuaagggac uuuauggcac 20

<210> SEQ ID NO 1521
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1521
cuaagggacu uuauggcacc 20

<210> SEQ ID NO 1522
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1522
uaagggacuu uauggcaccu 20

<210> SEQ ID NO 1523
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1523
aagggacuuu auggcaccua 20

<210> SEQ ID NO 1524
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1524
agggacuuua uggcaccuag 20

<210> SEQ ID NO 1525
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1525
gggacuuuau ggcaccuagu 20

<210> SEQ ID NO 1526
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1526
ggacuuuaug gcaccuaguu 20

<210> SEQ ID NO 1527
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1527
gacuuuaugg caccuaguuc 20

<210> SEQ ID NO 1528
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1528
acuuuauggc accuaguucc 20

<210> SEQ ID NO 1529
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1529
cuuuauggca ccuaguuccg 20

<210> SEQ ID NO 1530
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1530
uuuauggcac cuaguuccga 20

<210> SEQ ID NO 1531
<211> LENGTH: 20

<212> TYPE: RNA
<213> ORGANISM: Artificial Sequence
<220> FEATURE:
<223> OTHER INFORMATION: Synthetic Construct

<400> SEQUENCE: 1531
uuauggcacc uaguuccgag 20

<210> SEQ ID NO 1532
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1532
uauggcaccu aguuccgagu 20

<210> SEQ ID NO 1533
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1533
auggcaccua guuccgagua 20

<210> SEQ ID NO 1534
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1534
uggcaccuag uuccgaguag 20

<210> SEQ ID NO 1535
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1535
ggcaccuagu uccgaguagc 20

<210> SEQ ID NO 1536
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1536
gcaccuaguu ccgaguagcc 20

<210> SEQ ID NO 1537
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1537
caccuaguuc cgaguagccc 20

<210> SEQ ID NO 1538
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1538
accuaguucc gaguagccca 20

<210> SEQ ID NO 1539
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1539
ccuaguuccg aguagcccag 20

<210> SEQ ID NO 1540
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1540
cuaguuccga guagcccagg 20

<210> SEQ ID NO 1541
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1541
uaguuccgag uagcccaggg 20

<210> SEQ ID NO 1542
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1542
aguuccgagu agcccagggc 20

<210> SEQ ID NO 1543
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1543
guuccgagua gcccagggca 20

<210> SEQ ID NO 1544
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1544
ugauaaggcu cuuaagggu 19

<210> SEQ ID NO 1545
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1545
gauaaggcuc uuaaggguc 19

<210> SEQ ID NO 1546
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1546
auaaggcucu uaagggucu 19

<210> SEQ ID NO 1547
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1547
uaaggcucuu aagggucuc 19

<210> SEQ ID NO 1548
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1548
aaggcucuua agggucuca 19

<210> SEQ ID NO 1549
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1549
aggcucuuaa gggucucaa 19

<210> SEQ ID NO 1550
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1550
ggcucuuaag ggucucaaa 19

<210> SEQ ID NO 1551
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1551
gcucuuaagg gucucaaag 19

<210> SEQ ID NO 1552
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1552
cucuuaaggg ucucaaagc 19

<210> SEQ ID NO 1553
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1553
ucuuaagggu cucaaagcu 19

<210> SEQ ID NO 1554
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1554
cuuaaggguc ucaaagcuc 19

<210> SEQ ID NO 1555
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1555
uuaagggucu caaagcucu 19

<210> SEQ ID NO 1556
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1556
uaagggucuc aaagcucuu 19

<210> SEQ ID NO 1557
<211> LENGTH: 19
<212> TYPE: RNA
<213> ORGANISM: Artificial Sequence
<220> FEATURE:
<223> OTHER INFORMATION: Synthetic Construct -continued

<400> SEQUENCE: 1557
aagggucuca aagcucuua                                              19

<210> SEQ ID NO 1558
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1558
agggucucaa agcucuuag                                              19

<210> SEQ ID NO 1559
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1559
gggucucaaa gcucuuagg                                              19

<210> SEQ ID NO 1560
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1560
ggucucaaag cucuuaggg                                              19

<210> SEQ ID NO 1561
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1561
gucucaaagc ucuuagggu                                              19

<210> SEQ ID NO 1562
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1562
ucucaaagcu cuuaggguc                                              19

<210> SEQ ID NO 1563
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1563
cucaaagcuc uuagggucc                                              19

<210> SEQ ID NO 1564

<211> LENGTH: 19
<212> TYPE: RNA
<213> ORGANISM: Artificial Sequence
<220> FEATURE:
<223> OTHER INFORMATION: Synthetic Construct

<400> SEQUENCE: 1564
ucaaagcucu uagggguccu 19

<210> SEQ ID NO 1565
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1565
caaagcucuu aggguccua 19

<210> SEQ ID NO 1566
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1566
aaagcucuua ggguccuaa 19

<210> SEQ ID NO 1567
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1567
aagcucuuag gguccuaag 19

<210> SEQ ID NO 1568
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1568
agcucuuagg guccuaagg 19

<210> SEQ ID NO 1569
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1569
gcucuuaggg uccuaaggg 19

<210> SEQ ID NO 1570
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1570
cucuuagggu ccuaaggga                                        19

<210> SEQ ID NO 1571
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1571
ucuuaggguc cuaagggac                                        19

<210> SEQ ID NO 1572
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1572
cuuagggucc uaagggacu                                        19

<210> SEQ ID NO 1573
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1573
uuaggguccu aagggacuu                                        19

<210> SEQ ID NO 1574
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1574
uaggguccua agggacuuu                                        19

<210> SEQ ID NO 1575
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1575
aggguccuaa gggacuuua                                        19

<210> SEQ ID NO 1576
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1576
ggguccuaag ggacuuuau                                        19

<210> SEQ ID NO 1577
<211> LENGTH: 19
<212> TYPE: RNA

<213> ORGANISM: Artificial Sequence
<220> FEATURE:
<223> OTHER INFORMATION: Synthetic Construct

<400> SEQUENCE: 1577
gguccuaagg gacuuuaug 19

<210> SEQ ID NO 1578
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1578
guccuaaggg acuuuaugg 19

<210> SEQ ID NO 1579
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1579
uccuaaggga cuuuauggc 19

<210> SEQ ID NO 1580
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1580
ccuaagggac uuuauggca 19

<210> SEQ ID NO 1581
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1581
cuaagggacu uuauggcac 19

<210> SEQ ID NO 1582
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1582
uaagggacuu uauggcacc 19

<210> SEQ ID NO 1583
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1583
aagggacuuu auggcaccu 19

<210> SEQ ID NO 1584
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1584
agggacuuua uggcaccua 19

<210> SEQ ID NO 1585
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1585
gggacuuuau ggcaccuag 19

<210> SEQ ID NO 1586
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1586
ggacuuuaug gcaccuagu 19

<210> SEQ ID NO 1587
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1587
gacuuuaugg caccuaguu 19

<210> SEQ ID NO 1588
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1588
acuuuauggc accuaguuc 19

<210> SEQ ID NO 1589
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1589
cuuuauggca ccuaguucc 19

<210> SEQ ID NO 1590
<211> LENGTH: 19
<212> TYPE: RNA
<213> ORGANISM: Artificial Sequence
<220> FEATURE:

<223> OTHER INFORMATION: Synthetic Construct

<400> SEQUENCE: 1590
uuuauggcac cuaguuccg 19

<210> SEQ ID NO 1591
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1591
uuauggcacc uaguuccga 19

<210> SEQ ID NO 1592
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1592
uauggcaccu aguuccgag 19

<210> SEQ ID NO 1593
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1593
auggcaccua guuccgagu 19

<210> SEQ ID NO 1594
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1594
uggcaccuag uuccgagua 19

<210> SEQ ID NO 1595
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1595
ggcaccuagu uccgaguag 19

<210> SEQ ID NO 1596
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1596
gcaccuaguu ccgaguagc 19

<210> SEQ ID NO 1597
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1597
caccuaguuc cgaguagcc 19

<210> SEQ ID NO 1598
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1598
accuaguucc gaguagccc 19

<210> SEQ ID NO 1599
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1599
ccuaguuccg aguagccca 19

<210> SEQ ID NO 1600
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1600
cuaguuccga guagcccag 19

<210> SEQ ID NO 1601
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1601
uaguuccgag uagcccagg 19

<210> SEQ ID NO 1602
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1602
aguuccgagu agcccaggg 19

<210> SEQ ID NO 1603
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1603
guuccgagua gcccagggc 19

<210> SEQ ID NO 1604
<211> LENGTH: 19
<212> TYPE: RNA
<213> ORGANISM: Artificial Sequence
<220> FEATURE:
<223> OTHER INFORMATION: Synthetic Construct

<400> SEQUENCE: 1604
uuccgaguag cccagggca 19

<210> SEQ ID NO 1605
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1605
ugauaaggcu cuuaaggg 18

<210> SEQ ID NO 1606
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1606
gauaaggcuc uuaagggu 18

<210> SEQ ID NO 1607
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1607
auaaggcucu uaaggguc 18

<210> SEQ ID NO 1608
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1608
uaaggcucuu aagggucu 18

<210> SEQ ID NO 1609
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1609
aaggcucuua agggucuc 18

<210> SEQ ID NO 1610
<211> LENGTH: 18

<212> TYPE: RNA
<213> ORGANISM: Artificial Sequence
<220> FEATURE:
<223> OTHER INFORMATION: Synthetic Construct

<400> SEQUENCE: 1610
aggcucuuaa gggucuca 18

<210> SEQ ID NO 1611
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1611
ggcucuuaag ggucucaa 18

<210> SEQ ID NO 1612
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1612
gcucuuaagg gucucaaa 18

<210> SEQ ID NO 1613
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1613
cucuuaaggg ucucaaag 18

<210> SEQ ID NO 1614
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1614
ucuuaagggu cucaaagc 18

<210> SEQ ID NO 1615
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1615
cuuaaggguc ucaaagcu 18

<210> SEQ ID NO 1616
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1616
uuaagggucu caaagcuc 18

<210> SEQ ID NO 1617
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1617
uaagggucuc aaagcucu 18

<210> SEQ ID NO 1618
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1618
aagggucuca aagcucuu 18

<210> SEQ ID NO 1619
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1619
agggucucaa agcucuua 18

<210> SEQ ID NO 1620
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1620
gggucucaaa gcucuuag 18

<210> SEQ ID NO 1621
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1621
ggucucaaag cucuuagg 18

<210> SEQ ID NO 1622
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1622
gucucaaagc ucuuaggg 18

<210> SEQ ID NO 1623
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1623
ucucaaagcu cuuagggu 18

<210> SEQ ID NO 1624
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1624
cucaaagcuc uuaggguc 18

<210> SEQ ID NO 1625
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1625
ucaaagcucu uagggucc 18

<210> SEQ ID NO 1626
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1626
caaagcucuu aggguccu 18

<210> SEQ ID NO 1627
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1627
aaagcucuua ggguccua 18

<210> SEQ ID NO 1628
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1628
aagcucuuag gguccuaa 18

<210> SEQ ID NO 1629
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1629
agcucuuagg guccuaag 18

```
<210> SEQ ID NO 1630
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1630

gcucuuaggg uccuaagg                                                 18

<210> SEQ ID NO 1631
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1631

cucuuagggu ccuaaggg                                                 18

<210> SEQ ID NO 1632
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1632

ucuuaggguc cuaaggga                                                 18

<210> SEQ ID NO 1633
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1633

cuuagggucc uaagggac                                                 18

<210> SEQ ID NO 1634
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1634

uuaggguccu aagggacu                                                 18

<210> SEQ ID NO 1635
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1635

uaggguccua agggacuu                                                 18

<210> SEQ ID NO 1636
<211> LENGTH: 18
<212> TYPE: RNA
<213> ORGANISM: Artificial Sequence
<220> FEATURE:
<223> OTHER INFORMATION: Synthetic Construct
```

<400> SEQUENCE: 1636
aggguccuaa gggacuuu 18

<210> SEQ ID NO 1637
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1637
ggguccuaag ggacuuua 18

<210> SEQ ID NO 1638
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1638
gguccuaagg gacuuuau 18

<210> SEQ ID NO 1639
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1639
guccuaaggg acuuuaug 18

<210> SEQ ID NO 1640
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1640
uccuaaggga cuuuaugg 18

<210> SEQ ID NO 1641
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1641
ccuaagggac uuuauggc 18

<210> SEQ ID NO 1642
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1642
cuaagggacu uuauggca 18

<210> SEQ ID NO 1643

<211> LENGTH: 18
<212> TYPE: RNA
<213> ORGANISM: Artificial Sequence
<220> FEATURE:
<223> OTHER INFORMATION: Synthetic Construct

<400> SEQUENCE: 1643
uaagggacuu uauggcac 18

<210> SEQ ID NO 1644
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1644
aagggacuuu auggcacc 18

<210> SEQ ID NO 1645
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1645
agggacuuua uggcaccu 18

<210> SEQ ID NO 1646
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1646
gggacuuuau ggcaccua 18

<210> SEQ ID NO 1647
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1647
ggacuuuaug gcaccuag 18

<210> SEQ ID NO 1648
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1648
gacuuuaugg caccuagu 18

<210> SEQ ID NO 1649
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1649
acuuuauggc accuaguu 18

<210> SEQ ID NO 1650
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1650
cuuuauggca ccuaguuc 18

<210> SEQ ID NO 1651
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1651
uuuauggcac cuaguucc 18

<210> SEQ ID NO 1652
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1652
uuauggcacc uaguuccg 18

<210> SEQ ID NO 1653
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1653
uauggcaccu aguuccga 18

<210> SEQ ID NO 1654
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1654
auggcaccua guuccgag 18

<210> SEQ ID NO 1655
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1655
uggcaccuag uuccgagu 18

<210> SEQ ID NO 1656
<211> LENGTH: 18
<212> TYPE: RNA

<213> ORGANISM: Artificial Sequence
<220> FEATURE:
<223> OTHER INFORMATION: Synthetic Construct

<400> SEQUENCE: 1656
ggcaccuagu uccgagua 18

<210> SEQ ID NO 1657
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1657
gcaccuaguu ccgaguag 18

<210> SEQ ID NO 1658
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1658
caccuaguuc cgaguagc 18

<210> SEQ ID NO 1659
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1659
accuaguucc gaguagcc 18

<210> SEQ ID NO 1660
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1660
ccuaguuccg aguagccc 18

<210> SEQ ID NO 1661
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1661
cuaguuccga guagccca 18

<210> SEQ ID NO 1662
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1662
uaguuccgag uagcccag 18

<210> SEQ ID NO 1663
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1663
aguuccgagu agcccagg 18

<210> SEQ ID NO 1664
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1664
guuccgagua gcccaggg 18

<210> SEQ ID NO 1665
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1665
uuccgaguag cccagggc 18

<210> SEQ ID NO 1666
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1666
uccgaguagc ccagggca 18

<210> SEQ ID NO 1667
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1667
ugauaaggcu cuuaagg 17

<210> SEQ ID NO 1668
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1668
gauaaggcuc uuaaggg 17

<210> SEQ ID NO 1669
<211> LENGTH: 17
<212> TYPE: RNA
<213> ORGANISM: Artificial Sequence
<220> FEATURE:

```
<223> OTHER INFORMATION: Synthetic Construct

<400> SEQUENCE: 1669

auaaggcucu uaagggu                                                17

<210> SEQ ID NO 1670
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1670

uaaggcucuu aaggguc                                                17

<210> SEQ ID NO 1671
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1671

aaggcucuua agggucu                                                17

<210> SEQ ID NO 1672
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1672

aggcucuuaa gggucuc                                                17

<210> SEQ ID NO 1673
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1673

ggcucuuaag ggucuca                                                17

<210> SEQ ID NO 1674
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1674

gcucuuaagg gucucaa                                                17

<210> SEQ ID NO 1675
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1675

cucuuaaggg ucucaaa                                                17
```

<210> SEQ ID NO 1676
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1676
ucuuaagggu cucaaag 17

<210> SEQ ID NO 1677
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1677
cuuaaggguc ucaaagc 17

<210> SEQ ID NO 1678
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1678
uuaagggucu caaagcu 17

<210> SEQ ID NO 1679
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1679
uaagggucuc aaagcuc 17

<210> SEQ ID NO 1680
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1680
aagggucuca aagcucu 17

<210> SEQ ID NO 1681
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1681
agggucucaa agcucuu 17

<210> SEQ ID NO 1682
<211> LENGTH: 17
<212> TYPE: RNA
<213> ORGANISM: Artificial Sequence
<220> FEATURE:
<223> OTHER INFORMATION: Synthetic Construct -continued

```
<400> SEQUENCE: 1682

gggucucaaa gcucuua                                                     17

<210> SEQ ID NO 1683
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1683

ggucucaaag cucuuag                                                     17

<210> SEQ ID NO 1684
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1684

gucucaaagc ucuuagg                                                     17

<210> SEQ ID NO 1685
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1685

ucucaaagcu cuuaggg                                                     17

<210> SEQ ID NO 1686
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1686

cucaaagcuc uuagggu                                                     17

<210> SEQ ID NO 1687
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1687

ucaaagcucu uaggguc                                                     17

<210> SEQ ID NO 1688
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1688

caaagcucuu agggucc                                                     17

<210> SEQ ID NO 1689
<211> LENGTH: 17
```

<212> TYPE: RNA
<213> ORGANISM: Artificial Sequence
<220> FEATURE:
<223> OTHER INFORMATION: Synthetic Construct

<400> SEQUENCE: 1689
aaagcucuua ggguccu 17

<210> SEQ ID NO 1690
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1690
aagcucuuag gguccua 17

<210> SEQ ID NO 1691
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1691
agcucuuagg guccuaa 17

<210> SEQ ID NO 1692
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1692
gcucuuaggg uccuaag 17

<210> SEQ ID NO 1693
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1693
cucuuagggu ccuaagg 17

<210> SEQ ID NO 1694
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1694
ucuuaggguc cuaaggg 17

<210> SEQ ID NO 1695
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1695
cuuagggucc uaaggga 17

<210> SEQ ID NO 1696
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1696
uuaggguccu aagggac 17

<210> SEQ ID NO 1697
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1697
uaggguccua agggacu 17

<210> SEQ ID NO 1698
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1698
aggguccuaa gggacuu 17

<210> SEQ ID NO 1699
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1699
ggguccuaag ggacuuu 17

<210> SEQ ID NO 1700
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1700
gguccuaagg gacuuua 17

<210> SEQ ID NO 1701
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1701
guccuaaggg acuuuau 17

<210> SEQ ID NO 1702
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1702
uccuaaggga cuuuaug 17

<210> SEQ ID NO 1703
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1703
ccuaagggac uuuaugg 17

<210> SEQ ID NO 1704
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1704
cuaagggacu uuauggc 17

<210> SEQ ID NO 1705
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1705
uaagggacuu uauggca 17

<210> SEQ ID NO 1706
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1706
aagggacuuu auggcac 17

<210> SEQ ID NO 1707
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1707
agggacuuua uggcacc 17

<210> SEQ ID NO 1708
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1708
gggacuuuau ggcaccu 17

<210> SEQ ID NO 1709
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1709
ggacuuuaug gcaccua 17

<210> SEQ ID NO 1710
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1710
gacuuuaugg caccuag 17

<210> SEQ ID NO 1711
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1711
acuuuauggc accuagu 17

<210> SEQ ID NO 1712
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1712
cuuuauggca ccuaguu 17

<210> SEQ ID NO 1713
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1713
uuuauggcac cuaguuc 17

<210> SEQ ID NO 1714
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1714
uuauggcacc uaguucc 17

<210> SEQ ID NO 1715
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1715
uauggcaccu aguuccg 17

<210> SEQ ID NO 1716
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1716
auggcaccua guuccga 17

<210> SEQ ID NO 1717
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1717
uggcaccuag uuccgag 17

<210> SEQ ID NO 1718
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1718
ggcaccuagu uccgagu 17

<210> SEQ ID NO 1719
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1719
gcaccuaguu ccgagua 17

<210> SEQ ID NO 1720
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1720
caccuaguuc cgaguag 17

<210> SEQ ID NO 1721
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1721
accuaguucc gaguagc 17

<210> SEQ ID NO 1722

<211> LENGTH: 17
<212> TYPE: RNA
<213> ORGANISM: Artificial Sequence
<220> FEATURE:
<223> OTHER INFORMATION: Synthetic Construct

<400> SEQUENCE: 1722
ccuaguuccg aguagcc 17

<210> SEQ ID NO 1723
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1723
cuaguuccga guagccc 17

<210> SEQ ID NO 1724
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1724
uaguuccgag uagccca 17

<210> SEQ ID NO 1725
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1725
aguuccgagu agcccag 17

<210> SEQ ID NO 1726
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1726
guuccgagua gcccagg 17

<210> SEQ ID NO 1727
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1727
uuccgaguag cccaggg 17

<210> SEQ ID NO 1728
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1728
uccgaguagc ccagggc 17

<210> SEQ ID NO 1729
<211> LENGTH: 17
<212> TYPE: RNA
<213> ORGANISM: Artificial Sequence
<220> FEATURE:
<223> OTHER INFORMATION: Synthetic Construct

<400> SEQUENCE: 1729
ccgaguagcc cagggca 17

<210> SEQ ID NO 1730
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1730
ugauaaggcu cuuaag 16

<210> SEQ ID NO 1731
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1731
gauaaggcuc uuaagg 16

<210> SEQ ID NO 1732
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1732
auaaggcucu uaaggg 16

<210> SEQ ID NO 1733
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1733
uaaggcucuu aagggu 16

<210> SEQ ID NO 1734
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1734
aaggcucuua aggguc 16

<210> SEQ ID NO 1735
<211> LENGTH: 16
<212> TYPE: RNA

<213> ORGANISM: Artificial Sequence
<220> FEATURE:
<223> OTHER INFORMATION: Synthetic Construct

<400> SEQUENCE: 1735
aggcucuuaa gggucu 16

<210> SEQ ID NO 1736
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1736
ggcucuuaag ggucuc 16

<210> SEQ ID NO 1737
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1737
gcucuuaagg gucuca 16

<210> SEQ ID NO 1738
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1738
cucuuaaggg ucucaa 16

<210> SEQ ID NO 1739
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1739
ucuuaagggu cucaaa 16

<210> SEQ ID NO 1740
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1740
cuuaaggguc ucaaag 16

<210> SEQ ID NO 1741
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1741
uuaagggucu caaagc 16

<210> SEQ ID NO 1742
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1742
uaagggucuc aaagcu 16

<210> SEQ ID NO 1743
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1743
aagggucuca aagcuc 16

<210> SEQ ID NO 1744
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1744
agggucucaa agcucu 16

<210> SEQ ID NO 1745
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1745
gggucucaaa gcucuu 16

<210> SEQ ID NO 1746
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1746
ggucucaaag cucuua 16

<210> SEQ ID NO 1747
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1747
gucucaaagc ucuuag 16

<210> SEQ ID NO 1748
<211> LENGTH: 16
<212> TYPE: RNA
<213> ORGANISM: Artificial Sequence
<220> FEATURE:

<223> OTHER INFORMATION: Synthetic Construct

<400> SEQUENCE: 1748
ucucaaagcu cuuagg 16

<210> SEQ ID NO 1749
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1749
cucaaagcuc uuaggg 16

<210> SEQ ID NO 1750
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1750
ucaaagcucu uagggu 16

<210> SEQ ID NO 1751
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1751
caaagcucuu aggguc 16

<210> SEQ ID NO 1752
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1752
aaagcucuua ggaucc 16

<210> SEQ ID NO 1753
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1753
aagcucuuag gguccu 16

<210> SEQ ID NO 1754
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1754
agcucuuagg guccua 16

<210> SEQ ID NO 1755
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1755
gcucuuaggg uccuaa 16

<210> SEQ ID NO 1756
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1756
cucuuagggu ccuaag 16

<210> SEQ ID NO 1757
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1757
ucuuaggguc cuaagg 16

<210> SEQ ID NO 1758
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1758
cuuagggucc uaaggg 16

<210> SEQ ID NO 1759
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1759
uuaggguccu aaggga 16

<210> SEQ ID NO 1760
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1760
uaggguccua agggac 16

<210> SEQ ID NO 1761
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1761
aggguccuaa gggacu 16

<210> SEQ ID NO 1762
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1762
ggguccuaag ggacuu 16

<210> SEQ ID NO 1763
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1763
gguccuaagg gacuuu 16

<210> SEQ ID NO 1764
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1764
guccuaaggg acuuua 16

<210> SEQ ID NO 1765
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1765
uccuaaggga cuuuau 16

<210> SEQ ID NO 1766
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1766
ccuaagggac uuuaug 16

<210> SEQ ID NO 1767
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1767
cuaagggacu uuaugg 16

<210> SEQ ID NO 1768
<211> LENGTH: 16

<212> TYPE: RNA
<213> ORGANISM: Artificial Sequence
<220> FEATURE:
<223> OTHER INFORMATION: Synthetic Construct

<400> SEQUENCE: 1768
uaagggacuu uauggc 16

<210> SEQ ID NO 1769
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1769
aagggacuuu auggca 16

<210> SEQ ID NO 1770
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1770
agggacuuua uggcac 16

<210> SEQ ID NO 1771
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1771
gggacuuuau ggcacc 16

<210> SEQ ID NO 1772
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1772
ggacuuuaug gcaccu 16

<210> SEQ ID NO 1773
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1773
gacuuuaugg caccua 16

<210> SEQ ID NO 1774
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1774
acuuuauggc accuag 16

<210> SEQ ID NO 1775
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1775
cuuuauggca ccuagu 16

<210> SEQ ID NO 1776
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1776
uuuauggcac cuaguu 16

<210> SEQ ID NO 1777
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1777
uuauggcacc uaguuc 16

<210> SEQ ID NO 1778
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1778
uauggcaccu aguucc 16

<210> SEQ ID NO 1779
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1779
auggcaccua guuccg 16

<210> SEQ ID NO 1780
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1780
uggcaccuag uuccga 16

<210> SEQ ID NO 1781
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1781
ggcaccuagu uccgag 16

<210> SEQ ID NO 1782
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1782
gcaccuaguu ccgagu 16

<210> SEQ ID NO 1783
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1783
caccuaguuc cgagua 16

<210> SEQ ID NO 1784
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1784
accuaguucc gaguag 16

<210> SEQ ID NO 1785
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1785
ccuaguuccg aguagc 16

<210> SEQ ID NO 1786
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1786
cuaguuccga guagcc 16

<210> SEQ ID NO 1787
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1787
uaguuccgag uagccc 16

<210> SEQ ID NO 1788
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1788
aguuccgagu agccca 16

<210> SEQ ID NO 1789
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1789
guuccgagua gcccag 16

<210> SEQ ID NO 1790
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1790
uuccgaguag cccagg 16

<210> SEQ ID NO 1791
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1791
uccgaguagc ccaggg 16

<210> SEQ ID NO 1792
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1792
ccgaguagcc cagggc 16

<210> SEQ ID NO 1793
<211> LENGTH: 16
<212> TYPE: RNA
<213> ORGANISM: Artificial Sequence
<220> FEATURE:
<223> OTHER INFORMATION: Synthetic Construct

<400> SEQUENCE: 1793
cgaguagccc agggca 16

<210> SEQ ID NO 1794
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1794
ugauaaggcu cuuaa 15

<210> SEQ ID NO 1795
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1795
gauaaggcuc uuaag 15

<210> SEQ ID NO 1796
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1796
auaaggcucu uaagg 15

<210> SEQ ID NO 1797
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1797
uaaggcucuu aaggg 15

<210> SEQ ID NO 1798
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1798
aaggcucuua agggu 15

<210> SEQ ID NO 1799
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1799
aggcucuuaa ggguc 15

<210> SEQ ID NO 1800
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1800
ggcucuuaag ggucu 15

<210> SEQ ID NO 1801

<211> LENGTH: 15
<212> TYPE: RNA
<213> ORGANISM: Artificial Sequence
<220> FEATURE:
<223> OTHER INFORMATION: Synthetic Construct

<400> SEQUENCE: 1801
gcucuuaagg gucuc 15

<210> SEQ ID NO 1802
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1802
cucuuaaggg ucuca 15

<210> SEQ ID NO 1803
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1803
ucuuaagggu cucaa 15

<210> SEQ ID NO 1804
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1804
cuuaaggguc ucaaa 15

<210> SEQ ID NO 1805
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1805
uuaagggucu caaag 15

<210> SEQ ID NO 1806
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1806
uaagggucuc aaagc 15

<210> SEQ ID NO 1807
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1807
aagggucuca aagcu 15

<210> SEQ ID NO 1808
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1808
agggucucaa agcuc 15

<210> SEQ ID NO 1809
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1809
gggucucaaa gcucu 15

<210> SEQ ID NO 1810
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1810
ggucucaaag cucuu 15

<210> SEQ ID NO 1811
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1811
gucucaaagc ucuua 15

<210> SEQ ID NO 1812
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1812
ucucaaagcu cuuag 15

<210> SEQ ID NO 1813
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1813
cucaaagcuc uuagg 15

<210> SEQ ID NO 1814
<211> LENGTH: 15
<212> TYPE: RNA

<213> ORGANISM: Artificial Sequence
<220> FEATURE:
<223> OTHER INFORMATION: Synthetic Construct

<400> SEQUENCE: 1814
ucaaagcucu uaggg 15

<210> SEQ ID NO 1815
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1815
caaagcucuu agggu 15

<210> SEQ ID NO 1816
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1816
aaagcucuua ggguc 15

<210> SEQ ID NO 1817
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1817
aagcucuuag ggucc 15

<210> SEQ ID NO 1818
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1818
agcucuuagg guccu 15

<210> SEQ ID NO 1819
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1819
gcucuuaggg uccua 15

<210> SEQ ID NO 1820
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1820
cucuuagggu ccuaa 15

<210> SEQ ID NO 1821
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1821
ucuuaggguc cuaag 15

<210> SEQ ID NO 1822
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1822 cuuaggguce uaagg 15

<210> SEQ ID NO 1823
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1823 uuagggucc u aaggg 15

<210> SEQ ID NO 1824
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1824
uaggguccua aggga 15

<210> SEQ ID NO 1825
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1825
aggguccuaa gggac 15

<210> SEQ ID NO 1826
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1826
ggguccuaag ggacu 15

<210> SEQ ID NO 1827
<211> LENGTH: 15
<212> TYPE: RNA
<213> ORGANISM: Artificial Sequence
<220> FEATURE:

<223> OTHER INFORMATION: Synthetic Construct

<400> SEQUENCE: 1827
gguccuaagg gacuu 15

<210> SEQ ID NO 1828
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1828
guccuaaggg acuuu 15

<210> SEQ ID NO 1829
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1829
uccuaaggga cuuua 15

<210> SEQ ID NO 1830
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1830
ccuaagggac uuuau 15

<210> SEQ ID NO 1831
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1831
cuaagggacu uuaug 15

<210> SEQ ID NO 1832
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1832
uaagggacuu uaugg 15

<210> SEQ ID NO 1833
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1833
aagggacuuu auggc 15

<210> SEQ ID NO 1834
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1834
agggacuuua uggca 15

<210> SEQ ID NO 1835
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1835
gggacuuuau ggcac 15

<210> SEQ ID NO 1836
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1836
ggacuuuaug gcacc 15

<210> SEQ ID NO 1837
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1837
gacuuuaugg caccu 15

<210> SEQ ID NO 1838
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1838
acuuuauggc accua 15

<210> SEQ ID NO 1839
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1839
cuuuauggca ccuag 15

<210> SEQ ID NO 1840
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1840
uuuauggcac cuagu 15

<210> SEQ ID NO 1841
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1841
uuauggcacc uaguu 15

<210> SEQ ID NO 1842
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1842
uauggcaccu aguuc 15

<210> SEQ ID NO 1843
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1843
auggcaccua guucc 15

<210> SEQ ID NO 1844
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1844
uggcaccuag uuccg 15

<210> SEQ ID NO 1845
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1845
ggcaccuagu uccga 15

<210> SEQ ID NO 1846
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1846
gcaccuaguu ccgag 15

<210> SEQ ID NO 1847
<211> LENGTH: 15

<212> TYPE: RNA
<213> ORGANISM: Artificial Sequence
<220> FEATURE:
<223> OTHER INFORMATION: Synthetic Construct

<400> SEQUENCE: 1847
caccuaguuc cgagu 15

<210> SEQ ID NO 1848
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1848
accuaguucc gagua 15

<210> SEQ ID NO 1849
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1849
ccuaguuccg aguag 15

<210> SEQ ID NO 1850
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1850
cuaguuccga guagc 15

<210> SEQ ID NO 1851
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1851
uaguuccgag uagcc 15

<210> SEQ ID NO 1852
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1852
aguuccgagu agccc 15

<210> SEQ ID NO 1853
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1853
guuccgagua gccca 15

<210> SEQ ID NO 1854
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1854
uuccgaguag cccag 15

<210> SEQ ID NO 1855
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1855
uccgaguagc ccagg 15

<210> SEQ ID NO 1856
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1856
ccgaguagcc caggg 15

<210> SEQ ID NO 1857
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1857
cgaguagccc agggc 15

<210> SEQ ID NO 1858
<211> LENGTH: 15
<212> TYPE: RNA
<213> ORGANISM: Artificial Sequence
<220> FEATURE:
<223> OTHER INFORMATION: Synthetic Construct

<400> SEQUENCE: 1858
gaguagccca gggca 15

<210> SEQ ID NO 1859
<211> LENGTH: 51
<212> TYPE: DNA
<213> ORGANISM: Homo sapiens

<400> SEQUENCE: 1859
tagtctcttt agtcagcctt atagctaatg ccctgggcta ctcggaacta g 51

<210> SEQ ID NO 1860
<211> LENGTH: 51
<212> TYPE: RNA
<213> ORGANISM: Homo sapiens

<400> SEQUENCE: 1860
cuaguuccga guagcccagg gcauuagcua uaaggcugac uaaagagacu a 51

<210> SEQ ID NO 1861
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1861
cuaguuccga guagcccagg gcau 24

<210> SEQ ID NO 1862
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1862
uaguuccgag uagcccaggg cauu 24

<210> SEQ ID NO 1863
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1863
aguuccgagu agcccagggc auua 24

<210> SEQ ID NO 1864
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1864
guuccgagua gcccagggca uuag 24

<210> SEQ ID NO 1865
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1865
uuccgaguag cccagggcau uagc 24

<210> SEQ ID NO 1866
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1866
uccgaguagc ccagggcauu agcu 24

<210> SEQ ID NO 1867
<211> LENGTH: 24
<212> TYPE: RNA

<213> ORGANISM: Artificial Sequence
<220> FEATURE:
<223> OTHER INFORMATION: Synthetic Construct

<400> SEQUENCE: 1867
ccgaguagcc cagggcauua gcua 24

<210> SEQ ID NO 1868
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1868
cgaguagccc agggcauuag cuau 24

<210> SEQ ID NO 1869
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1869
gaguagccca gggcauuagc uaua 24

<210> SEQ ID NO 1870
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1870
aguagcccag ggcauuagcu auaa 24

<210> SEQ ID NO 1871
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1871
guagcccagg gcauuagcua uaag 24

<210> SEQ ID NO 1872
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1872
uagcccaggg cauuagcuau aagg 24

<210> SEQ ID NO 1873
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1873
agcccagggc auuagcuaua aggc 24

<210> SEQ ID NO 1874
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1874
gcccagggca uuagcuauaa ggcu 24

<210> SEQ ID NO 1875
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1875
cccagggcau uagcuauaag gcug 24

<210> SEQ ID NO 1876
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1876
ccagggcauu agcuauaagg cuga 24

<210> SEQ ID NO 1877
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1877
cagggcauua gcuauaaggc ugac 24

<210> SEQ ID NO 1878
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1878
agggcauuag cuauaaggcu gacu 24

<210> SEQ ID NO 1879
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1879
gggcauuagc uauaaggcug acua 24

<210> SEQ ID NO 1880
<211> LENGTH: 24
<212> TYPE: RNA
<213> ORGANISM: Artificial Sequence
<220> FEATURE:

<223> OTHER INFORMATION: Synthetic Construct

<400> SEQUENCE: 1880
ggcauuagcu auaaggcuga cuaa 24

<210> SEQ ID NO 1881
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1881
gcauuagcua uaaggcugac uaaa 24

<210> SEQ ID NO 1882
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1882
cauuagcuau aaggcugacu aaag 24

<210> SEQ ID NO 1883
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1883
auuagcuaua aggcugacua aaga 24

<210> SEQ ID NO 1884
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1884
uuagcuauaa ggcugacuaa agag 24

<210> SEQ ID NO 1885
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1885
uagcuauaag gcugacuaaa gaga 24

<210> SEQ ID NO 1886
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1886
agcuauaagg cugacuaaag agac 24

<210> SEQ ID NO 1887
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1887
gcuauaaggc ugacuaaaga gacu 24

<210> SEQ ID NO 1888
<211> LENGTH: 24
<212> TYPE: RNA
<213> ORGANISM: Artificial Sequence
<220> FEATURE:
<223> OTHER INFORMATION: Synthetic Construct

<400> SEQUENCE: 1888
cuauaaggcu gacuaaagag acua 24

<210> SEQ ID NO 1889
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1889
uaguuccgag uagcccaggg cau 23

<210> SEQ ID NO 1890
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1890
aguuccgagu agcccagggc auu 23

<210> SEQ ID NO 1891
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1891
guuccgagua gcccagggca uua 23

<210> SEQ ID NO 1892
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1892
uuccgaguag cccagggcau uag 23

<210> SEQ ID NO 1893
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1893
uccgaguagc ccagggcauu agc 23

<210> SEQ ID NO 1894
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1894
ccgaguagcc cagggcauua gcu 23

<210> SEQ ID NO 1895
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1895
cgaguagccc agggcauuag cua 23

<210> SEQ ID NO 1896
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1896
gaguagccca gggcauuagc uau 23

<210> SEQ ID NO 1897
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1897
aguagcccag ggcauuagcu aua 23

<210> SEQ ID NO 1898
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1898
guagcccagg gcauuagcua uaa 23

<210> SEQ ID NO 1899
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1899
uagcccaggg cauuagcuau aag 23

<210> SEQ ID NO 1900
<211> LENGTH: 23

<212> TYPE: RNA
<213> ORGANISM: Artificial Sequence
<220> FEATURE:
<223> OTHER INFORMATION: Synthetic Construct

<400> SEQUENCE: 1900
agcccagggc auuagcuaua agg 23

<210> SEQ ID NO 1901
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1901
gcccagggca uuagcuauaa ggc 23

<210> SEQ ID NO 1902
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1902
cccagggcau uagcuauaag gcu 23

<210> SEQ ID NO 1903
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1903
ccagggcauu agcuauaagg cug 23

<210> SEQ ID NO 1904
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1904
cagggcauua gcuauaaggc uga 23

<210> SEQ ID NO 1905
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1905
agggcauuag cuauaaggcu gac 23

<210> SEQ ID NO 1906
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1906
gggcauuagc uauaaggcug acu 23

<210> SEQ ID NO 1907
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1907
ggcauuagcu auaaggcuga cua 23

<210> SEQ ID NO 1908
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1908
gcauuagcua uaaggcugac uaa 23

<210> SEQ ID NO 1909
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1909
cauuagcuau aaggcugacu aaa 23

<210> SEQ ID NO 1910
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1910
auuagcuaua aggcugacua aag 23

<210> SEQ ID NO 1911
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1911
uuagcuauaa ggcugacuaa aga 23

<210> SEQ ID NO 1912
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1912
uagcuauaag gcugacuaaa gag 23

<210> SEQ ID NO 1913
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1913
agcuauaagg cugacuaaag aga 23

<210> SEQ ID NO 1914
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1914
gcuauaaggc ugacuaaaga gac 23

<210> SEQ ID NO 1915
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1915
cuauaaggcu gacuaaagag acu 23

<210> SEQ ID NO 1916
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1916
uauaaggcug acuaaagaga cua 23

<210> SEQ ID NO 1917
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1917
aguuccgagu agcccagggc au 22

<210> SEQ ID NO 1918
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1918
guuccgagua gcccagggca uu 22

<210> SEQ ID NO 1919
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1919
guuccgagua gcccagggca uu 22

<210> SEQ ID NO 1920
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1920
uuccgaguag cccagggcau ua 22

<210> SEQ ID NO 1921
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1921
ccgaguagcc cagggcauua gc 22

<210> SEQ ID NO 1922
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1922
cgaguagccc agggcauuag cu 22

<210> SEQ ID NO 1923
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1923
gaguagccca gggcauuagc ua 22

<210> SEQ ID NO 1924
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1924
aguagcccag ggcauuagcu au 22

<210> SEQ ID NO 1925
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1925
guagcccagg gcauuagcua ua 22

<210> SEQ ID NO 1926
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1926
uagcccaggg cauuagcuau aa 22

<210> SEQ ID NO 1927
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1927
agcccagggc auuagcuaua ag 22

<210> SEQ ID NO 1928
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1928
gcccagggca uuagcuauaa gg 22

<210> SEQ ID NO 1929
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1929
cccagggcau uagcuauaag gc 22

<210> SEQ ID NO 1930
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1930
ccagggcauu agcuauaagg cu 22

<210> SEQ ID NO 1931
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1931
cagggcauua gcuauaaggc ug 22

<210> SEQ ID NO 1932
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1932
agggcauuag cuauaaggcu ga 22

<210> SEQ ID NO 1933

<211> LENGTH: 22
<212> TYPE: RNA
<213> ORGANISM: Artificial Sequence
<220> FEATURE:
<223> OTHER INFORMATION: Synthetic Construct

<400> SEQUENCE: 1933
gggcauuagc uauaaggcug ac 22

<210> SEQ ID NO 1934
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1934
ggcauuagcu auaaggcuga cu 22

<210> SEQ ID NO 1935
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1935
gcauuagcua uaaggcugac ua 22

<210> SEQ ID NO 1936
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1936
cauuagcuau aaggcugacu aa 22

<210> SEQ ID NO 1937
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1937
auuagcuaua aggcugacua aa 22

<210> SEQ ID NO 1938
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1938
uuagcuauaa ggcugacuaa ag 22

<210> SEQ ID NO 1939
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1939
uagcuauaag gcugacuaaa ga 22

<210> SEQ ID NO 1940
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1940
agcuauaagg cugacuaaag ag 22

<210> SEQ ID NO 1941
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1941
gcuauaaggc ugacuaaaga ga 22

<210> SEQ ID NO 1942
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1942
cuauaaggcu gacuaaagag ac 22

<210> SEQ ID NO 1943
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1943
uauaaggcug acuaaagaga cu 22

<210> SEQ ID NO 1944
<211> LENGTH: 22
<212> TYPE: RNA
<213> ORGANISM: Artificial Sequence
<220> FEATURE:
<223> OTHER INFORMATION: Synthetic Construct

<400> SEQUENCE: 1944
auaaggcuga cuaaagagac ua 22

<210> SEQ ID NO 1945
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1945
guuccgagua gcccagggca u 21

<210> SEQ ID NO 1946
<211> LENGTH: 21
<212> TYPE: RNA

<213> ORGANISM: Artificial Sequence
<220> FEATURE:
<223> OTHER INFORMATION: Synthetic Construct

<400> SEQUENCE: 1946
uuccgaguag cccagggcau u 21

<210> SEQ ID NO 1947
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1947
uccgaguagc ccagggcauu a 21

<210> SEQ ID NO 1948
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1948
ccgaguagcc cagggcauua g 21

<210> SEQ ID NO 1949
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1949
cgaguagccc agggcauuag c 21

<210> SEQ ID NO 1950
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1950
gaguagccca gggcauuagc u 21

<210> SEQ ID NO 1951
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1951
aguagcccag ggcauuagcu a 21

<210> SEQ ID NO 1952
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1952
guagcccagg gcauuagcua u 21

<210> SEQ ID NO 1953
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1953
uagcccaggg cauuagcuau a 21

<210> SEQ ID NO 1954
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1954
agcccagggc auuagcuaua a 21

<210> SEQ ID NO 1955
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1955
gcccagggca uuagcuauaa g 21

<210> SEQ ID NO 1956
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1956
cccagggcau uagcuauaag g 21

<210> SEQ ID NO 1957
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1957
ccagggcauu agcuauaagg c 21

<210> SEQ ID NO 1958
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1958
cagggcauua gcuauaaggc u 21

<210> SEQ ID NO 1959
<211> LENGTH: 21
<212> TYPE: RNA
<213> ORGANISM: Artificial Sequence
<220> FEATURE:

<223> OTHER INFORMATION: Synthetic Construct

<400> SEQUENCE: 1959
agggcauuag cuauaaggcu g 21

<210> SEQ ID NO 1960
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1960
gggcauuagc uauaaggcug a 21

<210> SEQ ID NO 1961
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1961
ggcauuagcu auaaggcuga c 21

<210> SEQ ID NO 1962
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1962
gcauuagcua uaaggcugac u 21

<210> SEQ ID NO 1963
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1963
cauuagcuau aaggcugacu a 21

<210> SEQ ID NO 1964
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1964
auuagcuaua aggcugacua a 21

<210> SEQ ID NO 1965
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1965
uuagcuauaa ggcugacuaa a 21

<210> SEQ ID NO 1966
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1966
uagcuauaag gcugacuaaa g 21

<210> SEQ ID NO 1967
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1967
agcuauaagg cugacuaaag a 21

<210> SEQ ID NO 1968
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1968
gcuauaaggc ugacuaaaga g 21

<210> SEQ ID NO 1969
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1969
cuauaaggcu gacuaaagag a 21

<210> SEQ ID NO 1970
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1970
uauaaggcug acuaaagaga c 21

<210> SEQ ID NO 1971
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1971
auaaggcuga cuaaagagac u 21

<210> SEQ ID NO 1972
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1972
uaaggcugac uaaagagacu a 21

<210> SEQ ID NO 1973
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1973
uuccgaguag cccagggcau 20

<210> SEQ ID NO 1974
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1974
uccgaguagc ccagggcauu 20

<210> SEQ ID NO 1975
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1975
ccgaguagcc cagggcauua 20

<210> SEQ ID NO 1976
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1976
cgaguagccc agggcauuag 20

<210> SEQ ID NO 1977
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1977
gaguagccca gggcauuagc 20

<210> SEQ ID NO 1978
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1978
aguagcccag ggcauuagcu 20

<210> SEQ ID NO 1979
<211> LENGTH: 20

<212> TYPE: RNA
<213> ORGANISM: Artificial Sequence
<220> FEATURE:
<223> OTHER INFORMATION: Synthetic Construct

<400> SEQUENCE: 1979
guagcccagg gcauuagcua 20

<210> SEQ ID NO 1980
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1980
uagcccaggg cauuagcuau 20

<210> SEQ ID NO 1981
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1981
agcccagggc auuagcuaua 20

<210> SEQ ID NO 1982
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1982
gcccagggca uuagcuauaa 20

<210> SEQ ID NO 1983
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1983
cccagggcau uagcuauaag 20

<210> SEQ ID NO 1984
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1984
ccagggcauu agcuauaagg 20

<210> SEQ ID NO 1985
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1985
cagggcauua gcuauaaggc 20

<210> SEQ ID NO 1986
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1986
agggcauuag cuauaaggcu 20

<210> SEQ ID NO 1987
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1987
gggcauuagc uauaaggcug 20

<210> SEQ ID NO 1988
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1988
ggcauuagcu auaaggcuga 20

<210> SEQ ID NO 1989
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1989
gcauuagcua uaaggcugac 20

<210> SEQ ID NO 1990
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1990
cauuagcuau aaggcugacu 20

<210> SEQ ID NO 1991
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1991
auuagcuaua aggcugacua 20

<210> SEQ ID NO 1992
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1992
uuagcuauaa ggcugacuaa 20

<210> SEQ ID NO 1993
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1993
uagcuauaag gcugacuaaa 20

<210> SEQ ID NO 1994
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1994
agcuauaagg cugacuaaag 20

<210> SEQ ID NO 1995
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1995
gcuauaaggc ugacuaaaga 20

<210> SEQ ID NO 1996
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1996
cuauaaggcu gacuaaagag 20

<210> SEQ ID NO 1997
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1997
uauaaggcug acuaaagaga 20

<210> SEQ ID NO 1998
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1998
auaaggcuga cuaaagagac 20

<210> SEQ ID NO 1999
<211> LENGTH: 20
<212> TYPE: RNA
<213> ORGANISM: Artificial Sequence
<220> FEATURE:
<223> OTHER INFORMATION: Synthetic Construct

<400> SEQUENCE: 1999
uaaggcugac uaaagagacu 20

<210> SEQ ID NO 2000
<211> LENGTH: 20
<212> TYPE: RNA
<213> ORGANISM: Artificial Sequence
<220> FEATURE:
<223> OTHER INFORMATION: Synthetic Construct

<400> SEQUENCE: 2000
aaggcugacu aaagagacua 20

<210> SEQ ID NO 2001
<211> LENGTH: 19
<212> TYPE: RNA
<213> ORGANISM: Artificial Sequence
<220> FEATURE:
<223> OTHER INFORMATION: Synthetic Construct

<400> SEQUENCE: 2001
uccgaguagc ccagggcau 19

<210> SEQ ID NO 2002
<211> LENGTH: 19
<212> TYPE: RNA
<213> ORGANISM: Artificial Sequence
<220> FEATURE:
<223> OTHER INFORMATION: Synthetic Construct

<400> SEQUENCE: 2002
ccgaguagcc cagggcauu 19

<210> SEQ ID NO 2003
<211> LENGTH: 19
<212> TYPE: RNA
<213> ORGANISM: Artificial Sequence
<220> FEATURE:
<223> OTHER INFORMATION: Synthetic Construct

<400> SEQUENCE: 2003
cgaguagccc agggcauua 19

<210> SEQ ID NO 2004
<211> LENGTH: 19
<212> TYPE: RNA
<213> ORGANISM: Artificial Sequence
<220> FEATURE:
<223> OTHER INFORMATION: Synthetic Construct

<400> SEQUENCE: 2004
gaguagccca gggcauuag 19

<210> SEQ ID NO 2005
<211> LENGTH: 19
<212> TYPE: RNA
<213> ORGANISM: Artificial Sequence
<220> FEATURE:
<223> OTHER INFORMATION: Synthetic Construct

<400> SEQUENCE: 2005
aguagcccag ggcauuagc 19

<210> SEQ ID NO 2006
<211> LENGTH: 19
<212> TYPE: RNA
<213> ORGANISM: Artificial Sequence
<220> FEATURE:
<223> OTHER INFORMATION: Synthetic Construct

<400> SEQUENCE: 2006
guagcccagg gcauuagcu 19

<210> SEQ ID NO 2007
<211> LENGTH: 19
<212> TYPE: RNA
<213> ORGANISM: Artificial Sequence
<220> FEATURE:
<223> OTHER INFORMATION: Synthetic Construct

<400> SEQUENCE: 2007
uagcccaggg cauuagcua 19

<210> SEQ ID NO 2008
<211> LENGTH: 19
<212> TYPE: RNA
<213> ORGANISM: Artificial Sequence
<220> FEATURE:
<223> OTHER INFORMATION: Synthetic Construct

<400> SEQUENCE: 2008
agcccagggc auuagcuau 19

<210> SEQ ID NO 2009
<211> LENGTH: 19
<212> TYPE: RNA
<213> ORGANISM: Artificial Sequence
<220> FEATURE:
<223> OTHER INFORMATION: Synthetic Construct

<400> SEQUENCE: 2009
gcccagggca uuagcuaua 19

<210> SEQ ID NO 2010
<211> LENGTH: 19
<212> TYPE: RNA
<213> ORGANISM: Artificial Sequence
<220> FEATURE:
<223> OTHER INFORMATION: Synthetic Construct

<400> SEQUENCE: 2010
cccagggcau uagcuauaa 19

<210> SEQ ID NO 2011
<211> LENGTH: 19
<212> TYPE: RNA
<213> ORGANISM: Artificial Sequence
<220> FEATURE:
<223> OTHER INFORMATION: Synthetic Construct

<400> SEQUENCE: 2011
ccagggcauu agcuauaag 19

<210> SEQ ID NO 2012

<211> LENGTH: 19
<212> TYPE: RNA
<213> ORGANISM: Artificial Sequence
<220> FEATURE:
<223> OTHER INFORMATION: Synthetic Construct

<400> SEQUENCE: 2012
cagggcauua gcuauaagg 19

<210> SEQ ID NO 2013
<211> LENGTH: 19
<212> TYPE: RNA
<213> ORGANISM: Artificial Sequence
<220> FEATURE:
<223> OTHER INFORMATION: Synthetic Construct

<400> SEQUENCE: 2013
agggcauuag cuauaaggc 19

<210> SEQ ID NO 2014
<211> LENGTH: 19
<212> TYPE: RNA
<213> ORGANISM: Artificial Sequence
<220> FEATURE:
<223> OTHER INFORMATION: Synthetic Construct

<400> SEQUENCE: 2014
gggcauuagc uauaaggcu 19

<210> SEQ ID NO 2015
<211> LENGTH: 19
<212> TYPE: RNA
<213> ORGANISM: Artificial Sequence
<220> FEATURE:
<223> OTHER INFORMATION: Synthetic Construct

<400> SEQUENCE: 2015
ggcauuagcu auaaggcug 19

<210> SEQ ID NO 2016
<211> LENGTH: 19
<212> TYPE: RNA
<213> ORGANISM: Artificial Sequence
<220> FEATURE:
<223> OTHER INFORMATION: Synthetic Construct

<400> SEQUENCE: 2016
gcauuagcua uaaggcuga 19

<210> SEQ ID NO 2017
<211> LENGTH: 19
<212> TYPE: RNA
<213> ORGANISM: Artificial Sequence
<220> FEATURE:
<223> OTHER INFORMATION: Synthetic Construct

<400> SEQUENCE: 2017
cauuagcuau aaggcugac 19

<210> SEQ ID NO 2018
<211> LENGTH: 19
<212> TYPE: RNA
<213> ORGANISM: Artificial Sequence
<220> FEATURE:
<223> OTHER INFORMATION: Synthetic Construct

<400> SEQUENCE: 2018
auuagcuaua aggcugacu 19

<210> SEQ ID NO 2019
<211> LENGTH: 19
<212> TYPE: RNA
<213> ORGANISM: Artificial Sequence
<220> FEATURE:
<223> OTHER INFORMATION: Synthetic Construct

<400> SEQUENCE: 2019
uuagcuauaa ggcugacua 19

<210> SEQ ID NO 2020
<211> LENGTH: 19
<212> TYPE: RNA
<213> ORGANISM: Artificial Sequence
<220> FEATURE:
<223> OTHER INFORMATION: Synthetic Construct

<400> SEQUENCE: 2020
uagcuauaag gcugacuaa 19

<210> SEQ ID NO 2021
<211> LENGTH: 19
<212> TYPE: RNA
<213> ORGANISM: Artificial Sequence
<220> FEATURE:
<223> OTHER INFORMATION: Synthetic Construct

<400> SEQUENCE: 2021
agcuauaagg cugacuaaa 19

<210> SEQ ID NO 2022
<211> LENGTH: 19
<212> TYPE: RNA
<213> ORGANISM: Artificial Sequence
<220> FEATURE:
<223> OTHER INFORMATION: Synthetic Construct

<400> SEQUENCE: 2022
gcuauaaggc ugacuaaag 19

<210> SEQ ID NO 2023
<211> LENGTH: 19
<212> TYPE: RNA
<213> ORGANISM: Artificial Sequence
<220> FEATURE:
<223> OTHER INFORMATION: Synthetic Construct

<400> SEQUENCE: 2023
cuauaaggcu gacuaaaga 19

<210> SEQ ID NO 2024
<211> LENGTH: 19
<212> TYPE: RNA
<213> ORGANISM: Artificial Sequence
<220> FEATURE:
<223> OTHER INFORMATION: Synthetic Construct

<400> SEQUENCE: 2024
uauaaggcug acuaaagag 19

<210> SEQ ID NO 2025
<211> LENGTH: 19
<212> TYPE: RNA

<213> ORGANISM: Artificial Sequence
<220> FEATURE:
<223> OTHER INFORMATION: Synthetic Construct

<400> SEQUENCE: 2025
auaaggcuga cuaaagaga 19

<210> SEQ ID NO 2026
<211> LENGTH: 19
<212> TYPE: RNA
<213> ORGANISM: Artificial Sequence
<220> FEATURE:
<223> OTHER INFORMATION: Synthetic Construct

<400> SEQUENCE: 2026
uaaggcugac uaaagagac 19

<210> SEQ ID NO 2027
<211> LENGTH: 19
<212> TYPE: RNA
<213> ORGANISM: Artificial Sequence
<220> FEATURE:
<223> OTHER INFORMATION: Synthetic Construct

<400> SEQUENCE: 2027
aaggcugacu aaagagacu 19

<210> SEQ ID NO 2028
<211> LENGTH: 19
<212> TYPE: RNA
<213> ORGANISM: Artificial Sequence
<220> FEATURE:
<223> OTHER INFORMATION: Synthetic Construct

<400> SEQUENCE: 2028
aggcugacua aagagacua 19

<210> SEQ ID NO 2029
<211> LENGTH: 18
<212> TYPE: RNA
<213> ORGANISM: Artificial Sequence
<220> FEATURE:
<223> OTHER INFORMATION: Synthetic Construct

<400> SEQUENCE: 2029
ccgaguagcc cagggcau 18

<210> SEQ ID NO 2030
<211> LENGTH: 18
<212> TYPE: RNA
<213> ORGANISM: Artificial Sequence
<220> FEATURE:
<223> OTHER INFORMATION: Synthetic Construct

<400> SEQUENCE: 2030
cgaguagccc agggcauu 18

<210> SEQ ID NO 2031
<211> LENGTH: 18
<212> TYPE: RNA
<213> ORGANISM: Artificial Sequence
<220> FEATURE:
<223> OTHER INFORMATION: Synthetic Construct

<400> SEQUENCE: 2031
gaguagccca gggcauua 18

<210> SEQ ID NO 2032
<211> LENGTH: 18
<212> TYPE: RNA
<213> ORGANISM: Artificial Sequence
<220> FEATURE:
<223> OTHER INFORMATION: Synthetic Construct

<400> SEQUENCE: 2032
aguagcccag ggcauuag 18

<210> SEQ ID NO 2033
<211> LENGTH: 18
<212> TYPE: RNA
<213> ORGANISM: Artificial Sequence
<220> FEATURE:
<223> OTHER INFORMATION: Synthetic Construct

<400> SEQUENCE: 2033
guagcccagg gcauuagc 18

<210> SEQ ID NO 2034
<211> LENGTH: 18
<212> TYPE: RNA
<213> ORGANISM: Artificial Sequence
<220> FEATURE:
<223> OTHER INFORMATION: Synthetic Construct

<400> SEQUENCE: 2034
uagcccaggg cauuagcu 18

<210> SEQ ID NO 2035
<211> LENGTH: 18
<212> TYPE: RNA
<213> ORGANISM: Artificial Sequence
<220> FEATURE:
<223> OTHER INFORMATION: Synthetic Construct

<400> SEQUENCE: 2035
agcccagggc auuagcua 18

<210> SEQ ID NO 2036
<211> LENGTH: 18
<212> TYPE: RNA
<213> ORGANISM: Artificial Sequence
<220> FEATURE:
<223> OTHER INFORMATION: Synthetic Construct

<400> SEQUENCE: 2036
gcccagggca uuagcuau 18

<210> SEQ ID NO 2037
<211> LENGTH: 18
<212> TYPE: RNA
<213> ORGANISM: Artificial Sequence
<220> FEATURE:
<223> OTHER INFORMATION: Synthetic Construct

<400> SEQUENCE: 2037
cccagggcau uagcuaua 18

<210> SEQ ID NO 2038
<211> LENGTH: 18
<212> TYPE: RNA
<213> ORGANISM: Artificial Sequence
<220> FEATURE:

<223> OTHER INFORMATION: Synthetic Construct

<400> SEQUENCE: 2038
ccagggcauu agcuauaa 18

<210> SEQ ID NO 2039
<211> LENGTH: 18
<212> TYPE: RNA
<213> ORGANISM: Artificial Sequence
<220> FEATURE:
<223> OTHER INFORMATION: Synthetic Construct

<400> SEQUENCE: 2039
cagggcauua gcuauaag 18

<210> SEQ ID NO 2040
<211> LENGTH: 18
<212> TYPE: RNA
<213> ORGANISM: Artificial Sequence
<220> FEATURE:
<223> OTHER INFORMATION: Synthetic Construct

<400> SEQUENCE: 2040
agggcauuag cuauaagg 18

<210> SEQ ID NO 2041
<211> LENGTH: 18
<212> TYPE: RNA
<213> ORGANISM: Artificial Sequence
<220> FEATURE:
<223> OTHER INFORMATION: Synthetic Construct

<400> SEQUENCE: 2041
gggcauuagc uauaaggc 18

<210> SEQ ID NO 2042
<211> LENGTH: 18
<212> TYPE: RNA
<213> ORGANISM: Artificial Sequence
<220> FEATURE:
<223> OTHER INFORMATION: Synthetic Construct

<400> SEQUENCE: 2042
ggcauuagcu auaaggcu 18

<210> SEQ ID NO 2043
<211> LENGTH: 18
<212> TYPE: RNA
<213> ORGANISM: Artificial Sequence
<220> FEATURE:
<223> OTHER INFORMATION: Synthetic Construct

<400> SEQUENCE: 2043
gcauuagcua uaaggcug 18

<210> SEQ ID NO 2044
<211> LENGTH: 18
<212> TYPE: RNA
<213> ORGANISM: Artificial Sequence
<220> FEATURE:
<223> OTHER INFORMATION: Synthetic Construct

<400> SEQUENCE: 2044
cauuagcuau aaggcuga 18

<210> SEQ ID NO 2045
<211> LENGTH: 18
<212> TYPE: RNA
<213> ORGANISM: Artificial Sequence
<220> FEATURE:
<223> OTHER INFORMATION: Synthetic Construct

<400> SEQUENCE: 2045
auuagcuaua aggcugac 18

<210> SEQ ID NO 2046
<211> LENGTH: 18
<212> TYPE: RNA
<213> ORGANISM: Artificial Sequence
<220> FEATURE:
<223> OTHER INFORMATION: Synthetic Construct

<400> SEQUENCE: 2046
uuagcuauaa ggcugacu 18

<210> SEQ ID NO 2047
<211> LENGTH: 18
<212> TYPE: RNA
<213> ORGANISM: Artificial Sequence
<220> FEATURE:
<223> OTHER INFORMATION: Synthetic Construct

<400> SEQUENCE: 2047
uagcuauaag gcugacua 18

<210> SEQ ID NO 2048
<211> LENGTH: 18
<212> TYPE: RNA
<213> ORGANISM: Artificial Sequence
<220> FEATURE:
<223> OTHER INFORMATION: Synthetic Construct

<400> SEQUENCE: 2048
agcuauaagg cugacuaa 18

<210> SEQ ID NO 2049
<211> LENGTH: 18
<212> TYPE: RNA
<213> ORGANISM: Artificial Sequence
<220> FEATURE:
<223> OTHER INFORMATION: Synthetic Construct

<400> SEQUENCE: 2049
gcuauaaggc ugacuaaa 18

<210> SEQ ID NO 2050
<211> LENGTH: 18
<212> TYPE: RNA
<213> ORGANISM: Artificial Sequence
<220> FEATURE:
<223> OTHER INFORMATION: Synthetic Construct

<400> SEQUENCE: 2050
cuauaaggcu gacuaaag 18

<210> SEQ ID NO 2051
<211> LENGTH: 18
<212> TYPE: RNA
<213> ORGANISM: Artificial Sequence
<220> FEATURE:
<223> OTHER INFORMATION: Synthetic Construct

<400> SEQUENCE: 2051
uauaaggcug acuaaaga 18

<210> SEQ ID NO 2052
<211> LENGTH: 18
<212> TYPE: RNA
<213> ORGANISM: Artificial Sequence
<220> FEATURE:
<223> OTHER INFORMATION: Synthetic Construct

<400> SEQUENCE: 2052
auaaggcuga cuaaagag 18

<210> SEQ ID NO 2053
<211> LENGTH: 18
<212> TYPE: RNA
<213> ORGANISM: Artificial Sequence
<220> FEATURE:
<223> OTHER INFORMATION: Synthetic Construct

<400> SEQUENCE: 2053
uaaggcugac uaaagaga 18

<210> SEQ ID NO 2054
<211> LENGTH: 18
<212> TYPE: RNA
<213> ORGANISM: Artificial Sequence
<220> FEATURE:
<223> OTHER INFORMATION: Synthetic Construct

<400> SEQUENCE: 2054
aaggcugacu aaagagac 18

<210> SEQ ID NO 2055
<211> LENGTH: 18
<212> TYPE: RNA
<213> ORGANISM: Artificial Sequence
<220> FEATURE:
<223> OTHER INFORMATION: Synthetic Construct

<400> SEQUENCE: 2055
aggcugacua aagagacu 18

<210> SEQ ID NO 2056
<211> LENGTH: 18
<212> TYPE: RNA
<213> ORGANISM: Artificial Sequence
<220> FEATURE:
<223> OTHER INFORMATION: Synthetic Construct

<400> SEQUENCE: 2056
ggcugacuaa agagacua 18

<210> SEQ ID NO 2057
<211> LENGTH: 17
<212> TYPE: RNA
<213> ORGANISM: Artificial Sequence
<220> FEATURE:
<223> OTHER INFORMATION: Synthetic Construct

<400> SEQUENCE: 2057
cgaguagccc agggcau 17

<210> SEQ ID NO 2058
<211> LENGTH: 17

<212> TYPE: RNA
<213> ORGANISM: Artificial Sequence
<220> FEATURE:
<223> OTHER INFORMATION: Synthetic Construct

<400> SEQUENCE: 2058
gaguagccca gggcauu 17

<210> SEQ ID NO 2059
<211> LENGTH: 17
<212> TYPE: RNA
<213> ORGANISM: Artificial Sequence
<220> FEATURE:
<223> OTHER INFORMATION: Synthetic Construct

<400> SEQUENCE: 2059
aguagcccag ggcauua 17

<210> SEQ ID NO 2060
<211> LENGTH: 17
<212> TYPE: RNA
<213> ORGANISM: Artificial Sequence
<220> FEATURE:
<223> OTHER INFORMATION: Synthetic Construct

<400> SEQUENCE: 2060
guagcccagg gcauuag 17

<210> SEQ ID NO 2061
<211> LENGTH: 17
<212> TYPE: RNA
<213> ORGANISM: Artificial Sequence
<220> FEATURE:
<223> OTHER INFORMATION: Synthetic Construct

<400> SEQUENCE: 2061
uagcccaggg cauuagc 17

<210> SEQ ID NO 2062
<211> LENGTH: 17
<212> TYPE: RNA
<213> ORGANISM: Artificial Sequence
<220> FEATURE:
<223> OTHER INFORMATION: Synthetic Construct

<400> SEQUENCE: 2062
agcccagggc auuagcu 17

<210> SEQ ID NO 2063
<211> LENGTH: 17
<212> TYPE: RNA
<213> ORGANISM: Artificial Sequence
<220> FEATURE:
<223> OTHER INFORMATION: Synthetic Construct

<400> SEQUENCE: 2063
gcccagggca uuagcua 17

<210> SEQ ID NO 2064
<211> LENGTH: 17
<212> TYPE: RNA
<213> ORGANISM: Artificial Sequence
<220> FEATURE:
<223> OTHER INFORMATION: Synthetic Construct

<400> SEQUENCE: 2064
cccagggcau uagcuau 17

<210> SEQ ID NO 2065
<211> LENGTH: 17
<212> TYPE: RNA
<213> ORGANISM: Artificial Sequence
<220> FEATURE:
<223> OTHER INFORMATION: Synthetic Construct

<400> SEQUENCE: 2065
ccagggcauu agcuaua 17

<210> SEQ ID NO 2066
<211> LENGTH: 17
<212> TYPE: RNA
<213> ORGANISM: Artificial Sequence
<220> FEATURE:
<223> OTHER INFORMATION: Synthetic Construct

<400> SEQUENCE: 2066
cagggcauua gcuauaa 17

<210> SEQ ID NO 2067
<211> LENGTH: 17
<212> TYPE: RNA
<213> ORGANISM: Artificial Sequence
<220> FEATURE:
<223> OTHER INFORMATION: Synthetic Construct

<400> SEQUENCE: 2067
agggcauuag cuauaag 17

<210> SEQ ID NO 2068
<211> LENGTH: 17
<212> TYPE: RNA
<213> ORGANISM: Artificial Sequence
<220> FEATURE:
<223> OTHER INFORMATION: Synthetic Construct

<400> SEQUENCE: 2068
gggcauuagc uauaagg 17

<210> SEQ ID NO 2069
<211> LENGTH: 17
<212> TYPE: RNA
<213> ORGANISM: Artificial Sequence
<220> FEATURE:
<223> OTHER INFORMATION: Synthetic Construct

<400> SEQUENCE: 2069
ggcauuagcu auaaggc 17

<210> SEQ ID NO 2070
<211> LENGTH: 17
<212> TYPE: RNA
<213> ORGANISM: Artificial Sequence
<220> FEATURE:
<223> OTHER INFORMATION: Synthetic Construct

<400> SEQUENCE: 2070
gcauuagcua uaaggcu 17

<210> SEQ ID NO 2071
<211> LENGTH: 17
<212> TYPE: RNA
<213> ORGANISM: Artificial Sequence
<220> FEATURE:
<223> OTHER INFORMATION: Synthetic Construct

<400> SEQUENCE: 2071
cauuagcuau aaggcug 17

<210> SEQ ID NO 2072
<211> LENGTH: 17
<212> TYPE: RNA
<213> ORGANISM: Artificial Sequence
<220> FEATURE:
<223> OTHER INFORMATION: Synthetic Construct

<400> SEQUENCE: 2072
auuagcuaua aggcuga 17

<210> SEQ ID NO 2073
<211> LENGTH: 17
<212> TYPE: RNA
<213> ORGANISM: Artificial Sequence
<220> FEATURE:
<223> OTHER INFORMATION: Synthetic Construct

<400> SEQUENCE: 2073
uuagcuauaa ggcugac 17

<210> SEQ ID NO 2074
<211> LENGTH: 17
<212> TYPE: RNA
<213> ORGANISM: Artificial Sequence
<220> FEATURE:
<223> OTHER INFORMATION: Synthetic Construct

<400> SEQUENCE: 2074
uagcuauaag gcugacu 17

<210> SEQ ID NO 2075
<211> LENGTH: 17
<212> TYPE: RNA
<213> ORGANISM: Artificial Sequence
<220> FEATURE:
<223> OTHER INFORMATION: Synthetic Construct

<400> SEQUENCE: 2075
agcuauaagg cugacua 17

<210> SEQ ID NO 2076
<211> LENGTH: 17
<212> TYPE: RNA
<213> ORGANISM: Artificial Sequence
<220> FEATURE:
<223> OTHER INFORMATION: Synthetic Construct

<400> SEQUENCE: 2076
gcuauaaggc ugacuaa 17

<210> SEQ ID NO 2077
<211> LENGTH: 17
<212> TYPE: RNA
<213> ORGANISM: Artificial Sequence
<220> FEATURE:
<223> OTHER INFORMATION: Synthetic Construct

<400> SEQUENCE: 2077
cuauaaggcu gacuaaa 17

<210> SEQ ID NO 2078
<211> LENGTH: 17
<212> TYPE: RNA
<213> ORGANISM: Artificial Sequence
<220> FEATURE:
<223> OTHER INFORMATION: Synthetic Construct

<400> SEQUENCE: 2078
uauaaggcug acuaaag 17

<210> SEQ ID NO 2079
<211> LENGTH: 17
<212> TYPE: RNA
<213> ORGANISM: Artificial Sequence
<220> FEATURE:
<223> OTHER INFORMATION: Synthetic Construct

<400> SEQUENCE: 2079
auaaggcuga cuaaaga 17

<210> SEQ ID NO 2080
<211> LENGTH: 17
<212> TYPE: RNA
<213> ORGANISM: Artificial Sequence
<220> FEATURE:
<223> OTHER INFORMATION: Synthetic Construct

<400> SEQUENCE: 2080
uaaggcugac uaaagag 17

<210> SEQ ID NO 2081
<211> LENGTH: 17
<212> TYPE: RNA
<213> ORGANISM: Artificial Sequence
<220> FEATURE:
<223> OTHER INFORMATION: Synthetic Construct

<400> SEQUENCE: 2081
aaggcugacu aaagaga 17

<210> SEQ ID NO 2082
<211> LENGTH: 17
<212> TYPE: RNA
<213> ORGANISM: Artificial Sequence
<220> FEATURE:
<223> OTHER INFORMATION: Synthetic Construct

<400> SEQUENCE: 2082
aggcugacua aagagac 17

<210> SEQ ID NO 2083
<211> LENGTH: 17
<212> TYPE: RNA
<213> ORGANISM: Artificial Sequence
<220> FEATURE:
<223> OTHER INFORMATION: Synthetic Construct

<400> SEQUENCE: 2083
ggcugacuaa agagacu 17

<210> SEQ ID NO 2084
<211> LENGTH: 17
<212> TYPE: RNA
<213> ORGANISM: Artificial Sequence
<220> FEATURE:
<223> OTHER INFORMATION: Synthetic Construct

<400> SEQUENCE: 2084
gcugacuaaa gagacua 17

<210> SEQ ID NO 2085
<211> LENGTH: 16
<212> TYPE: RNA
<213> ORGANISM: Artificial Sequence
<220> FEATURE:
<223> OTHER INFORMATION: Synthetic Construct

<400> SEQUENCE: 2085
gaguagccca gggcau 16

<210> SEQ ID NO 2086
<211> LENGTH: 16
<212> TYPE: RNA
<213> ORGANISM: Artificial Sequence
<220> FEATURE:
<223> OTHER INFORMATION: Synthetic Construct

<400> SEQUENCE: 2086
aguagcccag ggcauu 16

<210> SEQ ID NO 2087
<211> LENGTH: 16
<212> TYPE: RNA
<213> ORGANISM: Artificial Sequence
<220> FEATURE:
<223> OTHER INFORMATION: Synthetic Construct

<400> SEQUENCE: 2087
guagcccagg gcauua 16

<210> SEQ ID NO 2088
<211> LENGTH: 16
<212> TYPE: RNA
<213> ORGANISM: Artificial Sequence
<220> FEATURE:
<223> OTHER INFORMATION: Synthetic Construct

<400> SEQUENCE: 2088
uagcccaggg cauuag 16

<210> SEQ ID NO 2089
<211> LENGTH: 16
<212> TYPE: RNA
<213> ORGANISM: Artificial Sequence
<220> FEATURE:
<223> OTHER INFORMATION: Synthetic Construct

<400> SEQUENCE: 2089
agcccagggc auuagc 16

<210> SEQ ID NO 2090
<211> LENGTH: 16
<212> TYPE: RNA
<213> ORGANISM: Artificial Sequence
<220> FEATURE:
<223> OTHER INFORMATION: Synthetic Construct

<400> SEQUENCE: 2090
gcccagggca uuagcu 16

<210> SEQ ID NO 2091

<211> LENGTH: 16
<212> TYPE: RNA
<213> ORGANISM: Artificial Sequence
<220> FEATURE:
<223> OTHER INFORMATION: Synthetic Construct

<400> SEQUENCE: 2091
cccagggcau uagcua 16

<210> SEQ ID NO 2092
<211> LENGTH: 16
<212> TYPE: RNA
<213> ORGANISM: Artificial Sequence
<220> FEATURE:
<223> OTHER INFORMATION: Synthetic Construct

<400> SEQUENCE: 2092
ccagggcauu agcuau 16

<210> SEQ ID NO 2093
<211> LENGTH: 16
<212> TYPE: RNA
<213> ORGANISM: Artificial Sequence
<220> FEATURE:
<223> OTHER INFORMATION: Synthetic Construct

<400> SEQUENCE: 2093
cagggcauua gcuaua 16

<210> SEQ ID NO 2094
<211> LENGTH: 16
<212> TYPE: RNA
<213> ORGANISM: Artificial Sequence
<220> FEATURE:
<223> OTHER INFORMATION: Synthetic Construct

<400> SEQUENCE: 2094
agggcauuag cuauaa 16

<210> SEQ ID NO 2095
<211> LENGTH: 16
<212> TYPE: RNA
<213> ORGANISM: Artificial Sequence
<220> FEATURE:
<223> OTHER INFORMATION: Synthetic Construct

<400> SEQUENCE: 2095
gggcauuagc uauaag 16

<210> SEQ ID NO 2096
<211> LENGTH: 16
<212> TYPE: RNA
<213> ORGANISM: Artificial Sequence
<220> FEATURE:
<223> OTHER INFORMATION: Synthetic Construct

<400> SEQUENCE: 2096
ggcauuagcu auaagg 16

<210> SEQ ID NO 2097
<211> LENGTH: 16
<212> TYPE: RNA
<213> ORGANISM: Artificial Sequence
<220> FEATURE:
<223> OTHER INFORMATION: Synthetic Construct

<400> SEQUENCE: 2097
gcauuagcua uaaggc 16

<210> SEQ ID NO 2098
<211> LENGTH: 16
<212> TYPE: RNA
<213> ORGANISM: Artificial Sequence
<220> FEATURE:
<223> OTHER INFORMATION: Synthetic Construct

<400> SEQUENCE: 2098
cauuagcuau aaggcu 16

<210> SEQ ID NO 2099
<211> LENGTH: 16
<212> TYPE: RNA
<213> ORGANISM: Artificial Sequence
<220> FEATURE:
<223> OTHER INFORMATION: Synthetic Construct

<400> SEQUENCE: 2099
auuagcuaua aggcug 16

<210> SEQ ID NO 2100
<211> LENGTH: 16
<212> TYPE: RNA
<213> ORGANISM: Artificial Sequence
<220> FEATURE:
<223> OTHER INFORMATION: Synthetic Construct

<400> SEQUENCE: 2100
uuagcuauaa ggcuga 16

<210> SEQ ID NO 2101
<211> LENGTH: 16
<212> TYPE: RNA
<213> ORGANISM: Artificial Sequence
<220> FEATURE:
<223> OTHER INFORMATION: Synthetic Construct

<400> SEQUENCE: 2101
uagcuauaag gcugac 16

<210> SEQ ID NO 2102
<211> LENGTH: 16
<212> TYPE: RNA
<213> ORGANISM: Artificial Sequence
<220> FEATURE:
<223> OTHER INFORMATION: Synthetic Construct

<400> SEQUENCE: 2102
agcuauaagg cugacu 16

<210> SEQ ID NO 2103
<211> LENGTH: 16
<212> TYPE: RNA
<213> ORGANISM: Artificial Sequence
<220> FEATURE:
<223> OTHER INFORMATION: Synthetic Construct

<400> SEQUENCE: 2103
gcuauaaggc ugacua 16

<210> SEQ ID NO 2104
<211> LENGTH: 16
<212> TYPE: RNA

<213> ORGANISM: Artificial Sequence
<220> FEATURE:
<223> OTHER INFORMATION: Synthetic Construct

<400> SEQUENCE: 2104
cuauaaggcu gacuaa 16

<210> SEQ ID NO 2105
<211> LENGTH: 16
<212> TYPE: RNA
<213> ORGANISM: Artificial Sequence
<220> FEATURE:
<223> OTHER INFORMATION: Synthetic Construct

<400> SEQUENCE: 2105
uauaaggcug acuaaa 16

<210> SEQ ID NO 2106
<211> LENGTH: 16
<212> TYPE: RNA
<213> ORGANISM: Artificial Sequence
<220> FEATURE:
<223> OTHER INFORMATION: Synthetic Construct

<400> SEQUENCE: 2106
auaaggcuga cuaaag 16

<210> SEQ ID NO 2107
<211> LENGTH: 16
<212> TYPE: RNA
<213> ORGANISM: Artificial Sequence
<220> FEATURE:
<223> OTHER INFORMATION: Synthetic Construct

<400> SEQUENCE: 2107
uaaggcugac uaaaga 16

<210> SEQ ID NO 2108
<211> LENGTH: 16
<212> TYPE: RNA
<213> ORGANISM: Artificial Sequence
<220> FEATURE:
<223> OTHER INFORMATION: Synthetic Construct

<400> SEQUENCE: 2108
aaggcugacu aaagag 16

<210> SEQ ID NO 2109
<211> LENGTH: 16
<212> TYPE: RNA
<213> ORGANISM: Artificial Sequence
<220> FEATURE:
<223> OTHER INFORMATION: Synthetic Construct

<400> SEQUENCE: 2109
aggcugacua aagaga 16

<210> SEQ ID NO 2110
<211> LENGTH: 16
<212> TYPE: RNA
<213> ORGANISM: Artificial Sequence
<220> FEATURE:
<223> OTHER INFORMATION: Synthetic Construct

<400> SEQUENCE: 2110
ggcugacuaa agagac 16

<210> SEQ ID NO 2111
<211> LENGTH: 16
<212> TYPE: RNA
<213> ORGANISM: Artificial Sequence
<220> FEATURE:
<223> OTHER INFORMATION: Synthetic Construct

<400> SEQUENCE: 2111
gcugacuaaa gagacu 16

<210> SEQ ID NO 2112
<211> LENGTH: 16
<212> TYPE: RNA
<213> ORGANISM: Artificial Sequence
<220> FEATURE:
<223> OTHER INFORMATION: Synthetic Construct

<400> SEQUENCE: 2112
cugacuaaag agacua 16

<210> SEQ ID NO 2113
<211> LENGTH: 15
<212> TYPE: RNA
<213> ORGANISM: Artificial Sequence
<220> FEATURE:
<223> OTHER INFORMATION: Synthetic Construct

<400> SEQUENCE: 2113
aguagcccag ggcau 15

<210> SEQ ID NO 2114
<211> LENGTH: 15
<212> TYPE: RNA
<213> ORGANISM: Artificial Sequence
<220> FEATURE:
<223> OTHER INFORMATION: Synthetic Construct

<400> SEQUENCE: 2114
guagcccagg gcauu 15

<210> SEQ ID NO 2115
<211> LENGTH: 15
<212> TYPE: RNA
<213> ORGANISM: Artificial Sequence
<220> FEATURE:
<223> OTHER INFORMATION: Synthetic Construct

<400> SEQUENCE: 2115
uagcccaggg cauua 15

<210> SEQ ID NO 2116
<211> LENGTH: 15
<212> TYPE: RNA
<213> ORGANISM: Artificial Sequence
<220> FEATURE:
<223> OTHER INFORMATION: Synthetic Construct

<400> SEQUENCE: 2116
agcccagggc auuag 15

<210> SEQ ID NO 2117
<211> LENGTH: 15
<212> TYPE: RNA
<213> ORGANISM: Artificial Sequence
<220> FEATURE:

<223> OTHER INFORMATION: Synthetic Construct

<400> SEQUENCE: 2117
gcccagggca uuagc 15

<210> SEQ ID NO 2118
<211> LENGTH: 15
<212> TYPE: RNA
<213> ORGANISM: Artificial Sequence
<220> FEATURE:
<223> OTHER INFORMATION: Synthetic Construct

<400> SEQUENCE: 2118
cccagggcau uagcu 15

<210> SEQ ID NO 2119
<211> LENGTH: 15
<212> TYPE: RNA
<213> ORGANISM: Artificial Sequence
<220> FEATURE:
<223> OTHER INFORMATION: Synthetic Construct

<400> SEQUENCE: 2119
ccagggcauu agcua 15

<210> SEQ ID NO 2120
<211> LENGTH: 15
<212> TYPE: RNA
<213> ORGANISM: Artificial Sequence
<220> FEATURE:
<223> OTHER INFORMATION: Synthetic Construct

<400> SEQUENCE: 2120
cagggcauua gcuau 15

<210> SEQ ID NO 2121
<211> LENGTH: 15
<212> TYPE: RNA
<213> ORGANISM: Artificial Sequence
<220> FEATURE:
<223> OTHER INFORMATION: Synthetic Construct

<400> SEQUENCE: 2121
agggcauuag cuaua 15

<210> SEQ ID NO 2122
<211> LENGTH: 15
<212> TYPE: RNA
<213> ORGANISM: Artificial Sequence
<220> FEATURE:
<223> OTHER INFORMATION: Synthetic Construct

<400> SEQUENCE: 2122
gggcauuagc uauaa 15

<210> SEQ ID NO 2123
<211> LENGTH: 15
<212> TYPE: RNA
<213> ORGANISM: Artificial Sequence
<220> FEATURE:
<223> OTHER INFORMATION: Synthetic Construct

<400> SEQUENCE: 2123
ggcauuagcu auaag 15

<210> SEQ ID NO 2124
<211> LENGTH: 15
<212> TYPE: RNA
<213> ORGANISM: Artificial Sequence
<220> FEATURE:
<223> OTHER INFORMATION: Synthetic Construct

<400> SEQUENCE: 2124
gcauuagcua uaagg 15

<210> SEQ ID NO 2125
<211> LENGTH: 15
<212> TYPE: RNA
<213> ORGANISM: Artificial Sequence
<220> FEATURE:
<223> OTHER INFORMATION: Synthetic Construct

<400> SEQUENCE: 2125
cauuagcuau aaggc 15

<210> SEQ ID NO 2126
<211> LENGTH: 15
<212> TYPE: RNA
<213> ORGANISM: Artificial Sequence
<220> FEATURE:
<223> OTHER INFORMATION: Synthetic Construct

<400> SEQUENCE: 2126
auuagcuaua aggcu 15

<210> SEQ ID NO 2127
<211> LENGTH: 15
<212> TYPE: RNA
<213> ORGANISM: Artificial Sequence
<220> FEATURE:
<223> OTHER INFORMATION: Synthetic Construct

<400> SEQUENCE: 2127
uuagcuauaa ggcug 15

<210> SEQ ID NO 2128
<211> LENGTH: 15
<212> TYPE: RNA
<213> ORGANISM: Artificial Sequence
<220> FEATURE:
<223> OTHER INFORMATION: Synthetic Construct

<400> SEQUENCE: 2128
uagcuauaag gcuga 15

<210> SEQ ID NO 2129
<211> LENGTH: 15
<212> TYPE: RNA
<213> ORGANISM: Artificial Sequence
<220> FEATURE:
<223> OTHER INFORMATION: Synthetic Construct

<400> SEQUENCE: 2129
agcuauaagg cugac 15

<210> SEQ ID NO 2130
<211> LENGTH: 15
<212> TYPE: RNA
<213> ORGANISM: Artificial Sequence
<220> FEATURE:
<223> OTHER INFORMATION: Synthetic Construct

<400> SEQUENCE: 2130
gcuauaaggc ugacu 15

<210> SEQ ID NO 2131
<211> LENGTH: 15
<212> TYPE: RNA
<213> ORGANISM: Artificial Sequence
<220> FEATURE:
<223> OTHER INFORMATION: Synthetic Construct

<400> SEQUENCE: 2131
cuauaaggcu gacua 15

<210> SEQ ID NO 2132
<211> LENGTH: 15
<212> TYPE: RNA
<213> ORGANISM: Artificial Sequence
<220> FEATURE:
<223> OTHER INFORMATION: Synthetic Construct

<400> SEQUENCE: 2132
uauaaggcug acuaa 15

<210> SEQ ID NO 2133
<211> LENGTH: 15
<212> TYPE: RNA
<213> ORGANISM: Artificial Sequence
<220> FEATURE:
<223> OTHER INFORMATION: Synthetic Construct

<400> SEQUENCE: 2133
auaaggcuga cuaaa 15

<210> SEQ ID NO 2134
<211> LENGTH: 15
<212> TYPE: RNA
<213> ORGANISM: Artificial Sequence
<220> FEATURE:
<223> OTHER INFORMATION: Synthetic Construct

<400> SEQUENCE: 2134
uaaggcugac uaaag 15

<210> SEQ ID NO 2135
<211> LENGTH: 15
<212> TYPE: RNA
<213> ORGANISM: Artificial Sequence
<220> FEATURE:
<223> OTHER INFORMATION: Synthetic Construct

<400> SEQUENCE: 2135
aaggcugacu aaaga 15

<210> SEQ ID NO 2136
<211> LENGTH: 15
<212> TYPE: RNA
<213> ORGANISM: Artificial Sequence
<220> FEATURE:
<223> OTHER INFORMATION: Synthetic Construct

<400> SEQUENCE: 2136
aggcugacua aagag 15

<210> SEQ ID NO 2137
<211> LENGTH: 15
<212> TYPE: RNA
<213> ORGANISM: Artificial Sequence
<220> FEATURE:
<223> OTHER INFORMATION: Synthetic Construct

<400> SEQUENCE: 2137
ggcugacuaa agaga 15

<210> SEQ ID NO 2138
<211> LENGTH: 15
<212> TYPE: RNA
<213> ORGANISM: Artificial Sequence
<220> FEATURE:
<223> OTHER INFORMATION: Synthetic Construct

<400> SEQUENCE: 2138
gcugacuaaa gagac 15

<210> SEQ ID NO 2139
<211> LENGTH: 15
<212> TYPE: RNA
<213> ORGANISM: Artificial Sequence
<220> FEATURE:
<223> OTHER INFORMATION: Synthetic Construct

<400> SEQUENCE: 2139
cugacuaaag agacu 15

<210> SEQ ID NO 2140
<211> LENGTH: 15
<212> TYPE: RNA
<213> ORGANISM: Artificial Sequence
<220> FEATURE:
<223> OTHER INFORMATION: Synthetic Construct

<400> SEQUENCE: 2140
ugacuaaaga gacua 15

<210> SEQ ID NO 2141
<211> LENGTH: 16
<212> TYPE: DNA
<213> ORGANISM: Artificial Sequence
<220> FEATURE:
<223> OTHER INFORMATION: Synthetic Construct

<400> SEQUENCE: 2141
gcatgcatgc atgcat 16

<210> SEQ ID NO 2142
<211> LENGTH: 14
<212> TYPE: DNA
<213> ORGANISM: Artificial Sequence
<220> FEATURE:
<223> OTHER INFORMATION: Synthetic Construct

<400> SEQUENCE: 2142
gcatgcatgc atgc 14

-continued

```
<210> SEQ ID NO 2143
<211> LENGTH: 14
<212> TYPE: DNA
<213> ORGANISM: Artificial Sequence
<220> FEATURE:
<223> OTHER INFORMATION: Synthetic Construct

<400> SEQUENCE: 2143

gcatttgcag cagc                                                    14
```